(12) United States Patent
Alper et al.

(10) Patent No.: US 9,695,223 B2
(45) Date of Patent: Jul. 4, 2017

(54) ENGINEERED XYLOSE TRANSPORTERS WITH REDUCED GLUCOSE INHIBITION

(71) Applicant: Board of Regents, The University of Texas System, Austin, TX (US)

(72) Inventors: Hal Alper, Austin, TX (US); Eric Young, Arlington, MA (US); Sunmi Lee, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/719,206

(22) Filed: May 21, 2015

(65) Prior Publication Data

US 2015/0344532 A1 Dec. 3, 2015

Related U.S. Application Data

(60) Provisional application No. 62/001,495, filed on May 21, 2014.

(51) Int. Cl.
| | |
|---|---|
| *C12N 9/00* | (2006.01) |
| *C07K 14/40* | (2006.01) |
| *C07K 14/33* | (2006.01) |
| *A61K 38/00* | (2006.01) |

(52) U.S. Cl.
CPC .............. *C07K 14/40* (2013.01); *C07K 14/33* (2013.01); *A61K 38/00* (2013.01)

(58) Field of Classification Search
CPC ................................. C07K 14/40; C07K 14/39
USPC .............................. 435/183, 252.3; 536/23.2
See application file for complete search history.

(56) References Cited

U.S. PATENT DOCUMENTS

| 7,910,718 B2 | 3/2011 | Simkin et al. |
| 2010/0017904 A1 | 1/2010 | Abad et al. |
| 2012/0329109 A1 | 12/2012 | Chua et al. |
| 2016/0280745 A1* | 9/2016 | Alper ................ C07K 14/40 |

FOREIGN PATENT DOCUMENTS

| WO | WO-2014/018552 A1 | 1/2014 |
| WO | WO-2015/179701 A1 | 11/2015 |

OTHER PUBLICATIONS

Written Opinion published in a related application: PCT/US15/32058, filed on May 21, 2015.*
Bengtsson, O. et al. (Nov. 2008). "Identification of common traits in improved xylose-growing *Saccharomyces cerevisiae* for inverse metabolic engineering," 25(11):835-847.
Curran, K.A. et al. (Jul. 2012). "Expanding the chemical palate of cells by combining systems biology and metabolic engineering," *Metab Eng* 14(4):289-297.
International Search Report mailed on Aug. 26, 2015, for PCT Application No. PCT/US2015/032058, filed May 21, 2015, 4 pages.
Wahlbom, C.F. et al. (Feb. 2003). "Molecular analysis of a *Saccharomyces cerevisiae* mutant with improved ability to utilize xylose shows enhanced expression of proteins involved in transport, initial xylose metabolism, and the pentose phosphate pathway," *Appl Environ Microbiol* 69(2):740-746.
Written Opinion mailed on Aug. 26, 2015, for PCT Application No. PCT/US2015/032058, filed May 21, 2015, 5 pages.
Young, E.M. et al. (Jan. 7, 2004, e-published Dec. 16, 2013). "Rewiring yeast sugar transporter preference through modifying a conserved protein motif," *Proc Natl Aced Sci USA* 111(1):131-136.

* cited by examiner

*Primary Examiner* — Tekchand Saidha
(74) *Attorney, Agent, or Firm* — Meunier Carlin & Curfman LLC

(57) ABSTRACT

Provided herein are compositions and methods useful for reducing glucose inhibition in transporting xylose, arabinose and other monosaccharides, into a yeast cell.

9 Claims, 12 Drawing Sheets

WT CiGXS1

CiGXS1 FIM

FIG. 9E

CiGXS1 (FIMH) Δ497

FIG. 9F

GXS1 (FIMH Δ497) with I171F

SEQUENCE LISTING

<160> NUMBER OF SEQ ID NOS: 130

<210> SEQ ID NO 1
<211> LENGTH: 522
<212> TYPE: PRT
<213> ORGANISM: Candida intermedia

<400> SEQUENCE: 1

```
Met Gly Leu Glu Asp Asn Arg Met Val Lys Arg Phe Val Asn Val Gly
1               5                   10                  15

Glu Lys Lys Ala Gly Ser Thr Ala Met Ala Ile Ile Val Gly Leu Phe
            20                  25                  30

Ala Ala Ser Gly Gly Val Leu Phe Gly Tyr Asp Thr Gly Thr Ile Ser
        35                  40                  45

Gly Val Met Thr Met Asp Tyr Val Leu Ala Arg Tyr Pro Ser Asn Lys
    50                  55                  60

His Ser Phe Thr Ala Asp Glu Ser Ser Leu Ile Val Ser Ile Leu Ser
65                  70                  75                  80

Val Gly Thr Phe Phe Gly Ala Leu Cys Ala Pro Phe Leu Asn Asp Thr
                85                  90                  95

Leu Gly Arg Arg Trp Cys Leu Ile Leu Ser Ala Leu Ile Val Phe Asn
            100                 105                 110

Ile Gly Ala Ile Leu Gln Val Ile Ser Thr Ala Ile Pro Leu Leu Cys
        115                 120                 125

Ala Gly Arg Val Ile Ala Gly Phe Gly Val Gly Leu Ile Ser Ala Thr
    130                 135                 140

Ile Pro Leu Tyr Gln Ser Glu Thr Ala Pro Lys Trp Ile Arg Gly Ala
145                 150                 155                 160

Ile Val Ser Cys Tyr Gln Trp Ala Ile Thr Ile Gly Leu Phe Leu Ala
                165                 170                 175

Ser Cys Val Asn Lys Gly Thr Glu His Met Thr Asn Ser Gly Ser Tyr
            180                 185                 190

Arg Ile Pro Leu Ala Ile Gln Cys Leu Trp Gly Leu Ile Leu Gly Ile
        195                 200                 205

Gly Met Ile Phe Leu Pro Glu Thr Pro Arg Phe Trp Ile Ser Lys Gly
    210                 215                 220

Asn Gln Glu Lys Ala Ala Glu Ser Leu Ala Arg Leu Arg Lys Leu Pro
225                 230                 235                 240

Ile Asp His Pro Asp Ser Leu Glu Glu Leu Arg Asp Ile Thr Ala Ala
                245                 250                 255

Tyr Glu Phe Glu Thr Val Tyr Gly Lys Ser Ser Trp Ser Gln Val Phe
            260                 265                 270

Ser His Lys Asn His Gln Leu Lys Arg Leu Phe Thr Gly Val Ala Ile
        275                 280                 285

Gln Ala Phe Gln Gln Leu Thr Gly Val Asn Phe Ile Phe Tyr Tyr Gly
    290                 295                 300
```

```
Thr Thr Phe Phe Lys Arg Ala Gly Val Asn Gly Phe Thr Ile Ser Leu
305                 310                 315                 320

Ala Thr Asn Ile Val Asn Val Gly Ser Thr Ile Pro Gly Ile Leu Leu
            325                 330                 335

Met Glu Val Leu Gly Arg Arg Asn Met Leu Met Gly Gly Ala Thr Gly
        340                 345                 350

Met Ser Leu Ser Gln Leu Ile Val Ala Ile Val Gly Val Ala Thr Ser
        355                 360                 365

Glu Asn Asn Lys Ser Ser Gln Ser Val Leu Val Ala Phe Ser Cys Ile
        370                 375                 380

Phe Ile Ala Phe Phe Ala Ala Thr Trp Gly Pro Cys Ala Trp Val Val
385                 390                 395                 400

Val Gly Glu Leu Phe Pro Leu Arg Thr Arg Ala Lys Ser Val Ser Leu
                405                 410                 415

Cys Thr Ala Ser Asn Trp Leu Trp Asn Trp Gly Ile Ala Tyr Ala Thr
                420                 425                 430

Pro Tyr Met Val Asp Glu Asp Lys Gly Asn Leu Gly Ser Asn Val Phe
            435                 440                 445

Phe Ile Trp Gly Gly Phe Asn Leu Ala Cys Val Phe Phe Ala Trp Tyr
450                 455                 460

Phe Ile Tyr Glu Thr Lys Gly Leu Ser Leu Glu Gln Val Asp Glu Leu
465                 470                 475                 480

Tyr Glu His Val Ser Lys Ala Trp Lys Ser Lys Gly Phe Val Pro Ser
                485                 490                 495

Lys His Ser Phe Arg Glu Gln Val Asp Gln Gln Met Asp Ser Lys Thr
                500                 505                 510

Glu Ala Ile Met Ser Glu Glu Ala Ser Val
            515                 520

<210> SEQ ID NO 2
<211> LENGTH: 522
<212> TYPE: PRT
<213> ORGANISM: Artificial sequence
<220> FEATURE:
<223> OTHER INFORMATION: Synthetic polypeptide

<400> SEQUENCE: 2

Met Gly Leu Glu Asp Asn Arg Met Val Lys Arg Phe Val Asn Val Gly
1               5                   10                  15

Glu Lys Lys Ala Gly Ser Thr Ala Met Ala Ile Ile Val Gly Leu Phe
            20                  25                  30

Ala Ala Ser Gly Gly Phe Ile Met Gly Tyr Asp Thr Gly Thr Ile Ser
        35                  40                  45

Gly Val Met Thr Met Asp Tyr Val Leu Ala Arg Tyr Pro Ser Asn Lys
    50                  55                  60

His Ser Phe Thr Ala Asp Glu Ser Ser Leu Ile Val Ser Ile Leu Ser
65                  70                  75                  80

Val Gly Thr Phe Phe Gly Ala Leu Cys Ala Pro Phe Leu Asn Asp Thr
                85                  90                  95

Leu Gly Arg Arg Trp Cys Leu Ile Leu Ser Ala Leu Ile Val Phe Asn
            100                 105                 110

Ile Gly Ala Ile Leu Gln Val Ile Ser Thr Ala Ile Pro Leu Leu Cys
        115                 120                 125

Ala Gly Arg Val Ile Ala Gly Phe Gly Val Gly Leu Ile Ser Ala Thr
    130                 135                 140
```

```
Ile Pro Leu Tyr Gln Ser Glu Thr Ala Pro Lys Trp Ile Arg Gly Ala
145                 150                 155                 160

Ile Val Ser Cys Tyr Gln Trp Ala Ile Thr Ile Gly Leu Phe Leu Ala
            165                 170                 175

Ser Cys Val Asn Lys Gly Thr Glu His Met Thr Asn Ser Gly Ser Tyr
        180                 185                 190

Arg Ile Pro Leu Ala Ile Gln Cys Leu Trp Gly Leu Ile Leu Gly Ile
    195                 200                 205

Gly Met Ile Phe Leu Pro Glu Thr Pro Arg Phe Trp Ile Ser Lys Gly
210                 215                 220

Asn Gln Glu Lys Ala Ala Glu Ser Leu Ala Arg Leu Arg Lys Leu Pro
225                 230                 235                 240

Ile Asp His Pro Asp Ser Leu Glu Glu Leu Arg Asp Ile Thr Ala Ala
            245                 250                 255

Tyr Glu Phe Glu Thr Val Tyr Gly Lys Ser Ser Trp Ser Gln Val Phe
        260                 265                 270

Ser His Lys Asn His Gln Leu Lys Arg Leu Phe Thr Gly Val Ala Ile
    275                 280                 285

Gln Ala Phe Gln Gln Leu Thr Gly Val Asn Phe Ile Phe Tyr Tyr Gly
290                 295                 300

Thr Thr Phe Phe Lys Arg Ala Gly Val Asn Gly Phe Thr Ile Ser Leu
305                 310                 315                 320

Ala Thr Asn Ile Val Asn Val Gly Ser Thr Ile Pro Gly Ile Leu Leu
            325                 330                 335

Met Glu Val Leu Gly Arg Arg Asn Met Leu Met Gly Gly Ala Thr Gly
        340                 345                 350

Met Ser Leu Ser Gln Leu Ile Val Ala Ile Val Gly Val Ala Thr Ser
    355                 360                 365

Glu Asn Asn Lys Ser Ser Gln Ser Val Leu Val Ala Phe Ser Cys Ile
370                 375                 380

Phe Ile Ala Phe Phe Ala Ala Thr Trp Gly Pro Cys Ala Trp Val Val
385                 390                 395                 400

Val Gly Glu Leu Phe Pro Leu Arg Thr Arg Ala Lys Ser Val Ser Leu
            405                 410                 415

Cys Thr Ala Ser Asn Trp Leu Trp Asn Trp Gly Ile Ala Tyr Ala Thr
        420                 425                 430

Pro Tyr Met Val Asp Glu Asp Lys Gly Asn Leu Gly Ser Asn Val Phe
    435                 440                 445

Phe Ile Trp Gly Gly Phe Asn Leu Ala Cys Val Phe Phe Ala Trp Tyr
450                 455                 460

Phe Ile Tyr Glu Thr Lys Gly Leu Ser Leu Glu Gln Val Asp Glu Leu
465                 470                 475                 480

Tyr Glu His Val Ser Lys Ala Trp Lys Ser Lys Gly Phe Val Pro Ser
            485                 490                 495

Lys His Ser Phe Arg Glu Gln Val Asp Gln Gln Met Asp Ser Lys Thr
        500                 505                 510

Glu Ala Ile Met Ser Glu Glu Ala Ser Val
    515                 520
```

<210> SEQ ID NO 3
<211> LENGTH: 522
<212> TYPE: PRT
<213> ORGANISM: Artificial sequence
<220> FEATURE:
<223> OTHER INFORMATION: Synthetic polypeptide

<400> SEQUENCE: 3

```
Met Gly Leu Glu Asp Asn Arg Met Val Lys Arg Phe Val Asn Val Gly
1               5                   10                  15

Glu Lys Lys Ala Gly Ser Thr Ala Met Ala Ile Ile Val Gly Leu Phe
            20                  25                  30

Ala Ala Ser Gly Gly Phe Ile Met Gly Tyr Asp Thr Gly Thr Ile Ser
        35                  40                  45

Gly Val Met Thr Met Asp Tyr Val Leu Ala Arg Tyr Pro Ser Asn Lys
    50                  55                  60

His Ser Phe Thr Ala Asp Glu Ser Ser Leu Ile Val Ser Ile Leu Ser
65                  70                  75                  80

Val Gly Thr Phe Phe Gly Ala Leu Cys Ala Pro Phe Leu Asn Asp Thr
                85                  90                  95

Leu Gly Arg Arg Trp Cys Leu Ile Leu Ser Ala Leu Ile Val Phe Asn
            100                 105                 110

Ile Gly Ala Ile Leu Gln Val Ile Ser Thr Ala Ile Pro Leu Leu Cys
            115                 120                 125

Ala Gly Arg Val Ile Ala Gly Phe Gly Val Gly Leu Ile Ser Ala Thr
130                 135                 140

Ile Pro Leu Tyr Gln Ser Glu Thr Ala Pro Lys Trp Ile Arg Gly Ala
145                 150                 155                 160

Ile Val Ser Cys Tyr Gln Trp Ala Ile Thr Ile Gly Leu Phe Leu Ala
                165                 170                 175

Ser Cys Val Asn Lys Gly Thr Glu His Met Thr Asn Ser Gly Ser Tyr
            180                 185                 190

Arg Ile Pro Leu Ala Ile Gln Cys Leu Trp Gly Leu Ile Leu Gly Ile
            195                 200                 205

Gly Met Ile Phe Leu Pro Glu Thr Pro Arg Phe Trp Ile Ser Lys Gly
210                 215                 220

Asn Gln Glu Lys Ala Ala Glu Ser Leu Ala Arg Leu Arg Lys Leu Pro
225                 230                 235                 240

Ile Asp His Pro Asp Ser Leu Glu Glu Leu Arg Asp Ile Thr Ala Ala
                245                 250                 255

Tyr Glu Phe Glu Thr Val Tyr Gly Lys Ser Ser Trp Ser Gln Val Phe
            260                 265                 270

Ser His Lys Asn His Gln Leu Lys Arg Leu Phe Thr Gly Val Ala Ile
            275                 280                 285

Gln Ala Phe Gln Gln Leu Thr Gly Val Asn Phe Ile Phe Tyr Tyr Gly
290                 295                 300

Thr Thr Phe Phe Lys Arg Ala Gly Val Asn Gly Phe Thr Ile Ser Leu
305                 310                 315                 320

Ala Thr Asn Ile Val His Val Gly Ser Thr Ile Pro Gly Ile Leu Leu
                325                 330                 335

Met Glu Val Leu Gly Arg Arg Asn Met Leu Met Gly Gly Ala Thr Gly
            340                 345                 350

Met Ser Leu Ser Gln Leu Ile Val Ala Ile Val Gly Val Ala Thr Ser
            355                 360                 365

Glu Asn Asn Lys Ser Ser Gln Ser Val Leu Val Ala Phe Ser Cys Ile
            370                 375                 380

Phe Ile Ala Phe Phe Ala Ala Thr Trp Gly Pro Cys Ala Trp Val Val
385                 390                 395                 400

Val Gly Glu Leu Phe Pro Leu Arg Thr Arg Ala Lys Ser Val Ser Leu
```

405                 410                 415
Cys Thr Ala Ser Asn Trp Leu Trp Asn Trp Gly Ile Ala Tyr Ala Thr
            420                 425                 430

Pro Tyr Met Val Asp Glu Asp Lys Gly Asn Leu Gly Ser Asn Val Phe
            435                 440                 445

Phe Ile Trp Gly Gly Phe Asn Leu Ala Cys Val Phe Phe Ala Trp Tyr
        450                 455                 460

Phe Ile Tyr Glu Thr Lys Gly Leu Ser Leu Glu Gln Val Asp Glu Leu
465                 470                 475                 480

Tyr Glu His Val Ser Lys Ala Trp Lys Ser Lys Gly Phe Val Pro Ser
            485                 490                 495

Lys His Ser Phe Arg Glu Gln Val Asp Gln Gln Met Asp Ser Lys Thr
            500                 505                 510

Glu Ala Ile Met Ser Glu Ala Ser Val
            515                 520

<210> SEQ ID NO 4
<211> LENGTH: 522
<212> TYPE: PRT
<213> ORGANISM: Artificial sequence
<220> FEATURE:
<223> OTHER INFORMATION: Synthetic polypeptide

<400> SEQUENCE: 4

Met Gly Leu Glu Asp Asn Arg Met Val Lys Arg Phe Val Asn Val Gly
1               5                   10                  15

Glu Lys Lys Ala Gly Ser Thr Ala Met Ala Ile Ile Val Gly Leu Phe
            20                  25                  30

Ala Ala Ser Gly Gly Phe Ile Met Gly Tyr Asp Thr Gly Thr Ile Ser
        35                  40                  45

Gly Val Met Thr Met Asp Tyr Val Leu Ala Arg Tyr Pro Ser Asn Lys
    50                  55                  60

His Ser Phe Thr Ala Asp Glu Ser Ser Leu Ile Val Ser Ile Leu Ser
65                  70                  75                  80

Val Gly Thr Phe Phe Gly Ala Leu Cys Ala Pro Phe Leu Asn Asp Thr
                85                  90                  95

Leu Gly Arg Arg Trp Cys Leu Ile Leu Ser Ala Leu Ile Val Phe Asn
            100                 105                 110

Ile Gly Ala Ile Leu Gln Val Ile Ser Thr Ala Ile Pro Leu Leu Cys
        115                 120                 125

Ala Gly Arg Val Ile Ala Gly Phe Gly Val Gly Leu Ile Ser Ala Thr
    130                 135                 140

Ile Pro Leu Tyr Gln Ser Glu Thr Ala Pro Lys Trp Ile Arg Gly Ala
145                 150                 155                 160

Ile Val Ser Cys Tyr Gln Trp Ala Ile Asn Ile Gly Leu Phe Leu Ala
                165                 170                 175

Ser Cys Val Asn Lys Gly Thr Glu His Met Thr Asn Ser Gly Ser Tyr
            180                 185                 190

Arg Ile Pro Leu Ala Ile Gln Cys Leu Trp Gly Leu Ile Leu Gly Ile
        195                 200                 205

Gly Met Ile Phe Leu Pro Glu Thr Pro Arg Phe Trp Ile Ser Lys Gly
    210                 215                 220

Asn Gln Glu Lys Ala Ala Glu Ser Leu Ala Arg Leu Arg Lys Leu Pro
225                 230                 235                 240

Ile Asp His Pro Asp Ser Leu Glu Glu Leu Arg Asp Ile Thr Ala Ala

```
                    245                 250                 255
Tyr Glu Phe Glu Thr Val Tyr Gly Lys Ser Ser Trp Ser Gln Val Phe
                260                 265                 270

Ser His Lys Asn His Gln Leu Lys Arg Leu Phe Thr Gly Val Ala Ile
            275                 280                 285

Gln Ala Phe Gln Gln Leu Thr Gly Val Asn Phe Ile Phe Tyr Tyr Gly
        290                 295                 300

Thr Thr Phe Phe Lys Arg Ala Gly Val Asn Gly Phe Thr Ile Ser Leu
305                 310                 315                 320

Ala Thr Asn Ile Val Asn Val Gly Ser Thr Ile Pro Gly Ile Leu Leu
                325                 330                 335

Met Glu Val Leu Gly Arg Arg Asn Met Leu Met Gly Gly Ala Thr Gly
            340                 345                 350

Met Ser Leu Ser Gln Leu Ile Val Ala Ile Val Gly Val Ala Thr Ser
        355                 360                 365

Glu Asn Asn Lys Ser Ser Gln Ser Val Leu Val Ala Phe Ser Cys Ile
370                 375                 380

Phe Ile Ala Phe Phe Ala Ala Thr Trp Gly Pro Cys Ala Trp Val Val
385                 390                 395                 400

Val Gly Glu Leu Phe Pro Leu Arg Thr Arg Ala Lys Ser Val Ser Leu
                405                 410                 415

Cys Thr Ala Ser Asn Trp Leu Trp Asn Trp Gly Ile Ala Tyr Ala Thr
            420                 425                 430

Pro Tyr Met Val Asp Glu Asp Lys Gly Asn Leu Gly Ser Asn Val Phe
        435                 440                 445

Phe Ile Trp Gly Gly Phe Asn Leu Ala Cys Val Phe Phe Ala Trp Tyr
    450                 455                 460

Phe Ile Tyr Glu Thr Lys Gly Leu Ser Leu Glu Gln Val Asp Glu Leu
465                 470                 475                 480

Tyr Glu His Val Ser Lys Ala Trp Lys Ser Lys Gly Phe Val Pro Ser
                485                 490                 495

Lys His Ser Phe Arg Glu Gln Val Asp Gln Gln Met Asp Ser Lys Thr
            500                 505                 510

Glu Ala Ile Met Ser Glu Glu Ala Ser Val
        515                 520

<210> SEQ ID NO 5
<211> LENGTH: 496
<212> TYPE: PRT
<213> ORGANISM: Artificial sequence
<220> FEATURE:
<223> OTHER INFORMATION: Synthetic polypeptide

<400> SEQUENCE: 5

Met Gly Leu Glu Asp Asn Arg Met Val Lys Arg Phe Val Asn Val Gly
1               5                   10                  15

Glu Lys Lys Ala Gly Ser Thr Ala Met Ala Ile Ile Val Gly Leu Phe
            20                  25                  30

Ala Ala Ser Gly Gly Phe Ile Met Gly Tyr Asp Thr Gly Thr Ile Ser
        35                  40                  45

Gly Val Met Thr Met Asp Tyr Val Leu Ala Arg Tyr Pro Ser Asn Lys
    50                  55                  60

His Ser Phe Thr Ala Asp Glu Ser Ser Leu Ile Val Ser Ile Leu Ser
65                  70                  75                  80

Val Gly Thr Phe Phe Gly Ala Leu Cys Ala Pro Phe Leu Asn Asp Thr
```

```
                        85                  90                  95
Leu Gly Arg Arg Trp Cys Leu Ile Leu Ser Ala Leu Ile Val Phe Asn
                100                 105                 110

Ile Gly Ala Ile Leu Gln Val Ile Ser Thr Ala Ile Pro Leu Leu Cys
                115                 120                 125

Ala Gly Arg Val Ile Ala Gly Phe Gly Val Gly Leu Ile Ser Ala Thr
                130                 135                 140

Ile Pro Leu Tyr Gln Ser Glu Thr Ala Pro Lys Trp Ile Arg Gly Ala
145                 150                 155                 160

Ile Val Ser Cys Tyr Gln Trp Ala Ile Thr Ile Gly Leu Phe Leu Ala
                165                 170                 175

Ser Cys Val Asn Lys Gly Thr Glu His Met Thr Asn Ser Gly Ser Tyr
                180                 185                 190

Arg Ile Pro Leu Ala Ile Gln Cys Leu Trp Gly Leu Ile Leu Gly Ile
                195                 200                 205

Gly Met Ile Phe Leu Pro Glu Thr Pro Arg Phe Trp Ile Ser Lys Gly
                210                 215                 220

Asn Gln Glu Lys Ala Ala Glu Ser Leu Ala Arg Leu Arg Lys Leu Pro
225                 230                 235                 240

Ile Asp His Pro Asp Ser Leu Glu Glu Leu Arg Asp Ile Thr Ala Ala
                245                 250                 255

Tyr Glu Phe Glu Thr Val Tyr Gly Lys Ser Ser Trp Ser Gln Val Phe
                260                 265                 270

Ser His Lys Asn His Gln Leu Lys Arg Leu Phe Thr Gly Val Ala Ile
                275                 280                 285

Gln Ala Phe Gln Gln Leu Thr Gly Val Asn Phe Ile Phe Tyr Tyr Gly
                290                 295                 300

Thr Thr Phe Phe Lys Arg Ala Gly Val Asn Gly Phe Thr Ile Ser Leu
305                 310                 315                 320

Ala Thr Asn Ile Val His Val Gly Ser Thr Ile Pro Gly Ile Leu Leu
                325                 330                 335

Met Glu Val Leu Gly Arg Arg Asn Met Leu Met Gly Gly Ala Thr Gly
                340                 345                 350

Met Ser Leu Ser Gln Leu Ile Val Ala Ile Val Gly Val Ala Thr Ser
                355                 360                 365

Glu Asn Asn Lys Ser Ser Gln Ser Val Leu Val Ala Phe Ser Cys Ile
                370                 375                 380

Phe Ile Ala Phe Phe Ala Ala Thr Trp Gly Pro Cys Ala Trp Val Val
385                 390                 395                 400

Val Gly Glu Leu Phe Pro Leu Arg Thr Arg Ala Lys Ser Val Ser Leu
                405                 410                 415

Cys Thr Ala Ser Asn Trp Leu Trp Asn Trp Gly Ile Ala Tyr Ala Thr
                420                 425                 430

Pro Tyr Met Val Asp Glu Asp Lys Gly Asn Leu Gly Ser Asn Val Phe
                435                 440                 445

Phe Ile Trp Gly Gly Phe Asn Leu Ala Cys Val Phe Phe Ala Trp Tyr
                450                 455                 460

Phe Ile Tyr Glu Thr Lys Gly Leu Ser Leu Glu Gln Val Asp Glu Leu
465                 470                 475                 480

Tyr Glu His Val Ser Lys Ala Trp Lys Ser Lys Gly Phe Val Pro Ser
                485                 490                 495

<210> SEQ ID NO 6
```

<211> LENGTH: 496
<212> TYPE: PRT
<213> ORGANISM: Artificial sequence
<220> FEATURE:
<223> OTHER INFORMATION: Synthetic polypeptide

<400> SEQUENCE: 6

Met Gly Leu Glu Asp Asn Arg Met Val Lys Arg Phe Val Asn Val Gly
1               5                   10                  15

Glu Lys Lys Ala Gly Ser Thr Ala Met Ala Ile Ile Val Gly Leu Phe
            20                  25                  30

Ala Ala Ser Gly Gly Phe Ile Met Gly Tyr Asp Thr Gly Thr Ile Ser
        35                  40                  45

Gly Val Met Thr Met Asp Tyr Val Leu Ala Arg Tyr Pro Ser Asn Lys
    50                  55                  60

His Ser Phe Thr Ala Asp Glu Ser Leu Ile Val Ser Ile Leu Ser
65                  70                  75                  80

Val Gly Thr Phe Phe Gly Ala Leu Cys Ala Pro Phe Leu Asn Asp Thr
                85                  90                  95

Leu Gly Arg Arg Trp Cys Leu Ile Leu Ser Ala Leu Ile Val Phe Asn
            100                 105                 110

Ile Gly Ala Ile Leu Gln Val Ile Ser Thr Ala Ile Pro Leu Leu Cys
        115                 120                 125

Ala Gly Arg Val Ile Ala Gly Phe Gly Val Gly Leu Ile Ser Ala Thr
    130                 135                 140

Ile Pro Leu Tyr Gln Ser Glu Thr Ala Pro Lys Trp Ile Arg Gly Ala
145                 150                 155                 160

Ile Val Ser Cys Tyr Gln Trp Ala Ile Thr Phe Gly Leu Phe Leu Ala
                165                 170                 175

Ser Cys Val Asn Lys Gly Thr Glu His Met Thr Asn Ser Gly Ser Tyr
            180                 185                 190

Arg Ile Pro Leu Ala Ile Gln Cys Leu Trp Gly Leu Ile Leu Gly Ile
        195                 200                 205

Gly Met Ile Phe Leu Pro Glu Thr Pro Arg Phe Trp Ile Ser Lys Gly
    210                 215                 220

Asn Gln Glu Lys Ala Ala Glu Ser Leu Ala Arg Leu Arg Lys Leu Pro
225                 230                 235                 240

Ile Asp His Pro Asp Ser Leu Glu Glu Leu Arg Asp Ile Thr Ala Ala
                245                 250                 255

Tyr Glu Phe Glu Thr Val Tyr Gly Lys Ser Ser Trp Ser Gln Val Phe
            260                 265                 270

Ser His Lys Asn His Gln Leu Lys Arg Leu Phe Thr Gly Val Ala Ile
        275                 280                 285

Gln Ala Phe Gln Gln Leu Thr Gly Val Asn Phe Ile Phe Tyr Tyr Gly
    290                 295                 300

Thr Thr Phe Phe Lys Arg Ala Gly Val Asn Gly Phe Thr Ile Ser Leu
305                 310                 315                 320

Ala Thr Asn Ile Val His Val Gly Ser Thr Ile Pro Gly Ile Leu Leu
                325                 330                 335

Met Glu Val Leu Gly Arg Arg Asn Met Leu Met Gly Gly Ala Thr Gly
            340                 345                 350

Met Ser Leu Ser Gln Leu Ile Val Ala Ile Val Gly Val Ala Thr Ser
        355                 360                 365

Glu Asn Asn Lys Ser Ser Gln Ser Val Leu Val Ala Phe Ser Cys Ile
    370                 375                 380

```
Phe Ile Ala Phe Phe Ala Ala Thr Trp Gly Pro Cys Ala Trp Val Val
385                 390                 395                 400

Val Gly Glu Leu Phe Pro Leu Arg Thr Arg Ala Lys Ser Val Ser Leu
            405                 410                 415

Cys Thr Ala Ser Asn Trp Leu Trp Asn Trp Gly Ile Ala Tyr Ala Thr
        420                 425                 430

Pro Tyr Met Val Asp Glu Asp Lys Gly Asn Leu Gly Ser Asn Val Phe
            435                 440                 445

Phe Ile Trp Gly Gly Phe Asn Leu Ala Cys Val Phe Phe Ala Trp Tyr
        450                 455                 460

Phe Ile Tyr Glu Thr Lys Gly Leu Ser Leu Glu Gln Val Asp Glu Leu
465                 470                 475                 480

Tyr Glu His Val Ser Lys Ala Trp Lys Ser Lys Gly Phe Val Pro Ser
            485                 490                 495

<210> SEQ ID NO 7
<211> LENGTH: 3086
<212> TYPE: DNA
<213> ORGANISM: Arabidopsis thaliana

<400> SEQUENCE: 7
cgaagatgag agataagcga ccaaaattag cgggagaatc ctcacttgtc tcactccgat      60
ccgatcatgg ctttcgctgt ctcggttcag tcacatttcg caatcagagc gttaaaacga     120
gaccacttca agaacccttc tcctcgtact ttctgctcgt gttttaaatc gaggcctgac     180
tcgtcttacc ttagtttaaa ggaacgtact tgcttcgttt ccaaaccggg tttagtcact     240
actagataca gacatatatt ccaggtgaaa agcaattttc tctgattttg atttcttcta     300
aaaaaaattc aaaagttttg attttttccgg ttttggttca tggttaggtc ggagctgaga     360
cgggaggaga gttcgccgac agtggagaag tagctgattc gcttgcttct gatgcaccag     420
agtcattttc ttggtcttct gtgatactcc cgtgcgtatt gatccttctc gttaatttga     480
atttaactgt tcctgagtaa tggatttgga ttgcctgtgt aatgatcttg cctaatgact     540
taatctctta gcaatgcctt atgtatcatc aattatagaa gatagaaaat tagttatttg     600
cctagattgc actgatttaa tagtaattta cttgaatcgt aggtttatct tcccggcttt     660
gggaggatta ttgtttgggt atgacattgg ggctacctcc ggtgctacgc tctcacttca     720
ggttatttta aagtatctat tttcatctag ttacatttta gctttcagaa ttttaacatt     780
atgtactgtc tcatatggtc ttgaacagtc acctgcgctt agcggaacta catggtttaa     840
cttctcacct gttcagctag gacttgtggt atgttatttg gagatcgata ttttctgtag     900
ttaagccata gagttagcag aaaatgatag ttttttactgc atttttgttgt gtaggttagc     960
ggatccttgt atggagccct tcttggctca atttctgtct atggcgttgc tgatttcctt    1020
ggtaagtctt gttttttttgg gttgacttct cgttcttctt aactgaatgc aagtatctca    1080
ttctggtttt cttcacatct ttatgaagga agaaggcggg aacttattat agctgctgtt    1140
ctctatctcc tcgggtctct gatcactggc tgtgcccctg atcttaatat tctcttagtt    1200
ggaaggcttc tctatggctt tggtattggt ttggtgagct ccggaaacct gaatcgttat    1260
ggtaatttct ttgttacttt tgttgttgat tgttagttaa tgttttatgt aaattggttt    1320
tgcttgatag gcaatgcatg gggctccccct ctatattgct gagacatgcc catctcaaat    1380
ccgtggaact ttgatatctc tgaaagaact cttcatcgta ttgggaattt tggtaagtgt    1440
ctgatgtcaa tctcttccca gtatgatttc tgcgtaaata ttgatttcct tcttgtgcag    1500
```

```
ttgggttttt ctgttggaag cttccagatt gatgtagttg gagggtggcg ttacatgtat    1560
ggatttggta cgcctgttgc tttgctgatg ggactaggca tgtggagtct ccctgcatct    1620
cctcgctggt tgctgcttag agctgtccaa ggtaaaggac aattacaaga atacaaagag    1680
aaggccatgc ttgccctcag caaattacgt ggcagacctc caggtgataa aatctcagag    1740
aagttggtag atgatgccta tttatctgtg aaaacggcct atgaagatga gaaatctggg    1800
ggaaacttcc tggaagtatt ccaagggcct aatttgaaag ctttgacaat tggtggaggt    1860
ttagtcctct tccaacaggt gattcttctt cgctgtttcc atttggatga atgtgtgagc    1920
attttttgaaa taatttacac tctgcttcgt tgtgacagat aactggacag cctagtgttc    1980
tttattatgc gggttcgatt cttcaggtat gctcgcctta acattgaaat gaatgagatt    2040
acctactaat ttttactgcc tttagtcgga tgtttaatga gactttatgc tcacttatct    2100
attcaaagac tgctggattc tctgctgctg ctgatgcaac tcgagtctct gttattattg    2160
gtgtttcaa ggtggcccctt tttattttt tgtttggatg tgtaaatatc ttattttcca    2220
acaagcttcc agttattcaa tactaacctc ttcaattgat aacgctctcg tagttactga    2280
tgacatgggt agctgttgcg aaagttgatg atctcggcag acgaccttta ctgattggag    2340
gtgtcagcgg cattgtatga attcatttta tgtctatatc ttctgttttct tattttccaa    2400
agaaaagata tcatttctta tatttcttcc aaattccagg cgttgtcctt gtttctactg    2460
tcagcatact acaagtttct cggaggcttt ccccttgtcg ctgttggtgc actgcttctc    2520
tatgttggtt gttaccaggt ttgtactcta gctcactgtt agctgtggct acatagtttt    2580
atctagcata ttactaaagt ctcagcgcga acagatctca tttggaccca tcagctggct    2640
aatggtgtca gagattttcc cgctccgcac aagagggaga gggatcagtc ttgcagttct    2700
tacaaacttt ggctccaatg ctattgtgac atttgcattt tcacctttaa aggtatattt    2760
ttctgttcct gcttgttcaa cccttgaagt tattagtaac tcttatcaaa atatgcattc    2820
tctgtaggaa tttcttggag ccgagaatct tttccttctc tttgggggca tagcactggt    2880
atcactgctg tttgtaatac tagtagttcc agagaccaag ggtctcagct tggaagaaat    2940
tgaatcaaaa atcttgaagt gaaacgttga agaacatatt tgttatagtt gattctggtg    3000
aaatacatgt atgaggatgt gactattctc tttgtaacat aatatgtttc gtaatcaatg    3060
ggaaaaccaa acctttttca tgatta                                         3086
```

<210> SEQ ID NO 8
<211> LENGTH: 5119
<212> TYPE: DNA
<213> ORGANISM: Arabidopsis thaliana

<400> SEQUENCE: 8

```
gtgaagatga ttcaatgtcg ttgagtggta gtagttaaat cttcaaaacc ccggagaatt     60
atatatatgg gtttcgttca gcaaacctaa ctaaactcag aaccagaatt catatttcgg    120
tcgctcaaat cacagctatg gcgcttgatc ctgagcagca gcaaccaatc tcctctgttt    180
ccagagaggt atacgtctcc tttcattgtc tacttcgtcg ttttgtttcc tgttcgatta    240
aacggtgtga gagagttttc atttgaagta tacgtctcct ttcatctgaa gcttaattct    300
ctagtaaatt cgtacttctt gacttgccac attaggaatg ttccttttga gatcaacttt    360
ggcttttagc tgacaaattt ctggaaaaat tctgaaattt gctatgttgg aatcttagag    420
attgtattta agagtcatat attcactttt tggggactcg cttcaattct gagaagaaat    480
```

```
ttagaggctt ttacggattt ttagccatca gcctcacagt tatctttaag catgaaattt      540 ttagaccta aatgctgtgt acaattggtt tgttggtttc atgatttgtg tgttccttac      600 tgttttttt tttttgggtg gcaactttct gaaactgttt atgcgtttta gtttggtaag      660
tcatctggtg agatcagccc agaaagggag cctcttatta aagagaatca tgtcccagaa      720
aactactctg tcgttgccgc cattctcccg tgagatctct catctcttct ccaagtttgg      780
tagttcttaa aatgattcaa atgaaacact cttgaacaat tccgatgtgt tctttgtttg      840
gttatattgt gtatcattta gcataatatg tatcctgact aggaaactag aacgctgtgt      900
atggtacctt gcatagcttt caaatagaat tccttatgga attacatacc atctgcagga      960
atttggacct atgtccttt gcgcatggta gtttttggt ttgtagctag tccattgatg     1020
attgatatat gcatgttaag aagtttctgt ttcattatca ggttttttatt tccagctctc     1080 ggaggactgc tttatggtta tgaaattggt gcaacttctt gtgcaaccat ttcacttcag     1140
gtaaagttaa aagttgtctg aaactatcta gtcctacaaa atttgttatc attcaactta     1200
tttttcaagt gcctagtcac tgttttcaaa gcctaaaatat tataaagctc tggaaattgg     1260
actgagatat cagtactgaa acatgatatt tcacacttgc cagaccattt tttcccttg     1320 atttctcctg tatattgttg tcacatgcat gtacgttatt tatatttgtc tacattcttt     1380
taggagccta tgactttgct atcttactat gctgttccct tttctgcagt cgccttcatt     1440
aagtggaatt tcatggtaca acttgtcctc agtggatgtt ggtctagttg taagtttcca     1500
agttatatgt gatacttctt ctttatcctg gtcattgctt atcatttatt cacctgccgc     1560
tcttggatat gtgtttgcca tttggagtaa agacaaattt gcttacaaaa tagtgttaaa     1620
ttttctccag accagtggct cactttacgg tgcattattt ggctcaattg tggcttttac     1680
tatcgctgac gttataggtt agttttactt ctcactatct tcattttgta ggcatgagta     1740
tttagcaatg tttgcttgtg gaaaaagata agttttggt tttgttgaat tggaaggaa      1800 gaagaaagga gctgatttg gctgcattat tgtatctcgt tggagccctt gtgactgcac     1860
tagccccaac ctattccgtt ctgataattg gacgggttat ttatgggggtc tcagttggac     1920 tggtaagact gatcatgctt cttattgtt tgacatctaa agactttctt atgcatgcca     1980
atggctcaaa cgttatatat tatgcatttg gcggtgtact aagaatcgca catctgttag     2040
gaggggagca aattaatgct ttataggact ttagggcacc cacactctta atttatagtg     2100
gtgactactt tccaaggtct tataatattt taacttgttc ccctcctaaa ggatgtggag     2160
ttcttatcat gtatataatc aacctaactt aaccttcca atgaatctaa cagttgatgc     2220
aaatatattt ccatctattg ctgagcatgg gttgttatcc agtgcatcat catagaaaca     2280
taattgatgt ctattctatg tacatgtata cagagtacac atatattgtg actgtattct     2340
tcgtccttcg tatttttat gttttccag cttaaaagcc agtgactaga aatcttgttt      2400
acctttcgaa aatattgttt atccatgtgc ttttgctgtg gattacatat agcagtactc     2460
ttgctacggg aactgaattg tttccctaca tttaggcaat gcatgcggct ccgatgtaca     2520
ttgcagagac tgctccaagt ccgatacgtg gacagctggt atcattaaag gaattcttca     2580
tagtccttgg gatggttgta agttcctgca accctgagat ttaggacgtt gattgcttta     2640
tgtgaagcag ttgagttgaa atctttgttc accaagttaa tctcacatat ccccatacaa     2700 aatttttacac agggaggtta tggaatcggt agtcttacag tcaatgttca ttctggttgg     2760
cgatacatgt atgcaacaag tgtccctttg gcagttatta tgggaattgg gatgtggtgg     2820
ctcccagcat cccctaggtg gcttttgttg cgcgtcatac aggggaaagg gaatgtggag     2880
```

```
aaccaacgag aggctgcaat caaatctctc tgctgcctta gaggccctgc ttttgttgat    2940
tcagctgctg aacaagtaaa tgagattttg gctgaactaa cttttgtggg cgaggataaa    3000
gaagtcacat ttggtgaatt atttcaaggg aagtgcttga aagctctcat cataggagga    3060
ggtctagtct tgtttcagca ggttggtata gtcaaatcta atcattgtgt tctcttgaaa    3120
gaataattac taatgaattc ttgtctaatg gcagataact ggacaaccaa gtgtgcttta    3180
ttatgcacca tcaatactgc aggttttctt cttctctaaa taaactttct gtatagtata    3240
atattggctt tgttgcactt cgaaactcac gactggattt ttaacttctc ccccatccc    3300 acatttcctg ttagaccgct ggcttttcag ccgcaggtga tgcaacaagg gtctcaattc    3360
tacttggtct attgaaggtt ttcactgttt cccacctggc taaaatttaa gttacttttc    3420
caatgtaata aagaaatgcc gttttagtta ttttgccttc aaagaaataa cacccgcctc    3480
tgttgttgca gttgattatg acaggagtag ctgttgtagt tatcgacaga cttggaagga    3540
gacctttact tcttggtgga gttggtggca tggtatgtcc tctgtcttta tcccttccct    3600
tttctcatcc atgttccgtt tatacacctt aagcaaaagt acagtaaatt taggtcaagc    3660
tcactaaatg ttcagctcaa tgatagagag aacccaatac tcctaataac attttatttt    3720
caatgtcaaa caggttgttt cattattcct gctggggtca tactacctct ttttcagcgc    3780
ctcaccagtt gttgctgtag ttgcactgct gctttatgtg ggctgttacc aggtaaacaa    3840
atagttgatt agaattttgc taatcaaact tcactaccac aatgtcaatg cttgtcctaa    3900
aagtatcata gacttttgga tataactcgt ggcatctaaa gttggagttc ttataacaag    3960
tagttccatt ggagtttatg tacaaaagtg attcatggat ttcattattt tcgccttaaa    4020
acttttgata tgcttctagt tcttttttc aacatgtttg gctttctact tttcaataag    4080
agcttgaacg tattaccatc aatcttgcag ctatcttttg gtccaattgg ttggctgatg    4140
atttcagaga tatttcccct taaactaaga ggtcgaggtc tcagtctagc agtgcttgtg    4200
aattttggtg caaacgcact tgtgacattt gcgttttcac ccctaaaggt aacctaccat    4260
tcccttgagg acaaaaattc tcgtttgttt aagcttggta tggccattac tgtagaaatg    4320
gtagcaaccc ttttgcaaga ctttttttact ttagaagaaa ttgtcaatca tatggttagt    4380
cgtggtgaaa ttctagtcga atgatatcga cacccacagt tagagtagtt tttcttctga    4440
tatctaactg gaacttttcg tttggctcaa atggctctgt tttgcaggaa ctgctgggag    4500
ctgggatact gttttgtggg tttggtgtga tatgtgtatt gtctctggta ttcatattct    4560
tcattgtgcc agagacaaag ggtctcactc ttgaggaaat tgaagccaaa tgtctctaaa    4620
aaagaggtct gttctttgct tagaaaccac aaagtcgtgt gcttcctcac atgattttga    4680
ttcatattgt taatcagtga ggaaaataat agtgcaggtt cagaaacaaa taaacatatg    4740
aatctgccgc acaagacggg aaatgaatct tcagagacca ctaagttatt tgaagcaatg    4800
ttacttcaaa ggctcggttg tttctagcaa aatacatgta cgagaattca taaatacaga    4860
aatctttgta atgattatta gcgctctgat gaagttagaa aataaaaaaa gaaaacatca    4920
tagaagaatt taaatttgta gaatatgtcc taaccagtga tgtttcgaaa tccgaaggtt    4980
tctcaaagtt tgtattttt ttaaacgatt ccacgattct gcaatgctgc attatgatat    5040
agaacattat gctgaataga agatattttt cgggatttgt aagacttgat gtgatatagt    5100
ataatggaac attgtggtc                                                 5119
```

<210> SEQ ID NO 9

```
<211> LENGTH: 1644
<212> TYPE: DNA
<213> ORGANISM: Candida intermedia

<400> SEQUENCE: 9
atgtcacaag attcgcattc ttctggtgcc gctacaccag tcaatggttc catccttgaa      60
aaggaaaaag aagactctcc agttcttcaa gttgatgccc acaaaaggg tttcaaggac     120
tacattgtca tttctatctt ctgttttatg gttgccttcg gtggtttcgt cttcggtttc     180
gacactggta ccatttccgg tttcgtgaac atgtctgact taaagacag attcggtcaa     240
caccacgctg atggtactcc ttacttgtcc gacgttagag ttggtttgat gatttctatt     300
ttcaacgttg gttgcgctgt cggtggtatt ttcctctgca aggtcgctga tgtctggggt     360
agaagaattg gtcttatgtt ctccatggct gtctacgttg ttggtattat tattcagatc     420
tcttcatcca ccaagtggta ccagttcttc attggtcgtc ttattgctgg tttggctgtt     480
ggtaccgttt ctgtcgtttc cccacttttc atctctgagg tttctccaaa gcaaattaga     540
ggtactttag tgtgctgctt ccagttgtgt atcaccttgg gtatcttctt gggttactgt     600
actacttacg gtactaagac ctacactgac tctagacagt ggagaattcc tttgggtttg     660
tgtttcgctt gggctatctt gttggttgtc ggtatgttga acatgccaga gtctccaaga     720
tacttggttg agaagcacag aattgatgag gccaagagat ccattgccag atccaacaag     780
atccctgagg aggacccatt cgtctacact gaggttcagc ttattcaggc cggtattgag     840
agagaagctt tggctggtca ggcatcttgg aaggagttga tcactggtaa gccaaagatc     900
ttcagaaagg ttatcatggg tattatgctt cagtccttgc aacagttgac cggtgacaac     960
tacttcttct actacggtac taccattttc caggctgtcg gtttgaagga ttctttccag    1020
acttctatca ttttgggtat tgtcaacttt gcttccacct tcgttggtat ctatgtcatt    1080
gagagattgg gtagaagatt gtgtcttttg accggttccg ctgctatgtt catctgtttc    1140
atcatctact ctttgattgg tactcagcac ttgtacaagc aaggttactc caacgagacc    1200
tccaacactt acaaggcttc tggtaacgct atgatcttca tcacttgtct ttacattttc    1260
ttctttgctt ctacctgggc tggtggtgtt tactgtatca tttccgagtc ctacccattg    1320
agaattagat ccaaggccat gtctattgct accgctgcta actggttgtg gggtttcttg    1380
atttccttct tcactccatt catcaccagt gccatccact tctactacgg tttcgttttc    1440
actggttgtt tggctttctc tttcttctac gtctacttct tcgtctacga aaccaagggt    1500
ctttctttgg aggaggttga tgagatgtac gcttccggtg ttcttccact caagtctgcc    1560
agctgggttc caccaaatct tgagcacatg gctcactctg ccggttacgc tggtgctgac    1620
aaggccaccg acgaacaggt ttaa                                           1644

<210> SEQ ID NO 10
<211> LENGTH: 1569
<212> TYPE: DNA
<213> ORGANISM: Candida intermedia

<400> SEQUENCE: 10 atgggttttgg aggacaatag aatggttaag cgtttcgtca acgttggcga aagaaggct      60
ggctctactg ccatggccat catcgtcggt cttttttgctg cttctggtgg tgtccttttc     120
ggatacgata ctggtactat ttctggtgtg atgaccatgg actacgttct tgctcgttac     180
ccttccaaca agcactcttt tactgctgat gaatcttctt tgattgtttc tatcttgtct     240
gttggtactt tcttttggtgc actttgtgct ccattcctta acgacaccct cggtagacgt     300
```

```
tggtgtctta ttctttctgc tcttattgtc ttcaacattg gtgctatctt gcaggtcatc      360
tctactgcca ttccattgct ttgtgctggt agagttattg caggttttgg tgtcggtttg      420
atttctgcta ctattccatt gtaccaatct gagactgctc caaagtggat cagaggtgcc      480
attgtctctt gttaccagtg ggctattacc attggtcttt tcttggcctc ttgtgtcaac      540
aagggtactg agcacatgac taactctgga tcttacagaa ttccacttgc tattcaatgt      600
ctttggggtc ttatcttggg tatcggtatg atcttcttgc cagagactcc aagattctgg      660
atctccaagg gtaaccagga gaaggctgct gagtctttgg ccagattgag aaagcttcca      720
attgaccacc cagactctct cgaggaatta agagacatca ctgctgctta cgagttcgag      780
actgtgtacg gtaagtcctc ttggagccag gtgttctctc acaagaacca ccagttgaag      840
agattgttca ctggtgtggc tatccaggct ttccagcaat tgaccggtgt taacttcatt      900
ttctactacg gtactacctt cttcaagaga gctggtgtta acggtttcac tatctccttg      960
gccactaaca ttgtcaatgt cggttctact attccaggta ttcttttgat ggaagtcctc     1020
ggtagaagaa acatgttgat gggtggtgct actggtatgt ctctttctca attgatcgtt     1080
gccattgttg gtgttgctac ctcggaaaac aacaagtctt cccagtccgt ccttgttgct     1140
ttctcctgta ttttcattgc cttcttcgct gccacctggg gtccatgtgc ttgggttgtt     1200
gttggtgagt tgttcccatt gagaaccaga gctaagtctg tctccttgtg tactgcttcc     1260
aactggttgt ggaactgggg tattgcttac gctactccat acatggtgga tgaagacaag     1320
ggtaacttgg gttccaatgt gttcttcatc tggggtggtt tcaacttggc ttgtgttttc     1380
ttcgcttggt acttcatcta cgagaccaag ggtctttctt tggagcaggt cgacgagttg     1440
tacgagcatg tcagcaaggc ttggaagtct aagggcttcg ttccatctaa gcactctttc     1500
agagagcagg tggaccagca aatggactcc aaaactgaag ctattatgtc tgaagaagct     1560
tctgttttaa                                                            1569
```

<210> SEQ ID NO 11
<211> LENGTH: 1584
<212> TYPE: DNA
<213> ORGANISM: Debaryomyces hansenii

<400> SEQUENCE: 11

```
atgggtttag aagataatgc gcttattaga aagtatgtca atgtcgggga aaaagggct        60 gggtcagcat ctatggggat tttcgtaggt gccttcgcag ctttcggggg tgttttgttc      120
gggtatgata ctggaaccat ttcaggtatc atggccatga actatgtcaa aggagaattt      180
cctgccaata aggagagttt tacgtcaaaa gaaagttcgt tgattgtttc catcttatca      240
gcaggtactt tcttcggtgc gttgttagca ccgtttatgt ctgatacttt aggtagaaga      300
tggtcattaa ttatttcaac attcattgtt ttcaacttgg gagtgatttt acaaactgtt      360
tcaactggta ttccattact atgtgctgga gagctattg ctggttttgg tgttggtctt       420
atatctgctg tcattccatt atatcaatca gaagccactc caaaatggat tagaggggct      480
gttgtatctt gttatcaatg ggccattact attggcttat tgttagcggc ttgtgttaac      540
caaggtactc ataatagaaa tgactcgggt tcatacagaa ttccaattgc tgttcaactt      600
ttatggtcgt taattttggg tactggtatg atcttcttgc ctgacacgcc acgtttctgg      660
atccacaaag gtaatgaatc tgaagctaag aaatcgttga gattttaag aaaattacca      720 cttgaccacc cagacttaat tgaagaatac gaagacatca aagctgctta cgatttcgag      780
```

```
tgttctttcg gaaaatcgtc ttggatggat cttttacca caaggaatag gcaattgaag      840
agattattta ccggtgttgc tcttcaagca tttcaacaat taactggtgt taactttatc     900
ttctattttg gtacctcttt cttcaagagt gctggtattg aaaacgaatt tcttatttct    960
ttagccacca gtattgttaa cgtaggtatg actgttccag gtatcttttt aattgaatta    1020
gtgggtcgtc gttctatgtt gttgtggggt gctgttggta tgtcggtttc tcaatttatc    1080
gttgctattg ttggtattgc cactgatagt gccgacgcta acaaagtctt gatcgcattc    1140
acttgtttct tcattgcatt ctttgcttct acctgggtc caattgcttg ggttgttgtt     1200
ggtgagattt tcccattaag aactagagct aagtccgttg cattatctgc cgcttccaac    1260
tggctttgga actgggctat cgcatacgct actccatact tggtagaaga tggtaagggt    1320
aatgctaact taggaacaaa cgttttcttc atctggggtg gatgtaactt tctttgtatt    1380
ttgttcactt acgtcttcat ttacgaaacc aagggttact ctttggaaca aattgatgaa    1440
ttatatgaaa aagttccaca tgcttggaaa tctcgtggct tcattccttc tgcccatgct    1500
ttcagagaag atgctccaga gtcaatcagc tctatgggaa aggatatgga aaaagttact    1560
gaaattgaaa ccacttcagt ctaa                                           1584
```

<210> SEQ ID NO 12
<211> LENGTH: 2196
<212> TYPE: DNA
<213> ORGANISM: Debaryomyces hansenii

<400> SEQUENCE: 12

```
atgtggccat ttctagatag gatcatgtat gatcactcga cggaggagga atattacaaa      60
aagatgcaac agaagtcgtc ttcgtcgagt gccattacag tggggctagt ggcggcggta    120
gggggatttt tgtatgggta cgatactggg ctcattaacg atattatgga gatgacgtac    180
gtgaaggata acttcccggc gaatggacat agcttcagcg tacacgagcg agcgttgata    240
acggccatct tgtcactcgg aacatttttt ggggcgttga tagcgccgtt gatatcggat    300
acgtggggta gaaagttttc gatcattgta tcgtcagctc tcatatttaa tgtgggaaac    360
atcttgcagg tgtcatccac agaggtggtg ctttttatgtg ttgggagagc tgtttcgggg    420
ttgtcagtgg gtatactctc agccattgtg ccgttgtatc aagctgaagc ttcgccaaaa    480
tgggtaagag gttccattgt gtatacttac caatgggcga taacatgggg gttgttgatt    540
gctagtgcta tatgtcaggg ggcaaaaaac attatgaatt cgggctcgta tagaataccg    600
gtgggaatac agttcttgtg ggcaattatt ttgtctgtcg ggatgctttt tttacccgaa    660
tctcctcgat tccatgtaca gaaggataat atccaagaag cattgaaatg cttagctaga    720
ctaagaaaag tgccgacaga tgaccctgat ttgatagaag aactagttga atcaaggcc    780 aactatgact acgagttatc gtttggaaag gcatcctata tagattgctt taagagtggt    840
ggaggaagaa ataagcaact cacgaggatg ctcacaggta ttggggtcca ggcattcaa     900 caaagttcag gaatcaattt tatttctat tacggggtta atttcttcgc aagttcagga    960
attaagaatt attacttaat gtcatttgta acttatgcag ttaacacact ttttacaata   1020
ccagggataa ttttgattga agtcatagga agaaggaaac tattattatt tggcggcatt   1080
ggaatggctg tttcaaattt cataatagca attgttggtg ttagtatgtc agatgagtca   1140
atcagttcta taatatgtgt gtcatttttcg tgtgtcttta ttgcattttt tgcatcatca   1200
tggggcggtg ccgtatgggc gctctcttca gatatatttg gtattggtat tagacaaaaa   1260
gcaatatcgc taacggcagc gacaaattgg ttagttaatt ttacctttgc atttataacg   1320
```

| | |
|---|---|
| ccatatttga ttgatactgg taaacatacc gcagcattgg gtaacaaaat ttttttatc | 1380 |
| tggggtggtt gtaatgctct aggcgtcgta tttgtgtact ttatggttta cgaaacgaaa | 1440 |
| ggattaaaat tggaagaaat tgatttcatg tacaaaaact gtgtgaacgc tagagcttcg | 1500 |
| actaagttca aatctcaaaa gattgtatac gccaatcaaa tttcaacacc gatctcagag | 1560 |
| cttcttaatc ccaaccgatc gcatattgcg attgagaaat caagtggaag taacaataat | 1620 |
| ggcgatgatg atgagaatag cgaagaaaat caccatgatt ttggtttaga gaacggaaac | 1680 |
| gtcttacaca acaatttgga taataggaat ataactctta tcccttataa gaatattatt | 1740 |
| tcacctctgc gatcattcag ttcagattct tcaagcgatt ccgactcatc ttcaccactc | 1800 |
| aatgattatg aaagatactt acatagcttg caaaagaag gcagccatca tgacacctct | 1860 |
| caaacttcaa cgtccttaat tactgacaat aagctaagtc atcttaattc catgcataat | 1920 |
| gcccactcac ggggtaattt tactgaggag gacttgaagt acctcaatga tgaatatgat | 1980 |
| ttagcgatgt cgcagaaata cccaggcaca actacggcgc tctaaaacc aagcacgaat | 2040 |
| atgactgtta tagcggcgcc attttttgac gctccaccaa gcgattcaga cacggacgac | 2100 |
| gaaagcgacg acgatgaagt cggtgacgaa gatagcgaaa cagaaccaga aactactaag | 2160 |
| ggctcaccgg ttgataccaa ggactctagt tcgtag | 2196 |

<210> SEQ ID NO 13
<211> LENGTH: 1593
<212> TYPE: DNA
<213> ORGANISM: Debaryomyces hansenii

<400> SEQUENCE: 13

| | |
|---|---|
| atgttcaata aaatcagatt tggtttctgc agcttaaaca aggagcttga taagtttcat | 60 |
| acgacatata atatatatgt tattgctatg attacaacaa tctcaggtat gatgtttgga | 120 |
| tttgatgtct cttcaatctc tgcatttata tctgaaccat cctacaggcg gttcttcaat | 180 |
| tatccaaact ctacgacaca gggtgcaatt actgcatcca tgtctgcagg gagcttcttg | 240 |
| ggtgcaatat tatcatcttt tgtatcagaa agaattggga gaagaacctc attgcttttt | 300 |
| tgtgccatgt tctgggtttt aggttccata atccaatcat catgcagaaa ccttggtcaa | 360 |
| ttaatcgcag gtcgcataat atccggggta ggtgttggta ttggatccgc aataacccca | 420 |
| atatattgtt cagaagtatc tcctgcccct tctagaggtg ttattggagg tttatttcaa | 480 |
| ttagctatca catttgggat attgataatg ttttacatag gatatggttg tacatttatt | 540 |
| aacggtcagg cgtctttcag attagcttgg gcgctacaaa tgattcccgg tttggttttg | 600 |
| tttgctggtg tattcatttt acctgagtca ccacgctggt tagcaaacaa tagtaagtgg | 660 |
| gagcaagcag aagaagtgat tcgaagaatt aacgaaaaag acaaaacagg aagatatttg | 720 |
| attgaattag aggagttgaa ggaaagtatc acaattcata aattatcaaa agatataggg | 780 |
| tacctagatc ttttcaggaa aaagaactat aaaagtagta ttgttggtat tcggctcaa | 840 |
| atctggaatc agcttaccgg aatgaacgtg atgatgtatt atatagtcta tatctttgaa | 900 |
| atggtgggat atactggaaa tacagttta gttagttcaa gtatccaata tgttatcaat | 960 |
| tttggcgtga ctttaatagc tttgcctta tctgattatg ttggaagaag aagactaatg | 1020 |
| ctaatcggtg gtgtactaat gatggcatgg ctatttgctg ttggtggact ctttgcagcc | 1080 |
| tattctgaaa aggtagaaaa cgtcaccagt gacgcaaccg tggttgttac tatccccgaa | 1140 |
| gaacatcgaa atattggaaa agccattgtt gcttgctctt atttattcgt tgccaccttc | 1200 |

```
gctagtacgt gggcagtatg ttcatggtgt tatttttctg aagtgctccc aactaggaca   1260
agatcaaaag caggactgtt agcagttgca agtgactggg caataaattt tgccatagct   1320 cttttttactt cttcagcatt tagaaatatt acttggaaaa cttactttgt ttttggaaca   1380
ttctgcggcg ctatgaccgt tcataccttc ctttcatacc ctgaaactcg tatgaaaacg   1440
ctagaagaaa ttgatatgac tttccaaaat tgtatcccac catggaggtc cgcgggagtt   1500
actattcaaa gtcttgacgg ttatttaagt gattctaagg aaaataacgt aacgcatgtc   1560
gaacaagtgg aatcaaatag cataagtaag tag                                1593

<210> SEQ ID NO 14
<211> LENGTH: 1731
<212> TYPE: DNA
<213> ORGANISM: Debaryomyces hansenii

<400> SEQUENCE: 14
atgtcttcgt tattgaccaa caaatatttc aaagactatt acaataatcc aagtccaacg     60
gcgattggta ctatgatcgc catcctagag attggtgctt tgatatcatc gttcgttgcg    120
ggtaaagttg gtgatcatat cggaagaaga cgcactatac gttatggatc gtttatcttc    180
ataatcgggg gcttatcca aacttcgtca atcaatatta ttaacttagg ggcaggaagg    240
tttatcagtg gtgtggcaat tgggttttg actactatca ttccatgcta tcagtctgaa    300
atcagtccac ctgatgatag aggattctat gcgtgcttag aatttactgg taacatcatt    360
ggttactcta caagtatttg ggtggattat gggttttcgt tcatagaaaa tgactactca    420
tggagaactc cattggccat ccaatgtgtc atgggtggcc ttttgtttat tggatcattc    480
gtaatcgtag aaactccaag atggctttta gatcatgatc atgatattga aggaatgatt    540
gtgatttctg atttgtatgg tgatggtgat gttgaagacg aattatctaa aacggaatat    600
agaaacatta aggaaaacat tctcatcgca agagtggaag gaggggaacg ttcatatcgt    660
tatatgttaa ctaagtataa gaaacgtctt tcagttgcgt gcttttcgca gatgtttgca    720
caattgaatg gtattaatat ggtttcctat tatgcgccta tgattttttga gctggccggt    780 tgggttggta gacaggccat tttaatgact ggtattaatt ccatagttta cgtattgagt    840
acaattccgc catggtattt ggtggatggt tggggcagaa agccgttatt gttgtctggc    900
gctgttgtca tgggtatacc attattagtg atttcgtatt cattattcct tgataacatt    960 tatacccccaa acatagtggt tgtatcggtg atcatattca atgctgcatt tggtgcaagt   1020
tgggggccaa tcccatggat gatgaatgaa gtattaccta atagtattag atctaaaggt   1080
gctgccatgt ccactgcaac taattggcta ttcaacttca tcgtagggga aatgaccccca  1140 atattgttgg ataccattaa atggagaacc tatttgatct cagccgtctc gtgtgcatta   1200
tcatttttat gcgtccactt cttgtttccg gaaacaaagg ggttgagctt agaggacatg   1260
ggctccgtat ttgatgataa ctcgtctatt ttttcgttcc attcgggtgc atccagtgga   1320
aacaatgcat caactactac tatcaataac tacgggctg cagatagaga tagcggtatc   1380
gaggttcgca gaactagtat ctccgttgaa actccaaacc atgcaaacat agttaatgaa   1440
gcatttcgcc aatccccagc atcaattgct cgtaattcaa aggccaaacc agagttagac   1500
ggtcttatta ctggtaatcc accacccgta ccacctgacc tctcggtctt ggactccaat   1560
gtacctccac aagaaatcga accaccttca ttcgacgtca ttttcaaata taaagttcgc   1620
caattagaga aaccaaacat attccaaaag gctttccgtg caatctccgg tgatagtacg   1680
ttcaaaccac cacagatcga cgaagaacgt actttgctct cgaataattg a            1731
```

<210> SEQ ID NO 15
<211> LENGTH: 1674
<212> TYPE: DNA
<213> ORGANISM: Debaryomyces hansenii

<400> SEQUENCE: 15

| | | | | | |
|---|---|---|---|---|---|
| atgactactg | ctgttggatt | agaagataat | tccaaaggga | atattattac | tgttatgagt | 60 |
| aaagatccgt | tagtgttttg | cataattgcg | tttgcatcta | ttgggggttt | actctttggg | 120 |
| tacgatcagg | gagttattag | tggtatagtt | actatggagt | catttgcggc | aaaattcccc | 180 |
| agaattttt | ccgatcctga | ttataagggt | tggtttgttt | ctacattttt | gttgtgtgct | 240 |
| tggtttggtt | cgttgataaa | ctctcctgtt | gttgatcgat | ttggaagaag | ggatactata | 300 |
| agaatagctt | gcgttgtatt | tgttatcgga | tctgtctttc | aatgtgcagg | tacgtcggtt | 360 |
| agtatgcttt | tcgctgggag | agcagttgct | ggtatcggtg | tcggacaatt | gactatggta | 420 |
| gtcccaattt | atatgtcgga | attagctcca | ccttcagtaa | gaggtggttt | agttgtaata | 480 |
| cagcaatttt | caataacaat | aggtattttg | atatcatttt | ggataaatta | tggcactcaa | 540 |
| tttattggag | gaactaaatg | tgctcctgac | caagattaca | aaggcgatac | tttcgaccca | 600 |
| tacattgatg | ttcctcaagg | tggttgttac | ggtcaaaaag | atgcttcctg | gagaattcca | 660 |
| tttgggttac | aaattgcacc | agctttcatt | ttaggtattg | gtatgtcttt | ttttccaaga | 720 |
| tcgccaagat | ggctcttatc | aagaaaaaga | gaagaggagg | catgggaggc | tttgaattat | 780 |
| ttgaggagaa | gaaataatcc | tgatatgatt | gatgctgaat | tcaatgaaat | taaatcggac | 840 |
| gtattatttg | aacaaaaata | taacgagagg | aaatttcaag | gaaaaacagg | aatgtctttc | 900 |
| tttataacat | cgtattggga | tctagtctct | accaaatcaa | attttaagag | agttttata | 960 |
| ggctctgcgg | ttatgttctt | ccaacaattt | attggttgta | atgcaattat | ttattacgca | 1020 |
| ccaacaatat | ttagtcaatt | aggaatggat | tccaacacca | cagcattgtt | aggaacaggg | 1080 |
| gtctatggga | ttgttaattg | cctttcaact | attcctgcta | tctttgcgat | tgacagattt | 1140 |
| ggtagaaaaa | ctttattgat | ggctggggca | gctggaactt | ttgtttcgtt | ggttatagta | 1200 |
| ggtgcaattg | tcggcacata | tggtgatact | ttatctaagc | ataaaactgc | tggtagagcg | 1260 |
| gcaatagctt | ttatttttat | atatgatttc | aacttttcat | atagctgggc | acctattgga | 1320 |
| tgggttttac | catccgaaat | cttctctatt | ggaatcagat | caaaagctat | atccattact | 1380 |
| acttcatcaa | catggatgaa | taatttcata | attggtttgg | tcaccccccg | tatgttggag | 1440 |
| acaatgaaat | ggggaacata | tatctttttt | gcagcatttg | ctataattgc | atttgctttc | 1500 |
| acttggtttg | ttatcccaga | aactaaagga | gtacctttag | aagaaatgga | tttagttttt | 1560 |
| ggtgatttag | atgcgttgca | agaaaagcaa | aacttctctc | gcatgaatga | attatcaaaa | 1620 |
| atggattcaa | ttaaagctac | aacagatatt | tcggaagcac | attattctga | ttaa | 1674 |

<210> SEQ ID NO 16
<211> LENGTH: 1476
<212> TYPE: DNA
<213> ORGANISM: Escherichia coli

<400> SEQUENCE: 16

| | | | | | |
|---|---|---|---|---|---|
| atgaataccc | agtataattc | cagttatata | ttttcgatta | ccttagtcgc | tacattaggt | 60 |
| ggtttattat | ttggctacga | caccgccgtt | atttccggta | ctgttgagtc | actcaatacc | 120 |
| gtctttgttg | ctccacaaaa | cttaagtgaa | tccgctgcca | actccctgtt | agggttttgc | 180 |

-continued

```
gtggccagcg ctctgattgg ttgcatcatc ggcggtgccc tcggtggtta ttgcagtaac      240
cgcttcggtc gtcgtgattc acttaagatt gctgctgtcc tgttttttat ttctggtgta      300
ggttctgcct ggccagaact tggttttacc tctataaacc cggacaacac tgtgcctgtt      360
tatctggcag gttatgtccc ggaatttgtt atttatcgca ttattggcgg tattggcgtt      420
ggtttagcct caatgctctc gccaatgtat attgcggaac tggctccagc tcatattcgc      480
gggaaactgg tctcttttaa ccagtttgcg attattttcg ggcaactttt agtttactgc      540
gtaaactatt ttattgcccg ttccggtgat gccagctggc tgaatactga cggctggcgt      600
tatatgtttg cctcggaatg tatccctgca ctgctgttct taatgctgct gtataccgtg      660
ccagaaagtc ctcgctggct gatgtcgcgc ggcaagcaag aacaggcgga aggtatcctg      720
cgcaaaatta tgggcaacac gcttgcaact caggcagtac aggaaattaa acactccctg      780
gatcatggcc gcaaaaccgg tggtcgtctg ctgatgtttg gcgtgggcgt gattgtaatc      840
ggcgtaatgc tctccatctt ccagcaattt gtcggcatca atgtggtgct gtactacgcg      900
ccggaagtgt tcaaaacgct gggggccagc acggatatcg cgctgttgca gaccattatt      960
gtcggagtta tcaacctcac cttcaccgtt ctggcaatta tgacggtgga taaatttggt     1020
cgtaagccac tgcaaattat cggcgcactc ggaatggcaa tcggtatgtt tagcctcggt     1080
accgcgtttt acactcaggc accgggtatt gtggcgctac tgtcgatgct gttctatgtt     1140
gccgcctttg ccatgtcctg gggtccggta tgctgggtac tgctgtcgga atcttcccg      1200 aatgctattc gtggtaaagc gctggcaatc gcggtggcgg cccagtggct ggcgaactac     1260
ttcgtctcct ggaccttccc gatgatggac aaaaactcct ggctggtggc ccatttccac     1320
aacggtttct cctactggat ttacggttgt atgggcgttc tggcagcact gtttatgtgg     1380
aaatttgtcc cggaaaccaa aggtaaaacc cttgaggagc tggaagcgct ctgggaaccg     1440
gaaacgaaga aaacacaaca aactgctacg ctgtaa                               1476
```

<210> SEQ ID NO 17
<211> LENGTH: 1701
<212> TYPE: DNA
<213> ORGANISM: Scheffersomyces stipitis

<400> SEQUENCE: 17

```
atgcacggtg gtggtgacgg taacgatatc acagaaatta ttgcagccag acgtctccag       60
atcgctggta agtctggtgt ggctggttta gtcgcaaact caagatcttt cttcatcgca      120
gtctttgcat ctcttggtgg attggtctac ggttacaatc aaggtatgtt cggtcaaatt      180
tccggtatgt actcattctc caaagctatt ggtgttgaaa agattcaaga caatcctact      240
ttgcaaggtt tgttgacttc tattcttgaa cttggtgcct gggttggtgt cttgatgaac      300
ggttacattg ctgatagatt gggtcgtaag aagtcagttg ttgtcggtgt tttcttcttc      360
ttcatcggtg tcattgtaca agctgttgct cgtggtggta actacgacta catcttaggt      420
ggtagatttg tcgtcggtat tggtgtgggt attctttcta tggttgtgcc attgtacaat      480
gctgaagttt ctccaccaga aattcgtggt tctttggttg ctttgcaaca attggctatt      540
actttcggta ttatgatttc ttactggatt acctacggta ccaactacat tggtggtact      600
ggctctggtc aaagtaaagc ttcttggttg gttcctattt gtatccaatt ggttccagct      660
ttgctcttgg gtgttggtat cttcttcatg cctgagtctc caagatggtt gatgaacgaa      720
gacagagaag acgaatgttt gtccgttctt tccaacttgc gttccttgag taaggaagat     780
actcttgttc aaatggaatt ccttgaaatg aaggcacaaa agttgttcga aagagaactt     840
```

```
tctgcaaagt acttccctca cctccaagac ggttctgcca agagcaactt cttgattggt    900
ttcaaccaat acaagtccat gattactcac tacccaacct tcaagcgtgt tgcagttgcc    960
tgtttaatta tgaccttcca acaatggact ggtgttaact tcatcttgta ctatgctcca   1020
ttcatcttca gttctttagg tttgtctgga aacaccattt ctcttttagc ttctggtgtt   1080
gtcggtatcg tcatgttcct tgctaccatt ccagctgttc tttgggtcga cagacttggt   1140
agaaagccag ttttgatttc cggtgccatt atcatgggta tttgtcactt tgttgtggct   1200
gcaatcttag gtcagttcgg tggtaacttt gtcaaccact ccggtgctgg ttgggttgct   1260
gttgtcttcg tttggatttt cgctatcggt ttcggttact cttggggtcc atgtgcttgg   1320
gtccttgttg ccgaagtctt cccattgggt ttgcgtgcta agggtgtttc tatcggtgcc   1380
tcttctaact ggttgaacaa cttcgctgtc gccatgtcta ccccagattt tgttgctaag   1440
gctaagttcg gtgcttacat tttcttaggt ttgatgtgta ttttcggtgc cgcatacgtt   1500
caattcttct gtccagaaac taagggtcgt accttggaag aaattgatga acttttcggt   1560
gacacctctg gtacttccaa gatggaaaag gaaatccatg agcaaaagct taaggaagtt   1620
ggtttgcttc aattgctcgg tgaagaaaat gcttctgaat ccgaaaacag caaggctgat   1680
gtctaccacg ttgaaaaata a                                             1701

<210> SEQ ID NO 18
<211> LENGTH: 1404
<212> TYPE: DNA
<213> ORGANISM: Scheffersomyces stipitis

<400> SEQUENCE: 18
atgaagtatt ttcaaatctg gaaatcaggc aaacaagtaa gctacgctgt tacattcact     60
tgtgaattgg catttattct ttttggtatt gaacagggta ttattggtaa tcttattaac    120
aaccaggact tcctaaacac ttttggaaac cccaccggta gttatttagg tattatcgtt    180
tctatctata ccttagggtg ttttttttggt tgtgttatga acttcttcat tggtgatcga    240
atgggcagaa gaagcaaaat tgcttcctca atgacagtta tcacaattgg tgttgctctt    300
caatgtagtt cctttttcagt tgaacaattg atgattggaa gatttatcac tgggcttgga    360
actggttggg aaacttctac ttgtccaatg tatcaggcag aactttcacc tccaaaagtt    420
agaggacgtt tggtgtgctc agaagcattg tttgttggag ttggtttaat ctatgcatat    480
tggtttgatt atgctctttc tttcacttct ggtcctattg catggagact tcctcttgcc    540
tctcagattg tgttcgcctt tgttgttttc tgtttcactt tcacaatacc cgaatcccct    600
agatacatgt tttacaaagg agagaagaa gaagccaaaa gaattttatc ttatgtcttt    660
ggaaagccag gagatcatcc tgacattctt aaggaatgga atgatattaa tgatgctgtt    720
attttggaaa cttcagaagg agcttttctcg tgggcaaaac ttttcaagcc cgataaggca    780
agaactggat acagagtctt cttggcatac atgagcatgt tgcgcaaaca gttgagtggt    840
gttaatgtag ttaattacta tattacatttt gttttgatta acagtgttgg catcgaagac    900
aacttggccc taattcttgg tggtgttgcc gtcatctgtt tcactgttgg ttcattagtt    960
cctactttct ttgctgatag gatgggaaga agattgcctt cagcagttgg agcttttggc   1020
tgtggtgttt gtatgatgct aatttcaatc ttattaagtt tcaagacaa tccaaagttg   1080
aagaagagca gtggagctgg tgctgtggct ttctttttcg ttttccaact tgtcttcggc   1140
tccactggta attgtattcc atggctgatg atttcagagc ttatccccct tcatgcacgt   1200
```

```
gctaaaggat cttcattagc tacatcaagt aactggcttt ggaatttctt tgttgttgag    1260
atcactccaa ctatcattga aaagttgaag tggaaagcat atttgatctt tatgtgctgc    1320
aacttctcct tcgtaccaat gttttacttt ttctttcccg agacaaagaa ccttacttta    1380
gaagccattg acgatttgtt ctca                                            1404
```

<210> SEQ ID NO 19
<211> LENGTH: 1656
<212> TYPE: DNA
<213> ORGANISM: Scheffersomyces stipitis

<400> SEQUENCE: 19

```
atgagagaag ttggtattct tgatgttgcc catggcaacg ttgtaactat aatgatgaaa      60
gatccagtag tatttttggt gattttattt gcatcccttg gaggtttgct ttttggttat    120
gatcaagggg ttattagtgg cattgtcaca atggaatctt ttggtgcaaa attccccaga    180 attttatgg atgccgatta caaggggtgg tttgtgtcta cttttttgct atgcgcatgg    240
tttggctcta ttattaatac tccaattgtt gataggtttg aagacgtga ttctatcaca    300 atctcttgtg ttattttgt cattggttct gcgttccaat gtgctggcat taatacaagt    360
atgttatttg gtgggcgtgc tgttgctggt cttgcagtcg gtcaattaac catggtagtt    420
ccaatgtaca tgtcggaatt ggctcctcca tcggtgagag gtgggttggt tgtaattcag    480
caactttcga ttacaattgg tatcatgatt cctattggt tggattatgg cactcatttt    540
attggaggta ctagatgtgc tcctagtcac ccataccaag gtgaaacttt taaccctaat    600
gtggatgttc ctccaggtgg ctgctatggt caaagtgatg ccagttggag aattcctttt    660
ggtgttcaga ttgctccagc agtgttgttg ggtattggaa tgatattttt cccaagatct    720
cccagatggt tactctctaa aggtcgcgac gaagaagctt ggagctcttt gaaatatctc    780
agaagaaaga gtcatgagga tcaagtcgaa agagagtttg ctgaaattaa ggcagaggtc    840
gtttatgaag acaagtacaa ggaaaagaga ttccctggta agactggagt tgctttaaca    900
cttactggat actgggatat tcttactact aaatctcact tcaagagagt tttattgga    960 tcagctgtca tgttcttcca acaattcatt ggctgcaatg caataattta ttacgcacct    1020
acaattttca cacaattggg aatgaactct acaactactt ccttgcttgg tactggtctt    1080
tatggtattg ttaattgtct ttccacccct tccagcagtgt tcttgatcga tagatgtgga    1140
agaaagactt tgttaatggc aggtgctatt ggaacttta tttccttggt tattgtcggc    1200
gcaatcgttg gcaagtatgg cgatcgtttta tctgaattca agacagcagg gagaactgca    1260
attgctttca ttttcattta tgatgtgaat ttctcgtaca gttgggctcc aattggatgg    1320
gttttaccct cagagatttt cccaatcggc atcagatcca atgccatctc cataactacc    1380
tcatctactt ggatgaataa ttttattatt ggcttggtca ctccacatat gttagaaaca    1440
atgaagtggg gcacttacat ttttttttgca gcgtttgcta ttattgcgtt cttttttcact    1500 tggcttatca tcccggaaac caagggagtt ccattggaag aaatggatgc cgtgtttggc    1560
gatactgcag cattgcagga aaagaatttg gttaccatta cgtcagtttc tgaatctgac    1620
gccaaggatc gcaactcgat tgaaatgtca gaataa                              1656
```

<210> SEQ ID NO 20
<211> LENGTH: 1629
<212> TYPE: DNA
<213> ORGANISM: Scheffersomyces stipitis

<400> SEQUENCE: 20

| | |
|---|---:|
| atgtcttcgt tattgactaa cgaatacttc aaagactact accacaaccc gactcctgtt | 60 |
| gaagtgggta ctatgattgc tatcttagag atcggcgcac ttttttcctc cttcatagct | 120 |
| ggaagagtag gtgacatcgt tggcagaaga agaaccatta gatacgggtc tttcattttt | 180 |
| gtagtaggcg gtcttgtaca agctacttcg gtcaatattg tcaatctctc actaggaaga | 240 |
| ttgattgccg gtattgccat tggcttttg acaaccatca tcccatgcta ccagtctgaa | 300 |
| atcagccccc cagacgatag aggtttctat gcctgtttgg agttcaccgg aaatatcatt | 360 |
| ggatatgcta gtagtatttg gtagactac gggttttcat ttttagacaa tgatttcagc | 420 |
| tggaggagcc cattgtatgt tcaggttgtt attggctcca tgttatttat tggttcattc | 480 |
| cttattgtag aaaccccctag atggctcttg gatcacaacc atgatatcga aggcatgatt | 540 |
| gtcatttctg acttgtatgc agatggtgat gtggaagacg atgatgctat tgctgagtac | 600 |
| agaaacataa aggaaagtgt cttgatagcc agagttgaag gcggagagag atcgtaccag | 660 |
| tatttgttca ccaaatatac caagagactt tctgtggcat gcttttcgca aatgtttgcc | 720 |
| cagatgaatg gtataaacat ggtatcttac tatgctccta tgatcttcga atctgctggc | 780 |
| tgggttggta gacaagctat cttgatgact ggtatcaact ccattatcta catctttagt | 840 |
| accattcctc catggtactt agttgattct tggggcagaa aacctttgct tttatctgga | 900 |
| tctgtgctca tgggtgttcc gctcttaacc attgcttgtt cgttattctt aaacaacaca | 960 |
| tacacacccg gggttgtggt tggcagtgta atcgtattca atgctgcttt tggatacagt | 1020 |
| tggggtccaa ttccttggct catgagcgaa gtgttcccta actcagttag atcaaaaggt | 1080 |
| gctgccatgt ctactgcaac caactggctc tttaacttta ttgttggaga gatgacacct | 1140 |
| attttgttgg atacaattac ctggagaact tacttgatcc cggcaacttc gtgtgtatta | 1200 |
| tcgtttttg ctgttggatt tttatttcca gagaccaagg gtttagcatt ggaggatatg | 1260 |
| ggctccgtat tcgatgataa ttcgtcaata ttttcatatc actcaactcc ttccactggg | 1320 |
| tatggtgcga ccgagtctaa cagtaatgcc aggagagcaa gtgtcatctc ttcagaaaac | 1380 |
| taccaggata gtttgcatca gacagcggct tcattggcta gaaatccttc aagcatgagg | 1440 |
| cctgattacg atggcataat cacaggagct gctacccttt cgccagtacc accattaaaa | 1500 |
| ccaataaagt ctgatgcgtc agtccattca gtcgatgcca taattccaag catttccagc | 1560 |
| aatattccgc aggaaattga accaccaacc tttgatgaaa tctttaagta caagttgaat | 1620 |
| gagatggaa | 1629 |

<210> SEQ ID NO 21
<211> LENGTH: 1488
<212> TYPE: DNA
<213> ORGANISM: Scheffersomyces stipitis

<400> SEQUENCE: 21

| | |
|---|---:|
| atgacggaaa gaagcattgg acctttaatc cccagaaata agcacttatt ctatggatcc | 60 |
| gtattattga tgagtattgt tcacccaact atcatgggat acgattccat gatggttggt | 120 |
| agtattctta atctagatgc atatgtaaat tatttccact taacggctgc taccactgga | 180 |
| ctcaatactg ctgcagtatg gcttgggcaa gtaattgcca cattgacagt tattctgtat | 240 |
| ttcaatgaca aatttggtag aagaagttca gtttgtataa gtattgcaat cagtttggtt | 300 |
| ggggttgcat tgcaatcagc agcccaaaac attgagatgt ttattatcgg aagaatagtt | 360 |
| attggttttg gaatatctat tggttttgtc tcatctacca ttttggtaag tgaactagcc | 420 |

```
cctccagaca aaagaggatt tattcttgga ttgagtttta caagctttct agtaggaagt      480
ttaattgcag caggtgtcac atatggaaca agaaatgctc ctggagactg gtgttggaga      540
atcccatcaa ttattcaagg ggctccagat attgttgcta ttattaacat actctttatt      600
tcagaatcac caaggtggtt gattgcaaag gaaagattca gcgaagctcg tgaaattatt      660
tctatcatta gtgatgttcc tattgaagat gcacatgaag aatgtgaaaa gatacatgcc      720
catattcaaa ctgagaagac tgctttccct ggcaataagt ggaaacaaat ggtgagctcc      780
aagagcaata caagaagagt tattatcttg ttcacacagg ccatagttac tgaaatggcc      840
ggttcttcag ttggatcgta ctattttttca attatattaa ctcaagctgg ggtcaaagat      900
tcgaatgata gactaagagt aaatattgtg atgagttcgt ggtcattggt aattgctctt      960
tccggatgtc taatgtttga cagaattgga agaaaaatgc aatcgctcat ttcgttatca     1020
ggtatgatca tatgctttat agttttaggt gttttggtta agaatatgg cgatggtcat      1080 agcaagagcg gaagttacgc agctgtcgcc atgatgtttt tattcacagg attttactca     1140
ttcactttca ctccattgaa ctctttgtac cctccagaat tgttcccccta cgtgttgaga     1200 agtacaggag ttacactctt taatattttc aacggctgct ggggactttt cgcaagtttc     1260
attttaccca ttgcaatgaa tggaattggc tggaaatttt acatcattaa tgcttgctat     1320
gacgtcatat tccttccaat aataatgttc tgttggattg agacaaaggg aattaatttg     1380
gatacaatta gtgaagtatt gcacggaaga ggacctgaag atgaagaaag cattgaagaa     1440
agtcacagcc taatcagaca aggttttgtt gttaatacaa agaagtaa                  1488
```

<210> SEQ ID NO 22
<211> LENGTH: 1635
<212> TYPE: DNA
<213> ORGANISM: Scheffersomyces stipitis

<400> SEQUENCE: 22

```
atgtccagtg ttgaaaaaag tgctgaaact gcttcctata cgtcgcaggt cagcgcaagc       60
ggctctgcaa agaccaacag ctaccttggc ctcagaggcc acaaacttaa ttttgctgtc      120
tcttgttttg ctggtgttgg tttcttactt ttcggttacg atcaaggtgt catgggttca      180
tgttgaccct tgccatcctt cgaaaacact ttcccggcca tgaaggctag caacaacgct      240
accttacaag gcgccgttat tgcactttat gaaatcggtt gtatgtcttc ttctttagca      300
accatttacc ttggtgacag attgggtaga ttgaagatca tgtttattgg ctgtgtaatt      360
gtctgtattg gtgctgcttt gcaagcttct gctttcacta ttgctcactt gactgttgct      420
agaattatca ctggtttagg tacaggtttc atcacttcta ctgttccagt ttaccaatcg      480
gagtgctctc cagccaagaa aagaggacag ttgatcatga tggaaggttc tcttatcgcc      540
cttggcattg ccatctcata ctggattgac tttggatttt actttttgag aaacgatggt      600
ttgcactcct cggcttcttg gagagcacct atcgcgcttc aatgtgtctt cgctgtcttg     660
ttgatttcca cagtcttctt cttcccagaa tctccaagat ggttgctcaa caaaggtagg      720
accgaagaag ctagagaagt ttttctgct ctttacgact tgccagccga ctctgaaaag      780
atttctattc aaattgaaga aattcaagct gctatagatt tagaaagaca agccggagaa      840
ggtttcgtac ttaaggaatt gttcactcag ggcccagcca gaaacttgca gcgtgtggcc      900
ttgtcatgtt ggtctcaaat aatgcaacaa atcactggta ttaacattat tacgtactat      960
gctggtacta tttttgaatc atacattggt atgagtccat ttatgtcaag aatcttggct     1020
gccttgaacg gtactgaata tttccttgtc tctcttattg ctttctacac cgtcgaaaga     1080
```

-continued

```
ttaggtagaa gattcctttt gttctggggt gccatcgcca tggctcttgt catggctggt   1140
ttaactgtta ccgttaaact tgccggtgaa ggcaacaccc atgctggtgt cggtgctgct   1200
gttcttttgt ttgcattcaa ctcattcttc ggcgtctcct ggttaggtgg atcctggttg   1260
ttaccacctg aattgttgtc tttgaaattg agagctcctg gtgctgcttt gtcgaccgct   1320
tctaactggg cttttaactt catggttgtc atgatcactc ctgtcggttt ccaaagtatt   1380
ggttcctaca cctaccttat ctttgctgcc atcaatttgt tgatggctcc ggtcatctac   1440
ttcttgtatc ccgaaaccaa gggtagatcg ttggaagaaa tggatatcat tttcaaccaa   1500
tgtcctgttt gggagccatg gaaggttgtc caaattgcca gagacctccc tattatgcac   1560
tcagaagttc ttgaccacga aaaggatgtc attattgaaa aatctagaat agagcatgtc   1620
gaaaacatca gctaa                                                    1635
```

<210> SEQ ID NO 23
<211> LENGTH: 1251
<212> TYPE: DNA
<213> ORGANISM: Scheffersomyces stipitis

<400> SEQUENCE: 23

```
acttttgcag ttaacttgta tgtgtttgca gttggtagag tgctttctgg ggtgggtgta     60
ggagttctat cgactatggt gccgtcctat caatgcgaaa ttagtcccag cgaagaaaga    120
ggcaagttgg tgtgtggaga gttcacggga aatatcactg gttatgctct cagtgtatgg    180
gccgattact tctgctactt tattcaagat ataggtgatg caagggagaa gcctcatagc    240
ttctttgccc acttgtcctg gcgattgcct ctattcatcc aggtggtgat agcggctgtt    300
ctctttgttg ggggattttt tattgtcgag tcacctcgtt ggttattaga tgtagaccag    360
gaccaacaag gattccatgt attagcgttg ctctatgatt cacatctaga tgataacaaa    420
ccacgtgaag agttctttat gatcaaaaac tccatcttgt tagaaagaga aactacacct    480
aagagcgaac gaacttggaa acatatgttc aagaactaca tgacccgagt gcttatagct    540
tgttcagcac ttggctttgc acagttcaac ggcataaata tcatttcgta ctatgccccc    600
atggtatttg aagaagcagg cttcaacaac tccaaggctt tacttatgac aggcatcaac    660
tctatagtat attggttcag tacgattcct ccgtggtttc tcgtggatca ttggggtaga    720
aagccaattt tgatatccgg gggtttatct atgggaatat gtattggttt gattgcggtg    780
gtaattctac tagacaagtc gttcacaccg tctatggttg cggtattggt gataatctac    840
aatgcatctt ttggctacag ttggggtcct atcggattct tgatcccgcc ggaggtgatg    900
ccattggcag ttagatcgaa aggtgtttct atttctacgg ctacaaactg gtttgccaat    960
tttgttgtgg gtcagatgac gccaattcta cagcagagat tgggctgggg aacttatcta   1020
ttcccggctg gtagttgtat catctcggtg atagtggtga ttttcttcta tccagagaca   1080
aagggtgcag agctagagga tatggactct gtgttcgaga gcttttacaa ctacaagtct   1140
ccgttcaaga tttcacgaaa gagacaccag aatgatggcc aggcgtacca aagggtagag   1200
aacgatatcc gccacaacga tgtagaaatg gacgatttgg acgatttgga c            1251
```

<210> SEQ ID NO 24
<211> LENGTH: 1638
<212> TYPE: DNA
<213> ORGANISM: Yarrowia lipolytica

<400> SEQUENCE: 24

| | |
|---|---:|
| atgattggaa acgctcaaat taaccaggtg ggagccttac agcaccggtt ccccaaactc | 60 |
| cacaatcctt acttaactgc ggccgtggcc accatgggtg gcctgctttt cggctttgat | 120 |
| atctcgtctg tttctgcctt tgtcgacacc aaaccctaca aggagtactt tgggtacccc | 180 |
| acctccatcc agcagggcgg tatcactgcc tcaatggccg gtggatcctt cctgtcgtct | 240 |
| ctggtggccg gctggatttc cgaccgactt ggtcgacgtt tcgccatcca ctttgcttcc | 300 |
| ttttggtggg tggttggagc tgccatccag tcctcagccc aaaacaaggg ccaattgatc | 360 |
| gccggtcgac tcatttccgg ccttggtatc ggtctgggct cctcggttat ccccgtctac | 420 |
| atctccgagc tgtctcccaa gaagattcga ggtcggcttg tcggtctctt caatgggcc | 480 |
| gttacctggg gtatcctcat catgttctac atttccttcg gtctcagtaa catccacgga | 540 |
| gtcgccggat tcagagtcgc ctggggtctg cagatcatcc ccggtctgct catgtctctc | 600 |
| ggttgtttgt tcctggaaga gtctccgcga tggctagcca agcaggacaa ctgggacgag | 660 |
| tccgtgcgag tgcttcgagc catccaccag ggaggctacg gcaccgaaga agacattttg | 720 |
| ttagagattg aagagatccg agaagcagtc cgaatcgagc atgagaccaa aaacctgcga | 780 |
| ttctggcacc tgttccaaaa ggactctatc aaccgaacaa tggtgggtat ctgggcccag | 840 |
| atctggcagc agctcaccgg catgaacgtc atgatgtatt acattgtgct gattttcacc | 900 |
| atggctggat acactggaaa cgccaatctg gtggcctcgt ctatccagta cgtcatcaac | 960 |
| atgatcatga ccatccccgc tcttctgttc attgaccgag tggacgacg accctgctg | 1020 |
| ctgttcggat caatcgtcat gatgatctgg ctgtttgccg tcgctggtat ccttgcagtg | 1080 |
| tacgaaactc agatccccgg tggactcgac ggagacgcat tcacaaccat tgtcattgag | 1140 |
| cccactcaca agcctgccca aaagggagtc attgcgtgct cgtacctgtt tgtggccacc | 1200 |
| tttgcgccta cctggggccc cggtatctgg ctgtactgct ccgagctgtt ccctctgaag | 1260 |
| cagcgagctg tggctgccgg tgtaaccgcc tctgccaact ggatcttcaa cttttgctctc | 1320 |
| gctctattcg tgccctcggc cttcaagaac atcaactgga agacctacat catctttgga | 1380 |
| gtcttctgta tcgtcatgac catccacgtc tttgtcctct tccccgaaac caagggcaag | 1440 |
| accctcgaag agattgatat gatgtgggcc gcccgagttc ctgcctggag aaccgcaaac | 1500 |
| tgggtgcctg accacgttcc tggcgccctt cccgaagacg agaaacactc ggaggagatg | 1560 |
| gtcgaggccg tcgaatccaa tgaagaggag cccaagatag ccagtgctaa cgtcgacgcc | 1620 |
| cctccctctc aattgtaa | 1638 |

<210> SEQ ID NO 25
<211> LENGTH: 1665
<212> TYPE: DNA
<213> ORGANISM: Yarrowia lipolytica

<400> SEQUENCE: 25

| | |
|---|---:|
| atgtacaagg tccataaccc ctacctcacg gcggcggtag ccaccatggg cggaatgctc | 60 |
| tttggtttcg atatctcgtc cgtgtcggcc tttgtggggcg aagataacta catgaactac | 120 |
| tttggtcatc ccacctcctt ccagcaggga ggtatcaccg cctccatggc cggaggatcc | 180 |
| atgctgtcgt gtgcgtttgc cggctacatt tccgaccggg ttggccgaaa gcccaccatt | 240 |
| caatttgccg ccgcctggtg gatggttggc gcctccattc aatgctctgc cagaatatg | 300 |
| ggccaactga ttgccggccg ggccattccc gggcttggaa tcggcctcgg ctcgtcccag | 360 |
| atccccgtct tcatctccga gttgtccccc aagaagatcc gaggccggct cgtcggctgc | 420 |
| ttccaatggt ccgttaccctg gggtattctc atcatgttct acatttcgtt cggctgctca | 480 |

```
tacatcaagg gccactcgtc cttccgactg gcgtggggca tccagctgat tccaggagcc    540
atgttggcgt tcggaatgat gctgctggac gaatcgccgc gatggctggc gtccaaagac    600
cgctgggaag aggccatcca gatcatccgc tccatcaatg ccaactacgg atccgaggag    660
gacattctca tggaaatcga agatctgcga gaggtggtgc gaatcgacca cgagtccaag    720
tcggtcacca tctgggacct gttccgaaaa gactccatca accgaaccat ggtcggagtg    780
tgggcccaga tctggcaaca actgactgga atgaacatca tgatgtacta cgtggtcatc    840
atcttcaaaa tggccggcta ctcgggcaaa agtgccgtca ttgtctccgg ctccatccag    900
tacatcatca acgtggtcat gaccatcccg gcgctgcttt tcattgataa aatcggacga    960
agacccctgc tcctctgtgg aagcatgctc atggccacct ggctgctagc tgtcggagga   1020
atgctaggag cctacggaat ccaaatgccc aaggtctac cggcagtacc ctccaaaaac   1080
caggcagcgg acccctacac caccatctac attcccgaca accaggcgcc ggcccgaaag   1140
gccattatcg cctgttgcta tctgtttgtc gcctcttttg cacccacctg ggcccccggc   1200
atctggctct actgctccga gatcttcccc aacaaacaac gagcgctggc caactcgctg   1260
accgccggcg ccaactgggg cttcaacttt gccctggccc tgtttgtgcc caccgccttc   1320
aagaacatca actggaaggt gtacatcatc ttcggtgtct tctgcatcgt catgtccatc   1380
cacgtcttcc tgctcttccc cgaaaccaag ggcaagagtc tggaggtgat tgaccagatg   1440
tgggacgccc gcgtgcccgc ttggaaaacc gcctcctggg tccccgacca catgccttct   1500
cattacgcag gggaccagga ggaaaagccc accgacgaac tggccgaggc gccgtttcac   1560
gaggagaatg ccccggtgaa caccgagacc cctcctcatg aggatgagcc cacttttgcg   1620
gagaccgagc caagaccca gtatcctgga actgagcatg tctaa                    1665

<210> SEQ ID NO 26
<211> LENGTH: 1599
<212> TYPE: DNA
<213> ORGANISM: Yarrowia lipolytica

<400> SEQUENCE: 26 atgtttcgt taacgggcaa accgctgctc tattttacgt cagtgttcgt ctctctgggc     60
gtgttcctgt ttggatacga ccagggagtc atgtccggca tcatcacggg cttctacttc    120
aaggagtact tccatgagcc cacccgagcc gaaatcggaa ccatggtgtc gattcttgag    180
gtcggagcgt ttgtctcgtc gctcatggtc ggccgaatcg gtgacattat tggccgacga    240
aaaaccatca tgtacggtgc cttcatcttc atcatcggag gtgccttcca gacatttgcc    300
gtcagcatgt ccgagatgat tttgggccga gtagtggccg gtttcggcgt tggtatgctg    360
tcgaccattg tgccagtcta tcagtctgag atctcgcctc ctcacaaccg aggcaagctc    420
gcgtgcatcg agttcacggg aaacattgtg ggctatgcca gctcagtgtg ggtggactac    480
ttctgcagtt tcatcaattc caacatgagc tggcgtatcc cactgttttct gcagtgtgct    540 atgggcgctc ttttgtttgg aggctcgttc ctaattgccg agactcctcg atggttgctg    600
gataacgacc atgacgagga gggattggtt gtcctggcca acctgcatgg aggaggagac    660
attgactctc ctctggctaa gcaggaatat cgggagatta agcagtccgt tttgatccac    720
cggctcgagg gcgagcgatc atataccgac atgtggaaga agtacaagaa gcgagtgctg    780
attgccatgt cgtcgcagat gtttgcccag ctcaacggta tcaacgtcat ctcttactac    840
gctcctctgg tgtttgaaga ggcaggatgg gtcggacggt ctgctattct catgaccggt    900
```

```
atcaacggta tcgtctacgt gtgttccact attccccgt ggtacctcgt ggacaaatgg      960
ggccgaagac ctattcttct gtccggtgca gtaattatgg ctatttccct ggcgtctgtg     1020
gcgttctgga tgcgtctaga cttgcacat acaccggctc tggtggtgat ttccgtcgtc     1080
atcttcaacg ctgcttttgg atactcgtgg ggcccattc cctggctcta tccccctgag      1140
attatgcctc ttaccatccg agccaaggga gcttctctgt caaccgccac caactgggcc     1200
tttaactggc tggtgggata tatgaccccc attctccagg agaccatcaa gtggcgactg     1260
tatttgatgc atgccgcctt ctgtagtctt tcgtttgttc tcgtctactt cacctacccg     1320
gagacctcgg gaatcaactt ggaagacatg gactcgttgt tcggcgacaa gtctgttgtg     1380 aacaccccg actcgcggtc tttgcttggt gatcgagaca ctccagagcc tgacgtgcct      1440
cacagttata ctgatgctgc caccgatcga ctgcctgctg gtatgcaggg ctatggctcc     1500
gctcccagct cgagaggagg cagtgtggtc ggaagtcccc gacgaggaaa cagtgtggtt     1560
gggtctccca agcgggactt ccctcaacct ccggtataa                            1599

<210> SEQ ID NO 27
<211> LENGTH: 1548
<212> TYPE: DNA
<213> ORGANISM: Yarrowia lipolytica

<400> SEQUENCE: 27
atgggactcg ctaacatcat caaccgtgga gaaaagcccg agggctcggc cttcatggcg       60
gcctttgtgg ccgtgtttgt cgcgtttgga ggtattctgt ttggatacga cactggaacc      120
atttccggcg tcatggccat gccattcgtc aagaagacct ttacagatga cggcctggag      180
ttcacttctg agcagacctc gctcatcact tccattcttt ctgcaggcac cttcactgga      240
gccatttctg ctccctgggc ctctgatact ctgggaagac gactgggtct gatcctcttc      300
tgtgtcgtct tctctgttgg cgctattctt cagactgctg ccaccggccg aacgcttttg      360
attgtcggac gagttgttgc tggtcttggt gttggtggag tctcttccat cgttcctctt      420
taccagtctg aggttgcccc caagtggatc cgaggtgccg ttgtctccat ctaccagttt      480
gccatcacca ttggtcttct gctggctgcc attgtcaaca acgcaaccaa aaacaaagac      540
aacagtgctt cctaccgaat tcctctcggc cttcagcttc tgtgggccgt catcctgagt      600
ggaggtctca tcctgctacc ggagactcct cgattctgga tcaagaaggg cgagtacgac      660
aaggccgccg attccctgcg acgactacga cgacttcctg ttgagcacga ggctgtacag      720
aaggagctcc tggagatcca atcttctcac gaccacgaga tgcagatcgg tagcgccacc      780
tgggccgcct gcttctcccc caaggggtcc cagctgaagc gaatgctgac cggtattgcc      840
attcaggccc tgcagcagct caccggtatc aacttcatct tctactacgg aaccgagttc      900
ttcaagaagt ccaacatctc caaccccttc ctcatccaga tgatcaccaa cattgtcaac      960
gtggttatga ccatcccgg tatcatgttt gttgatcgag tcggacgacg aaagctgctg     1020
ttgatcggag ctatcgtcat gtgctcttcc gagtttatcg tggcggctgt tggtactgcc     1080
attgataacg agacctcctc aaaggttctg attgccttca cttgtacctt cattgccggt     1140
ttcgccgcca cctgggggtcc tattgcctgg ttgtcattg gagagatttt ccctctacga     1200
atccgagcca agggtgttgc tctatgcgcc gcctccaact ggcttttcaa cttttgccatt    1260 gcctttgcaa cccctacct cgtcgacgag gcccctggat cggccggtct caagaccaag     1320
gtcttcttca tctggggagg ctgcaacttc ctgtgcatcg ccttcactta cttcttcatc     1380
tacgagacca agggtcttac tctggaggag gtggaccaga tgtacgccga gatcaagatt     1440
```

```
gcttctcgat cccaccagtt tgtgcctacc actcgagtcg ctgcttacga cgagcacgct      1500
tctgacgaca agaaggacgg acagcacgtc tacattgagt ctgtctag                  1548

<210> SEQ ID NO 28
<211> LENGTH: 1485
<212> TYPE: DNA
<213> ORGANISM: Yarrowia lipolytica

<400> SEQUENCE: 28
atggccatta ttgtggctgt atttgtggct tttggaggac ttctctacgg ctacgacaca       60
ggaactattg ctggaatcat gaccatgggc tatgtgaaag aacactttac agactttggg      120
aagaacgact tcacctcggg ccaatcatct ctcaccacat ctatcctatc tgtgggcaca      180
tttaccggag ccatcgttgc tcccttagct gctgacacgg ctggtcgacg tctgggtctt      240
ctgttgtatt gtcttgtatt ctctgtgggt gctattttgc agaccgtcac aaccggaaga      300
gtcttgctaa ttgtgggacg ggtgattgct ggtcttggtg tgggaggtat ctcgtccatt      360
gtgcctctct atcagtcaga agtgtctccc aaatggatca gaggggccgt tgtttctgtc      420
taccagtttg ccatcactgt gggtcttcta ctggcagcta ttgtcaacaa tgccactaag      480
gaccgtccaa atacgtcatc ataccgtatc cctcttggta ttcaactcat ttgggctctt      540
attctttcag caggacttgt gtttcttcct gagactcctc gtttctgggt caagaagaac      600
cggccagaga agccgccga agcactctca cggctaagaa ggctaccaac agactcgaaa      660
ccggtaaaaa aggaactgct tgaactacag aagtcgttcg aaatggaaat ggaggttgga      720
aactcctcct ggaaggcttg tttcagtcca catggatcac agctcaaaag actgctgaca      780
ggagtctcaa tccaggctct gcaacaacta acaggcatca atttcatatt ctactatgga      840
accaactttt tcaaaacagc tggcataaaa gatccctttg tggtgtccat gatcacctct      900
gccgtcaatg tggccttcac ccttccgggt attctgtttg tcgacaaagt gggccgaaga      960
aagctgctct tgattggagc cgtggtaatg tgtgtttcag aattaattgt ggcagctgta     1020
ggagcagctc tggatagcca ggtgtcttcc aaggtcctta ttgccttcac ttgtacgttc     1080
atcgcaggct ttgcatccac ctggggacct atagcctggg tggttgttgc ggagattttc     1140
ccgcttcgaa tccgggccaa gggagtggct atcagtgtgg ctgccaactg gattttcaac     1200
tttgccattg cctttgcaac tccgtacttg gtcgacaaga aacctgggtc tgccggtctc     1260
gagtccaagg tgttttttcat ctggggaggt tgcaattttc tagccattgc ctttgtgtac     1320
ttgtttgtct atgaaaccaa agggttgtca ctggagcagg tggacgaaat gtactcggag     1380
gtcaagtacg cctggcagag tgataggttc cagaccgaga tcatgtctgg aaagacggag     1440
gtttcgccgg atcagagctg cgattctgga tttgattcgg attag                     1485

<210> SEQ ID NO 29
<211> LENGTH: 2881
<212> TYPE: DNA
<213> ORGANISM: Cryptococcus neoformans

<400> SEQUENCE: 29
atgcccgatc cctctattcc ggtagtcggt cacaagactc agcgtaggct ggtcggacat       60
aacctactgt acagtgtttc agtgtttctt agcataggag tctggttatt tgggtaggtg      120
ttttgtgaat ccgatggtg ttgtgctgat atgataaccg ttaagatat gaccaggggt       180 aagttcactt caagcgctta tccttaagct tcgctgatca tggccttcaa actgtgaaag      240
```

```
agtaatgtcc ggtaagttgg tatcaccatc acatatctcg atagctagtt gactttctac    300
gtaaggaatt attaccggcc catactttaa gtaggtatga agtaaatact gagtatcttt    360
cattaacatt tatggcacgt gtctacagag cttattgtga gtaaagccct aatcaagcaa    420
actaagctga cgttttagt caaccaacca acgtcaacgc agattggcaa gtaagttagt     480
cattcagtgc cagtagcaat gtctgaacat tcgatagtat ggtggccgtt ttggagattg    540
gtgccttcag taagattatt ccatgtcatg tcattctttc aagaactcac ggcaatcacg    600
cagttacttc tctggctgcc gctcatattg cagataatta tggaaggcgt atgacccttc    660
gcacaggtgc aatagtcttc accattggag gtgctataca gacttttgc gttggatata    720 attccatggt acttggaaga attgtcagcg gctttggggt agggatgttg agtatggtcg    780
tgccaatcta tcaggtatgt ggtttacaat agtaaaggcg cggagcataa gccaatgtgt    840
gtcaccctcg cgcagtccga aatatctcct gcagaccatg taagaaacac ttcaatattt    900
ccagaagatt tttctaataa aacacgatga tagcgaggcc ttttgggctc tgtcgaattc    960
acaggtaata tcattggcta tgcctcctct gttgtacgat gtgtcacctg cctatgtcaa   1020
gcaccatgct cactcaacgt tcatagtgga tcgactatgc ctgttcattc ttccagtctg   1080
actggtcttg gcgcctcccg cttttctgttc aatgtatagg cggctctgtt ctcttcatcg   1140
gcagcttcgt cacaccagag tctccccggt aagccttcta tatgtgcatc atatgtaggt   1200
gcagaactaa gagctgttca aaggtatctt gtcgatacag accaagaggt ggaaggttta   1260
gcagtcatcg ctgattttca agggaaagcg ctggacgata tttcagtgca agccgagtac   1320
aaagaaattc gagatgctgt tctagccgac gtgagacaat cctctcaacg ttatccccat   1380
acacttgctt attctgtttt gtttttttt tactagagag ctgtcggaga tagaagctat   1440
agggctttat ggaggagata caaaggacga gttctgattg caatgagcag tcaattgttt   1500
gctcaactgg tgagtcaatc tttgcaaaag tcaaagaaac atgaaaataa agcggtctgt   1560
actaatgatt attggcagaa tggcatcaat ggtgagctta gagagcgctg caaacaatta   1620
ctaaccattt ggccagtcat ctcatattat gcacgtgcgt cccatctcat tctgccgatc   1680
attcttgaca gctgatgtgg attacagctc ttgtctttga acgttagtct cactgaagac   1740
ctaatactgc cgtgttacta atggtggtga agaggcgggg tggattggac gtgacgctat   1800
ccttatgaca ggtatcaatg ccttatttta tgtggcaagc tcacttccgc cgtaagtcca   1860
ggtccatccg aaattatgca cattctcaaa ttattactag atggtatctc atggatcgag   1920
cgggtcgaag gcccattttg ctctcgggag cagtggccat ggcgattgca ctgacggcta   1980
caggatggtg gatatatatt gatcaagcaa taacacccaa tgctggctcg tcttttgttc   2040
tgccatgtcg gatgaagctg atggtatttg tcgatagtgg tcatttgcgt agtgatttat   2100
aattccgcat ttggcatgag ctggggacct gtcccatggt atgtgtcatt gacatatggc   2160
cggttggaag tgaagttaat taattaattg atcccaggct ttatcctccg gaaatcatgc   2220
cgttgtcatt ccgagcaaag ggagtatcct tatctactgc tacagtacgt ccaatttat    2280 cccgaatgca caacgatggg ctaatttgag ttatcagaac tggatctcag tgggtctgga   2340
gcgctttaat cctgcttttt gctaacgact gttgtatctg cagaattggt gggtaggggt   2400
ttcaacaccg ctctttcaag aacttatcgg atggcgatta tatccgatgc acgcattctt   2460
ttgtgcatta tcattcatcc tcgtgtactt ccgtgagttg tcagccgaga ttcgtaaacc   2520
accactcatg cacatggaac tagtctatcc cgaaacccga ggcgtaccgc ttgaagaaat   2580
ggacaaattg tttggggatg aaagtgatga agacgaggtt gattcggact tcgatgaagt   2640
```

```
tgaggaagcc gaatcagaaa tatcctctct agtcagcaat cctcgacacc gacgccgctc    2700
ggccagctct tcattgggcc catctttgcc gacctcccga aaaccgtcac ccataccctc    2760
tagggaggct tcatctagcc gaggactgtt tggacgtata actgactcgg tgaatggtct    2820
gattggaagc acaaaacagc aaagcaggag cgtggggtat actgctgtca acgaggaata    2880
g                                                                    2881
```

<210> SEQ ID NO 30
<211> LENGTH: 1713
<212> TYPE: DNA
<213> ORGANISM: Saccharomyces cerevisiae

<400> SEQUENCE: 30

```
atgtcacaag acgctgctat tgcagagcaa actcctgtgg agcatctctc tgctgttgac      60
tcagcctccc actcggtttt atctacacca tcaaacaagg ctgaaagaga tgaaataaaa     120
gcttatggtg aaggtgaaga gcacgaacct gtcgttgaaa ttccaaagag accagcttct     180
gcctatgtca ctgtctctat tatgtgtatc atgatcgcct ttggtggttt cgttttcggt     240
tgggatactg gtaccatttc tggtttcatc aatcaaaccg atttcatcag aagatttggt     300
atgaagcata agatggtac taattatttg tctaaggtta gaactggttt gattgtctcc     360
attttcaaca ttggttgtgc cattggtggt attattcttt ccaaattggg tgatatgtac     420
ggtcgtaagg tgggtttgat tgtcgttgtt gtcatctaca tcatcggtat tattattcaa     480
attgcatcta tcaacaaatg gtaccaatat ttcatcggta gaattatttc cggtttgggt     540
gttggtggta ttgccgtttt atctcctatg ttgatttctg aagtatcccc aaagcattta     600
aggggtactt tagtctcttg ctaccaattg atgattactg ccggtatttt cttgggttac     660
tgtaccaact tcggtactaa gaactactcc aactctgtgc aatggagagt tccattaggt     720
ttgtgttttg cctgggcttt gtttatgatt ggtggtatga catttgttcc agagtctcca     780
cgttatttgg ctgaagtcgg taagatcgaa gaagccaaac gttctattgc cgtttctaac     840
aaggttgctg ttgatgatcc atctgttttg gctgaagtcg aagctgtctt ggctggtgta     900
gaggcagaga aattagctgg taatgcatcc tggggtgaat tgtttagtag caagacaaag     960
gtccttcagc gtttgatcat gggtgctatg attcaatctc tacaacaatt gacaggtgat    1020
aactatttct tctactatgg tactactatt ttcaaggctg ttggtttgag tgactctttc    1080
gaaacctcta ttgtcttggg tattgttaac tttgcttcca cctttgttgg tatttacgtt    1140
gttgagagat atggtcgtcg tacttgtttg ctatggggtg ctgcatccat gactgcttgt    1200
atggttgtct atgcttccgt gggtgtcacc agattatggc caaatggtca agaccaacca    1260
tcttccaagg gtgctggtaa ctgtatgatt gtctttgcct gtttctatat tttctgtttt    1320
gctactacat gggctccaat tccttatgtc gttgtttctg aaactttccc attgagagtc    1380
aagtctaagg ctatgtctat tgctacagct gctaattggt tgtggggttt cttgattggt    1440
ttcttcactc catttattac tggtgctatt aacttctact acggttacgt tttcatgggc    1500
tgtttggtct tcatgttctt ctatgttttg ttagttgttc cagaaactaa gggtttgact    1560
ttggaagaag tcaacaccat gtgggaagaa ggtgttctac catggaagtc tgcctcatgg    1620
gttccaccat ccagaagagg tgccaactac gacgctgaag aaatgactca cgatgacaag    1680
ccattgtaca agagaatgtt cagcaccaaa taa                                 1713
```

<210> SEQ ID NO 31

```
<211> LENGTH: 1695
<212> TYPE: DNA
<213> ORGANISM: Saccharomyces cerevisiae

<400> SEQUENCE: 31
atgtctagtg cgcaatcctc tattgatagc gatggagatg ttcgagatgc tgatattcat      60
gtcgcaccac ccgtggaaaa agagtggtca gatggatttg atgacaacga agtcataaac     120
ggggataacg ttgagccacc aaaaagaggg ctcataggtt atcttgtcat ttacttactg     180
tgttatccaa tatcctttgg gggtttcctg cctggttggg atagtggtat cacagcaggt     240
ttcattaaca tggacaactt taaaatgaac ttcggttctt acaagcatag cactggtgaa     300
tattatttga gcaacgtgcg tatgggtctt cttgtggcta tgttcagtat ggatgtgcc      360
ataggtggcc ttattttgc ccgtcttgct gatactttag gtagaaggct ggcaattgtg     420
atcgtggtgt tggtatatat ggttggtgca attattcaga tcagttcaaa tcacaaatgg     480
taccagtact ttgtcggtaa gatcatctac ggtcttggtg ctggtggctg ttcggtgttg     540
tgtccaatgc ttttgtctga aatagccccc acagatttga gaggtggact ggtctcattg     600
taccaactga acatgacgtt cggtattttc ttgggttatt gtagcgttta tggtacgaga     660
aaatacgata acactgcaca atggagagtc ccccttgggc tttgcttttt atgggctttg     720
attatcatca ttggtatgtt attggttcca gagtccccaa gatatctgat tgaatgtgag     780
agacacgaag aggcccgtgc ttccattgcc aaaatcaaca aggtttcacc agaggatcca     840
tgggtactca aacaggctga tgaaatcaac gccggtgtcc ttgcccaaag ggaactagga     900
gaagcttcat ggaagaact tttctctgta aaaactaaag tccttcaacg tttgatcaca     960
ggtattcttg tgcaaacctt tttgcaactt actggtgaaa actacttctt cttctacgga    1020
actaccattt ttaaatcagt cggtcttact gatgggtttg agacgtcgat cgtcctaggt    1080
acagtgaact tcttctccac tattattgct gttatggtcg tagacaaaat tggccgtcgt    1140
aaatgtctgt tatttggtgc agctgggatg atggcttgta tggtcatatt tgcaagtatc    1200
ggggtgaaat gtctttaccc tcatggccag gacggtcctt cttcgaaagg tgcaggtaat    1260
gccatgattg tgttcacttg tttctatata ttctgctttg caacgacatg ggctcctgtt    1320
gcttatattg tggttgccga gtcgttccct tcgaaggtca agtctagagc catgtcgatt    1380
tcaactgcat gcaactggtt atggcaattt ttgatcggtt ttttcacacc attcattact    1440
gggtctatcc acttctatta tggttatgtg ttcgtaggtt gtttggttgc tatgttttg    1500
tacgttttct tcttttacc agaaacgatt ggtctatctt tggaggaaat ccaattacta    1560
tacgaagaag gtataaaacc atggaaatct gcatcttggg tcccaccttc taggagaggt    1620
atttcttccg aagaaagtaa gaccgagaag aaggattgga gaaattttt gaagttctca    1680
aagaattctg attga                                                     1695

<210> SEQ ID NO 32
<211> LENGTH: 1704
<212> TYPE: DNA
<213> ORGANISM: Saccharomyces cerevisiae

<400> SEQUENCE: 32
atgaattcaa ctccagattt aatatctcca caaaagtcaa gtgagaattc gaatgctgac      60
ctgccttcga atagctctca ggtaatgaac atgcctgaag aaaaaggtgt tcaagatgat     120
ttccaagctg aggccgacca agtacttacc aacccaaata caggtaaagg tgcatatgtc     180
actgtgtcta tctgttgtgt tatggttgcc ttcggtggtt tcgttttcgg ttgggatact     240
```

```
ggtaccattt ctggtttcgt cgcccaaact gatttcttga gaagattcgg tatgaagcat    300
aaagatggta gttattattt gtctaaggtt agaactggtt taattgtctc cattttcaac    360
attggttgtg ccattggtgg tattattttg gctaaattgg gtgatatgta cggtcgtaaa    420
atgggtttga ttgtcgttgt tgttatctac atcatcggta ttattattca aattgcatcc    480
atcaacaaat ggtaccaata tttcatcggt agaattattt ccggtttggg tgttggtggt    540
attgccgttt tatctcctat gttgatttct gaagtcgctc taaggaaat  gagaggtact    600 ttagtctcct gttaccaact gatgattacc ttgggtattt tcttgggtta ctgtaccaac    660
ttcggtacta agaactactc caactctgtg caatggagag ttccattagg tttgtgtttt    720
gcctgggctt tgtttatgat cggtggtatg actttcgttc agaatcccc  acgttatttg    780 gttgaagctg gtcaaattga cgaagcaaga gcatctcttt ccaaagttaa caaggttgcc    840
ccagaccatc cattcattca acaagagttg gaagttattg aagctagtgt tgaagaagct    900
agagctgctg gttcagcatc atggggtgag ttgttcactg gtaagccggc catgtttaag    960
cgtactatga tgggtatcat gatccaatct ctacaacaat tgactggtga taactatttc   1020
ttctactatg gtactaccgt ttttaacgct gttggtatga gtgattcttt cgaaacttct   1080
attgttttcg gtgtcgtcaa cttcttctct acttgttgtt ctttgtacac tgtcgatcgt   1140
tttggacgtc gtaactgttt gttatatggt gccattggta tggtctgctg ttatgtagtt   1200
tacgcttctg ttggtgtcac cagactatgg ccaaatggtg aaggtaatgg ttcatccaag   1260
ggtgctggta actgtatgat tgtctttgcc tgtttctata ttttctgttt tgctaccact   1320
tgggctccaa ttgcttatgt tgttatttct gaaactttcc cattgagagt caagtctaag   1380
gctatgtcta ttgctacagc tgctaattgg ttgtgggggtt tcttgattgg tttcttcact   1440
ccatttatta ctggtgctat taacttctac tacggttacg ttttcatggg ctgtatggtt   1500
ttcgcctact tctacgtttt cttctttgtg ccagaaacta aggggtttgac tttggaagaa   1560 gtcaatgata tgtacgctga aggtgttcta ccatggaagt ctgcttcatg ggttccaaca   1620
tctcaaagag gtgctaacta cgatgctgat gcattgatgc atgatgacca gccattctac   1680
aagaaaatgt tcggcaagaa ataa                                           1704

<210> SEQ ID NO 33
<211> LENGTH: 1713
<212> TYPE: DNA
<213> ORGANISM: Saccharomyces cerevisiae

<400> SEQUENCE: 33
atgaattcaa ctcccgatct aatatctcct cagaaatcca attcatccaa ctcatatgaa     60
ttggaatctg gtcgttcaaa ggccatgaat actccagaag gtaaaaatga agttttcac    120 gacaacttaa gtgaaagtca agtgcaaccc gccgttgccc ctccaaacac cggaaaaggt    180
gtctacgtaa cggtttctat ctgttgtgtt atggttgctt tcggtggttt catatttgga    240
tgggatactg gtaccatttc tggttttgtt gctcaaactg attttctaag aagatttggt    300
atgaagcacc acgacggtag tcattacttg tccaaggtga aactggtttt aattgtctct    360
atttttaaca ttggttgtgc cattggtggt atcgtcttag ccaagctagg tgatatgtat    420
ggtcgtagaa tcggtttgat tgtcgttgta gtaatctaca ctatcggtat cattattcaa    480
atagcctcga tcaacaagtg gtaccaatat ttcattggta gaattatctc tggtttaggt    540
gtcggtggta tcacagtttt atctcccatg ctaatatctg aggtcgcccc cagtgaaatg    600
```

```
agaggcacct tggtttcatg ttaccaagtc atgattactt taggtatttt cttaggttac      660
tgtaccaatt ttggtaccaa gaattactca aactctgtcc aatggagagt tccattaggt      720
ttgtgtttcg cctgggcctt atttatgatt ggtggtatga tgtttgttcc tgaatctcca      780
cgttatttgg ttgaagctgg cagaatcgac gaagccaggg cttctttagc taaagttaac      840
aaatgcccac ctgaccatcc atacattcaa tatgagttgg aaactatcga agccagtgtc      900
gaagaaatga gagccgctgg tactgcatct tggggcgaat tattcactgg taaaccagcc      960
atgtttcaac gtactatgat gggtatcatg attcaatctc tacaacaatt aactggtgat     1020
aactatttct tctactacgg taccattgtt ttccaggctg tcggtttaag tgactctttt     1080
gaaacttcta ttgtctttgg tgtcgtcaac ttcttctcca cttgttgttc tctgtacacc     1140
gttgaccgtt ttggccgtcg taactgtttg atgtggggtg ctgtcggtat ggtctgctgt     1200
tatgttgtct atgcctctgt tggtgttacc agattatggc aaacggtca agatcaacca      1260 tcttcaaagg gtgctggtaa ctgtatgatt gttttcgcat gttttctacat tttctgtttc     1320 gctactacct gggccccaat tgcttacgtt gttatttcag aatgtttccc attaagagtc     1380
aaatccaagt gtatgtctat tgccagtgct gctaactgga tctggggttt cttgattagt     1440
ttcttcaccc catttattac tggtgccatc aacttctact acgttacgt tttcatgggc      1500 tgtatggttt tcgcttactt ttacgtcttt ttcttcgttc cagaaactaa aggtttatca     1560
ttagaagaag ttaatgatat gtacgccgaa ggtgttctac catggaaatc agcttcctgg     1620
gttccagtat ccaagagagg cgctgactac aacgctgatg acctaatgca tgatgaccaa     1680 ccatttttaca agagtttgtt tagcaggaaa taa                                 1713
```

<210> SEQ ID NO 34  
<211> LENGTH: 1644  
<212> TYPE: DNA  
<213> ORGANISM: Debaryomyces hansenii

<400> SEQUENCE: 34

```
atgggttacg aagataaatt agtggctcct gctttaaagt ttagaaactt tttggacaag       60
actccaaata tctataatgt ttttgttatt gctctgattt catgtatctc cggggttgatg     120 tttggtattg atatctcatc tatgtcttta tttattgggg atgacaaata cattaaatac      180
ttccataaac ctagcacaac catgcaatcg tttattactt cggctatgtc tttgggttca      240
ttttttggat caatatgttc ttcttttgtg tccgaaccat ttggcagaag atcatcgtta      300
atggtatgtg ggttttctg gtgtgttggt gctgctattc aatcatctgc tcaaaatcaa       360
gcgcaattga ttatcggccg ttttatttct ggttttggtg ttggtttcgg ttcatcagtt      420
gctccagttt atggatctga attagctcct agaaagatca gaggtttaat tggggggtctt    480 tttcaattct ctgtcacttt gggtatctta atcatgttct atatctgtta tggtttgaat      540
tttattaacg gtgtcgcatc cttcagagtt gcttggggtt tacaaatcat accaggttta     600
gttttgatcc ttggttgttt ctttattcca gaatctccta gatggttagc taaacaaggt     660
tactgggaag atgctgaata tgttgttgcc aagatccaag ctaagggtaa cagagaagat    720
ccagatgttt taattgaaat gtctgaaatt aaggaacaaa ttatgttaga tgaacacatc    780
aaggctttca catatgctga tttgttcact aagaagtata tattgagaac tgttactgct    840
tgttgggctc aagctggca acaattaacc ggtatgaata ctttgatgta ttatattgtt     900 tatgtttttcc aaatggccgg ttacgaaggt gatgctaatt tggttgctag ttccattcaa    960
tactgtctta acactggtat gaccattccc gcattatact tcatggataa gcttggtaga   1020
```

```
agaccagttt tattaactgg ggctgcattc atgatggctt ggcaattcgc cgttggtgga    1080
ttattggcaa cttacagtgt tgataaccct atcagtgaaa ccgtcagaat tcaaattcca    1140
gaagaacatg gcaaggccgc caaagctgtc attgcttgct gttatttatt cgttgtttct    1200
ttcgcttgta gttggggtgt ttgtatttgg gtttactgtg ctgaagtctg ggtgatagt     1260 gcttcaagac aaagaggtgc tgctcttacc acttctgtta attggatttt caatttcgcc    1320
attgctatgt tcactccaag tgctttcaag aacattactt ggaagactta catggtcttc    1380
gctacattct gtggttgtat gtttatccat gtcttcttct tcttcccaga aactaagggt    1440
aagagattgg aagaaattgg tcaaatgtgg gccgaaggtg taccagcttg gaagtctgct    1500
tcttggcaac catctattcc aatcgtgtcc gataatgaat tacataacaa gatgaagatt    1560
gaccataatg aagataactt attaaattct tcttcacatt ctgaagtatc ccaagagaag    1620
ggcgatactt ctcacatgac ttaa                                           1644

<210> SEQ ID NO 35
<211> LENGTH: 1638
<212> TYPE: DNA
<213> ORGANISM: Debaryomyces hansenii

<400> SEQUENCE: 35
atgggatatg aagaaaagtt ggtcgcacca gctctaaaac taagattatt cttagataaa      60
cttccaaaca tttataatat ttatgtcatt gctactattt cgtgtatttc ggggttgatg     120
ttcggtatcg acatttcatc gatgtcggcg ttccttagta atgacgctta ccttaaaatat   180 tttggtaccc ctgaacctga tatgcaagga ttcattactg ctgctatgtc tcttgggtca    240
ttctttgggt ctcttgcatc ggcattttgt tcagagccat tggtagaag agcttcattg     300 ttgctttgtg gattcttttg gtctgttggg gctgcaattc aatcttcatc acagaatgtc    360
gcccagttaa ttattggtcg ttttatttct ggttttggaa ttggtttcgg ctcatctgtg    420
gcacccgtgt atggatcaga gttggcacct agaaaaatta gagggttaat tggtggtctt    480
ttccaacttt cagttacctt aggtattttg attatgttct atatctgtta cgggttaggt    540
aaaatccaag ccgtcggctc attcagaact gcgtggggtt tgcaaattat cccaggattg    600
atcttaatac ttggatgttt ctttattcca gaatcaccta gatggttagc caaacagaac    660
tactgggaag aggcggagga cattgtcgct agagtccaag ctaaaggtaa cagagaagac    720
cctgaagtat taattgaaat ggctgaaatt agagaccaga ttctgacgtt agacaaagtt    780
aagtctttta cttatattga tttattcaaa agaagtatc ttcttagaac tgtaacggca     840
atatttgctc aaatttggca acaattaaca ggtatgaaca ccttaatgta ttatattgtc    900
tatgttttcg aaatggctgg ttatcatggt gatgcaaatt tggttgcctc ttcaattcaa    960
tattgtatca attttgccat gactattcct gcattgtact aatggataa ggtcggtagg     1020 agaccagtgt tgttaactgg agctgcgctc atgatggcct ggcaatttgc tatagggggc    1080
ttgcttgcca cttatgctga acccaccgat atttttgggg gtaataatac cgttaaaatc    1140
agtatcccag aagatgaatc tcctgccgcc aaggctgtta ttgcatgttg ttacttattc    1200
gttgtttcat ttgcgtctac ttggggtgtt ggtatctggg tttactgtgc tgaagtctgg    1260
ggtgatagtg cctcaagaca aagaggtgcg tgtgttgcaa ctgctggtaa ttggatttt    1320 aatttcgcaa ttgcaatgtt cactccgcac gctttcagta ctattacttg gaaaacatac    1380
atgatttttg ctactttctg tgcatgtatg tttcttcatg ttttcttctt tttccctgaa    1440
```

```
actaagggta aaagattgga agaaattggt caaatgtggg acgagcatgt tccagcttgg    1500
aagtctgctt cgtggcaacc acacgtacca ctcgtttcag ataatgaaat acacgggaag    1560
atggattctg cgcatgatga acattcatct cgttcggagt ctactggaga aaaggtggtc    1620
gcagatcaca ttgcttga                                                  1638
```

<210> SEQ ID NO 36
<211> LENGTH: 1638
<212> TYPE: DNA
<213> ORGANISM: Debaryomyces hansenii

<400> SEQUENCE: 36

```
atgggatacg aagataaatt actagggcca gccttaaagt ttagaaactt cttggacaaa      60
tttccgaaca tccataatgt ctatattgtt gttggtatttt cttgtatatc tggtatgatg    120
tttggcattg atatttcttc aatgtcttta ttcattggag atgataaata tttagactat    180
ttcaattcac cagattctac acttcaaggg tttattacag catccatgtc tttagggtct    240
ttctttgggg ccttatttc cgcatttata tcagaacctt tcggtagaag aatgtcgttg    300
atgttctgtg catttttttg gtgtgttgga gctgccattc aatcatcgtc acagaacgtc    360
gtccagttaa ttataggtcg ttttatttct ggttttggtg ttggatttgg atcctcagta    420
gccccagttt atggtacaga attggcacca agaaaaataa gaggattaat tggtggatta    480
tttcagcttt cggtcacttt gggaattttg gttatgttct atgtttgtta tgcattacat    540
tatatcaatg gtgtggcttc tttagatta tcttgggggt tacaaatagt tcctggtctt    600
cttttgttca ttggctgttt tttcatccct gaatcaccta gatggttagc aaagcaaggc    660
tgttgggagg aggctgaata cattgtggca atgattcagg ccaaaggcaa tagggaagat    720
cccgatgtca tgattgagat tactgagatc aaagatcaaa ttttgacaga ggaaaatatt    780
aaggctttca cttatgcaga tttattcaag cgcaaatatc tccttagaac tgtcaccgca    840
acatttgctc aaatatggca acaattaacg ggtatgaata cattaatgta ttatattgtt    900
tatgtttttg atatggctgg ctatcagggc gatgcaaatt taattgcatc ttcaattcaa    960
tacgttcttt ttttcgttat gactgcccct tcattatatt taatggataa acttggtaga   1020
aggcccattt tgttaagcgg tgctgcattc atgatgatat ggcaattcgc agtcggtggt   1080
ttgctttcca cttatgctga gcccaccaat gatgttggtg aaatgatac tgtcagatta   1140 aggatcccag ctgataactc aaccgctgcc aagggtgtaa ttgcatgttg ctatttgttt   1200
gttgtatcat ttgcatatag ttggggtgtt tgtatctgga tgtattgtgc tgaagtttgg   1260
ggtgatagcg cctcaagaca aagaggggcc tgttttacaa cttcagctaa ttggattttt   1320
aacttcgcga tcgcaatgtt tacccctctc tgcgttcaaaa acattacttg gaaaacatac   1380 atgattttttg ctacgttctg cggttgtatg ttccttcacg tattttttctt tttcccagaa   1440 actaaaggta aaagattgga ggaaattggc caaatgtggg atgaaggaat tccagcatgg   1500
agaacagccg catgggagcc atctattcca ttccttatctg ataatgactt gcgtgaaaag   1560
ctagaagtaa aacacgtcga agattcaaac tccagtaatt cggatgctga aaagcctagt   1620
gctgtccata ttgcttag                                                 1638
```

<210> SEQ ID NO 37
<211> LENGTH: 1851
<212> TYPE: DNA
<213> ORGANISM: Saccharomyces cerevisiae

<400> SEQUENCE: 37

```
atgaaaaata tcatttcatt ggtaagcaag aagaaggctg cctcaaaaaa tgaggataaa      60
aacatttctg agtcttcaag agatattgta aaccaacagg aggttttcaa tactgaagat     120
tttgaagaag ggaaaaagga tagtgccttt gagctagacc acttagagtt caccaccaat     180
tcagcccagt taggagattc tgacgaagat aacgagaatg tgattaatga gatgaacgct     240
actgatgatg caaatgaagc taacagcgag gaaaaaagca tgactttgaa gcaggcgttg     300
ctaaaatatc caaaagcagc cctgtggtcc atattagtgt ctactaccct ggttatggaa     360
ggttatgata ccgcactact gagcgcactg tatgccctgc cagttttttca gagaaaattc     420 ggtactttga acggggaggg ttcttacgaa attacttccc aatggcagat tggttttaaac    480 atgtgtgtcc tttgtggtga gatgattggt ttgcaaatca cgacttatat ggttgaattt     540
atggggaatc gttatacgat gattacagca cttggtttgt taactgctta tatctttatc     600
ctctactact gtaaaagttt agctatgatt gctgtgggac aaattctctc agctatacca     660
tggggttgtt tccaaagttt ggctgttact tatgcttcgg aagtttgccc tttagcatta     720
agatattaca tgaccagtta ctccaacatt tgttggttat ttggtcaaat cttcgcctct     780
ggtattatga aaaactcaca agagaattta gggaactccg acttgggcta taaattgcca     840
tttgctttac aatggatttg gcctgctcct ttaatgatcg gtatctttttt cgctcctgag     900 tcgccctggt ggttggtgag aaaggatagg gtcgctgagg caagaaaatc tttaagcaga     960
attttgagtg gtaaaggcgc cgagaaggac attcaagttg atcttacttt aaagcagatt    1020
gaattgacta ttgaaaaaga aagactttta gcatctaaat caggatcatt ctttaattgt    1080
ttcaagggag ttaatggaag aagaacgaga cttgcatgtt taacttgggt agctcaaaat    1140
agtagcggtg ccgttttact tggttactcg acatattttt ttgaaagagc aggtatggcc    1200
accgacaagg cgtttacttt ttctctaatt cagtactgtc ttgggttagc gggtacactt    1260
tgctcctggg taatatctgg ccgtgttggt agatggacaa tactgaccta tggtcttgca    1320
tttcaaatgg tctgcttatt tattattggt ggaatggggt ttggttctgg aagcagcgct    1380
agtaatggtg ccggtggttt attgctggct ttatcattct tttacaatgc tggtatcggt    1440
gcagttgttt actgtatcgt tgctgaaatt ccatcagcgg agttgagaac taagactata    1500
gtgctggccc gtatttgcta caatctcatg gccgttatta acgctatatt aacgccctat    1560
atgctaaacg tgagcgattg gaactggggt gccaaaactg gtctatactg gggtggtttc    1620
acagcagtca ctttagcttg ggtcatcatc gatctgcctg agacaactgg tagaaccttc    1680
agtgaaatta tgaactttt caaccaaggg gttcctgcca gaaaatttgc atctactgtg    1740
gttgatccat tcggaaaggg aaaaactcaa catgattcgc tagctgatga gagtatcagt    1800
cagtcctcaa gcataaaaca gcgagaatta aatgcagctg ataaatgtta a             1851
```

<210> SEQ ID NO 38
<211> LENGTH: 1710
<212> TYPE: DNA
<213> ORGANISM: Saccharomyces cerevisiae

<400> SEQUENCE: 38

```
atgaaggatt taaaattatc gaatttcaaa ggcaaattta taagcagaac cagtcactgg      60
ggacttacgg gtaagaagtt gcggtatttc atcactatcg catctatgac gggcttctcc     120
ctgtttggat acgaccaagg gttgatggca agtctaatta ctggtaaaca gttcaactat     180
gaatttccag caaccaaaga aaatggcgat catgacagac acgcaactgt agtgcagggc     240
```

```
gctacaacct cctgttatga attaggttgt ttcgcaggtt ctctattcgt tatgttctgc    300
ggtgaaagaa ttggtagaaa accattaatc ctgatgggtt ccgtaataac catcattggt    360
gccgttattt ctacatgcgc atttcgtggt tactgggcat taggccagtt tatcatcgga    420
agagtcgtca ccggtgttgg aacagggttg aatacatcta ctattcccgt ttggcaatca    480
gaaatgtcaa aagctgaaaa tagagggttg ctggtcaatt tagaaggttc cacaattgct    540
tttggtacta tgattgctta ttggattgat tttgggttgt cttataccaa cagttctgtt    600
cagtggagat tccccgtgtc aatgcaaatc gttttttgctc tcttcctgct tgctttcatg    660
attaaactac ctgaatcgcc acgttggctg atttctcaaa gtcgaacaga agaagctcgc    720
tacttggtag gaacactaga cgacgcggat ccaaatgatg aggaagttat aacagaagtt    780
gctatgcttc acgatgctgt taacaggacc aaacacgaga acattcact gtcaagtttg    840 ttctccagag gcaggtccca aaatcttcag agggctttga ttgcagcttc aacgcaattt    900
ttccagcaat ttactggttg taacgctgcc atatactact ctactgtatt attcaacaaa    960
acaattaaat tagactatag attatcaatg atcataggtg gggtcttcgc aacaatctac   1020
gccttatcta ctattggttc atttttttcta attgaaaagc taggtagacg taagctgttt   1080
ttattaggtg ccacaggtca agcagtttca ttcacaatta catttgcatg cttggtcaaa   1140
gaaaataaag aaaacgcaag aggtgctgcc gtcggcttat ttttgttcat tacattcttt   1200
ggtttgtctt tgctatcatt accatggata tacccaccag aaattgcatc aatgaaagtt   1260
cgtgcatcaa caaacgcttt ctccacatgt actaattggt tgtgtaactt tgcggttgtc   1320
atgttcaccc caatatttat tggacagtcc ggttggggtt gctacttatt ttttgctgtt   1380
atgaattatt tatacattcc agttatcttc tttttctacc ctgaaaccgc cggaagaagt   1440
ttggaggaaa tcgacatcat ctttgctaaa gcatacgagg atggcactca accatggaga   1500
gttgctaacc atttgcccaa gttatcccta caagaagtcg aagatcatgc caatgcattg   1560
ggctcttatg acgacgaaat ggaaaaagag gactttggtg aagatagagt agaagacacc   1620
tataaccaaa ttaacggcga taattcgtct agttcttcaa acatcaaaaa tgaagataca   1680
gtgaacgata aagcaaattt tgagggttga                                     1710

<210> SEQ ID NO 39
<211> LENGTH: 1626
<212> TYPE: DNA
<213> ORGANISM: Saccharomyces cerevisiae

<400> SEQUENCE: 39
atgtctgaat tcgctactag ccgcgttgaa agtggctctc aacaaacttc tatccactct     60
actccgatag tgcagaaatt agagacggat gaatctccta ttcaaaccaa atctgaatac    120
actaacgctg aactcccagc aaagccaatc gccgcatatt ggactgttat ctgtttatgt    180
ctaatgattg catttggtgg gtttgtcttt ggttgggata ctggtaccat ctctggtttt    240
gttaatcaaa ccgatttcaa aagaagattt ggtcaaatga atctgatgg tacctattat    300 ctttcggacg tccggactgg tttgatcgtt ggtatcttca atattggttg tgcctttggt    360
gggttaacct aggacgtct gggtgatatg tatggacgta gaattggttt gatgtgcgtc    420
gttctggtat acatcgttgg tattgtgatt caaattgctt ctagtgacaa atggtaccaa    480
tatttcattg gtagaattat ctctggtatg gtgtcggtg tattgctgt cctatctcca    540 actttgattt ccgaaacagc accaaaacac attagaggta cctgtgtttc tttctatcag    600
ttaatgatca ctctaggtat tttcttaggt tactgtacca actatggtac taaagactac    660
```

```
tccaattcag ttcaatggag agtgcctttg ggtttgaact ttgccttcgc tattttcatg    720
atcgctggta tgctaatggt tccagaatct ccaagattct tagtcgaaaa aggcagatac    780
gaagacgcta acgttctttt ggcaaaatct aacaaagtca ccattgaaga tccaagtatt    840
gttgctgaaa tggatacaat tatggccaac gttgaaactg aaagattagc cggtaacgct    900
tcttggggtg agttattctc caacaaaggt gctattttac ctcgtgtgat tatgggtatt    960
atgattcaat ccttacaaca attaactggt aacaattact tcttctatta tggtactact   1020
attttcaacg ccgtcggtat gaaagattct ttccaaactt ccatcgtttt aggtatagtc   1080
aacttcgcat ccactttcgt ggccttatac actgttgata aatttggtcg tcgtaagtgt   1140
ctattgggtg gttctgcttc catggccatt tgttttgtta tcttctctac tgtcggtgtc   1200
acaagcttat atccaaatgg taaagatcaa ccatcttcca aggctgccgg taacgtcatg   1260
attgtcttta cctgtttatt cattttcttc ttcgctatta gttgggcccc aattgcctac   1320
gttattgttg ccgaatccta tcctttgcgt gtcaaaaatc gtgctatggc tattgctgtt   1380
ggtgccaact ggatttgggg tttcttgatt ggtttcttca ctcccttcat tacaagtgca   1440
attggatttt catacgggta tgtcttcatg ggctgtttgg tattttcatt cttctacgtg   1500
tttttctttg tctgtgaaac caagggctta acattagagg aagttaatga aatgtatgtt   1560
gaaggtgtca aaccatggaa atctggtagc tggatctcaa aagaaaaaag agtttccgag   1620
gaataa                                                              1626

<210> SEQ ID NO 40
<211> LENGTH: 1710
<212> TYPE: DNA
<213> ORGANISM: Saccharomyces cerevisiae

<400> SEQUENCE: 40
atgactgatc gtaaaaccaa cttgccagaa gaaccgattt tcgaagaggc agaagatgat     60
ggctgccctt cgatagaaaa ttcttcacat ctgtcagtac ctacagtgga ggaaaacaag    120
gacttttccg agtataatgg ggaagaggca gaggaagttg ttgttccaga aaagcctgct    180
tcagcctatg ctactgtttc tatcatgtgt ttatgtatgg ctttcggtgg atttatgtcc    240
ggttgggaca caggtacgat ttctggtttc gtcaatcaga ctgattttttt aagaagattt    300
ggtaattata gccattccaa gaacacttac tacttatcta atgtgagaac tgggttgatt    360
gtgtccatct tcaatgtggg aagcgccatt ggctgtcttt tcttgtctaa attgggtgat    420
atttacggcc gctgcatggg tttgattata gttattgtcg tttatatggt tggtattgtc    480
attcaaattg cctctatagg taagtggtat cagtatttta ttggaagaat tatcgctggt    540
ataggtgctg gttccattag tgttcttgcc ccgatgctta tttcggaaac tgcgccaaag    600
catatcagag gtacgttgct agcttgttgg caattgatgg tgactttcgc aattttcttg    660
ggttattgta ccaattatgg taccaagact tactcgaatt ctgtccagtg gcgtgttccg    720
cttggtctat gttttgcatg ggctattatt atgattggtg gtatgacgtt tgttccggaa    780
tctcctcggt ttttggtgca agtcggtaag attgagcaag ctaaagcttc ttttgccaag    840
tcgaacaagc ttagtgttga cgatcctgct gtggttgcag agattgatct tcttgttgct    900
ggtgtggagg cagaagaagc aatgggaact gcttcatgga aggaattatt tcgagaaag    960
actaaagttt ttcaacgttt aacgatgaca gtcatgatta actctctgca gcaactaacc   1020
ggtgacaact atttcttcta ctacggtact actatcttca aatctgtcgg tatgaatgac   1080
```

```
tcttttgaga cttcaattgt cttgggtatt gtgaattttg cttcttgctt cttttcactt      1140
tattctgttg ataagttggg ccgtcgtaga tgtcttttac ttggagcagc caccatgacg      1200
gcgtgcatgg ttatttacgc ctccgttggc gtcacaagac tatatccgaa cggtaaaagt      1260
gaaccatcat ctaaaggtgc tggtaattgt acgattgttt tcacgtgttt ttacattttc      1320
tgcttttcct gcacctgggg acctgtatgt tatgtgatta tttctgaaac atttccatta      1380
agggtgagat ccaagtgtat gtccgttgca acagcggcca acttattgtg ggggttccta      1440
atcgggtttt tcactccttt tattacttcg gcaattaatt tctactacgg ttacgttttc      1500
atgggttgct tagcgttttc atattttac gtcttttct ttgttccaga aacaaaaggt      1560
ctaactttag aagaagttga tgagatgtgg atggacggtg tattaccttg gaaatctgaa      1620
tcctgggtac cagcttctag aagggatggt gattatgata acgaaaaatt acagcatgac      1680
gagaaaccct tctacaaaag aatgttttag                                       1710

<210> SEQ ID NO 41
<211> LENGTH: 1704
<212> TYPE: DNA
<213> ORGANISM: Saccharomyces cerevisiae

<400> SEQUENCE: 41
atgtccggtg ttaataatac atccgcaaat gatttatcca ctaccgagtc taactctaac        60
tcagtagcaa atgcaccatc tgtaaaaact gagcataatg actctaaaaa ctccctcaac       120
ctggatgcca ctgaaccacc tattgactta cctcaaaaac ccctctctgc atataccacc       180
gtcgcaatcc tgtgtttgat gattgcattt ggcggcttca tctttggttg ggataccggt       240
accatttctg gttttgttaa cctttctgat ttcatcagaa ggttcggtca aaaaaatgac       300
aagggaacct actacttatc gaaagtaaga atgggtttga tcgtctcaat attcaacatt       360
ggctgcgcca taggcggaat tgtcttgtca aaagtcggtg atatatatgg tcgtcgtatt       420
ggattgatta cagttactgc catttacgtt gtaggcatcc taatccaaat aacttccata       480
aacaagtggt accaatactt cattggaaga attatttctg gcctaggagt gggaggcatt       540
gctgtccttt ccccaatgtt gatatctgaa gttgctccca acaaatcag aggaaccctg       600 gtccaattgt accagctgat gtgtacgatg gtatttttc taggatactg taccaattac       660
ggtaccaaga actatcacaa cgccactcaa tggagagtcg gccttggtct ttgctttgcc       720
tggactacat tcatggttag tggaatgatg tttgtaccag aatcaccacg ttacctgatt       780
gaggttggta agatgagga agcgaaacgt tcactttcga atccaacaa agtctcagtc       840 gacgatccag ccttgttagc agaatatgac actataaagg cgggaatcga acttgaaaag       900
ctggcaggta acgcatcatg gtctgaacta ctctccacta aaacaaaggt ctttcagcgt       960
gttctcatgg gagtgatgat ccaatcgctg cagcaattaa ccggtgataa ctacttcttt      1020
tactacggca ccaccatctt caaatctgtc ggtctaaagg actcctttca gcttcgatc      1080 attatcggtg tggttaattt tttctcttca ttcatagcgg tataccacct tgagaggttt      1140
ggacgccgta cgtgtctatt gtggggtgct gcttctatgc tatgctgctt tgctgtgttt      1200
gcctccgtcg gtgtgacaaa gttgtggcct caaggaagca gtcaccaaga cattacttct      1260
cagggcgccg gtaactgtat gattgtgttt actatgttct tcattttttc gttcgccacc      1320
acttgggcag gcggctgtta cgttattgtc tcagagacgt ttcctcttag ggtcaaatca      1380
agaggaatgg caatcgcaac agctgcaaac tggatgtggg gttcctgat tagtttcttt      1440 accccattca ttaccggggc aatcaacttt tactacggtt atgtattctt aggctgtctg      1500
```

-continued

| | |
|---|---|
| gtttttgcat actttttatgt cttttttcttt gtcccagaaa caaaaggcct gacgctggag | 1560 |
| gaggtgaata ctatgtggct ggaaggtgtg ccagcatgga aatcagcctc atgggtgcca | 1620 |
| ccagaaagaa gaaccgcaga ttacgatgct gacgccatag accatgacga tagaccaatc | 1680 |
| tacaagaggt tcttttccag ctaa | 1704 |

<210> SEQ ID NO 42
<211> LENGTH: 1641
<212> TYPE: DNA
<213> ORGANISM: Saccharomyces cerevisiae

<400> SEQUENCE: 42

| | |
|---|---|
| atggttagtt caagtgtttc cattttgggg actagcgcca aggcatccac ttctctaagt | 60 |
| agaaaggatg aaattaaact aacccctgaa acaaggaagg ctagcttgga cattccatac | 120 |
| aaacccatta ttgcatactg gacggtgatg ggtctctgtc tgatgattgc ctttggtgga | 180 |
| ttcattttg gttgggatac aggaaccatt tcagggttta ttaaccaaac agatttcaag | 240 |
| agaaggtttg gtgagttaca aagggacggc agttttcaac tatcagatgt caggacaggg | 300 |
| ctaattgtcg gtatcttcaa cataggttgt gctttaggtg gcctaacgct gggacgcctg | 360 |
| ggcgatattt atgggcgtaa aatcggctta atgtgtgtta ctggtgtgta tgttgttggt | 420 |
| atcgtgatcc agattgcttc ctctgacaaa tggtatcaat attttattgg tagaattgtt | 480 |
| tctggaatgg gtgttggagg tgttgctgtg ctgtcgccaa ctttgatctc agaaatttcc | 540 |
| ccaaagcacc taagaggcac ttgtgtctct ttttaccagc taatgattac ccttggaatt | 600 |
| ttcttgggct actgtaccaa ttatggtaca agaaatatt caaattcaat acagtggcgg | 660 |
| gttcccttgg gtttgtgttt tgcgtgggca atctttatgg tgattggaat ggttatggtt | 720 |
| ccggaatcgc ccagatattt agtagaaaaa ggtaagtatg aagaagctag aaggtctttg | 780 |
| gccaaatcaa acaaggtcac agttactgat ccaggcgttg ttttttgagtt tgatactata | 840 |
| gttgcaaata tggaattaga aagggctgtt ggaaatgcca gttggcacga actcttctca | 900 |
| aataaaggag caattctacc aagggtaata atgggaatcg ttatccagtc actgcaacag | 960 |
| cttactggct gtaattattt tttctactac ggcacgacca ttttcaatgc tgttggaatg | 1020 |
| caagactctt tcgagacttc cattgtcctt ggggctgtta attttgcttc tacatttgtt | 1080 |
| gcactataca ttgtggataa atttgggcgt cgaaaatgtt tattgtgggg gtctgcctcg | 1140 |
| atggcaattt gtttcgtcat attcgccacc gttggcgtca ctagattatg gccacaaggg | 1200 |
| aaagaccaac cttcttcgca aagtgctggt aatgttatga tcgtttttac ttgtttcttc | 1260 |
| attttctctt tgccattac ttgggctcct atcgcctatg tcattgtggc agaaacttat | 1320 |
| ccattaagag ttaaaaatcg tgccatggcc attgcggttg gtgcgaactg gatgtggggt | 1380 |
| ttcttgattg gattttttcac accctttatc actagatcca taggatttc ttatggctat | 1440 |
| gttttcatgg gttgcttaat cttttcgtac ttctacgttt tcttctttgt ttgcgaaaca | 1500 |
| aagggattaa ctctggagga agttaatgaa atgtacgaag aaagaataaa gccatggaag | 1560 |
| tccggaggtt ggattcccag ttctagaaga acaccacaac caacaagcag tacaccatta | 1620 |
| gttattgttg atagtaaata a | 1641 |

<210> SEQ ID NO 43
<211> LENGTH: 1623
<212> TYPE: DNA
<213> ORGANISM: Saccharomyces cerevisiae

<400> SEQUENCE: 43

```
atgactgctc agattccgta tcaacatagc tcgggataca tctctcattt tcacaataat      60
gagcttgatg caggcagggg aagggattat aatgtaacca ttaagtatct agatgataaa     120
gaagaaaata tagaaggcca agcagcaaag attagtcaca atgcgagtct gcatattccc     180
gttttattgt gcttggtaat ctcgcttggt ggctttattt ttggatggga cattggaacc     240
atcggtggaa tgacaaatat ggttagcttt caagaaaaat ttggcacaac taatattatc     300
catgacgatg aaacaatttt tgtatctact aagaaactta ctgatctgca ataggccta      360
attatcagta ttttttaacat cagttgtggc gtaggggctt taactctgtc aaaaatcggt    420
gattggattg gtaggaaagg tggtatatgg tttgccttag tagtgtactg catcggtata     480
accattcaaa ttctctccta tggaaggtgg tattttttga cattgggaag agccgtaacg    540
ggaatcggtg tgggagtaac cactgtcttg gtgccaatgt ttctctccga gaattctcca    600
ctaaaaatca gaggctccat ggtatctacg tatcaattga ttgtaacatt tggcatacta    660
atgggaaaca ttttaaattt catatgcgaa agatgttata aagatcctac acaaaatata    720
gcctggcaat tgccattgtt cttgggatac atttgggcaa ttataattgg aatgtcactt    780
gtttacgttc ctgaatctcc acagtacttg gcaaaaatca aaaatgatgt gccctctgct    840
aaatactctt ttgcgaggat gaatggcatc cctgcgacgg atagcatggt aattgaattc    900
atcgatgatt tgctggaaaa taactataat aatgaggaaa ctaacaacga atcaaaaag    960
caaagcttag ttaaaagaaa cacatttgaa tttattatgg gaaagccaaa gttatggttg   1020
agactgatta ttggtatgat gataatggca tttcaacagc tgtccggaat aaattatttc   1080
ttttattacg gaacgtctgt tttcaaaggt gtcgggatta aggatcctta tattacttca   1140
atcatactgt caagtgttaa cttcctttct acgatattag gcatatatta cgtggagaaa   1200
tggggccaca agacatgttt attatatggt tcaacaaatt tattatttta tatgatgaca   1260
tatgctactg tggggacatt tggaagagaa acggacttct caaatattgt tttaattatc   1320
gtgacttgtt gttttatttt ttggtttgca ataacattgg gcccagttac atttgtacta   1380
gtgtccgaat tgttccctct aagaacgagg gccatatcaa tggctatttg cacatttatc   1440
aattggatgt tcaatttctt aatatcactt ttaacaccaa tgattgtatc caaaattgat   1500
ttcaaactag gatacatatt tgctgcttgc ctattagcgt tgataatatt cagttggata   1560
ctagttcctg aaacgaggaa aaagaatgag caagagatca ataaaatatt tgaaccggag   1620
tag                                                                  1623
```

<210> SEQ ID NO 44
<211> LENGTH: 2067
<212> TYPE: DNA
<213> ORGANISM: Scheffersomyces stipitis

<400> SEQUENCE: 44

```
ctacaagtga cagtcagtcg attagacttt gcatccactt gagtttgaca attgatatat     60
tccactagag acaatgagtg ctgacgaaaa agtcgctgct gccggccagg acggcttgtt    120
tgaacacaac agttccactt cgagcatcga ggacaagaag ccctccaaga gctccgatgt    180
cgattccgtg aactcgcaat tagtagacaa ctcggtagag ggcaacatct tgtcccagta    240
caccgaaagt caggtgatgc agatgggtag aagctatgcc accagcacg gcttggaccc    300
agaattgttc gccaaggcag ctgctgttgc cagaactcct cttggtttca actccatgcc    360
cttcttgaca gaggaagaga aggttggttt gaatgccgaa gccactaata gtggcacat    420
```

```
tccacccaga ttgatcgggg ttattgcctt gggttctatg gccgctgctg tgcagggtat      480
ggacgaatcg gtcattaacg gtgccaactt gttctacccc aaggctttcg gagtcgacac      540
catgcacaat tcggacttga ttgaaggttt gatcaatggt gctccttacc tttgctgtgg      600
tattctttcc tgttggttgt ctgacgcttg taaccgtcgt cttggtagaa aatggaccat      660
tttctggtgt tgtgtcattt ctgccatcac ctgtgtctgg caaggtcttg tcaacaactg      720
gtaccatttg ttcattgctc gtttcttcct tggatttggt gttggtatca agtccgccac      780
tgttcctgcc tactctgccg aatgtactcc taaacacatc agaggttcgt tagtcatgtt      840
gtggcaattc ttcacagctg ttggtattat gtttggttat gttgcttcct ggcttttcta      900
caatgtcgga gatagaggaa tccattacgg gttgaactgg agattgatgc ttggttcggc      960
cgctattcct gctgtcatca tcttgttcca aattcctttc gctcctgaat ctccacgttg     1020
gttaatgggt aaggacagac accttgaagc ctttgagtcc ttgaagcaat tgagatacga     1080
agaacttgct gctgctcgtg actgtttcta ccagtacgtc ttgttagctg aagaaggttc     1140
ttacaagatc ccaaccctca ccagatttaa ggaaatgttc accaagagaa gaaacagaaa     1200
cggtgccatc ggtgcattta ttgtcatgtt catgcaacag ttctgtggta tcaacgtcat     1260
tgcttactac tcttcgtcta tctttgtcca atctggtttc tctcaaactt ctgctttgat     1320
cgcttcttgg ggtttcggta tgcttaactt cacctttgcc attcctgcct tcttcacaat     1380
cgatcgtttc ggtagaagat ccttattgtt ggttaccttc cccttgatgg ctattttctt     1440
attgattgcc ggtttcggtt tcttgataaa cgaagaaaca aactccaagg gaagattggg     1500
aatgatcatc atcggtatct atatgttcac catctgttac tcttccggtg aaggtccagt     1560
tcctttcacc tactctgccg aagccttccc attgtacatc agagacttgg gtatgtcttt     1620
tgctactgcc acctgttgga ctttcaactt catcttggcc ttcacctgga acagattggt     1680
caatgcattc acatctactg gtgccttcgg cttctacgct gcttggaaca tcattggttt     1740
cttcttggtc ttatggttct tgccagaaac caagggcttg accttggaag aattggacga     1800
agtcttcgcc gtttccgccg tccaacacgc caagtaccaa accaagagtt tgatcaactt     1860
catccaaaga tacgttttac gttccaaggt ggctccattg cctccattgt acgaccacca     1920
gagattggct gtcaccaacc cagaatggaa cgacaagcca gaagtctctt atgtcgagta     1980
ggctccttga taacacattc atttatttcc tctttataat taatagttaa cttagttgtt     2040
caattcttca catcgcctag atagtaa                                         2067
```

<210> SEQ ID NO 45
<211> LENGTH: 1629
<212> TYPE: DNA
<213> ORGANISM: Scheffersomyces stipitis

<400> SEQUENCE: 45

```
atgagctacg aagataaact cgttcaacct gccttgaagt tcaggacctt cttggacaga       60
cttccaaaca tttacaatgt gtacattatt gcatctattt cctgtatttc aggtatgatg      120
ttcggttttg atatttcatc tatgtctgct tttataggtg aagatgacta caagaacttt      180
ttcaataatc caggctcaga catccaaggt tttatcactt cctgtatggc tttaggttct      240
ttcttcggtt ccatcgtctc ttccttcatt tccgaaccat tggtagaag agcatccttg      300 ttgttgtgtt cattcttctg gatggtcggg gctgctgtac aatcatcttc tcaaaacaga      360
gcccaattga tgatcggacg tatcatcgct ggtttcggtg ttggttttgg ttcttctgtt      420
```

-continued

```
gctccagttt acggttccga attggctcca agaaagatta gaggttttgt tggtggtatt    480
ttccaattct gtgttacctt gggtatcttg attatgttct acatttgtta cggtttgcat    540
ttcattaacg gtgttggctc tttcagaatt gcttggggtt tacaaattgt cccaggtttg    600 gtttatttg tcggttgttt ctttattcca gaatccccaa gatggttagc caaacatggt    660
tactgggatg aagcagaatt catcgttgcc caaattcaag ctaagggtaa tagagaagac    720
ccagacgtgt tgattgaaat ctccgaaatc aaggaccaaa ttttgattga agaaaacctc    780
aagagtttcg gttacgttga cttattcacc aagaagtata tcagaagaac tttaactgcc    840
atatttgctc aaatctggca acaattgacc ggtatgaatg tcatgatgta ctatattgtc    900
tacattttca acatggccgg ttactctaac aacgcaaact tggttgcctc ttccatccaa    960
tacgtcttga acactgctgc aactgttcca gctttgtttt taatggatta cattggtaga   1020
agaagattgt tgattggtgg tgccatcatg atgatgattt tccaatttgg tgttgctggt   1080
atcttaggta aatactccgt ccccgttcca ggcggtcttc caggtaaccc aactgtcacc   1140
atccaaatcc cagaagataa caagtcagct gctagaggtg ttattgcttg ttgttactta   1200
ttcgttgtat cattcgctct gagttggggt gtcggtatct gggtctactg ttcagaagtt   1260
tggggtgact ctgcttccag acagagaggt gctgctgttt caactgctgc caactggatt   1320
cttaactttg ctattgccat gtacactcca tcttccttca agaatatcac ctggaagact   1380
tacatcatct acgccgtctt ctgtcttgtt atggcaatcc atgtctactt ggattccca    1440 gaaaccaagg gcaagcgttt ggaagaagtc ggacaaatgt gggacgaaaa tgttcccgca   1500
tggagatctt ccagctggca accaactgtt ccattgttgt cagatgccga cttggcacac   1560
aagatggatg tttcccacaa ggaagagcaa tctccagatg ccgagtcaag ttctgaggaa   1620
aagccttaa                                                           1629
```

<210> SEQ ID NO 46
<211> LENGTH: 1673
<212> TYPE: DNA
<213> ORGANISM: Scheffersomyces stipitis

<400> SEQUENCE: 46

```
acaaaaatgg gtttagaaga cagtgctctc ttgcaaaagt acatcaactt cggtgaaaag    60
aaggctggtt ccaccaccat gggtatctgt gttggttttgt tcgcagcctt cggtggtatc   120
cttttcggtt atgacactgg taccatctcc ggtatcatgg ccatggacta cgtcactgcc   180
agattcccat ccaaccacca atctttcagt tcttctgaat cttcccttat tgtttccatt   240
ttgtctgttg gtaccttctt tggttctctt tctgcatctt tcatctccga cagattgggt   300
cgtagattga cttttaatgat ctccaccttg atcatcttca atgtcggtat tatcttgcaa    360
actgcctcta ctagcattcc acttttgtgt gttggtagag ttcttgctgg tcttggtgtt    420
ggtctcattt ccgctgttat tccattgtac caagctgaaa cagttccaaa gtggatcaga    480
ggtgctgttg tctcctgtta ccaatgggcc attacccttg gtttgttgtt ggctgctgtt    540
gttaaccaag gtacccacaa cagaaatgac tctggttcct acagaatccc aattgctatc    600
caattcttgt gggctttgat tttgggaggt ggtatgtgtt tgttgccaga accccaaga    660 ttctgggttt ctaaaggtga caacgacaga gccaaggact ccttgagaag attgagaaag    720
ttgcccctcg accatcccga cttgattgaa gaatacgaag aaatcaaggc taactacgaa    780
tacgaagctc aatacggttc aggttcttgg agtcaagttt tgctaacaa gaaccaccaa    840 agaaagagat tggccatggg tgttggtatc caagccttgc aacaattgac cggtattaac    900
```

| | |
|---|---|
| tttatcttct actatggtac taacttcttc aagggttctg gtatcaaaaa cgaattcctt | 960 |
| atccaaatgg ccactaacat tgtcaacttc ggttctactg tcccaggtat tcttttggtt | 1020 |
| gaaattattg gtagaagaaa gttgttgttg ggtggttctg cagttatgtc catttctcaa | 1080 |
| ttgattgttg ctattgtcgg tgttgccgct ggtgaaggtt caacttctgc caacaagtgt | 1140 |
| ttggttgcct tcgtttgtat cttcattgct gctttcgcag ccacttgggg tcctcttttgt | 1200 |
| tgggctgtca ttgccgaatg ttacccactt acagttagac aaaagtccat ctccttgtgt | 1260 |
| acagcttcca actggttgtg gaactggggt attgcctacg ctactcctta catggtcaac | 1320 |
| tccggtccag gtaacgccaa cttgggttcc aaggttttct tcatctgggg tggttgtaat | 1380 |
| atcattggtg gtcttttcgt gtggtacctt gtctacgaaa ctaagggctt gaccttagaa | 1440 |
| caaatcgatg aaatgtacga aaaggttcca aaggcttggc aatctaccag attcattcca | 1500 |
| tccgaacatg cattcactca accatccgca gctgcctctg tctcttctgg taaggctgaa | 1560 |
| ggtgtttctg aagttgaaga agcttctgta tagatacctc atgcacatta atcgacttac | 1620 |
| gtctttatga attttacttt ctcctaatat aatattatgg ccaattaacg ttg | 1673 |

<210> SEQ ID NO 47
<211> LENGTH: 1650
<212> TYPE: DNA
<213> ORGANISM: Debaryomyces hansenii

<400> SEQUENCE: 47

| | |
|---|---|
| atggctttaa aaatctttc tagaaccaac actatggggt taaggggtaa acgtcttaga | 60 |
| gtaatgttca ctgtggtggc tactcttggg ttctccttat tcggttacga tcaaggttta | 120 |
| atgtctggtc ttattactgg tgagcaattc aatgctgaat ccctccaac agcaggtaag | 180 |
| gatcactggg cttctgttaa tcaaggtgcc gttaccgcct gttacgaaat tggatgtttg | 240 |
| tttggtgctt tatttgtttt attctatggt gataaaacag gtagaagaat tttagttgtt | 300 |
| tgcggttctt tgattattat tattggtacc gtcatttcta ctgcggcatt tggtccacaa | 360 |
| tggggtttag gtcagtttgt tgtcggaaga gtggttacag gtgtaggtaa tggtttgaat | 420 |
| accgctacaa ttccagtttg gcaatctgaa atgtctaaag ccgaaaacag aggtcttta | 480 |
| gtcaacttcg aaggttctgt cattgcagtg ggtacctttg ttgcttactg gatcgatttc | 540 |
| ggattatctt atgttgatag ttctgtccaa tggagattcc cagttgcttt ccaagcatta | 600 |
| tttgcaatct tcttgttatt tggagctatt gaaatgccag aatctccaag atggatgttc | 660 |
| gctcacgata tgaaagctga aggtatgaa gttttagctg caatgaaaga tatttctcca | 720 |
| gatgatgatg aaatctacgc agaatatacg ttcattactg actcgattaa gagattcgat | 780 |
| aataaccaag ccggattcaa ggaattattc aaaggtggta aagagcaata ctttgctaga | 840 |
| atgataattg gttcatctgg tcaattttc caacaattta ctggttgtaa tgcggcaatt | 900 |
| tattattcta ccgtgttatt tgaagatact attcatttag aaagaagatt ggctttgatt | 960 |
| ttaggtggtg tttttgcaac cgtctatgcc ttatccacaa ttccttcgtt cttcttggtt | 1020 |
| gatacacttg gtagaagaaa cttattctta attggtgcaa ttggtcaagc tatctcattt | 1080 |
| acaattacat ttgcctgttt gattccagaa gatggagaaa cactcaagat gccaaaggt | 1140 |
| gctgctgttg gtcttttctt gtttattgtc ttttcggtt ttactatctt accaatgcct | 1200 |
| tggatttatc caccagaaat caatccaatg aagacaagaa ccgtagcttc agctgtttcc | 1260 |
| acctgtacta actggttaac taatttcggg gttgttatgt tcaccccaat tttcattgca | 1320 |

```
caaagtacct ttggatgtta tttattcttt gcgcttatga attatacttt cattccaatt    1380
attttcttct tttatccaga aactgccggt cgttccttag aagagattga tatcattttc    1440
gccaaagcac atgttgacaa tagattacca ttcagagttg cagctactat gccacgttta    1500
tctgtcaaag atattgaaga atacaatgtt caattaggtc ttgatgatga cttcgataag    1560
gaacagaatg aattgcaaga gaatgcctcc tccaattcag aaaaatcacc tgatgacact    1620
ccagaaggta tcttaactcc taatgcttaa                                     1650
```

<210> SEQ ID NO 48
<211> LENGTH: 1650
<212> TYPE: DNA
<213> ORGANISM: Debaryomyces hansenii

<400> SEQUENCE: 48

```
atgtataaaa tatggtcaaa aactaacact atgggactca gaggtaaacc tcttagagtt     60
gccatcacta tatgctgtac tattggattt tcattattcg gttacgacca aggattaatg    120
tcgggaatta ttactggtaa acaattcaat gaggaatttc cacccactca cggtacagat    180
cagcatgcta ctgttataca aggtgcagtc acgtcgtgct acgagttagg ctgttttttt    240
ggtgctttgt ttgcgttgtt tcaaggtgat aagtatggta aaggccaat gattattgtt    300 ggatctctgc tcattgtcat aggtactgtt attgcagttt ctgcatttgg tccgcaatgg    360
ggattgggcc aatttgttat ggtagagtt atcacaggat taggtaacgg catggatacg    420
gctactattc cggtgtggca atcggaaatt tctaaggcag aaaatagagg tcttttggtt    480
aacttggaag gttccatggt tgcggttggg acatttattg catattggtt agattttggg    540
ttatcatatg tcgatacttc agttcagtgg agattcccag ttgctttttca gatagtattt    600 gctcttttct tgtttcttgg cgttgcacaa ttaccggaat cacctagatg gttaattgct    660
catggcctca aggatgaagc tcattatgta ttggcaactt taaatgacgt tgatattgat    720
gatgagttcg taattgaaga agcgccatt ataactgatg gtgtcaatag atttgccaga    780
acccaaattg ggttcaaaga actatttcc ggcggcaagc aacagaactt cgctagaatg    840
ataattggtg catctacaca attctttcag caatttactg gatgtaacgc ttccatctat    900
tattcaactg ttttatttga aaatagtatt ggattgaccg gtaaattgcc cttaattcta    960
ggaggtgttt ttgctaccat ttatgcttta tctactattc catctttctt cttgattgat   1020
aggctaggca gaagagcttt gttttgatc ggtgccaccg gtcaaggcat atcattcacc   1080 atcactttg catgcttgat ccctgataat ggacaaaata ggaaacagc caaaggtgct   1140 gccgttggta tcttcttgtt tatcgttttt tttgcgttca ctattttacc attgccatgg   1200
atttaccctc cagaaatcaa ccccttgaga acaagaacag ttgctactgc ggtatcaaca   1260
tgtactaatt ggctaacaaa ctttgcagtc gttatgttta ctcctatttt tattggtgca   1320
agtagttatg gctgttactt attctttgct ataatgaatt tccttttcat tcctgtcatt   1380
ttctggtttt atcccgagac tgctggtcgt gagttggaag agattgatat tattttcgca   1440
aaggcatacg ttgataatag actaccatgg agagttgctg ctactttacc acacttgaat   1500
ttcaaggaac aagaacaaga gggaatcaaa ttgggtcttt atgatgactt cgaaaaggaa   1560
gcacctgaac atgtaaacac tttgtccgac gcctcaggct cagaagatgg ctcaaatgaa   1620
gccgcttcag ttaagcctgc ggaagtttaa                                     1650
```

<210> SEQ ID NO 49
<211> LENGTH: 1980

<212> TYPE: DNA
<213> ORGANISM: Yarrowia lipolytica

<400> SEQUENCE: 49

```
atggtttttg gacgagaaaa agacgactct gagggtatcg aacatgtgcc ctcccccaa      60
gacaacccgt cagatcagac gtcagacatc atcgctctga acgagaaggc ttctaatgaa    120
catgatgatc tccccactat ccccaaaccc gagggagatg ccccagtcaa ctctgaactg    180
gaccccgaca atccgctgat tcgatacagt cgcgctgagc tcctcgagat tgccacccag    240
tttgcggtgg ataacgacct tgccgacaaa gcggaagcat tcagaaaggg cgccctagtg    300
gcccaagacc cttccggttt cgagaacatc gacatacttg atgacgacga cagatactgg    360
cttaaccgtg agatcaccaa taagtgggat catcccatga aggtttacta ccttgttgtg    420
tgctgctcct ggctgctgc tgtccagggt atggatgaga ctgttatcaa cggcgccaac    480
atcattttcc ctgctcagtt tggtatcaag gaggattccg gtgttgtgtc tcgaaagagt    540
tggctgcttg gtcttgtcaa ctctgctcct tatttgtgtt gtgcatgcat ctcgtgctgg    600
atgactgacc ctatcaacaa agtacttggc cgaaaatgga cagtgttctg acctgtttc    660
tgggccggag ccacctgttt ctggtctggt ttcgtcaaca cctggtggca tctgttatt    720
gcccggttct tcctgggatt cggtattggt cccaagtccg ccacagttcc cgtgtacgct    780
gccgagtgtg ctcctcccag gattcgaggt gccatggtta tgatgtggca gatgtggact    840
gcttttggta tcatgatggg ctatgttatg gatcttgcat tctactacgt caaggataga    900
ggaactattg tcggcctaaa ttggagactg atgcttggtt ctgctttgat tcctgctctt    960
ctggtctgta ttttattgt caaatgtcct gagtctccca gatggcacct cgctcgagga   1020
gagatccgaa agtcgtttga gtgcatgcga gaaattcgac acactgacat acaagccgct   1080
cgagatacct tctacgccca cgttcttctg atcgaagaga acgagatgaa gaaaggaaag   1140
aaccgatttg tggagctctt taccgttcct cgaaaccggc gagcagcctg gcttctttc   1200
attgtcatgt tcatgcagca gttctgtggt atcaatgtta ttgcctacta ctcctccaac   1260
attttcatgg agtctggttt tggtgctatc caagctcttc tggcttcgtt tggttttggt   1320
gctatcaact tgtgttttgc gttgccagct gtttacacta tcgacacatt tggtagacgg   1380
gcactattac tggcgacctt ccctctgatg gctatattct tgctatttgc tggtttctgt   1440
ttctacattg gccagaacga tcccacccac tctcatgctc gtgtcggttt aattgctcta   1500
ggtatctatc tcttctcagc agtttactcc tgtggagaag gtccagtgcc cttcacctac   1560
tcggctgaag cctcccttt gtacgttcga gatttgggta tgtcgtttgc caccgccgtt   1620
tgctggctct ttaattttgt tctagccgtc acgtggccct ctctcctggc agccttcact   1680
ccgcagggtg cctccggatg gtatgctgcg tggaatgttg tcggattctt cttggtcctg   1740
tgtttcttgc ccgagaccaa gaacctgact ctggaagagc ttgacaaggt cttcagtgtc   1800
cccacccgag tccacatgaa gtaccagttc aacgccttca aaatcaacat tcagcgaaca   1860
atattacgaa aggatgtgcc caagcctcct ccgctctatg cccacgaagc cggtattggt   1920
ggtacttctc actggagctc caagcctcag cccaacgcga acactgccga gttcgtttaa   1980
```

<210> SEQ ID NO 50
<211> LENGTH: 1587
<212> TYPE: DNA
<213> ORGANISM: Scheffersomyces stipitis

<400> SEQUENCE: 50

```
atggcatatc ttgattggtt aacagctaga accaacactt tcgggttgag gggcaagaag      60
ttgagagcct tcatcactgt agtggctgtc actggtttct cattattcgg atatgatcaa     120
gggttgatgt ccggaattat tactgctgat caattcaact ctgagtttcc cgccactaga     180
aataacagta ctatccaagg tgccgtcacc tcctgttacg agcttggttg tttctttggt     240
gctgtgtttg ccttgttaag aggtgaaaga attggaagaa gacctcttgt gctttgtggc     300
tcgcttatta tcatcttggg aacagttatt tctgtaaccg ccttccatcc acactggtca     360
ttaggtcagt ttgttattgg tagagttatc actggtattg gtaatggtat gaatactgcc     420
accattccag tttggcaatc ggaaatgtca agagctgaaa acagaggaag attggtcaac     480
ttggaaggtt ccgttgtcgc tgtgggtaca tgtattgcct actggttgga tttcggtttg     540
tcttatgtcg acaattcagt ttcctggaga tttccagttg ctttccaaat agtgtttgct     600
tccgttttat ttgtgggaat gttgcaattg cccgactctc aagatggtt ggttgctaac      660
cacagaagag cagaggctct tcaagtgttg tctgctttga agacttgcc cgaagacgac      720
gaagaaattc ttaatgaagc tgaagttatt caggaaagtg tagacaagtt tgctggacat     780
gcttccgtca aggaagtgtt tactggtggt aagacccagc actggcaaag aatggttatt     840
ggatccagca cccaattctt tcagcagttc actggttgta acgctgccat ttactattcc     900
actgtcttgt ttcaagacac tattggttta gaaagaagaa tggcattgat tatcggtggt     960
gttttcgcaa ctgtctacgc cattttcaca attccttcct tcttcttggt cgatactctc    1020
ggacgtagaa acttgttctt gattggtgct atgggacaag gtattgcatt cactatcacc    1080
tttgcctgtt tgattgacga tactgaaaac aacgccaagg gtgccgcagt tggtttattc    1140
ttgtttattt gtttcttcgc cttcaccatc ttgccattgc catgggtata cccaccagaa    1200
atcaatcctt tgagaactag aactatagct tctgcaattt ccacttgtac caactggatc    1260
tgtaactttg ctgttgttat gttcaccct gtctttgtca ctaacaccag atggggagcc     1320
tatctttct ttgctgtgat gaacttcctt ttcgttccta ttattttctt cttctaccca     1380
gaaacagctg aagatcgtt ggaagaaatc gatatcatct ttgcgaaggc attcgttgac      1440
aaaagacagc catggagagt tgctgcaacc atgccaaagt tgtccaacca cgaaattgaa    1500
gacgaagcca acagattggg cttgtttgac gatggtacat tcgacaagga agcatttgaa    1560
accaaagaaa acgcatccag cagctct                                        1587
```

<210> SEQ ID NO 51
<211> LENGTH: 51
<212> TYPE: PRT
<213> ORGANISM: Artificial sequence
<220> FEATURE:
<223> OTHER INFORMATION: Synthetic polypeptide

<400> SEQUENCE: 51

Lys Phe Arg Asn Phe Leu Asp Lys Thr Pro Asn Ile Tyr Asn Val Phe
1               5                   10                  15

Val Ile Ala Ser Ile Ser Cys Ile Ser Gly Leu Met Phe Gly Ile Asp
            20                  25                  30

Ile Ser Ser Met Ser Leu Phe Ile Gly Asp Asp Lys Tyr Ile Lys Tyr
        35                  40                  45

Phe His Lys
    50

<210> SEQ ID NO 52
<211> LENGTH: 51

<212> TYPE: PRT
<213> ORGANISM: Artificial sequence
<220> FEATURE:
<223> OTHER INFORMATION: Synthetic polypeptide

<400> SEQUENCE: 52

Lys Leu Arg Leu Phe Leu Asp Lys Leu Pro Asn Ile Tyr Asn Ile Tyr
1               5                   10                  15

Val Ile Ala Thr Ile Ser Cys Ile Ser Gly Leu Met Phe Gly Ile Asp
            20                  25                  30

Ile Ser Ser Met Ser Ala Phe Leu Ser Asn Asp Ala Tyr Leu Lys Tyr
        35                  40                  45

Phe Gly Thr
    50

<210> SEQ ID NO 53
<211> LENGTH: 51
<212> TYPE: PRT
<213> ORGANISM: Artificial sequence
<220> FEATURE:
<223> OTHER INFORMATION: Synthetic polypeptide

<400> SEQUENCE: 53

Lys Phe Arg Asn Phe Leu Asp Lys Phe Pro Asn Ile His Asn Val Tyr
1               5                   10                  15

Ile Val Val Gly Ile Ser Cys Ile Ser Gly Met Met Phe Gly Ile Asp
            20                  25                  30

Ile Ser Ser Met Ser Leu Phe Ile Gly Asp Asp Lys Tyr Leu Asp Tyr
        35                  40                  45

Phe Asn Ser
    50

<210> SEQ ID NO 54
<211> LENGTH: 51
<212> TYPE: PRT
<213> ORGANISM: Artificial sequence
<220> FEATURE:
<223> OTHER INFORMATION: Synthetic polypeptide

<400> SEQUENCE: 54

Lys Phe Arg Thr Phe Leu Asp Arg Leu Pro Asn Ile Tyr Asn Val Tyr
1               5                   10                  15

Ile Ile Ala Ser Ile Ser Cys Ile Ser Gly Met Met Phe Gly Phe Asp
            20                  25                  30

Ile Ser Ser Met Ser Ala Phe Ile Gly Phe Asp Tyr Lys Asn Phe
        35                  40                  45

Phe Asn Asn
    50

<210> SEQ ID NO 55
<211> LENGTH: 51
<212> TYPE: PRT
<213> ORGANISM: Artificial sequence
<220> FEATURE:
<223> OTHER INFORMATION: Synthetic polypeptide

<400> SEQUENCE: 55

Ser Leu Asn Lys Phe Leu Asp Lys Phe His Thr Thr Tyr Asn Ile Tyr
1               5                   10                  15

Val Ile Ala Met Ile Thr Thr Ile Ser Gly Met Met Phe Gly Phe Asp
            20                  25                  30

Val Ser Ser Ile Ser Ala Phe Ile Ser Glu Pro Ser Tyr Arg Arg Phe
            35                  40                  45

Phe Asn Tyr
    50

<210> SEQ ID NO 56
<211> LENGTH: 51
<212> TYPE: PRT
<213> ORGANISM: Artificial sequence
<220> FEATURE:
<223> OTHER INFORMATION: Synthetic polypeptide

<400> SEQUENCE: 56

Gln Val Gly Ala Leu Gln His Arg Phe Pro Lys Leu His Asn Pro Tyr
1               5                   10                  15

Leu Thr Ala Ala Val Ala Thr Met Gly Gly Leu Leu Phe Gly Phe Asp
            20                  25                  30

Ile Ser Ser Val Ser Ala Phe Val Asp Thr Lys Pro Tyr Lys Glu Tyr
            35                  40                  45

Phe Gly Tyr
    50

<210> SEQ ID NO 57
<211> LENGTH: 43
<212> TYPE: PRT
<213> ORGANISM: Artificial sequence
<220> FEATURE:
<223> OTHER INFORMATION: Synthetic polypeptide

<400> SEQUENCE: 57

Met Tyr Lys Val His Asn Pro Tyr Leu Thr Ala Ala Val Ala Thr Met
1               5                   10                  15

Gly Gly Met Leu Phe Gly Phe Asp Ile Ser Ser Val Ser Ala Phe Val
            20                  25                  30

Gly Phe Asp Asn Tyr Met Asn Tyr Phe Gly His
            35                  40

<210> SEQ ID NO 58
<211> LENGTH: 52
<212> TYPE: PRT
<213> ORGANISM: Artificial sequence
<220> FEATURE:
<223> OTHER INFORMATION: Synthetic polypeptide

<400> SEQUENCE: 58

Met Gly Arg Ile Thr Asn Pro Tyr Val Leu Thr Ala Leu Ala Cys Thr
1               5                   10                  15

Gly Gly Leu Leu Phe Gly Phe Asp Ile Ser Ser Met Ser Ala Ile Ile
            20                  25                  30

Ser Ser Pro Asn Tyr Leu Thr Tyr Phe Gly Pro Lys Asp Leu Thr Val
            35                  40                  45

Glu Cys Pro Asp
    50

<210> SEQ ID NO 59
<211> LENGTH: 55
<212> TYPE: PRT
<213> ORGANISM: Artificial sequence
<220> FEATURE:
<223> OTHER INFORMATION: Synthetic polypeptide

<400> SEQUENCE: 59

```
Leu Ala Ser Asp Ala Pro Glu Ser Phe Ser Trp Ser Ser Val Ile Leu
1               5                   10                  15

Pro Phe Ile Phe Pro Ala Leu Gly Gly Leu Leu Phe Gly Tyr Asp Ile
                20                  25                  30

Gly Ala Thr Ser Gly Ala Thr Leu Ser Leu Gln Ser Pro Ala Leu Ser
            35                  40                  45

Gly Thr Thr Trp Phe Asn Phe
        50                  55
```

<210> SEQ ID NO 60
<211> LENGTH: 56
<212> TYPE: PRT
<213> ORGANISM: Artificial sequence
<220> FEATURE:
<223> OTHER INFORMATION: Synthetic polypeptide

<400> SEQUENCE: 60

```
His Val Pro Glu Asn Tyr Ser Val Val Ala Ala Ile Leu Pro Phe Leu
1               5                   10                  15

Phe Pro Ala Leu Gly Gly Leu Leu Tyr Gly Tyr Glu Ile Gly Ala Thr
                20                  25                  30

Ser Cys Ala Thr Ile Ser Leu Gln Glu Pro Met Thr Leu Leu Ser Tyr
            35                  40                  45

Tyr Ala Val Pro Phe Ser Ala Val
        50                  55
```

<210> SEQ ID NO 61
<211> LENGTH: 56
<212> TYPE: PRT
<213> ORGANISM: Artificial sequence
<220> FEATURE:
<223> OTHER INFORMATION: Synthetic polypeptide

<400> SEQUENCE: 61

```
Leu Asn Ala Glu Ala Thr Asn Lys Trp His Ile Pro Pro Arg Leu Ile
1               5                   10                  15

Gly Val Ile Ala Leu Gly Ser Met Ala Ala Ala Val Gln Gly Met Asp
                20                  25                  30

Glu Ser Val Ile Asn Gly Ala Asn Leu Phe Tyr Pro Lys Ala Phe Gly
            35                  40                  45

Val Asp Thr Met His Asn Ser Asp
        50                  55
```

<210> SEQ ID NO 62
<211> LENGTH: 60
<212> TYPE: PRT
<213> ORGANISM: Artificial sequence
<220> FEATURE:
<223> OTHER INFORMATION: Synthetic polypeptide

<400> SEQUENCE: 62

```
Leu Asn Arg Phe Ile Thr Asn Lys Trp Asp His Pro Met Lys Val Tyr
1               5                   10                  15

Tyr Leu Val Val Cys Cys Ser Leu Ala Ala Ala Val Gln Gly Met Asp
                20                  25                  30

Glu Thr Val Ile Asn Gly Ala Asn Ile Ile Phe Pro Ala Gln Phe Gly
            35                  40                  45

Ile Lys Glu Asp Ser Gly Val Val Ser Arg Lys Ser
        50                  55                  60
```

```
<210> SEQ ID NO 63
<211> LENGTH: 55
<212> TYPE: PRT
<213> ORGANISM: Artificial sequence
<220> FEATURE:
<223> OTHER INFORMATION: Synthetic polypeptide

<400> SEQUENCE: 63

Phe Leu Gly Met Arg Gly Ile Lys Leu Asn Trp Ala Ile Gly Phe Ala
1               5                   10                  15

Ala Ser Ala Gly Phe Leu Leu Phe Gly Tyr Asp Gln Gly Val Leu Gly
            20                  25                  30

Ser Leu Tyr Thr Leu Pro Ser Trp Asn Ala Gln Phe Pro Glu Ile Asn
        35                  40                  45

Thr Ala Ala Val Gly Asp Ser
    50                  55

<210> SEQ ID NO 64
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 64

Ala Lys Thr Asn Ser Tyr Leu Gly Leu Arg Gly His Lys Leu Asn Phe
1               5                   10                  15

Ala Val Ser Cys Phe Ala Gly Val Gly Phe Leu Leu Phe Gly Tyr Asp
            20                  25                  30

Gln Gly Val Met Gly Ser Leu Leu Thr Leu Pro Ser Phe Glu Asn Thr
        35                  40                  45

Phe Pro Ala Met Lys
    50

<210> SEQ ID NO 65
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 65

Lys Thr Asn Thr Met Gly Leu Arg Gly Lys Pro Leu Arg Val Ala Ile
1               5                   10                  15

Thr Ile Cys Cys Thr Ile Gly Phe Ser Leu Phe Gly Tyr Asp Gln Gly
            20                  25                  30

Leu Met Ser Gly Ile Ile Thr Gly Lys Gln Phe Asn Glu Glu Phe Pro
        35                  40                  45

Pro Thr His Gly Thr
    50

<210> SEQ ID NO 66
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 66

Arg Thr Asn Thr Met Gly Leu Arg Gly Lys Arg Leu Arg Val Met Phe
1               5                   10                  15

Thr Val Val Ala Thr Leu Gly Phe Ser Leu Phe Gly Tyr Asp Gln Gly
```

-continued

```
                20                  25                  30
Leu Met Ser Gly Leu Ile Thr Gly Glu Gln Phe Asn Ala Glu Phe Pro
            35                  40                  45

Pro Thr Ala Gly Lys
        50

<210> SEQ ID NO 67
<211> LENGTH: 51
<212> TYPE: PRT
<213> ORGANISM: Artificial sequence
<220> FEATURE:
<223> OTHER INFORMATION: Synthetic polypeptide

<400> SEQUENCE: 67

Arg Thr Asn Thr Phe Gly Leu Arg Gly Lys Lys Leu Arg Ala Phe Ile
1               5                   10                  15

Thr Val Val Ala Val Thr Gly Phe Ser Leu Phe Gly Tyr Asp Gln Gly
            20                  25                  30

Leu Met Ser Gly Ile Ile Thr Ala Asp Gln Phe Asn Ser Glu Phe Pro
        35                  40                  45

Ala Thr Arg
        50

<210> SEQ ID NO 68
<211> LENGTH: 55
<212> TYPE: PRT
<213> ORGANISM: Artificial sequence
<220> FEATURE:
<223> OTHER INFORMATION: Synthetic polypeptide

<400> SEQUENCE: 68

Arg Thr Ser His Trp Gly Leu Thr Gly Lys Lys Leu Arg Tyr Phe Ile
1               5                   10                  15

Thr Ile Ala Ser Met Thr Gly Phe Ser Leu Phe Gly Tyr Asp Gln Gly
            20                  25                  30

Leu Met Ala Ser Leu Ile Thr Gly Lys Gln Phe Asn Tyr Phe Phe Pro
        35                  40                  45

Ala Thr Lys Glu Asn Gly Asp
        50                  55

<210> SEQ ID NO 69
<211> LENGTH: 49
<212> TYPE: PRT
<213> ORGANISM: Artificial sequence
<220> FEATURE:
<223> OTHER INFORMATION: Synthetic polypeptide

<400> SEQUENCE: 69

Ile Asp Val Gly Leu Arg Gly Asn Trp Leu Leu Thr Val Ile Thr Ala
1               5                   10                  15

Ser Cys Ala Ala Gly Phe Leu Leu Phe Gly Tyr Asp Asn Gly Val Met
            20                  25                  30

Gly Gly Val Val Gly Leu Gly Glu Phe Asn Lys Thr Phe Asn Asn Pro
        35                  40                  45

Asp

<210> SEQ ID NO 70
<211> LENGTH: 44
<212> TYPE: PRT
<213> ORGANISM: Artificial sequence
<220> FEATURE:
```

<223> OTHER INFORMATION: Synthetic polypeptide

<400> SEQUENCE: 70

Gly Lys Gln Val Ser Tyr Ala Val Thr Phe Thr Cys Glu Leu Ala Phe
1               5                   10                  15

Ile Leu Phe Gly Ile Glu Gln Gly Ile Ile Gly Asn Leu Ile Asn Asn
            20                  25                  30

Gln Asp Phe Leu Asn Thr Phe Gly Asn Pro Thr Gly
        35                  40

<210> SEQ ID NO 71
<211> LENGTH: 52
<212> TYPE: PRT
<213> ORGANISM: Artificial sequence
<220> FEATURE:
<223> OTHER INFORMATION: Synthetic polypeptide

<400> SEQUENCE: 71

His Lys Thr Gln Arg Arg Leu Val Gly His Asn Leu Leu Tyr Ser Val
1               5                   10                  15

Ser Val Phe Leu Ser Ile Gly Gly Val Leu Phe Gly Tyr Asp Gln Gly
            20                  25                  30

Val Met Ser Gly Ile Ile Thr Gly Pro Tyr Phe Lys Ala Tyr Phe Asn
        35                  40                  45

Gln Pro Thr Ser
    50

<210> SEQ ID NO 72
<211> LENGTH: 49
<212> TYPE: PRT
<213> ORGANISM: Artificial sequence
<220> FEATURE:
<223> OTHER INFORMATION: Synthetic polypeptide

<400> SEQUENCE: 72

Met Phe Ser Leu Thr Gly Lys Pro Leu Leu Tyr Phe Thr Ser Val Phe
1               5                   10                  15

Val Ser Leu Gly Val Phe Leu Phe Gly Tyr Asp Gln Gly Val Met Ser
            20                  25                  30

Gly Ile Ile Thr Gly Phe Tyr Phe Lys Phe Tyr Phe His Glu Pro Thr
        35                  40                  45

Arg

<210> SEQ ID NO 73
<211> LENGTH: 55
<212> TYPE: PRT
<213> ORGANISM: Artificial sequence
<220> FEATURE:
<223> OTHER INFORMATION: Synthetic polypeptide

<400> SEQUENCE: 73

Val Gly Ala Thr Gly Ala Lys Gly Leu Ile Lys Asn Ala Arg Thr Phe
1               5                   10                  15

Ala Ile Ala Val Phe Ala Ser Met Gly Gly Leu Ile Tyr Gly Tyr Asn
            20                  25                  30

Gln Gly Met Phe Gly Gln Ile Leu Ser Met His Ser Phe Gln Phe Ala
        35                  40                  45

Ser Gly Val Lys Gly Ile Thr
    50                  55

```
<210> SEQ ID NO 74
<211> LENGTH: 56
<212> TYPE: PRT
<213> ORGANISM: Artificial sequence
<220> FEATURE:
<223> OTHER INFORMATION: Synthetic polypeptide

<400> SEQUENCE: 74

Ala Gly Lys Ser Gly Val Ala Gly Leu Val Ala Asn Ser Arg Ser Phe
1               5                   10                  15

Phe Ile Ala Val Phe Ala Ser Leu Gly Gly Leu Val Tyr Gly Tyr Asn
                20                  25                  30

Gln Gly Met Phe Gly Gln Ile Ser Gly Met Tyr Ser Phe Ser Lys Ala
            35                  40                  45

Ile Gly Val Glu Lys Ile Gln Asp
        50                  55

<210> SEQ ID NO 75
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 75

Ala His Gly Asn Val Val Thr Ile Met Met Lys Asp Pro Val Val Phe
1               5                   10                  15

Leu Val Ile Leu Phe Ala Ser Leu Gly Gly Leu Leu Phe Gly Tyr Asp
                20                  25                  30

Gln Gly Val Ile Ser Gly Ile Val Thr Met Glu Ser Phe Gly Ala Lys
            35                  40                  45

Phe Pro Arg Ile Phe Met
        50

<210> SEQ ID NO 76
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 76

Ala His Gly Asn Val Val Thr Ile Met Met Lys Asp Pro Val Val Phe
1               5                   10                  15

Leu Val Ile Leu Phe Ala Ser Leu Gly Gly Leu Leu Phe Gly Tyr Asp
                20                  25                  30

Gln Gly Val Ile Ser Gly Ile Val Thr Met Glu Ser Phe Gly Ala Lys
            35                  40                  45

Phe Pro Arg Ile Phe Met
        50

<210> SEQ ID NO 77
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 77

Ala His Gly Asn Val Val Thr Ile Met Met Lys Asp Pro Val Val Phe
1               5                   10                  15

Leu Val Ile Leu Phe Ala Ser Leu Gly Gly Leu Leu Phe Gly Tyr Asp
```

```
                    20                  25                  30

Gln Gly Val Ile Ser Gly Ile Val Thr Met Glu Ser Phe Gly Ala Lys
            35                  40                  45

Phe Pro Arg Ile Phe Met
    50

<210> SEQ ID NO 78
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 78

Ser Lys Gly Asn Ile Ile Thr Val Met Ser Lys Asp Pro Leu Val Phe
1               5                   10                  15

Cys Ile Ile Ala Phe Ala Ser Ile Gly Gly Leu Leu Phe Gly Tyr Asp
            20                  25                  30

Gln Gly Val Ile Ser Gly Ile Val Thr Met Glu Ser Phe Ala Ala Lys
            35                  40                  45

Phe Pro Arg Ile Phe Ser
    50

<210> SEQ ID NO 79
<211> LENGTH: 57
<212> TYPE: PRT
<213> ORGANISM: Artificial sequence
<220> FEATURE:
<223> OTHER INFORMATION: Synthetic polypeptide

<400> SEQUENCE: 79

Pro Ile Glu Ile Pro Lys Lys Pro Met Ser Glu Tyr Val Thr Val Ser
1               5                   10                  15

Leu Leu Cys Leu Cys Val Ala Phe Gly Gly Phe Met Phe Gly Trp Asp
            20                  25                  30

Thr Gly Thr Ile Ser Gly Phe Val Gln Thr Asp Phe Leu Arg Arg
            35                  40                  45

Phe Gly Met Lys His Lys Asp Gly Thr
    50                  55

<210> SEQ ID NO 80
<211> LENGTH: 58
<212> TYPE: PRT
<213> ORGANISM: Artificial sequence
<220> FEATURE:
<223> OTHER INFORMATION: Synthetic polypeptide

<400> SEQUENCE: 80

Glu Val Val Val Pro Glu Lys Pro Ala Ser Ala Tyr Ala Thr Val Ser
1               5                   10                  15

Ile Met Cys Leu Cys Met Ala Phe Gly Gly Phe Met Ser Gly Trp Asp
            20                  25                  30

Thr Gly Thr Ile Ser Gly Phe Val Asn Gln Thr Asp Phe Leu Arg Arg
            35                  40                  45

Phe Gly Asn Tyr Ser His Ser Lys Asn Thr
    50                  55

<210> SEQ ID NO 81
<211> LENGTH: 57
<212> TYPE: PRT
<213> ORGANISM: Artificial sequence
```

```
<220> FEATURE:
<223> OTHER INFORMATION: Synthetic polypeptide

<400> SEQUENCE: 81

Ala Val Ala Pro Pro Asn Thr Gly Lys Gly Val Tyr Val Thr Val Ser
1               5                   10                  15

Ile Cys Cys Val Met Val Ala Phe Gly Gly Phe Ile Phe Gly Trp Asp
            20                  25                  30

Thr Gly Thr Ile Ser Gly Phe Val Ala Gln Thr Asp Phe Leu Arg Arg
        35                  40                  45

Phe Gly Met Lys His His Asp Gly Ser
    50                  55

<210> SEQ ID NO 82
<211> LENGTH: 57
<212> TYPE: PRT
<213> ORGANISM: Artificial sequence
<220> FEATURE:
<223> OTHER INFORMATION: Synthetic polypeptide

<400> SEQUENCE: 82

Val Leu Thr Asn Pro Asn Thr Gly Lys Gly Ala Tyr Val Thr Val Ser
1               5                   10                  15

Ile Cys Cys Val Met Val Ala Phe Gly Gly Phe Val Phe Gly Trp Asp
            20                  25                  30

Thr Gly Thr Ile Ser Gly Phe Val Ala Gln Thr Asp Phe Leu Arg Arg
        35                  40                  45

Phe Gly Met Lys His Lys Asp Gly Ser
    50                  55

<210> SEQ ID NO 83
<211> LENGTH: 57
<212> TYPE: PRT
<213> ORGANISM: Artificial sequence
<220> FEATURE:
<223> OTHER INFORMATION: Synthetic polypeptide

<400> SEQUENCE: 83

Val Val Glu Ile Pro Lys Arg Pro Ala Ser Ala Tyr Val Thr Val Ser
1               5                   10                  15

Ile Met Cys Ile Met Ile Ala Phe Gly Gly Phe Val Phe Gly Trp Asp
            20                  25                  30

Thr Gly Thr Ile Ser Gly Phe Ile Asn Gln Thr Asp Phe Ile Arg Arg
        35                  40                  45

Phe Gly Met Lys His Lys Asp Gly Thr
    50                  55

<210> SEQ ID NO 84
<211> LENGTH: 57
<212> TYPE: PRT
<213> ORGANISM: Artificial sequence
<220> FEATURE:
<223> OTHER INFORMATION: Synthetic polypeptide

<400> SEQUENCE: 84

Pro Ile Asp Leu Pro Gln Lys Pro Leu Ser Ala Tyr Thr Thr Val Ala
1               5                   10                  15

Ile Leu Cys Leu Met Ile Ala Phe Gly Gly Phe Ile Phe Gly Trp Asp
            20                  25                  30

Thr Gly Thr Ile Ser Gly Phe Val Asn Leu Ser Asp Phe Ile Arg Arg
        35                  40                  45
```

```
Phe Gly Gln Lys Asn Asp Lys Gly Thr
    50                  55

<210> SEQ ID NO 85
<211> LENGTH: 57
<212> TYPE: PRT
<213> ORGANISM: Artificial sequence
<220> FEATURE:
<223> OTHER INFORMATION: Synthetic polypeptide

<400> SEQUENCE: 85

Asn Ala Glu Leu Pro Ala Lys Pro Ile Ala Ala Tyr Trp Thr Val Ile
1               5                   10                  15

Cys Leu Cys Leu Met Ile Ala Phe Gly Gly Phe Val Phe Gly Trp Asp
                20                  25                  30

Thr Gly Thr Ile Ser Gly Phe Val Asn Gln Thr Asp Phe Lys Arg Arg
            35                  40                  45

Phe Gly Gln Met Lys Ser Asp Gly Thr
    50                  55

<210> SEQ ID NO 86
<211> LENGTH: 57
<212> TYPE: PRT
<213> ORGANISM: Artificial sequence
<220> FEATURE:
<223> OTHER INFORMATION: Synthetic polypeptide

<400> SEQUENCE: 86

Ser Leu Asp Ile Pro Tyr Lys Pro Ile Ile Ala Tyr Trp Thr Val Met
1               5                   10                  15

Gly Leu Cys Leu Met Ile Ala Phe Gly Gly Phe Ile Phe Gly Trp Asp
                20                  25                  30

Thr Gly Thr Ile Ser Gly Phe Ile Asn Gln Thr Asp Phe Lys Arg Arg
            35                  40                  45

Phe Gly Glu Leu Gln Arg Asp Gly Ser
    50                  55

<210> SEQ ID NO 87
<211> LENGTH: 57
<212> TYPE: PRT
<213> ORGANISM: Artificial sequence
<220> FEATURE:
<223> OTHER INFORMATION: Synthetic polypeptide

<400> SEQUENCE: 87

Gln Val Asp Ala Pro Gln Lys Gly Phe Lys Asp Tyr Ile Val Ile Ser
1               5                   10                  15

Ile Phe Cys Phe Met Val Ala Phe Gly Gly Phe Val Phe Gly Phe Asp
                20                  25                  30

Thr Gly Thr Ile Ser Gly Phe Val Asn Met Ser Asp Phe Lys Asp Arg
            35                  40                  45

Phe Gly Gln His His Ala Asp Gly Thr
    50                  55

<210> SEQ ID NO 88
<211> LENGTH: 58
<212> TYPE: PRT
<213> ORGANISM: Artificial sequence
<220> FEATURE:
<223> OTHER INFORMATION: Synthetic polypeptide

<400> SEQUENCE: 88
```

```
Asn Val Glu Pro Pro Lys Arg Gly Leu Ile Gly Tyr Leu Val Ile Tyr
1               5                   10                  15

Leu Leu Cys Tyr Pro Ile Ser Phe Gly Gly Phe Leu Pro Gly Trp Asp
            20                  25                  30

Ser Gly Ile Thr Ala Gly Phe Ile Asn Met Asp Asn Phe Lys Met Asn
        35                  40                  45

Phe Gly Ser Tyr Lys His Ser Thr Gly Glu
    50                  55
```

<210> SEQ ID NO 89
<211> LENGTH: 58
<212> TYPE: PRT
<213> ORGANISM: Artificial sequence
<220> FEATURE:
<223> OTHER INFORMATION: Synthetic polypeptide

<400> SEQUENCE: 89

```
Met Val Phe Gln Val Arg Gly Thr Pro Ile Gly Ala Leu Thr Leu Phe
1               5                   10                  15

Ile Ala Met Leu Ala Ser Met Gly Gly Phe Leu Phe Gly Trp Asp Thr
            20                  25                  30

Gly Gln Ile Ser Gly Leu Thr Gln Met Ala Asp Phe Arg Gln Arg Phe
        35                  40                  45

Ala Thr Val Asp Asn Pro Asp Ala Ile Gly
    50                  55
```

<210> SEQ ID NO 90
<211> LENGTH: 60
<212> TYPE: PRT
<213> ORGANISM: Artificial sequence
<220> FEATURE:
<223> OTHER INFORMATION: Synthetic polypeptide

<400> SEQUENCE: 90

```
Gly Gln Ala Ala Lys Ile Ser His Asn Ala Ser Leu His Ile Pro Val
1               5                   10                  15

Leu Leu Cys Leu Val Ile Ser Leu Gly Gly Phe Ile Phe Gly Trp Asp
            20                  25                  30

Ile Gly Thr Ile Gly Gly Met Thr Asn Met Val Ser Phe Gln Glu Lys
        35                  40                  45

Phe Gly Thr Thr Asn Ile Ile His Asp Asp Glu Thr
    50                  55                  60
```

<210> SEQ ID NO 91
<211> LENGTH: 59
<212> TYPE: PRT
<213> ORGANISM: Artificial sequence
<220> FEATURE:
<223> OTHER INFORMATION: Synthetic polypeptide

<400> SEQUENCE: 91

```
Gly Pro Val Ala Arg Pro Ala Ser Val Lys Gln Ser Leu Pro Ala Ile
1               5                   10                  15

Leu Val Ala Ala Ala Ser Ala Phe Gly Gly Val Leu Phe Gly Tyr Asp
            20                  25                  30

Thr Gly Thr Ile Ser Gly Leu Ile Val Met Pro Asn Phe Gln Thr Glu
        35                  40                  45

Gly Lys Pro Val Pro Gly Ser Thr Thr Gly Ala
    50                  55
```

<210> SEQ ID NO 92
<211> LENGTH: 60
<212> TYPE: PRT
<213> ORGANISM: Artificial sequence
<220> FEATURE:
<223> OTHER INFORMATION: Synthetic polypeptide

<400> SEQUENCE: 92

Gly Pro Val Ala Arg Pro Ala Ser Val Lys Gln Ser Leu Pro Ala Ile
1               5                   10                  15

Leu Val Ala Ala Ala Ser Ala Phe Gly Gly Val Leu Phe Gly Tyr Asp
                20                  25                  30

Thr Gly Thr Ile Ser Gly Leu Ile Val Met Pro Asn Phe Gln Glu Thr
            35                  40                  45

Phe Gly Lys Pro Val Pro Gly Ser Thr Thr Gly Ala
    50                  55                  60

<210> SEQ ID NO 93
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 93

Phe Val Asn Val Gly Glu Lys Lys Ala Gly Ser Thr Ala Met Ala Ile
1               5                   10                  15

Ile Val Gly Leu Phe Ala Ala Ser Gly Gly Val Leu Phe Gly Tyr Asp
                20                  25                  30

Thr Gly Thr Ile Ser Gly Val Met Thr Met Asp Tyr Val Leu Ala Arg
            35                  40                  45

Tyr Pro Ser Asn Lys
    50

<210> SEQ ID NO 94
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 94

Phe Val Asn Val Gly Glu Lys Lys Ala Gly Ser Thr Ala Met Ala Ile
1               5                   10                  15

Ile Val Gly Leu Phe Ala Ala Ser Gly Gly Val Leu Val Gly Tyr Asp
                20                  25                  30

Thr Gly Thr Ile Ser Gly Val Met Thr Met Asp Tyr Val Leu Ala Arg
            35                  40                  45

Tyr Pro Ser Asn Lys
    50

<210> SEQ ID NO 95
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 95

Phe Val Asn Val Gly Glu Lys Lys Ala Gly Ser Thr Ala Met Ala Ile
1               5                   10                  15

Ile Val Gly Leu Phe Ala Ala Phe Gly Gly Val Leu Ser Gly Tyr Asp
            20                  25                  30

Thr Gly Thr Ile Ser Gly Val Met Thr Met Asp Tyr Val Leu Ala Arg
        35                  40                  45

Tyr Pro Ser Asn Lys
    50

<210> SEQ ID NO 96
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 96

Tyr Val Asn Val Gly Glu Lys Arg Ala Gly Ser Ala Ser Met Gly Ile
1               5                   10                  15

Phe Val Gly Ala Phe Ala Ala Phe Gly Gly Val Leu Phe Gly Tyr Asp
            20                  25                  30

Thr Gly Thr Ile Ser Gly Ile Met Ala Met Asn Tyr Val Lys Gly Glu
        35                  40                  45

Phe Pro Ala Asn Lys
    50

<210> SEQ ID NO 97
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 97

Tyr Val Asn Val Gly Glu Lys Arg Ala Gly Ser Ala Ser Met Gly Ile
1               5                   10                  15

Phe Val Gly Ala Phe Ala Ala Phe Gly Gly Val Leu Phe Gly Tyr Asp
            20                  25                  30

Thr Gly Thr Ile Ser Gly Ile Met Ala Met Asn Tyr Val Lys Gly Glu
        35                  40                  45

Phe Pro Ala Asn Lys
    50

<210> SEQ ID NO 98
<211> LENGTH: 53
<212> TYPE: PRT
<213> ORGANISM: Artificial sequence
<220> FEATURE:
<223> OTHER INFORMATION: Synthetic polypeptide

<400> SEQUENCE: 98

Tyr Ile Asn Phe Gly Glu Lys Lys Ala Gly Ser Thr Thr Met Gly Ile
1               5                   10                  15

Cys Val Gly Leu Phe Ala Ala Phe Gly Gly Ile Leu Phe Gly Tyr Asp
            20                  25                  30

Thr Gly Thr Ile Ser Gly Ile Met Ala Met Asp Tyr Val Thr Ala Arg
        35                  40                  45

Phe Pro Ser Asn His
    50

<210> SEQ ID NO 99
<211> LENGTH: 53
<212> TYPE: PRT

<213> ORGANISM: Artificial sequence
<220> FEATURE:
<223> OTHER INFORMATION: Synthetic polypeptide

<400> SEQUENCE: 99

Ile Ile Asn Arg Gly Glu Lys Pro Glu Gly Ser Ala Phe Met Ala Ala
1               5                   10                  15

Phe Val Ala Val Phe Val Ala Phe Gly Gly Ile Leu Phe Gly Tyr Asp
                20                  25                  30

Thr Gly Thr Ile Ser Gly Val Met Ala Met Pro Phe Val Lys Lys Thr
            35                  40                  45

Phe Thr Asp Asp Gly
    50

<210> SEQ ID NO 100
<211> LENGTH: 41
<212> TYPE: PRT
<213> ORGANISM: Artificial sequence
<220> FEATURE:
<223> OTHER INFORMATION: Synthetic polypeptide

<400> SEQUENCE: 100

Met Ala Ile Ile Val Ala Val Phe Val Ala Phe Gly Gly Leu Leu Tyr
1               5                   10                  15

Gly Tyr Asp Thr Gly Thr Ile Ala Gly Ile Met Thr Met Gly Tyr Val
                20                  25                  30

Lys Phe His Phe Thr Asp Phe Gly Lys
            35                  40

<210> SEQ ID NO 101
<211> LENGTH: 52
<212> TYPE: PRT
<213> ORGANISM: Artificial sequence
<220> FEATURE:
<223> OTHER INFORMATION: Synthetic polypeptide

<400> SEQUENCE: 101

Tyr Tyr Lys Lys Met Gln Gln Lys Ser Ser Ser Ser Ala Ile Thr
1               5                   10                  15

Val Gly Leu Val Ala Ala Val Gly Gly Phe Leu Tyr Gly Tyr Asp Thr
                20                  25                  30

Gly Leu Ile Asn Asp Ile Met Phe Met Thr Tyr Val Lys Asp Asn Phe
            35                  40                  45

Pro Ala Asn Gly
    50

<210> SEQ ID NO 102
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 102

Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
                20                  25                  30

Gly Thr Val Glu Ser Leu His Thr Val Phe Val Ala Pro Gln Asn Leu
            35                  40                  45

Ser Glu Ser Ala Ala Asn

```
<210> SEQ ID NO 103
<211> LENGTH: 50
<212> TYPE: PRT
<213> ORGANISM: Artificial sequence
<220> FEATURE:
<223> OTHER INFORMATION: Synthetic polypeptide

<400> SEQUENCE: 103

Arg Ser Ile Gly Pro Leu Ile Pro Arg Asn Lys His Leu Phe Tyr Gly
1               5                   10                  15

Ser Val Leu Leu Met Ser Ile Val His Pro Thr Ile Met Gly Tyr Asp
            20                  25                  30

Ser Met Met Val Gly Ser Ile Leu Asn Leu Asp Ala Tyr Val Asn Tyr
        35                  40                  45

Phe His
    50

<210> SEQ ID NO 104
<211> LENGTH: 57
<212> TYPE: PRT
<213> ORGANISM: Artificial sequence
<220> FEATURE:
<223> OTHER INFORMATION: Synthetic polypeptide

<400> SEQUENCE: 104

Lys Ser Met Thr Leu Lys Gln Ala Leu Leu Lys Tyr Pro Lys Ala Ala
1               5                   10                  15

Leu Trp Ser Ile Leu Val Ser Thr Thr Leu Val Met Glu Gly Tyr Asp
            20                  25                  30

Thr Ala Leu Leu Ser Ala Leu Tyr Ala Leu Pro Val Phe Gln Arg Lys
        35                  40                  45

Phe Gly Thr Leu Asn Gly Glu Gly Ser
    50                  55

<210> SEQ ID NO 105
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 105

Gly Gly Leu Ile Phe Gly
1               5

<210> SEQ ID NO 106
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 106

Gly Gly Phe Ile Phe Gly
1               5

<210> SEQ ID NO 107
<211> LENGTH: 6
<212> TYPE: PRT
<213> ORGANISM: Artificial sequence
<220> FEATURE:
<223> OTHER INFORMATION: Synthetic polypeptide
```

```
<400> SEQUENCE: 107

Gly Gly Phe Ile Met Gly
1               5

<210> SEQ ID NO 108
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 108

Gly Phe Phe Ile Met Gly
1               5

<210> SEQ ID NO 109
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 109

Gly Gly Phe Ile Ser Gly
1               5

<210> SEQ ID NO 110
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 110

Gly Phe Phe Ile Ser Gly
1               5

<210> SEQ ID NO 111
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 111

Gly Gly Phe Ile Thr Gly
1               5

<210> SEQ ID NO 112
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 112

Gly Phe Phe Ile Thr Gly
1               5

<210> SEQ ID NO 113
<211> LENGTH: 6
<212> TYPE: PRT
<213> ORGANISM: Artificial sequence
<220> FEATURE:
<223> OTHER INFORMATION: Synthetic polypeptide
```

```
<400> SEQUENCE: 113

Gly Gly Phe Leu Met Gly
1               5

<210> SEQ ID NO 114
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 114

Gly Phe Phe Leu Met Gly
1               5

<210> SEQ ID NO 115
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 115

Gly Gly Phe Leu Ser Gly
1               5

<210> SEQ ID NO 116
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 116

Gly Phe Phe Leu Ser Gly
1               5

<210> SEQ ID NO 117
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 117

Gly Gly Phe Leu Thr Gly
1               5

<210> SEQ ID NO 118
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 118

Gly Phe Phe Leu Thr Gly
1               5

<210> SEQ ID NO 119
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 119
```

```
Gly Gly Phe His Met Gly
1               5

<210> SEQ ID NO 120
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 120

Gly Phe Phe His Met Gly
1               5

<210> SEQ ID NO 121
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 121

Gly Gly Phe His Ser Gly
1               5

<210> SEQ ID NO 122
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 122

Gly Phe Phe His Ser Gly
1               5

<210> SEQ ID NO 123
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 123

Gly Gly Phe His Thr Gly
1               5

<210> SEQ ID NO 124
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 124

Gly Phe Phe His Thr Gly
1               5

<210> SEQ ID NO 125
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 125
```

```
Gly Gly Leu Val Tyr Gly
1               5

<210> SEQ ID NO 126
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 126

Gly Gly Phe Val Phe Gly
1               5

<210> SEQ ID NO 127
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 127

Gly Gly Arg Pro Thr Gly
1               5

<210> SEQ ID NO 128
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 128

Gly Phe Arg Pro Thr Gly
1               5

<210> SEQ ID NO 129
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 129

Gly Gly Thr Pro Thr Gly
1               5

<210> SEQ ID NO 130
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 130

Gly Phe Thr Pro Thr Gly
1               5
```

ENGINEERED XYLOSE TRANSPORTERS WITH REDUCED GLUCOSE INHIBITION

CROSS-REFERENCES TO RELATED APPLICATIONS

This application claims priority to U.S. Provisional Application No. 62/001,495, filed May 21, 2014, the disclosure of which is incorporated herein in its entirety and for all purposes.

STATEMENT AS TO RIGHTS TO INVENTIONS MADE UNDER FEDERALLY SPONSORED RESEARCH AND DEVELOPMENT

This invention was made with government support under grant no. CBET1067506, awarded by the National Science Foundation. The government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file 48932-525001US_ST25.TXT, created on May 21, 2015, 171,093 bytes, machine format IBM-PC, MS Windows operating system, is hereby incorporated by reference.

BACKGROUND OF THE INVENTION

The quest for an optimal xylose pathway in yeast is of utmost importance along the way to realizing the potential of lignocellulosic biomass conversion into fuels and chemicals. An often overlooked aspect of this catabolic pathway is the molecular transport of this sugar. Molecular transporter proteins facilitate monosaccharide uptake and serve as the first step in catabolic metabolism. In this capacity, the preferences, regulation, and kinetics of these transporters ultimately dictate total carbon flux (1-3); and optimization of intracellular catabolic pathways only increases the degree to which transport exerts control over metabolic flux (4, 5). Thus, monosaccharide transport profiles and rates are important design criteria and a driving force to enable metabolic engineering advances (6-10). Furthermore, the presence of other hexose sugars, such as glucose, can hamper efficient transport of xylose by inhibiting sugar transporters. There is a need in the art for efficient transport systems for xylose in yeast when glucose is present. Provided herein are solutions to these and other problems in the art.

BRIEF SUMMARY OF THE INVENTION

Provided herein are compositions and methods useful for transporting xylose, arabinose, and galactose into a yeast cell in the presence of glucose.

Recombinant transporter proteins are provided herein that transport hexoses or pentoses. In one aspect, the recombinant transporter is a recombinant xylose transporter protein that includes a xylose transporter motif sequence and a glucose mitigation mutation. In another aspect, the recombinant transporter is a recombinant arabinose transporter protein that includes an arabinose transporter motif sequence and a glucose mitigation mutation. In yet another aspect, the recombinant transporter protein is a recombinant galactose transporter protein that includes a galactose transporter motif sequence and a glucose mitigation mutation.

Also provided herein are nucleic acids that encode recombinant transporter proteins described herein. Thus, in one aspect is a nucleic acid encoding a recombinant xylose transporter as described herein, including embodiments thereof. In another aspect is a nucleic acid encoding a recombinant arabinose transporter as described herein, including embodiments thereof. In yet another aspect is a nucleic acid encoding a recombinant galactose transporter as described herein, including embodiments thereof.

Recombinant yeast cells are described herein which include a recombinant transporter protein as described herein. In one aspect is a recombinant yeast cell that includes a recombinant xylose transporter as described herein, including embodiments thereof. In another aspect is a recombinant yeast cell that includes a recombinant arabinose transporter as described herein, including embodiments thereof. In another aspect is a recombinant yeast cell that includes a recombinant galactose transporter as described herein, including embodiments thereof.

Methods of transporting xylose into a recombinant yeast cell are also described herein. In one aspect, the method includes contacting a recombinant yeast cell with a xylose compound, where the recombinant yeast cell includes a recombinant xylose transporter protein as described herein, including embodiments thereof. The recombinant xylose transporter protein transports the xylose compound into the recombinant yeast cell. In another aspect, the method includes contacting a recombinant yeast cell with a xylose compound, where the xylose compound is the only sugar (i.e. carbon source) in the media, and where the recombinant yeast cell includes a recombinant xylose transporter protein as described herein, including embodiments thereof.

In another aspect is a method of transporting arabinose into a recombinant yeast cell. The method includes contacting a recombinant yeast cell with an arabinose compound, where the recombinant yeast cell includes a recombinant arabinose transporter protein as described herein, including embodiments thereof. The recombinant arabinose transporter protein transports the arabinose compound into the recombinant yeast cell. In another aspect, the method includes contacting a recombinant yeast cell with an arabinose compound, where the arabinose compound is the only sugar (i.e. carbon source) in the media, and where the recombinant yeast cell includes a recombinant arabinose transporter protein as described herein, including embodiments thereof.

In another aspect is a method of transporting galactose into a recombinant yeast cell. The method includes contacting a recombinant yeast cell with a galactose compound, where the recombinant yeast cell includes a recombinant galactose transporter protein as described herein, including embodiments thereof. The recombinant galactose transporter protein transports the galactose compound into the recombinant yeast cell. In another aspect, the method includes contacting a recombinant yeast cell with a galactose compound, where the galactose compound is the only sugar (i.e. carbon source) in the media, and where the recombinant yeast cell includes a recombinant galactose transporter protein as described herein, including embodiments thereof.

BRIEF DESCRIPTION OF THE DRAWINGS

Figures 9E, 9F:
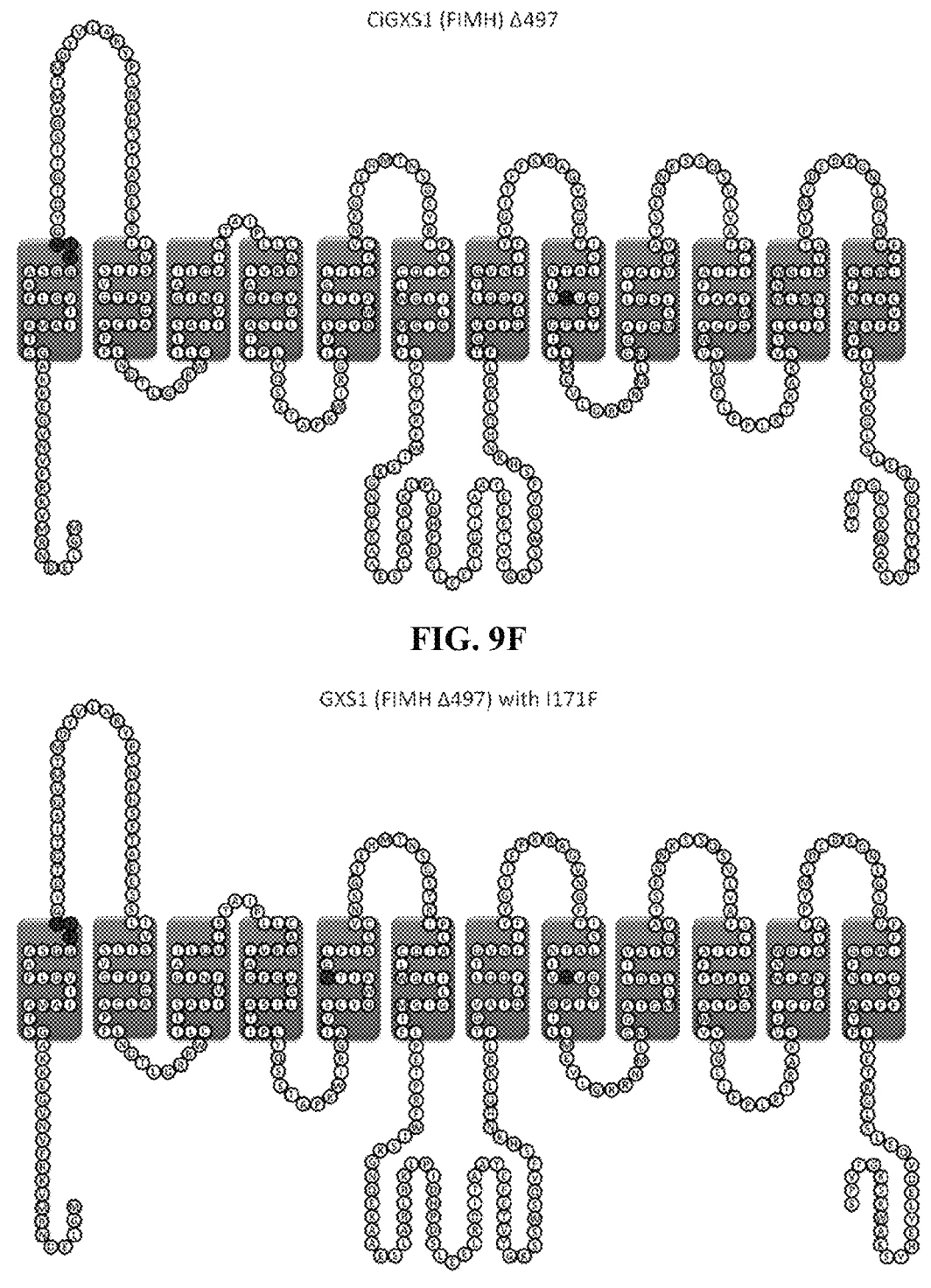

FIG. 9A-9F: Schematics of the transporter structures for the wild-type GXS1 and gxs1 mutant showing the location of the F-I-M xylose transporter sequence motif. FIG. 9A: WT CiGXS1 (SEQ ID NO:1). FIG. 9B: CiGXS1FIM (SEQ ID NO:2). FIG. 9C: CiGXS1FIM N326H (SEQ ID NO:3). FIG. 9D: CiGXS1FIM T170N (SEQ ID NO:4). FIG. 9E: CiGXS1(FIMH)Δ497 (SEQ ID NO:5). FIG. 9F: CiGXS1 (FIMH-Δ497) with I171F (SEQ ID NO:6).

DETAILED DESCRIPTION OF THE INVENTION

Figure 1:
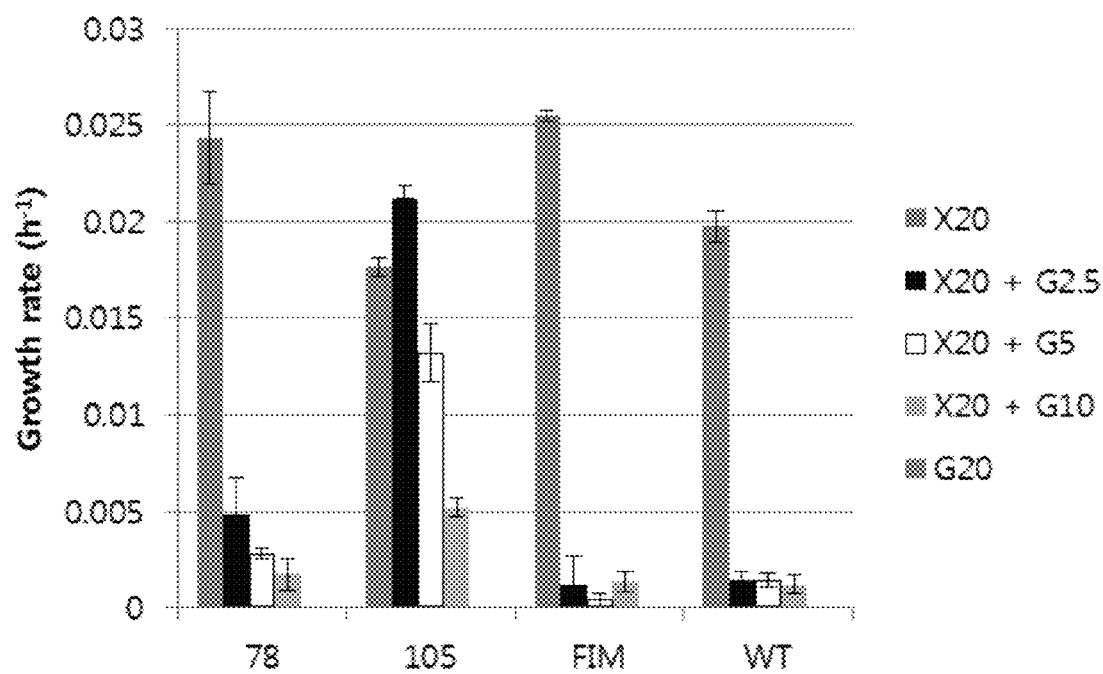
FIG. 1: The growth of *S. cerevisiae* expressing mutants (78 and 105), FIM, wild-type CiGXS1 transporters on xylose medium supplemented with different concentration of glucose: X20: xylose 20 g/L, X20+G2.5: xylose 20 g/L+glucose 2.5 g/L, X20+G5: xylose 20 g/L+glucose 5 g/L, X20+G10: xylose 20 g/L+glucose 10 g/L, G20: glucose 20 g/L.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as a naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)). In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions. In some embodiments, there may be 1, 2, 3, 4, 5, 6, 7, 8, 9, 10, 15, 20, 25, 30, 35, or 40 conservative substitutions.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

An amino acid or nucleotide base "position" is denoted by a number that sequentially identifies each amino acid (or nucleotide base) in the reference sequence based on its position relative to an N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to a reference sequence. In embodiments the reference sequence is a *Candida intermedia* GXS1 protein having SEQ ID NO: 1. In embodiments, the comparison to the reference sequence is a sequence alignment between the given amino acid or polynucleotide sequence and the reference sequence.

"GXS1 protein" or "*Candida intermedia* GXS1 protein" is used according to its common, ordinary meaning and refers to proteins of the same or similar names and functional fragments and homologs thereof. The term includes recombinant or naturally occurring forms of GXS1 protein (e.g. Genbank ID: CAI44932.1; GI: 85057135; SEQ ID NO: 1), or variants thereof that maintain GXS1 protein activity (e.g. within at least 30%, 40%, 50%, 60%, 70%, 80%, 90%, 95%, or 100% as compared to SEQ ID NO: 1). The term includes recombinant or naturally occurring forms of GXS1 protein or variants thereof that have sequence identity to SEQ ID NO: 1 (e.g. about 65%, 70%, 75%, 80%, 85%, 90%, 95%, 99% or 100% identity to SEQ ID NO: 1). GXS1 protein may refer to variants having mutated amino acid residues that modulate (e.g. increase or decrease when compared to GXS1 protein) GXS1 protein activity, expression, cellular targeting, or protein translocation. GXS1 protein may be modified as described herein (e.g. modified with a transporter motif sequence and/or glucose mitigation mutation).

```
SEQ ID NO: 1:
MGLEDNRMVK RFVNVGEKKA GSTAMAIIVG LFAASGGVLF

GYDTGTISGV MTMDYVLARY PSNKHSFTAD ESSLIVSILS

VGTFFGALCA PFLNDTLGRR WCLILSALIV FNIGAILQVI

STAIPLLCAG RVIAGFGVGL ISATIPLYQS ETAPKWIRGA

IVSCYQWAIT IGLFLASCVN KGTEHMTNSG SYRIPLAIQC

LWGLILGIGM IFLPETPRFW ISKGNQEKAA ESLARLRKLP

IDHPDSLEEL RDITAAYEFE TVYGKSSWSQ VFSHKNHQLK

RLFTGVAIQA FQQLTGVNFI FYYGTTFFKR AGVNGFTISL

ATNIVNVGST IPGILLMEVL GRRNMLMGGA TGMSLSQLIV

AIVGVATSEN NKSSQSVLVA FSCIFIAFFA ATWGPCAWVV

VGELFPLRTR AKSVSLCTAS NWLWNWGIAY ATPYMVDEDK

GNLGSNVFFI WGGFNLACVF FAWYFIYETK GLSLEQVDEL

YEHVSKAWKS KGFVPSKHSF REQVDQQMDS KTEAIMSEEA

SV
```

Residues corresponding to positions 36-41 are underlined and bolded for reference. Residues corresponding to positions 155, 225, 326, 354, 361, 407 and 446 are underlined for reference.

The term "recombinant" when used with reference to, for example, a cell, nucleic acid, or protein, indicates that the cell, nucleic acid, or protein, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express genes otherwise modified from those found in the native form of a cell (e.g. genes encoding a mutation in a native or non-native transporter protein, such as a transporter motif sequence as described herein). For example, a recombinant protein may be a protein that is expressed by a cell or organism that has been modified by the introduction of a heterologous nucleic acid (e.g. encoding the recombinant protein).

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 Molecular Cloning: A Laboratory Manual, 18.1-18.88).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "isolated" refers to a nucleic acid, polynucleotide, polypeptide, protein, or other component that is partially or completely separated from components with which it is normally associated (other proteins, nucleic acids, cells, etc.). In embodiments, an isolated polypeptide or protein is a recombinant polypeptide or protein.

A "yeast cell" as used herein, refers to a eukaryotic unicellular microorganism carrying out metabolic or other function sufficient to preserve or replicate its genomic DNA. Yeast cells may carry out fermentation of sugars described herein. In embodiments, fermentation may convert the sugar to a biofuel or biochemical as set forth herein. Yeast cells referenced herein include, for example, the following species: *Candida intermedia, Cryptococcos neoformans, Debaryomyces hansenii, Saccharomyces cerevisiae, Scheffersomyces stipitis*, or *Yarrowia lipolytica*. A "recombinant yeast cell" is a yeast cell which expresses a recombinant transporter protein.

The term "biofuel" as used herein refers to a convenient energy containing substance produced from living organisms (e.g. biomass conversion to a fuel). Thus, biofuels may be produced through, for example, fermentation of carbohydrates (e.g. sugars) found in biomass (e.g. lignocellulosic biomass). Biofuels may be solid, liquid, or gas forms. Biofuels include, for example, ethanol, biodiesel, vegetable oil, ether (oxygenated fuels), or gas (e.g. methane).

The term "biochemical" as used herein refers to production of chemicals by living organisms. Biochemicals herein include production of alcohols (e.g. methanol, butanol, ethanol, isobutanol, 2,3-butanediol, propanol); sugars (e.g. erythritol, mannitol, riboflavin); carotenoids (e.g. β-carotene, lycopene, astaxanthin); fatty acids (e.g. ricinoleic acid, linolenic acid, tetracetyl phytosphingosine); amino acids (e.g. valine, lysine, threonine); aromatics (e.g. indigo, vanillin, sytrene, p-hydroxystyrene); flavonoids (e.g. naringenin, genistein, kaempferol, quercetin, chrysin, apigenin, luteolin); stillbenoids (e.g. resveratrol); terpenoids (e.g. β-amyrin, taxadiene, miltiradiene, paclitaxel, artemisinin, bisabolane); polyketides (e.g. aureothin, spectinabilin, lovastatin, geodin); acetone; or organic acids (e.g. citric acid, succinic acid, malic acid, lactic acid, polylactic acid, adipic acid, glucaric acid). See e.g. Curran K. A., Alper H. S., Metabolic Engineering 14:289-297 (2012).

A "transporter motif sequence" as used herein refers to an amino acid sequence that, when present in a protein (e.g. a sugar transporter protein such as a MFS transporter protein), increases the ability of the protein to transport a sugar or sugar-containing compound into a yeast cell. In embodiments, the transporter motif sequence imparts a hexose sugar transport preference or pentose sugar transport preference to the protein. Correspondingly, a transporter motif may refer to the specific sugar it transports into a yeast cell. For example, the transporter motif sequence may impart preference to hexose sugars to a transporter protein, thereby allowing the recombinant transporter protein to preferentially transport hexoses into a yeast cell. Such transporter motif sequences may be referred to herein as a "hexose transporter motif sequence." In embodiments the transporter motif sequence imparts preference to a single hexose. The hexose may be galactose or mannose. Such transporter motif sequences may be referred to herein as a "galactose transporter motif sequence" and a "mannose transporter motif sequence" respectively. In embodiments, the transporter motif sequence imparts preference to more than one hexose sugar.

The transporter motif sequence may impart preference to pentose sugars to a transporter protein, thereby allowing the recombinant transporter protein to preferentially transport pentose into a yeast cell. In embodiments the transporter motif sequence imparts preference to a single pentose (e.g. xylose). The pentose may be xylose or arabinose. Such transporter motif sequences may be referred to herein as a "xylose transporter motif sequence" and an "arabinose transporter motif sequence" respectively. In embodiments the transporter motif sequence imparts preference to more than one pentose sugar (e.g. xylose and arabinose). Such transporter motif sequences may be referred to as a "xylose/arabinose transporter motif sequence."

In embodiments, the transporter motif sequence imparts preference to a hexose and a pentose. That is, in embodiments, the recombinant transporter protein having such a transporter motif sequence preferentially transports one hexose and/or one pentose. Such transporter motif sequences may be referred to by the sugars which are transported (e.g. galactose and arabinose). Accordingly, in embodiments, the transporter motif sequence imparts preference to galactose and arabinose. Such a transporter motif is herein referred to as a "galactose-arabinose transporter motif sequence" (i.e. a recombinant transporter protein that transports both galactose and arabinose, or transports galactose or arabinose).

The transporter motif sequence as described herein corresponds to residues corresponding to positions 36-41 of the *Candida intermedia* GXS1 protein ("GXS1 motif sequence"). One skilled in the art will immediately recognize the identity and location of residues corresponding to positions 36-41 of the *Candida intermedia* GXS1 protein in other transporter proteins with different numbering systems. For example, by performing a simple sequence alignment with *Candida intermedia* GXS1 protein the identity and location of residues corresponding to positions 36-41 of the *Candida intermedia* GXS1 protein are identified in other yeast transport proteins as illustrated in Table 1. Insertion (e.g. substitution) of a transporter motif sequence into a yeast transport protein may thereby be performed resulting in a functional yeast transporter protein with an altered sugar transport preference (e.g. changing a preference for hexoses to a preference for pentoses). For example, amino acid residue positions 75-81 of *S. cerevisiae* HXT7 protein correspond to amino acid residue positions 36-41 of the *Candida intermedia* GXS1 protein (see Table 1).

TABLE 1

Sequence alignment of 54 sequences from major facilitator superfamily sugar transporter proteins (SEQ ID NOs: 51-104, respectively in order of appearance in Table 1). Putative transporter motif sequences are illustrated in the box and corresponds as described herein to residue positions 36-41 of *C. intermedia* GXS1 protein.

```
Dh2C02530p    KFRNFLDKTPNIYNVFVIASISCI SGLM FGIDISSMSLFIGDDKYIKYFHK--------- 63
Dh2E01166p    KLRLFLDKLPNIYNIYVIATISCI SGLM FGIDISSMSAFLSNDAYLKYFGT--------- 63
Dh2E01298p    KFRNFLDKFPNIHNVYIVVGISCI SGMM FGIDISSMSLFIGDDKYLDYFNS--------- 63
SsHGT2        KFRTFLDRLPNIYNVYIIASISCI SGMM FGFDISSMSAFIGEDDYKNFFNN--------- 63
Dh2A14300p    SLNKELDKFHTTYNIYVIAMITTI SGMM FGFDVSSISAFISEPSYRRFFNY--------- 61
Y10B06391p    QVGALQHRFPKLHNPYLTAAVATM GGLL FGFDISSVSAFVDTKPYKEYFGY--------- 59
Y10B01342p    --------MYKVHNPYLTAAVATM GGML FGFDISSVSAFVGEDNYMNYFGH--------- 43
BmHGT2        --------MGRITNPYVLTALACT GGLL FGFDISSMSAIISSPNYLTYFGPKDLTVECPD 52
At5g59250     LASDAPESFSWSSVILPFIFP-AL GGLL FGYDIGATSGATLSLQSP----ALSGTTWFNF 139
At5g17010     ---HVPENYSVVAAILPFLFP-AL GGLL YGYEIGATSCATISLQEPMTLLSYYAVPFSAV 89
SsAUT1        LNAEATNKWHIPPRLIGVIALGSM AAAV QGMDESVINGANLFYPKAFGVD----TMHNSD 161
Y10D00132     LNREITNKWDHPMKVYYLVVCCSL AAAV QGMDETVINGANIIFPAQFGIKEDSGVVSRKS 180
BmSTL1        -----FLGMRGIKLNWAIGFAASA GFLL FGYDQGVLGSLYTLPSWNAQFPEINTAAVGDS 73
SsXUT6        AKTNSYLGLRGHKLNFAVSCFAGV GFLL FGYDQGVMGSLLTLPSFENTFPAMK------- 75
Dh2E01386p    --KTNTMGLRGKPLRVAITICCTI GFSL FGYDQGLMSGIITGKQFNEEPPTHGT------ 59
Dh2B05060p    --RTNTMGLRGKRLRVMFTVVATL GFSL FGYDQGLMSGLITGEQFNAEFPPTAGK----- 60
SsSTL1        --RRNRMGLRGKRLRVMFTVVATL GFSL FGYDQGLMSGLITGEQFNAEFPPTAGK----- 60
ScSTL1        --RTSHWGLTGKKLRYFITIASMT GFSL FGYDQGLMASLITGKQFNYEFPATKENG---D 70
BmHXT10       ----IDVGLRGNWLLTVITASCAA GFLL VGYDNGVMGGVVGLGEFNKTFNNPD------- 66
SsXUT2        ----------GKQVSYAVTFTCEL AFIL FGIEQGIIGNLINNQDFLNTFGNPTG------ 53
CnBC3990p     --HKTQRRLVGHNLLYSVSVFLSI GVWL FGYDQGVMSGIITGPYFKAYFNQPTS------ 62
Y10F06776p    -----MFSLTGKPLLYFTSVFVSL GVFL FGYDQGVMSGIITGFYFKEYPHEPTR------ 49
BmXUT3        VGATGAKGLIKNARTFAIAVFASM GGLI YGYNQGMFGQILSMHSFQEASGVKGIT----- 78
SsXUT1        AGKSGVAGLVANSRSFFIAVFASL GGLV YGYNQGMFGQISGMYSFSKAIGVEKIQD---- 77
SsXUT3        AHGNVVTIMMKDPVVFLVILFASL GGLL FGYDQGVISGIVTMESF--GAKFPRIFM---- 63

SsXUT3-A      AHGNVVTIMMKDPVVFLVILFASL GGLL FGYDQGVISGIVTMESF--GAKFPRIFM---- 63
SsXUT3-B      AHGNVVTIMMKDPVVFLVILFASL GGLL FGYDQGVISGIVTMESF--GAKFPRIFM---- 63
DhXy1HP       SKGNIITVMSKDPLVFCIIAFASI GGLL FGYDQGVISGIVTMESF--AAKFPRIFS---- 64
ScGAL2        PIEIPKKPMSEYVTVSLLCLCVAF GGFM FGWDTGTISGFVVQTDFLRRFG-MKHKDGT-- 113
ScHXT8        EVVVPEKPASAYATVSIMCLCMAF GGFM SGWDTGTISGFVNQTDFLRRFGNYSHSKNT-- 109
ScHXT1        AVAPPNTGKGVYVTVSICCVMVAF GGFI FGWDTGTISGFVAQTDFLRRFG-MKHHDGS-- 107
ScHXT3        VLTNPNTGKGAYVTVSICCVMVAF GGFV FGWDTGTISGFVAQTDFLRRFG-MKHHDGS-- 104
ScHXT7        VVEIPKRPASAYVTVSIMCIMIAF GGFV FGWDTGTISGFINQTDFIRRFG-MKHKDGT-- 107
ScHXT9        PIDLPQKPLSAYTTVAILCLMIAF GGFI FGWDTGTISGFVNLSDFIRRFG-QKNDKGT-- 103
ScHXT2        NAELPAKPIAAYWTVICLCLMIAF GGFV FGWDTGTISGFVNQTDFKRRFG-QMKSDGT-- 98
ScHXT10       SLDIPYKPIIAYWTVMGLCLMIAF GGFI FGWDTGTISGFINQTDFKRRFG-ELQRDGS-- 91
CiGXF1        QVDAPQKGFKDYIVISIFCFMVAF GGFV FGFDTGTISGFVNMSDFKDRFG-QHHADGT-- 86
ScHXT13       NVEPPKRGLIGYLVIYLLCYPISF GGFL PGWDSGITAGFINMDNFKMNFGSYKHSTGE-- 100
BmGXF1        -MVFQVRGTPIGALTLFIAMLASM GGFL FGWDTGQISGLTQMADFRQRFATVDNPDAIG- 58
```

TABLE 1-continued

Sequence alignment of 54 sequences from major facilitator superfamily sugar transporter proteins (SEQ ID NOs: 51-104, respectively in order of appearance in Table 1). Putative transporter motif sequences are illustrated in the box and corresponds as described herein to residue positions 36-41 of C. intermedia GXS1 protein.

```
ScHXT14     GQAAKISHNASLHIPVLLCLVISLGGFIFGWDIGTIGGMTNMVSFQEKFGTTNIIHDDET  105
BmGXS1      GPVARPASVKQSLPAILVAAASAFGGVLFGYDTGTISGLIVMPNFQETFGKPVPGSTTGA   74
BmRGT2      GPVARPASVKQSLPAILVAAASAFGGVLFGYDTGTISGLIVMPNFQETFGKPVPGSTTGA   74
CiGXS1      FVNVGEKKAGSTAMAIIVGLFAASGGVLFGYDTGTISGVMTMDYVLARY------PSNK-   64
CiGXS1-A    FVNVGEKKAGSTAMAIIVGLFAASGGVLVGYDTGTISGVMTMDYVLARY------PSNK-   64
CiGXS1-B    FVNVGEKKAGSTAMAIIVGLFAAFGGVLSGYDTGTISGVMTMDYVLARY------PSNK-   64
Dh2D01474   YVNVGEKRAGSASMGIFVGAFAAFGGVLFGYDTGTISGIMAMNYVKGEF------PANK-   64
Dh0D02167p  YVNVGEKRAGSASMGIFVGAFAAFGGVLFGYDTGTISGIMAMNYVKGEF------PANK-   64
SsRGT2      YINFGEKKAGSTTMGICVGLFAAFGGILFGYDTGTISGIMAMDYVTARF------PSNH-   64
Y10C06424p  IINRGEKPEGSAFMAAFVAVFVAFGGILFGYDTGTISGVMAMPFVKKTF------TDDG-   58
Y10C08943p  -------------MAIIVAVFVAFGGLLYGYDTGTIAGIMTMGYVKEHF------TDFGK   41
Dh2B14278p  YYKKMQQKS-SSSSAITVGLVAAVGGFLYGYDTGLINDIMEMTYVKDNF------PANG-   69
EcXy1E      -----MNTQYNSSYIFSITLVATLGGLLFGYDTAVISGTVESLHTVFVAPQNLSESAAN-   54
SsXUT5      RSIGPLIPRNKHLFYGSVLLMSIVHPTIMGYDSMMVGSILNLDAYVNYFH---------   53
ScMAL11     KSMTLKQALLKYPKAALWSILVSTTLVMEGYDTALLSALYALPVFQRKFGTLNGEGS---  148
```

A "glucose mitigation mutation" as used herein refers to an amino acid mutation that, when present in a recombinant transporter protein, reduces, minimizes, diminishes, or in certain embodiments, eliminates the inhibitory effect of glucose on the recombinant transporter when transporting a sugar other than glucose (e.g. xylose) into a yeast cell. A glucose mitigation mutation may, in embodiments, increase the ability of a recombinant transporter protein to transport a preferred sugar or sugar-containing compound into a yeast cell. Thus, in embodiments, a glucose mitigation mutation may increase the ability of a recombinant transporter protein to transport xylose into a yeast cell. A glucose mitigation mutation may include a single amino acid residue mutation (e.g. a "point mutation") in a recombinant transporter protein. A glucose mitigation mutation may include two or more mutations (e.g. a "substitution set") in a recombinant transporter protein. The glucose mitigation mutation may be in a transmembrane domain, an extracellular loop, or cytoplasmic loop of a recombinant transporter protein. In embodiments, the glucose mitigation mutation may be localized (i.e. glucose mitigation mutations located within a specified domain or region of a recombinant transporter protein) or distributed (i.e. glucose mitigation mutations located throughout the sequence of the recombinant transporter protein).

A "recombinant transporter protein" as used herein refers to a recombinantly expressed transmembrane protein which transports a sugar or sugar-containing compound (e.g. hexoses and pentoses) into a yeast cell. In embodiments, the recombinant transporter protein is a yeast recombinant transporter protein. In embodiments, the recombinant transporter protein is a transporter protein belonging to the major facilitator superfamily ("MFS") transporter proteins. In embodiments, a recombinant transporter protein may transport a hexose (e.g. galactose) into a yeast cell. In embodiments, a recombinant transporter protein may transport a pentose (e.g. xylose or arabinose) into a yeast cell. A recombinant transporter protein may be engineered, using the transporter motif sequences described herein, to alter its sugar preference (e.g. a transporter protein having a preference to transport a hexose compound may be converted to a transporter protein having a preference to transport a pentose compound). A recombinant transporter protein may be characterized by the sugar it transports. Thus, a recombinant transporter protein transporting xylose is herein referred to a "recombinant xylose transporter protein." Likewise, recombinant transporter proteins transporting arabinose or galactose are herein referred to as a "recombinant arabinose transporter protein" and a "recombinant galactose transporter protein" respectively.

A recombinant transporter protein may be characterized as a transporter protein derived from a particular organism. Where a recombinant transporter protein is derived from a particular organism, the endogenous sequence of the recombinant transporter protein may be maintained and residues corresponding to positions 36-41 of the Candida intermedia GXS1 protein may be replaced with a transporter motif sequence. As an example, a C. intermedia gxs1 transporter protein is a gxs1 transporter protein, a homolog thereof, or a functional fragment thereof, found in C. intermedia. Amino acids 75-81 of S. cerevisiae hxt7 transporter protein may be replace with a transporter motif sequence thereby forming a recombinant transporter protein with desired sugar transport characteristics as described herein. In embodiments, the recombinant transporter protein is a protein, functional fragment, or homolog thereof, identified by the following NCBI gene ID or NCBI accession numbers: 836043, 831564, AJ937350.1, AJ875406.1, 2901237, 2913528, 8998057, 8999011, 50419288, 948529, 4839826, 4852047, 4851844, 4840896, 4840252, 4841106, 4851701, 2907283, 2906708, 2908504, 2909312, 2909701, 4935064, 851943, 856640, 851946, 856494, 8998297, 2902950, 2902912, 853207, 852149, 855023, 853216, 853236, 850536, 855398, 4836720, 4836632, 4840859, 2913215, 2902914, 2910370, and 4838168 (SEQ ID NOs:7-50, respectively in order of appearance). Such recombinant transporter proteins may further be characterized by the sugar preference conferred (e.g. a Candida intermedia GXS1 recombinant xylose transporter protein).

A "pentose compound" or "pentose" is a monosaccharide-containing compound having 5 carbon atoms. Pentose compounds include aldopentoses (e.g. pentose compounds having an aldehyde moiety at carbon 1) and ketopentoses (e.g. pentose compounds having a ketone moiety at carbon 2 or carbon 3). Pentose compounds include, for example, D/L-arabinose, D/L-lyxose, D/L-ribose, D/L-xylose, D/L-ribulose, and D/L-xylulose. The term "monosaccharide-containing" refers to a compound that includes at least one monosaccharide.

A "hexose compound" "or "hexose" is a monosaccharide-containing compound having 6 carbon atoms. Hexose compounds include aldohexoses (e.g. hexose compounds having an aldehyde moiety at carbon 1) and ketohexoses (e.g. hexose compounds having a ketone moiety at carbon 2). Hexose compounds include, for example, D/L-allose, D/L-altrose, D/L-glucose, D/L-mannose, D/L-glucose, D/L-idose, D/L-galactose, and D/L-talose.

A "xylose compound" is xylose or a xylose-containing compound including at least one xylose moiety. Thus as used herein, the term xylose compound represents a single xylose, a chain including one or more xylose moieties, or a xylose moiety covalently or non-covalently bound to another chemical moiety (e.g. another sugar forming a xylose containing polysaccharide or xylose bound to lignin). An "arabinose compound" is arabinose or an arabinose-containing compound including at least one arabinose moiety. Thus as used herein, the term arabinose compound represents a single arabinose, a chain including one or more arabinose moieties, or an arabinose moiety covalently or non-covalently bound to another chemical moiety (e.g. another sugar forming an arabinose containing polysaccharide or arabinose bound to lignin). A "galactose compound" is galactose or a galactose-containing compound including at least one galactose moiety. Thus as used herein, the term galactose compound represents a single galactose, a chain including one or more galactose moieties, or a galactose moiety covalently or non-covalently bound to another chemical moiety (e.g. another sugar forming a galactose containing polysaccharide or bound to lignin).

A "sugar" as set forth herein, refers to monosaccharide and polysaccharide compounds metabolized by a yeast cell. In embodiments, a sugar may be a hexose sugar as described herein or a pentose sugar as described herein.

Polysaccharides herein include hexose-only polysaccharides, pentose-only polysaccharides, and hexose-pentose mixture polysaccharides. In embodiments, the xylose compound, the arabinose compound, or the galactose compound may be derived from or form part of a lignocellulosic biomass (e.g. plant dry matter that may used in as a source for pentose compounds or hexose compounds and for production of biofuels or biochemicals), hemicellulose, marine biomass (e.g. seaweeds or algae that may used in as a source for pentose compounds or hexose compounds and for production of biofuels or biochemicals) or other natural or synthetic sources for xylose, arabinose, or galactose, including but not limited to xylan or pectin. "Derived from" refers to extraction, removal, purification, or otherwise freeing a xylose compound, arabinose compound, or galactose compound from a source (e.g. lignocellulosic biomass) by either chemical processes (e.g. acid hydrolysis, ammonium explosion, or ionic liquids extraction) or through natural biological processes by organisms capable of using such sources for energy.

A "xylose growth media" refers to a yeast cell media containing a xylose compound in amounts sufficient to serve as a nutrient for growing or culturing recombinant yeast cells. The term refers to a media substantially free of glucose, and, in embodiments, is "glucose free" (i.e. the media contains no glucose). In embodiments, a xylose growth media includes trace amounts of glucose which are undetectable using known methods and which are insufficient to support significant growth of yeast cells. In embodiments, a xylose growth media includes trace amounts of glucose which are insufficient to cause inhibition of activity of a recombinant transporter protein (e.g. a recombinant xylose transporter protein) as described herein.

A "xylose-glucose growth media" refers to a yeast cell media containing a xylose compound in an amount sufficient to serve as a nutrient for growing or culturing recombinant yeast cells and a glucose compound. The term refers to a media that includes glucose in an amount sufficient to serve as a nutrient for growth or culturing recombinant yeast cells or in an amount sufficient to cause inhibition of activity of a recombinant transporter protein as described herein. The glucose may be present in the xylose-glucose growth media at a pre-determined concentration as described herein.

Xylose growth media and xylose-glucose growth media may be supplemented with other hexoses or pentoses described herein (e.g. mannose, galactose, or arabinose). Growth of a recombinant yeast cell in a xylose growth media may be compared to growth of a recombinant yeast cell in a xylose-glucose growth media. Thus, in embodiments, a recombinant xylose transporter protein may be selected for its xylose selectivity and/or its rate of transfer of a xylose compound into a yeast cell by comparing its growth in xylose growth media to its growth in xylose-glucose growth media. In embodiments, recombinant yeast cells having impaired growth in xylose-glucose growth media may indicate that the recombinant xylose transporter protein in the recombinant yeast is inhibited, at least in part, by glucose.

An "arabinose growth media" refers to a yeast cell media containing an arabinose compound in amounts sufficient to serve as a nutrient for growing or culturing recombinant yeast cells. The term refers to a media substantially free of glucose, and, in embodiments, is "glucose free" (i.e. the media contains no glucose). In embodiments, an arabinose growth media includes trace amounts of glucose which are undetectable using known methods and which are insufficient to support significant growth of yeast cells. In embodiments, an arabinose growth media includes trace amounts of glucose which are insufficient to cause inhibition of activity of a recombinant transporter protein (e.g. a recombinant arabinose transporter protein) as described herein.

An "arabinose-glucose growth media" refers to a yeast cell media containing an arabinose compound in an amount sufficient to serve as a nutrient for growing or culturing recombinant yeast cells and a glucose compound. The term refers to a media that includes glucose in an amount sufficient to serve as a nutrient for growth or culturing recombinant yeast cells or in an amount sufficient to cause inhibition of activity of a recombinant transporter protein as described herein. The glucose may be present in the arabinose-glucose growth media at a pre-determined concentration as described herein.

Arabinose growth media and arabinose-glucose growth media may be supplemented with other hexoses or pentoses described herein (e.g. mannose, galactose, or xylose). Growth of a recombinant yeast cell in an arabinose growth media may be compared to growth of a recombinant yeast cell in an arabinose-glucose growth media. Thus, in embodiments, a recombinant arabinose transporter may be selected for its arabinose selectivity and/or its rate of transfer of an arabinose compound into a yeast cell by comparing its growth in arabinose growth media to its growth in arabinose-glucose growth media. In embodiments, recombinant yeast cells having impaired growth in arabinose-glucose growth media may indicate that the recombinant arabinose transporter protein in the recombinant yeast is inhibited, at least in part, by glucose.

A "galactose growth media" refers to a yeast cell media containing a galactose compound in amounts sufficient to serve as a nutrient for growing or culturing recombinant yeast cells. The term refers to a media substantially free of glucose, and, in embodiments, is "glucose free" (i.e. the media contains no glucose). In embodiments, a galactose growth media includes trace amounts of glucose which are undetectable using known methods and which are insufficient to support significant growth of yeast cells. In embodiments, a galactose growth media includes trace amounts of glucose which are insufficient to cause inhibition of activity of a recombinant transporter protein (e.g. a recombinant galactose transporter protein) as described herein.

A "galactose-glucose growth media" refers to a yeast cell media containing a galactose compound in an amount sufficient to serve as a nutrient for growing or culturing recombinant yeast cells and a glucose compound. The term refers to a media that includes glucose in an amount sufficient to serve as a nutrient for growth or culturing recombinant yeast cells or in an amount sufficient to cause inhibition of activity of a recombinant transporter protein as described herein. The glucose may be present in the galactose-glucose growth media at a pre-determined concentration as described herein.

Galactose growth media and galactose-glucose growth media may be supplemented with other hexoses or pentoses described herein (e.g. mannose, arabinose, or xylose). Growth of a recombinant yeast cell in a galactose growth media may be compared to growth of a recombinant yeast cell in a galactose-glucose growth media. Thus, in embodiments, a recombinant galactose transporter may be selected for its galactose selectivity and/or its rate of transfer of a galactose compound into a yeast cell by comparing its growth in galactose growth media to its growth in galactose-glucose growth media. In embodiments, recombinant yeast cells having impaired growth in galactose-glucose growth media may indicate that the recombinant galactose transporter protein in the recombinant yeast is inhibited, at least in part, by glucose.

As defined herein, the term "inhibition", "inhibit", "inhibiting" and the like refers to negatively affecting (e.g. decreasing) the activity or function of a recombinant transporter protein (e.g. recombinant xylose transporter protein) relative to the activity or function of the protein in the absence of the inhibitor (e.g. glucose). In embodiments, inhibition refers to a reduction in the growth rate of a recombinant yeast cell.

"Contacting" is used in accordance with its plain ordinary meaning and refers to the process of allowing at least two distinct species (e.g. chemical compounds including sugars, biomolecules or cells) to become sufficiently proximal to react, interact or physically touch. The term "contacting" includes allowing two species to react, interact, or physically touch, where the two species may be a sugar as described herein and a recombinant transporter protein as described herein. In embodiments contacting includes allowing a sugar described herein to interact with a recombinant transporter protein that is involved in transporting hexose or pentose compounds into a yeast cell.

I. Compositions

Provided herein are recombinant transporter proteins that include a transporter motif sequence and a glucose mitigation mutation. In one aspect, the recombinant transporter protein is a recombinant xylose transporter protein that includes a xylose transporter motif sequence and a glucose mitigation mutation.

1. Recombinant Xylose Transporter Protein

The xylose transporter motif sequence may correspond to amino acid residue positions 36, 37, 38, 39, 40, and 41 of *Candida intermedia* GXS1 protein (SEQ ID NO: 1). In embodiments, the xylose transporter motif sequence corresponds to amino acid residue positions 36, 37, 38, 39, 40, and 41 of SEQ ID NO:1. The transporter motif sequence may have the sequence -G-G/F-$X^1$-$X^2$-$X^3$-G-. $X^1$ is D, C, G, H, I, L, or F. $X^2$ is A, D, C, E, G, H, or I. $X^3$ is N, C, Q, F, G, L, M, S, T, or P. In embodiments, the transporter motif sequence is not -G-G-L-I-F-G- (SEQ ID NO:105) or -G-G-F-I-F-G- (SEQ ID NO:106).

$X^1$ may be D, C, G, I, L, or F. $X^1$ may be D, C, G, H, or F. $X^1$ may be D. $X^1$ may be C. $X^1$ may be G. $X^1$ may be I. $X^1$ may be L. $X^1$ may be H. $X^1$ may be F. $X^2$ may be D, C, E, G, H, or I. $X^2$ may be E, G, H, or I. $X^2$ may be H or I. $X^2$ may be H. $X^2$ may be I. $X^3$ may be N, Q, F, M, S, T, or P. $X^3$ may be F, M, S, or T. $X^3$ may be S, T, or M. $X^3$ may be T. $X^3$ may be S. $X^3$ may be M. In embodiments, when $X^1$ is F, $X^2$ may be I and $X^3$ may be M or S.

The xylose transporter motif sequence may be -G-G-F-I-M-G- (SEQ ID NO:107), -G-F-F-I-M-G- (SEQ ID NO:108), -G-G-F-I-S-G- (SEQ ID NO:109), -G-F-F-I-S-G- (SEQ ID NO:110), -G-G-F-I-T-G- (SEQ ID NO:111), -G-F-F-I-T-G- (SEQ ID NO:112), -G-G-F-L-M-G- (SEQ ID NO:113), -G-F-F-L-M-G- (SEQ ID NO:114), -G-G-F-L-S-G- (SEQ ID NO:115), -G-F-F-L-S-G- (SEQ ID NO:116), -G-G-F-L-T-G- (SEQ ID NO:117), -G-F-F-L-T-G- (SEQ ID NO:118), -G-G-F-H-M-G- (SEQ ID NO:119), -G-F-F-H-M-G- (SEQ ID NO:120), -G-G-F-H-S-G- (SEQ ID NO:121), -G-F-F-H-S-G- (SEQ ID NO:122), -G-G-F-H-T-G- (SEQ ID NO:123) or -G-F-F-H-T-G- (SEQ ID NO:124). In embodiments, the xylose transporter motif sequence is -G-G-F-I-M-G- (SEQ ID NO:107), -G-F-F-I-M-G- (SEQ ID NO:108), -G-G-F-I-S-G- (SEQ ID NO:109), -G-F-F-I-S-G- (SEQ ID NO:110), -G-G-F-I-T-G- (SEQ ID NO:111), or -G-F-F-I-T-G- (SEQ ID NO:112). In embodiments, the xylose transporter motif sequence is -G-G-F-I-M-G- (SEQ ID NO:107), -G-F-F-I-M-G- (SEQ ID NO:108), -G-G-F-I-S-G- (SEQ ID NO:109), or -G-F-F-I-S-G- (SEQ ID NO:110). In embodiments, the xylose transporter motif sequence is -G-G-F-I-M-G- (SEQ ID NO:107), or -G-F-F-I-M-G- (SEQ ID NO:108). The xylose transporter motif sequence may be -G-G-F-I-M-G- (SEQ ID NO:107). The xylose transporter motif sequence may be -G-F-F-I-M-G- (SEQ ID NO:108). The xylose transporter motif sequence may be -G-G-F-I-S-G- (SEQ ID NO:109). The xylose transporter motif sequence may be -G-F-F-I-S-G- (SEQ ID NO:110). The xylose transporter motif sequence may be -G-G-F-I-T-G- (SEQ ID NO:111). The xylose transporter motif sequence may be -G-F-F-I-T-G- (SEQ ID NO:112). The xylose transporter motif sequence may be -G-G-F-L-M-G- (SEQ ID NO:113). The xylose transporter motif sequence may be -G-F-F-L-M-G- (SEQ ID NO:114). The xylose transporter motif sequence may be -G-G-F-L-S-G- (SEQ ID NO:115). The xylose transporter motif sequence may be -G-F-F-L-S-G- (SEQ ID NO:116). The xylose transporter motif sequence may be -G-G-F-L-T-G- (SEQ ID NO:117). The xylose transporter motif sequence may be -G-F-F-L-T-G- (SEQ ID NO:118). The xylose transporter motif sequence may be -G-G-F-H-M-G- (SEQ ID NO:119). The xylose transporter motif sequence may be -G-F-F-H-M-G- (SEQ ID NO:120). The xylose transporter motif sequence may be -G-G-F-H-S-G- (SEQ ID NO:121). The xylose transporter motif sequence may be -G-F-F-H-S-G- (SEQ ID NO:122). The xylose transporter motif sequence may be -G-G-F-H-T-G- (SEQ ID NO:123). The xylose transporter motif sequence may be -G-F-F-H-T-G- (SEQ ID NO:124).

The glucose mitigation mutation may be within a protein domain corresponding to a transmembrane of a recombinant transporter protein (e.g. one or more of transmembrane domains 1-12). The glucose mitigation mutation may be within two or more protein domains corresponding to transmembranes of a recombinant transporter protein. The glucose mitigation mutation may be within a protein domain corresponding to a transmembrane of *Candida intermedia* GXS1 protein. The transmembrane may be a protein domain corresponding to transmembrane 1, 2, 3, 4, 5, 6, 7, 8, 9, 10, 11, or 12 of *Candida intermedia* GXS1 protein. The transmembrane may be a protein domain corresponding to a transmembrane a protein of SEQ ID NO:51-104. The glucose mitigation mutation may be within a protein domain corresponding to transmembrane 1 of *Candida intermedia* GXS1 protein. The glucose mitigation mutation may be within a protein domain corresponding to transmembrane 2 of *Candida intermedia* GXS1 protein. The glucose mitigation mutation may be within a protein domain corresponding to transmembrane 3 of *Candida intermedia* GXS1 protein. The glucose mitigation mutation may be within a protein domain corresponding to transmembrane 4 of *Candida intermedia* GXS1 protein. The glucose mitigation mutation may be within a protein domain corresponding to transmembrane 5 of *Candida intermedia* GXS1 protein.

In embodiments, the glucose mitigation mutation is within a protein domain corresponding to transmembrane 5 of SEQ ID NO:1. In embodiments, the glucose mitigation mutation is within a protein domain corresponding to residue 160-179 of SEQ ID NO:1. In embodiments, the glucose mitigation mutation is at a position corresponding to T170 or I171 of SEQ ID NO:1. In embodiments, the glucose mitigation mutation is a T170N mutation. In embodiments, the glucose mitigation mutation is a I171F mutation.

The glucose mitigation mutation may be within a protein domain corresponding to transmembrane 6 of *Candida intermedia* GXS1 protein. The glucose mitigation mutation may be within a protein domain corresponding to transmembrane 7 of *Candida intermedia* GXS1 protein. The glucose mitigation mutation may be within a protein domain corresponding to transmembrane 8 of *Candida intermedia* GXS1 protein. The glucose mitigation mutation may be within a protein domain corresponding to transmembrane 9 of *Candida intermedia* GXS1 protein. The glucose mitigation mutation may be within a protein domain corresponding to transmembrane 8 or 9 of *Candida intermedia* GXS1 protein. The glucose mitigation mutation may be within a protein domain corresponding to transmembrane 8 and 9 of *Candida intermedia* GXS1 protein (e.g. amino acid residues about 347 to about 366 of *Candida intermedia* GXS1 amino acid sequence (SEQ ID NO: 1)). The glucose mitigation mutation may be within a protein domain corresponding to transmembrane 10 of *Candida intermedia* GXS1 protein. The glucose mitigation mutation may be within a protein domain corresponding to transmembrane 11 of *Candida intermedia* GXS1 protein. The glucose mitigation mutation may be within a protein domain corresponding to transmembrane 12 of *Candida intermedia* GXS1 protein. The glucose mitigation mutation may be within a protein domain corresponding to transmembrane 9 of *Candida intermedia* GXS1.

In embodiments, the glucose mitigation mutation is within a protein domain corresponding to an extracellular domain of *Candida intermedia* GXS1 protein. The glucose mitigation mutation may be in a protein domain corresponding to the 11-12 extracellular domain of *Candida intermedia* GXS1 protein. The glucose mitigation mutation may be within a protein domain corresponding to a cytoplasmic domain (i.e. intracellular) of *Candida intermedia* GXS1 protein. In embodiments, the glucose mitigation mutation is in a protein domain corresponding to the 4-5 cytoplasmic domain (i.e. an intracellular domain between protein domains corresponding to transmembranes 4 and 5 of *Candida intermedia* GXS1 protein); the central cytoplasmic domain (i.e. an intracellular domain between protein domains corresponding to transmembranes 6 and 7 of *Candida intermedia* GXS1 protein); or the 10-11 cytoplasmic domain (i.e. an intracellular domain between protein domains corresponding to transmembranes 10 and 11 of *Candida intermedia* GXS1 protein) of *Candida intermedia* GXS1 protein.

The glucose mitigation mutation may be at a position corresponding to K155, T170, I171, N225, S354, A361, L407, or N446 of *Candida intermedia* GXS1 protein. The glucose mitigation mutation may be at a position corresponding to T170 of *Candida intermedia* GXS1 protein. The glucose mitigation mutation may be at a position corresponding to I171 of *Candida intermedia* GXS1 protein. The glucose mitigation mutation may be at a position corresponding to K155 of *Candida intermedia* GXS1 protein. The glucose mitigation mutation may be a conservative mutation at position 155 as described herein. In embodiments, the glucose mitigation mutation is a K155E mutation. The glucose mitigation mutation may be at a position corresponding to N225 of *Candida intermedia* GXS1 protein. The glucose mitigation mutation may be a conservative mutation at position 225 as described herein. In embodiments, the glucose mitigation mutation is a N225D mutation. The glucose mitigation mutation may be at a position corresponding to S354 of *Candida intermedia* GXS1 protein. The glucose mitigation mutation may be a conservative mutation at position 354 as described herein. In embodiments, the glucose mitigation mutation is a S354T mutation. The glucose mitigation mutation may be at a position corresponding to A361 of *Candida intermedia* GXS1 protein. The glucose mitigation mutation may be a conservative mutation at position 361 as described herein. In embodiments, the glucose mitigation mutation is a A361T mutation. The glucose mitigation mutation may be at a position corresponding to L407 of *Candida intermedia* GXS1 protein. The glucose mitigation mutation may be a conservative mutation at position 407 as described herein. In embodiments, the glucose mitigation mutation is a L407M mutation. The glucose mitigation mutation may be at a position corresponding to N446 of *Candida intermedia* GXS1 protein. The glucose mitigation mutation may be a conservative mutation at position 446 as described herein. In embodiments, the glucose mitigation mutation is a N446S mutation. The glucose mitigation mutation may be at a position corresponding to N326 of *Candida intermedia* GXS1 protein. The glucose mitigation mutation may be a conservative mutation at position 326 as described herein. In embodiments, the glucose mitigation mutation is a N326S mutation. In embodiments, the glucose mitigation mutation is a N326H mutation.

The glucose mitigation mutation may include two or more positions corresponding to K155, T170, I171, N225, N326, S354, A361, L407, or N446 of *Candida intermedia* GXS1 protein as described hereinabove. The glucose mitigation mutation may include three or more positions corresponding to K155, T170, I171, N225, N326, S354, A361, L407, or N446 of *Candida intermedia* GXS1 protein as described hereinabove. The glucose mitigation mutation may include four or more positions corresponding to K155, T170, I171, N225, N326, S354, A361, L407, or N446 of *Candida intermedia* GXS1 protein as described hereinabove. The glucose mitigation mutation may include five or more positions corresponding to K155, T170, I171, N225, N326, S354, A361, L407, or N446 of *Candida intermedia* GXS1 protein as described hereinabove. The glucose mitigation mutation may include six or more positions corresponding to K155, T170, I171, N225, N326, S354, A361, L407, or N446 of *Candida intermedia* GXS1 protein as described hereinabove. The glucose mitigation mutation may include mutation at positions corresponding to K155, T170, I171, N225, N326, S354, A361, L407, and N446 of *Candida intermedia* GXS1 protein as described hereinabove. The glucose mitigation mutation may include mutation at positions corresponding to K155, T170, I171, N225, S354, A361, L407, and N446 of *Candida intermedia* GXS1 protein as described hereinabove.

The recombinant xylose transporter protein provided herein including embodiments thereof may further include an amino acid deletion. An amino acid deletion as provided herein is a deletion of at least one amino acid residue of a *Candida intermedia* GXS1 protein as described hereinabove. Thus, the sequence of a *Candida intermedia* GXS1 protein including an amino acid deletion includes at least one amino acid residue less relative to the sequence of a *Candida intermedia* GXS1 protein lacking said deletion. In embodiments, the deletion is at least 5 amino acids in length. In embodiments, the deletion is at least 10 amino acids in length. In embodiments, the deletion is at least 15 amino acids in length. In embodiments, the deletion is at least 20 amino acids in length. In embodiments, the deletion is at least 25 amino acids in length. In embodiments, the deletion is at least 30 amino acids in length. In embodiments, the deletion is at least 35 amino acids in length. In embodiments, the deletion is at least 40 amino acids in length. In embodiments, the deletion is at least 45 amino acids in length. In embodiments, the deletion is at least 50 amino acids in length. In embodiments, the deletion is at least 55 amino acids in length. In embodiments, the deletion is at least 60 amino acids in length. In embodiments, the deletion is at least 65 amino acids in length. In embodiments, the deletion is at least 70 amino acids in length. In embodiments, the deletion is at least 75 amino acids in length. In embodiments, the deletion is at least 80 amino acids in length. In embodiments, the deletion is at least 85 amino acids in length. In embodiments, the deletion is at least 90 amino acids in length. In embodiments, the deletion is at least 95 amino acids in length. In embodiments, the deletion is at least 100 amino acids in length.

In embodiments, the deletion is less than 50 amino acids in length. In embodiments, the deletion is less than 45 amino acids in length. In embodiments, the deletion is less than 40 amino acids in length. In embodiments, the deletion is less than 35 amino acids in length. In embodiments, the deletion is less than 30 amino acids in length. In embodiments, the deletion is less than 25 amino acids in length. In embodiments, the deletion is less than 20 amino acids in length. In embodiments, the deletion is less than 15 amino acids in length. In embodiments, the deletion is less than 10 amino acids in length. In embodiments, the deletion is within a protein domain corresponding to residue 497-522 of SEQ ID NO:1. In embodiments, the deletion is within a protein domain corresponding to residue 497-522 of a *Candida intermedia* GXS1 protein as described hereinabove.

2. Recombinant Arabinose Transporter Protein

Also provided herein is a recombinant arabinose transporter protein that includes an arabinose transporter motif sequence and a glucose mitigation mutation.

The arabinose transporter motif sequence may correspond to residue positions 36, 37, 38, 39, 40, and 41 of *Candida intermedia* GXS1 protein. The arabinose transporter motif sequence may have the sequence -G-G/F-$X^4$-$X^5$-$X^6$-G-. $X^4$ is D, C, F, G, H, L, R, T, or P. $X^5$ is A, C, E, F, H, K, S, P, or V. $X^6$ is R, D, E, F, H, I, M, T, or Y. In embodiments, the arabinose transporter is not -G-G-L-V-Y-G- (SEQ ID NO:125), or -G-G-F-V-F-G- (SEQ ID NO:126).

$X^4$ may be D, F, G, L, R, or T. $X^4$ may be R, T, H, or F. $X^4$ may be R. $X^4$ may be T. $X^4$ may be H. $X^4$ may be F. $X^5$ may be A, E, F, P, H, or V. $X^5$ may be P, H, or V. $X^5$ may be P. $X^5$ may be H. $X^5$ may be V. $X^6$ may be T, H, F, M, or Y. $X^6$ may be F or Y. $X^6$ may be T or M. $X^6$ may be T. $X^6$ may be H. $X^6$ may be F. $X^6$ may be M. $X^6$ may be Y. In embodiments, $X^4$ is F or T, $X^5$ is P or I, and $X^6$ is M or T.

The arabinose transporter motif sequence may be -G-G-F-H-M-G- (SEQ ID NO:119), -G-F-F-H-M-G- (SEQ ID NO:120), -G-G-R-P-T-G- (SEQ ID NO:127), -G-F-R-P-T-G- (SEQ ID NO:128), -G-G-T-P-T-G- (SEQ ID NO:129), or -G-F-T-P-T-G- (SEQ ID NO:130). The arabinose transporter motif sequence may be -G-G-F-H-M-G- (SEQ ID NO:119), or -G-F-F-H-M-G- (SEQ ID NO:120). The arabinose transporter motif sequence may be -G-G-R-P-T-G- (SEQ ID NO:127), -G-F-R-P-T-G- (SEQ ID NO:128). The arabinose transporter motif sequence may be -G-G-T-P-T-G- (SEQ ID NO:129) or -G-F-T-P-T-G- (SEQ ID NO:130). The arabinose transporter motif sequence may be -G-G-F-H-M-G- (SEQ ID NO:119). The arabinose transporter motif sequence may be -G-F-F-H-M-G- (SEQ ID NO:120). The arabinose transporter motif sequence may be -G-G-R-P-T-G- (SEQ ID NO:127). The arabinose transporter motif sequence may be -G-F-R-P-T-G- (SEQ ID NO:128). The arabinose transporter motif sequence may be -G-G-T-P-T-G- (SEQ ID NO:129). The arabinose transporter motif sequence may be -G-F-T-P-T-G- (SEQ ID NO:130).

The glucose mitigation mutation of the recombinant arabinose transporter protein is as described hereinabove for the "recombinant xylose transporter protein" and includes embodiments thereof.

3. Recombinant Galactose Transporter Protein

Provided herein is a recombinant galactose transporter protein that includes an galactose transporter motif sequence and a glucose mitigation mutation.

The galactose transporter motif sequence is as described hereinabove for the "arabinose transporter motif sequence" and includes embodiments thereof. The glucose mitigation mutation of the recombinant arabinose transporter protein is as described hereinabove for the "recombinant xylose transporter protein" and includes embodiments thereof.

Also provided herein is a recombinant galactose-arabinose transporter protein that includes a galactose-arabinose transporter motif sequence and a glucose mitigation mutation. The galactose-arabinose transporter motif sequence may be as described hereinabove for the "arabinose transporter motif sequence" and includes embodiments thereof. The glucose mitigation mutation of the recombinant galactose-arabinose transporter protein is as described hereinabove for the "recombinant xylose transporter protein" and includes embodiments thereof.

II. Nucleic Acids

In another aspect is a nucleic acid encoding a recombinant xylose transporter protein described herein, including embodiments thereof. In yet another aspect is a nucleic acid encoding a recombinant arabinose transporter protein described herein, including embodiments thereof. In still another aspect is a nucleic acid encoding a recombinant galactose transporter protein described herein, including embodiments thereof. In another aspect is a nucleic acid encoding a recombinant galactose-arabinose transporter protein described herein, including embodiments thereof. The nucleic acids may be RNA or DNA. The nucleic acids may be cDNA. The nucleic acids may be single- or double-stranded RNA or single- or double-stranded DNA. The nucleic acids may be located on a plasmid or other vector. The nucleic acids may be introduced and expressed by a yeast cell using conventional techniques known to those in the art.

III. Recombinant Yeast Cells

Provided herein are recombinant yeast cells that include a recombinant transporter protein as described herein, including embodiments thereof. Also provided herein are recombinant yeast cells that include a nucleic acid encoding a recombinant xylose transporter protein described herein, including embodiments thereof.

1. Recombinant Yeast Cell Including a Recombinant Xylose Transporter Protein

In one aspect is a recombinant yeast cell that includes a recombinant xylose transporter protein as described herein, including embodiments thereof. In embodiments, the growth rate of the recombinant yeast cell including a recombinant transporter protein as described herein can be measured. The growth rate may be determined in xylose growth media (i.e. in the absence of glucose). The growth rate may be determined in xylose-glucose growth media. In embodiments, the growth rates (i.e. growth rate in the absence and presence of glucose) are compared to determine the differential growth rate of the recombinant yeast cells. If the growth rate of recombinant yeast cells grown in xylose-glucose growth media is less than the growth rate of recombinant yeast cells grown in xylose growth media, the differential growth rate may indicate the presence of glucose inhibition of the recombinant transporter protein. As described herein, inclusion of a glucose mitigating mutation decreases, minimizes, or may eliminate glucose inhibition of a recombinant xylose transporter protein.

In embodiments, the growth rate of the recombinant yeast cell in a xylose-glucose growth media is about 5% to about 150% of the growth rate of the recombinant yeast cell in xylose growth media. The growth rate of the recombinant yeast cell in a xylose-glucose growth media may be about 5% to about 140% of the growth rate of the recombinant yeast cell in xylose growth media. The growth rate of the recombinant yeast cell in a xylose-glucose growth media may be about 5% to about 130% of the growth rate of the recombinant yeast cell in xylose growth media. The growth rate of the recombinant yeast cell in a xylose-glucose growth media may be about 5% to about 120% of the growth rate of the recombinant yeast cell in xylose growth media. The growth rate of the recombinant yeast cell in a xylose-glucose growth media may be about 5% to about 110% of the growth rate of the recombinant yeast cell in xylose growth media.

The growth rate of the recombinant yeast cell in a xylose-glucose growth media may be about 5% to about 100% of the growth rate of the recombinant yeast cell in xylose growth media. The growth rate of the recombinant yeast cell in a xylose-glucose growth media may be about 5% to about 90% of the growth rate of the recombinant yeast cell in xylose growth media. The growth rate of the recombinant yeast cell in a xylose-glucose growth media may be about 5% to about 80% of the growth rate of the recombinant yeast cell in xylose growth media. The growth rate of the recombinant yeast cell in a xylose-glucose growth media may be about 5% to about 70% of the growth rate of the recombinant yeast cell in xylose growth media. The growth rate of the recombinant yeast cell in a xylose-glucose growth media may be about 5% to about 60% of the growth rate of the recombinant yeast cell in xylose growth media. The growth rate of the recombinant yeast cell in a xylose-glucose growth media may be about 5% to about 50% of the growth rate of the recombinant yeast cell in xylose growth media. The growth rate of the recombinant yeast cell in a xylose-glucose growth media may be about 5% to about 40% of the growth rate of the recombinant yeast cell in xylose growth media. The growth rate of the recombinant yeast cell in a xylose-glucose growth media may be about 5% to about 30% of the growth rate of the recombinant yeast cell in xylose growth media. The growth rate of the recombinant yeast cell in a xylose-glucose growth media may be about 5% to about 20% of the growth rate of the recombinant yeast cell in xylose growth media. The growth rate of the recombinant yeast cell in a xylose-glucose growth media may be about 5% to about 10% of the growth rate of the recombinant yeast cell in xylose growth media.

The growth rate of the recombinant yeast cell in a xylose-glucose growth media may be about 10% to about 150% of the growth rate of the recombinant yeast cell in xylose growth media. The growth rate of the recombinant yeast cell in a xylose-glucose growth media may be about 10% to about 140% of the growth rate of the recombinant yeast cell in xylose growth media. The growth rate of the recombinant yeast cell in a xylose-glucose growth media may be about 10% to about 130% of the growth rate of the recombinant yeast cell in xylose growth media. The growth rate of the recombinant yeast cell in a xylose-glucose growth media may be about 10% to about 120% of the growth rate of the recombinant yeast cell in xylose growth media. The growth rate of the recombinant yeast cell in a xylose-glucose growth media may be about 10% to about 110% of the growth rate of the recombinant yeast cell in xylose growth media.

The growth rate of the recombinant yeast cell in a xylose-glucose growth media may be about 10% to about 100% of the growth rate of the recombinant yeast cell in xylose growth media. The growth rate of the recombinant yeast cell in a xylose-glucose growth media may be about 10% to about 90% of the growth rate of the recombinant yeast cell in xylose growth media. The growth rate of the recombinant yeast cell in a xylose-glucose growth media may be about 10% to about 80% of the growth rate of the recombinant yeast cell in xylose growth media. The growth rate of the recombinant yeast cell in a xylose-glucose growth media may be about 10% to about 70% of the growth rate of the recombinant yeast cell in xylose growth media. The growth rate of the recombinant yeast cell in a xylose-glucose growth media may be about 10% to about 60% of the growth rate of the recombinant yeast cell in xylose growth media. The growth rate of the recombinant yeast cell in a xylose-glucose growth media may be about 10% to about 50% of the growth rate of the recombinant yeast cell in xylose growth media. The growth rate of the recombinant yeast cell in a xylose-glucose growth media may be about 10% to about 40% of the growth rate of the recombinant yeast cell in xylose growth media. The growth rate of the recombinant yeast cell in a xylose-glucose growth media may be about 10% to about 30% of the growth rate of the recombinant yeast cell in xylose growth media. The growth rate of the recombinant yeast cell in a xylose-glucose growth media may be about 10% to about 20% of the growth rate of the recombinant yeast cell in xylose growth media.

The growth rate of the recombinant yeast cell in a xylose-glucose growth media may be about 5% of the growth rate of the recombinant yeast cell in xylose growth media. The growth rate of the recombinant yeast cell in a xylose-glucose growth media may be about 10% of the growth rate of the recombinant yeast cell in xylose growth media. The growth rate of the recombinant yeast cell in a xylose-glucose growth media may be about 20% of the growth rate of the recombinant yeast cell in xylose growth media. The growth rate of the recombinant yeast cell in a xylose-glucose growth media may be about 30% of the growth rate of the recombinant yeast cell in xylose growth media. The growth rate of the recombinant yeast cell in a xylose-glucose growth media may be about 40% of the growth rate of the recombinant yeast cell in xylose growth media. The growth rate of the recombinant yeast cell in a xylose-glucose growth media may be about 50% of the growth rate of the recombinant yeast cell in xylose growth media. The growth rate of the recombinant yeast cell in a xylose-glucose growth media may be about 60% of the growth rate of the recombinant yeast cell in xylose growth media. The growth rate of the recombinant yeast cell in a xylose-glucose growth media may be about 70% of the growth rate of the recombinant yeast cell in xylose growth media. The growth rate of the recombinant yeast cell in a xylose-glucose growth media may be about 80% of the growth rate of the recombinant yeast cell in xylose growth media. The growth rate of the recombinant yeast cell in a xylose-glucose growth media may be about 90% of the growth rate of the recombinant yeast cell in xylose growth media. The growth rate of the recombinant yeast cell in a xylose-glucose growth media may be about 100% of the growth rate of the recombinant yeast cell in xylose growth media. The growth rate of the recombinant yeast cell in a xylose-glucose growth media may be about equal to the growth rate of the recombinant yeast cell in xylose growth media. Thus, in embodiments, the growth rate of the recombinant yeast cell is not inhibited in the presence of glucose. The growth rate of the recombinant yeast cell in a xylose-glucose growth media may be greater than the growth rate of the recombinant yeast cell in xylose growth media.

The growth rate of the recombinant yeast cell in a xylose-glucose growth media may be about 110% of the growth rate of the recombinant yeast cell in xylose growth media. The growth rate of the recombinant yeast cell in a xylose-glucose growth media may be about 120% of the growth rate of the recombinant yeast cell in xylose growth media. The growth rate of the recombinant yeast cell in a xylose-glucose growth media may be about 130% of the growth rate of the recombinant yeast cell in xylose growth media. The growth rate of the recombinant yeast cell in a xylose-glucose growth media may be about 140% of the growth rate of the recombinant yeast cell in xylose growth media. The growth rate of the recombinant yeast cell in a xylose-glucose growth media may be about 150% of the growth rate of the recombinant yeast cell in xylose growth media. The growth rate of the recombinant yeast cell in a xylose-glucose growth media may be about 160% of the growth rate of the recombinant yeast cell in xylose growth media. The growth rate of the recombinant yeast cell in a xylose-glucose growth media may be about 170% of the growth rate of the recombinant yeast cell in xylose growth media. The growth rate of the recombinant yeast cell in a xylose-glucose growth media may be about 180% of the growth rate of the recombinant yeast cell in xylose growth media. The growth rate of the recombinant yeast cell in a xylose-glucose growth media may be about 190% of the growth rate of the recombinant yeast cell in xylose growth media. The growth rate of the recombinant yeast cell in a xylose-glucose growth media may be about 200% of the growth rate of the recombinant yeast cell in xylose growth media.

In embodiments, the recombinant yeast cells have a growth rate of about $0.005$ $hr^{-1}$ to about $0.05$ $hr^{-1}$. The recombinant yeast cells may have a growth rate of about $0.005$ $hr^{-1}$ to about $0.04$ $hr^{-1}$. The recombinant yeast cells may have a growth rate of about $0.005$ $hr^{-1}$ to about $0.03$ $hr^{-1}$. The recombinant yeast cells may have a growth rate of about $0.005$ $hr^{-1}$ to about $0.025$ $hr^{-1}$. The recombinant yeast cells may have a growth rate of about $0.005$ $hr^{-1}$ to about $0.0225$ $hr^{-1}$. The recombinant yeast cells may have a growth rate of about $0.005$ $hr^{-1}$ to about $0.02$ $hr^{-1}$. The recombinant yeast cells may have a growth rate of about $0.005$ $hr^{-1}$ to about $0.0175$ $hr^{-1}$. The recombinant yeast cells may have a growth rate of about $0.005$ $hr^{-1}$ to about $0.015$ $hr^{-1}$. The recombinant yeast cells may have a growth rate of about $0.005$ $hr^{-1}$ to about $0.0125$ $hr^{-1}$. The recombinant yeast cells may have a growth rate of about $0.005$ $hr^{-1}$ to about $0.01$ $hr^{-1}$. The recombinant yeast cells may have a growth rate of about $0.005$ $hr^{-1}$ to about $0.0075$ $hr^{-1}$. In embodiments, the recombinant yeast cells are cultured in a xylose growth media and the growth rate is measured in the xylose growth media. In embodiments, the recombinant yeast cells are cultured in lignocellulosic biomass, hemicellulose, or xylan and the growth rate is measured in the lignocellulosic biomass, hemicellulose, or xylan respectively.

In embodiments, the recombinant yeast cells have a growth rate of about $0.005$ $hr^{-1}$. The recombinant yeast cells may have a growth rate of about $0.0075$ $hr^{-1}$. The recombinant yeast cells may have a growth rate of about $0.01$ $hr^{-1}$. The recombinant yeast cells may have a growth rate of about $0.0125$ $hr^{-1}$. The recombinant yeast cells may have a growth rate of about $0.015$ $hr^{-1}$. The recombinant yeast cells may have a growth rate of about $0.0175$ $hr^{-1}$. The recombinant yeast cells may have a growth rate of about $0.02$ $hr^{-1}$. The recombinant yeast cells may have a growth rate of about $0.0225$ $hr^{-1}$. The recombinant yeast cells may have a growth rate of about $0.025$ $hr^{-1}$. The recombinant yeast cells may have a growth rate of about $0.0275$ $hr^{-1}$. The recombinant yeast cells may have a growth rate of about $0.03$ $hr^{-1}$. The recombinant yeast cells may have a growth rate of about $0.0325$ $hr^{-1}$. The recombinant yeast cells may have a growth rate of about $0.035$ $hr^{-1}$. The recombinant yeast cells may have a growth rate of about $0.0375$ $hr^{-1}$. The recombinant yeast cells may have a growth rate of about $0.04$ $hr^{-1}$. The recombinant yeast cells may have a growth rate of about $0.0425$ $hr^{-1}$. The recombinant yeast cells may have a growth rate of about $0.045$ $hr^{-1}$. The recombinant yeast cells may have a growth rate of about $0.0475$ $hr^{-1}$. The recombinant yeast cells may have a growth rate of about $0.05$ $hr^{-1}$. In embodiments, the recombinant yeast cells are cultured in a xylose growth media and the growth rate is measured in the xylose growth media. In embodiments, the recombinant yeast cells are cultured in lignocellulosic biomass, hemicellulose, or xylan and the growth rate is measured in the lignocellulosic biomass, hemicellulose, or xylan respectively.

In embodiments, the recombinant yeast cells have a growth rate of about $0.05$ $hr^{-1}$ to about $0.1$ $hr^{-1}$. The recombinant yeast cells may have a growth rate of about $0.05$ $hr^{-1}$ to about $0.125$ $hr^{-1}$. The recombinant yeast cells may have a growth rate of about $0.05$ $hr^{-1}$ to about $0.15$ $hr^{-1}$. The recombinant yeast cells may have a growth rate of about $0.05$ $hr^{-1}$ to about $0.175$ $hr^{-1}$. The recombinant yeast cells may have a growth rate of about 0.05 hr$^{-1}$ to about 0.2 hr$^{-1}$. The recombinant yeast cells may have a growth rate of about 0.05 hr$^{-1}$ to about 0.225 hr$^{-1}$. The recombinant yeast cells may have a growth rate of about 0.05 hr$^{-1}$ to about 0.25 hr$^{-1}$. The recombinant yeast cells may have a growth rate of about 0.05 hr$^{-1}$ to about 0.275 hr$^{-1}$. The recombinant yeast cells may have a growth rate of about 0.05 hr$^{-1}$ to about 0.3 hr$^{-1}$. The recombinant yeast cells may have a growth rate of about 0.05 hr$^{-1}$ to about 0.325 hr$^{-1}$. The recombinant yeast cells may have a growth rate of about 0.05 hr$^{-1}$ to about 0.35 hr$^{-1}$. The recombinant yeast cells may have a growth rate of about 0.05 hr$^{-1}$ to about 0.375 hr$^{-1}$. The recombinant yeast cells may have a growth rate of about 0.05 hr$^{-1}$ to about 0.4 hr$^{-1}$. The recombinant yeast cells may have a growth rate of about 0.05 hr$^{-1}$ to about 0.425 hr$^{-1}$. The recombinant yeast cells may have a growth rate of about 0.05 hr$^{-1}$ to about 0.45 hr$^{-1}$. The recombinant yeast cells may have a growth rate of about 0.05 hr$^{-1}$ to about 0.475 hr$^{-1}$. The recombinant yeast cells may have a growth rate of about 0.05 hr$^{-1}$ to about 0.5 hr$^{-1}$. The recombinant yeast cells may have a growth rate of about 0.05 hr$^{-1}$ to about 0.525 hr$^{-1}$. The recombinant yeast cells may have a growth rate of about 0.05 hr$^{-1}$ to about 0.5 hr$^{-1}$. The recombinant yeast cells may have a growth rate of about 0.05 hr$^{-1}$ to about 0.575 hr$^{-1}$. The recombinant yeast cells may have a growth rate of about 0.05 hr$^{-1}$ to about 0.6 hr$^{-1}$. The recombinant yeast cells may have a growth rate of about 0.05 hr$^{-1}$ to about 0.65 hr$^{-1}$. The recombinant yeast cells may have a growth rate of about 0.05 hr$^{-1}$ to about 0.7 hr$^{-1}$. The recombinant yeast cells may have a growth rate of about 0.05 hr$^{-1}$ to about 0.75 hr$^{-1}$. The recombinant yeast cells may have a growth rate of about 0.05 hr$^{-1}$ to about 0.8 hr$^{-1}$. The recombinant yeast cells may have a growth rate of about 0.05 hr$^{-1}$ to about 0.85 hr$^{-1}$. The recombinant yeast cells may have a growth rate of about 0.05 hr$^{-1}$ to about 0.9 hr$^{-1}$. The recombinant yeast cells may have a growth rate of about 0.05 hr$^{-1}$ to about 0.95 hr$^{-1}$. The recombinant yeast cells may have a growth rate of about 0.05 hr$^{-1}$ to about 1 hr$^{-1}$. In embodiments, the recombinant yeast cells are cultured in a xylose growth media and the growth rate is measured in the xylose growth media. In embodiments, the recombinant yeast cells are cultured in lignocellulosic biomass, hemicellulose, or xylan and the growth rate is measured in the lignocellulosic biomass, hemicellulose, or xylan respectively.

In embodiments, the recombinant yeast cells have a growth rate of about 0.1 hr$^{-1}$. The recombinant yeast cells may have a growth rate of about 0.125 hr$^{-1}$. The recombinant yeast cells may have a growth rate of about 0.15 hr$^{-1}$. The recombinant yeast cells may have a growth rate of about 0.175 hr$^{-1}$. The recombinant yeast cells may have a growth rate of about 0.2 hr$^{-1}$. The recombinant yeast cells may have a growth rate of about 0.225 hr$^{-1}$. The recombinant yeast cells may have a growth rate of about 0.25 hr$^{-1}$. The recombinant yeast cells may have a growth rate of about 0.275 hr$^{-1}$. The recombinant yeast cells may have a growth rate of about 0.3 hr$^{-1}$. The recombinant yeast cells may have a growth rate of about 0.325 hr$^{-1}$. The recombinant yeast cells may have a growth rate of about 0.35 hr$^{-1}$. The recombinant yeast cells may have a growth rate of about 0.375 hr$^{-1}$. The recombinant yeast cells may have a growth rate of about 0.4 hr$^{-1}$. The recombinant yeast cells may have a growth rate of about 0.425 hr$^{-1}$. The recombinant yeast cells may have a growth rate of about 0.45 hr$^{-1}$. The recombinant yeast cells may have a growth rate of about 0.475 hr$^{-1}$. The recombinant yeast cells may have a growth rate of about 0.5 hr$^{-1}$. The recombinant yeast cells may have a growth rate of about 0.525 hr$^{-1}$. The recombinant yeast cells may have a growth rate of about 0.5 hr$^{-1}$. The recombinant yeast cells may have a growth rate of about 0.575 hr$^{-1}$. The recombinant yeast cells may have a growth rate of about 0.6 hr$^{-1}$. The recombinant yeast cells may have a growth rate of about 0.65 hr$^{-1}$. The recombinant yeast cells may have a growth rate of about 0.7 hr$^{-1}$. The recombinant yeast cells may have a growth rate of about 0.75 hr$^{-1}$. The recombinant yeast cells may have a growth rate of about 0.8 hr$^{-1}$. The recombinant yeast cells may have a growth rate of about 0.85 hr$^{-1}$. The recombinant yeast cells may have a growth rate of about 0.9 hr$^{-1}$. The recombinant yeast cells may have a growth rate of about 0.95 hr$^{-1}$. The recombinant yeast cells may have a growth rate of about 1 hr$^{-1}$. In embodiments, the recombinant yeast cells are cultured in a xylose growth media and the growth rate is measured in the xylose growth media. In embodiments, the recombinant yeast cells are cultured in lignocellulosic biomass, hemicellulose, or xylan and the growth rate is measured in the lignocellulosic biomass, hemicellulose, or xylan respectively.

The recombinant yeast cells may have a growth rate of about 0.005 hr$^{-1}$ in xylose-glucose growth media that includes 2.5 g/L glucose. The recombinant yeast cells may have a growth rate of about 0.0075 hr$^{-1}$ in xylose-glucose growth media that includes 2.5 g/L glucose. The recombinant yeast cells may have a growth rate of about 0.01 hr$^{-1}$ in xylose-glucose growth media that includes 2.5 g/L glucose. The recombinant yeast cells may have a growth rate of about 0.0125 hr$^{-1}$ in xylose-glucose growth media that includes 2.5 g/L glucose. The recombinant yeast cells may have a growth rate of about 0.015 hr$^{-1}$ in xylose-glucose growth media that includes 2.5 g/L glucose. The recombinant yeast cells may have a growth rate of about 0.0175 hr$^{-1}$ in xylose-glucose growth media that includes 2.5 g/L glucose. The recombinant yeast cells may have a growth rate of about 0.02 hr$^{-1}$ in xylose-glucose growth media that includes 2.5 g/L glucose. The recombinant yeast cells may have a growth rate of about 0.0225 hr$^{-1}$ in xylose-glucose growth media that includes 2.5 g/L glucose. The recombinant yeast cells may have a growth rate of about 0.025 hr$^{-1}$ in xylose-glucose growth media that includes 2.5 g/L glucose. The recombinant yeast cells may have a growth rate of about 0.0275 hr$^{-1}$ in xylose-glucose growth media that includes 2.5 g/L glucose. The recombinant yeast cells may have a growth rate of about 0.03 hr$^{-1}$ in xylose-glucose growth media that includes 2.5 g/L glucose. The recombinant yeast cells may have a growth rate of about 0.0325 hr$^{-1}$ in xylose-glucose growth media that includes 2.5 g/L glucose. The recombinant yeast cells may have a growth rate of about 0.035 hr$^{-1}$ in xylose-glucose growth media that includes 2.5 g/L glucose. The recombinant yeast cells may have a growth rate of about 0.0375 hr$^{-1}$ in xylose-glucose growth media that includes 2.5 g/L glucose. The recombinant yeast cells may have a growth rate of about 0.04 hr$^{-1}$ in xylose-glucose growth media that includes 2.5 g/L glucose. The recombinant yeast cells may have a growth rate of about 0.0425 hr$^{-1}$ in xylose-glucose growth media that includes 2.5 g/L glucose. The recombinant yeast cells may have a growth rate of about 0.045 hr$^{-1}$. The recombinant yeast cells may have a growth rate of about 0.0475 hr$^{-1}$ in xylose-glucose growth media that includes 2.5 g/L glucose. The recombinant yeast cells may have a growth rate of about 0.05 hr$^{-1}$ in xylose-glucose growth media that includes 2.5 g/L glucose.

In embodiments, the recombinant yeast cells have a growth rate of about 0.1 hr$^{-1}$ in xylose-glucose growth media that includes 2.5 g/L glucose. The recombinant yeast cells may have a growth rate of about 0.125 hr$^{-1}$ in xylose-glucose growth media that includes 2.5 g/L glucose. The recombinant yeast cells may have a growth rate of about 0.15 hr$^{-1}$ in xylose-glucose growth media that includes 2.5 g/L glucose. The recombinant yeast cells may have a growth rate of about 0.175 hr$^{-1}$ in xylose-glucose growth media that includes 2.5 g/L glucose. The recombinant yeast cells may have a growth rate of about 0.2 hr$^{-1}$ in xylose-glucose growth media that includes 2.5 g/L glucose. The recombinant yeast cells may have a growth rate of about 0.225 hr$^{-1}$ in xylose-glucose growth media that includes 2.5 g/L glucose. The recombinant yeast cells may have a growth rate of about 0.25 hr$^{-1}$ in xylose-glucose growth media that includes 2.5 g/L glucose. The recombinant yeast cells may have a growth rate of about 0.275 hr$^{-1}$ in xylose-glucose growth media that includes 2.5 g/L glucose. The recombinant yeast cells may have a growth rate of about 0.3 hr$^{-1}$ in xylose-glucose growth media that includes 2.5 g/L glucose. The recombinant yeast cells may have a growth rate of about 0.325 hr$^{-1}$ in xylose-glucose growth media that includes 2.5 g/L glucose. The recombinant yeast cells may have a growth rate of about 0.35 hr$^{-1}$ in xylose-glucose growth media that includes 2.5 g/L glucose. The recombinant yeast cells may have a growth rate of about 0.375 hr$^{-1}$ in xylose-glucose growth media that includes 2.5 g/L glucose. The recombinant yeast cells may have a growth rate of about 0.4 hr$^{-1}$ in xylose-glucose growth media that includes 2.5 g/L glucose. The recombinant yeast cells may have a growth rate of about 0.425 hr$^{-1}$ in xylose-glucose growth media that includes 2.5 g/L glucose. The recombinant yeast cells may have a growth rate of about 0.45 hr$^{-1}$ in xylose-glucose growth media that includes 2.5 g/L glucose. The recombinant yeast cells may have a growth rate of about 0.475 hr$^{-1}$ in xylose-glucose growth media that includes 2.5 g/L glucose. The recombinant yeast cells may have a growth rate of about 0.5 hr$^{-1}$ in xylose-glucose growth media that includes 2.5 g/L glucose. The recombinant yeast cells may have a growth rate of about 0.525 hr$^{-1}$ in xylose-glucose growth media that includes 2.5 g/L glucose. The recombinant yeast cells may have a growth rate of about 0.5 hr$^{-1}$ in xylose-glucose growth media that includes 2.5 g/L glucose. The recombinant yeast cells may have a growth rate of about 0.575 hr$^{-1}$ in xylose-glucose growth media that includes 2.5 g/L glucose. The recombinant yeast cells may have a growth rate of about 0.6 hr$^{-1}$ in xylose-glucose growth media that includes 2.5 g/L glucose. The recombinant yeast cells may have a growth rate of about 0.65 hr$^{-1}$ in xylose-glucose growth media that includes 2.5 g/L glucose. The recombinant yeast cells may have a growth rate of about 0.7 hr$^{-1}$ in xylose-glucose growth media that includes 2.5 g/L glucose. The recombinant yeast cells may have a growth rate of about 0.75 hr$^{-1}$ in xylose-glucose growth media that includes 2.5 g/L glucose. The recombinant yeast cells may have a growth rate of about 0.8 hr$^{-1}$ in xylose-glucose growth media that includes 2.5 g/L glucose. The recombinant yeast cells may have a growth rate of about 0.85 hr$^{-1}$ in xylose-glucose growth media that includes 2.5 g/L glucose. The recombinant yeast cells may have a growth rate of about 0.9 hr$^{-1}$ in xylose-glucose growth media that includes 2.5 g/L glucose. The recombinant yeast cells may have a growth rate of about 0.95 hr$^{-1}$ in xylose-glucose growth media that includes 2.5 g/L glucose. The recombinant yeast cells may have a growth rate of about 1 hr$^{-1}$ in xylose-glucose growth media that includes 2.5 g/L glucose.

In embodiments, the recombinant yeast cells have a growth rate of about 0.005 hr$^{-1}$ in xylose-glucose growth media that includes 5 g/L glucose. The recombinant yeast cells may have a growth rate of about 0.0075 hr$^{-1}$ in xylose-glucose growth media that includes 5 g/L glucose. The recombinant yeast cells may have a growth rate of about 0.01 hr$^{-1}$ in xylose-glucose growth media that includes 5 g/L glucose. The recombinant yeast cells may have a growth rate of about 0.0125 hr$^{-1}$ in xylose-glucose growth media that includes 5 g/L glucose. The recombinant yeast cells may have a growth rate of about 0.015 hr$^{-1}$ in xylose-glucose growth media that includes 5 g/L glucose. The recombinant yeast cells may have a growth rate of about 0.0175 hr$^{-1}$ in xylose-glucose growth media that includes 5 g/L glucose. The recombinant yeast cells may have a growth rate of about 0.02 hr$^{-1}$ in xylose-glucose growth media that includes 5 g/L glucose. The recombinant yeast cells may have a growth rate of about 0.0225 hr$^{-1}$ in xylose-glucose growth media that includes 5 g/L glucose. The recombinant yeast cells may have a growth rate of about 0.025 hr$^{-1}$ in xylose-glucose growth media that includes 5 g/L glucose. The recombinant yeast cells may have a growth rate of about 0.0275 hr$^{-1}$ in xylose-glucose growth media that includes 5 g/L glucose. The recombinant yeast cells may have a growth rate of about 0.03 hr$^{-1}$ in xylose-glucose growth media that includes 5 g/L glucose. The recombinant yeast cells may have a growth rate of about 0.0325 hr$^{-1}$ in xylose-glucose growth media that includes 5 g/L glucose. The recombinant yeast cells may have a growth rate of about 0.035 hr$^{-1}$ in xylose-glucose growth media that includes 5 g/L glucose. The recombinant yeast cells may have a growth rate of about 0.0375 hr$^{-1}$ in xylose-glucose growth media that includes 5 g/L glucose. The recombinant yeast cells may have a growth rate of about 0.04 hr$^{-1}$ in xylose-glucose growth media that includes 5 g/L glucose. The recombinant yeast cells may have a growth rate of about 0.0425 hr$^{-1}$ in xylose-glucose growth media that includes 5 g/L glucose. The recombinant yeast cells may have a growth rate of about 0.045 hr$^{-1}$. The recombinant yeast cells may have a growth rate of about 0.0475 hr$^{-1}$ in xylose-glucose growth media that includes 5 g/L glucose. The recombinant yeast cells may have a growth rate of about 0.05 hr$^{-1}$ in xylose-glucose growth media that includes 5 g/L glucose.

In embodiments, the recombinant yeast cells have a growth rate of about 0.1 hr$^{-1}$ in xylose-glucose growth media that includes 5 g/L glucose. The recombinant yeast cells may have a growth rate of about 0.125 hr$^{-1}$ in xylose-glucose growth media that includes 5 g/L glucose. The recombinant yeast cells may have a growth rate of about 0.15 hr$^{-1}$ in xylose-glucose growth media that includes 5 g/L glucose. The recombinant yeast cells may have a growth rate of about 0.175 hr$^{-1}$ in xylose-glucose growth media that includes 5 g/L glucose. The recombinant yeast cells may have a growth rate of about 0.2 hr$^{-1}$ in xylose-glucose growth media that includes 5 g/L glucose. The recombinant yeast cells may have a growth rate of about 0.225 hr$^{-1}$ in xylose-glucose growth media that includes 5 g/L glucose. The recombinant yeast cells may have a growth rate of about 0.25 hr$^{-1}$ in xylose-glucose growth media that includes 5 g/L glucose. The recombinant yeast cells may have a growth rate of about 0.275 hr$^{-1}$ in xylose-glucose growth media that includes 5 g/L glucose. The recombinant yeast cells may have a growth rate of about 0.3 hr$^{-1}$ in xylose-glucose growth media that includes 5 g/L glucose. The recombinant yeast cells may have a growth rate of about 0.325 hr$^{-1}$ in xylose-glucose growth media that includes 5 g/L glucose. The recombinant yeast cells may have a growth rate of about 0.35 hr$^{-1}$ in xylose-glucose growth media that includes 5 g/L glucose. The recombinant yeast cells may have a growth rate of about 0.375 hr$^{-1}$ in xylose-glucose growth media that includes 5 g/L glucose. The recombinant yeast cells may have a growth rate of about 0.4 hr$^{-1}$ in xylose-glucose growth media that includes 5 g/L glucose. The recombinant yeast cells may have a growth rate of about 0.425 hr$^{-1}$ in xylose-glucose growth media that includes 5 g/L glucose. The recombinant yeast cells may have a growth rate of about 0.45 hr$^{-1}$ in xylose-glucose growth media that includes 5 g/L glucose. The recombinant yeast cells may have a growth rate of about 0.475 hr$^{-1}$ in xylose-glucose growth media that includes 5 g/L glucose. The recombinant yeast cells may have a growth rate of about 0.5 hr$^{-1}$ in xylose-glucose growth media that includes 5 g/L glucose. The recombinant yeast cells may have a growth rate of about 0.525 hr$^{-1}$ in xylose-glucose growth media that includes 5 g/L glucose. The recombinant yeast cells may have a growth rate of about 0.5 hr$^{-1}$ in xylose-glucose growth media that includes 5 g/L glucose. The recombinant yeast cells may have a growth rate of about 0.575 hr$^{-1}$ in xylose-glucose growth media that includes 5 g/L glucose. The recombinant yeast cells may have a growth rate of about 0.6 hr$^{-1}$ in xylose-glucose growth media that includes 5 g/L glucose. The recombinant yeast cells may have a growth rate of about 0.65 hr$^{-1}$ in xylose-glucose growth media that includes 5 g/L glucose. The recombinant yeast cells may have a growth rate of about 0.7 hr$^{-1}$ in xylose-glucose growth media that includes 5 g/L glucose. The recombinant yeast cells may have a growth rate of about 0.75 hr$^{-1}$ in xylose-glucose growth media that includes 5 g/L glucose. The recombinant yeast cells may have a growth rate of about 0.8 hr$^{-1}$ in xylose-glucose growth media that includes 5 g/L glucose. The recombinant yeast cells may have a growth rate of about 0.85 hr$^{-1}$ in xylose-glucose growth media that includes 5 g/L glucose. The recombinant yeast cells may have a growth rate of about 0.9 hr$^{-1}$ in xylose-glucose growth media that includes 5 g/L glucose. The recombinant yeast cells may have a growth rate of about 0.95 hr$^{-1}$ in xylose-glucose growth media that includes 5 g/L glucose. The recombinant yeast cells may have a growth rate of about 1 hr$^{-1}$ in xylose-glucose growth media that includes 5 g/L glucose.

In embodiments, the recombinant yeast cells have a growth rate of about 0.005 hr$^{-1}$ in xylose-glucose growth media that includes 10 g/L glucose. The recombinant yeast cells may have a growth rate of about 0.0075 hr$^{-1}$ in xylose-glucose growth media that includes 10 g/L glucose. The recombinant yeast cells may have a growth rate of about 0.01 hr$^{-1}$ in xylose-glucose growth media that includes 10 g/L glucose. The recombinant yeast cells may have a growth rate of about 0.0125 hr$^{-1}$ in xylose-glucose growth media that includes 10 g/L glucose. The recombinant yeast cells may have a growth rate of about 0.015 hr$^{-1}$ in xylose-glucose growth media that includes 10 g/L glucose. The recombinant yeast cells may have a growth rate of about 0.0175 hr$^{-1}$ in xylose-glucose growth media that includes 10 g/L glucose. The recombinant yeast cells may have a growth rate of about 0.02 hr$^{-1}$ in xylose-glucose growth media that includes 10 g/L glucose. The recombinant yeast cells may have a growth rate of about 0.0225 hr$^{-1}$ in xylose-glucose growth media that includes 10 g/L glucose. The recombinant yeast cells may have a growth rate of about 0.025 hr$^{-1}$ in xylose-glucose growth media that includes 10 g/L glucose. The recombinant yeast cells may have a growth rate of about 0.0275 hr$^{-1}$ in xylose-glucose growth media that includes 10 g/L glucose. The recombinant yeast cells may have a growth rate of about 0.03 hr$^{-1}$ in xylose-glucose growth media that includes 10 g/L glucose. The recombinant yeast cells may have a growth rate of about 0.0325 hr$^{-1}$ in xylose-glucose growth media that includes 10 g/L glucose. The recombinant yeast cells may have a growth rate of about 0.035 hr$^{-1}$ in xylose-glucose growth media that includes 10 g/L glucose. The recombinant yeast cells may have a growth rate of about 0.0375 hr$^{-1}$ in xylose-glucose growth media that includes 10 g/L glucose. The recombinant yeast cells may have a growth rate of about 0.04 hr$^{-1}$ in xylose-glucose growth media that includes 10 g/L glucose. The recombinant yeast cells may have a growth rate of about 0.0425 hr$^{-1}$ in xylose-glucose growth media that includes 10 g/L glucose. The recombinant yeast cells may have a growth rate of about 0.045 hr$^{-1}$. The recombinant yeast cells may have a growth rate of about 0.0475 hr$^{-1}$ in xylose-glucose growth media that includes 10 g/L glucose. The recombinant yeast cells may have a growth rate of about 0.05 hr$^{-1}$ in xylose-glucose growth media that includes 10 g/L glucose.

In embodiments, the recombinant yeast cells have a growth rate of about 0.1 hr$^{-1}$ in xylose-glucose growth media that includes 10 g/L glucose. The recombinant yeast cells may have a growth rate of about 0.125 hr$^{-1}$ in xylose-glucose growth media that includes 10 g/L glucose. The recombinant yeast cells may have a growth rate of about 0.15 hr$^{-1}$ in xylose-glucose growth media that includes 10 g/L glucose. The recombinant yeast cells may have a growth rate of about 0.175 hr$^{-1}$ in xylose-glucose growth media that includes 10 g/L glucose. The recombinant yeast cells may have a growth rate of about 0.2 hr$^{-1}$ in xylose-glucose growth media that includes 10 g/L glucose. The recombinant yeast cells may have a growth rate of about 0.225 hr$^{-1}$ in xylose-glucose growth media that includes 10 g/L glucose. The recombinant yeast cells may have a growth rate of about 0.25 hr$^{-1}$ in xylose-glucose growth media that includes 10 g/L glucose. The recombinant yeast cells may have a growth rate of about 0.275 hr$^{-1}$ in xylose-glucose growth media that includes 10 g/L glucose. The recombinant yeast cells may have a growth rate of about 0.3 hr$^{-1}$ in xylose-glucose growth media that includes 10 g/L glucose. The recombinant yeast cells may have a growth rate of about 0.325 hr$^{-1}$ in xylose-glucose growth media that includes 10 g/L glucose. The recombinant yeast cells may have a growth rate of about 0.35 hr$^{-1}$ in xylose-glucose growth media that includes 10 g/L glucose. The recombinant yeast cells may have a growth rate of about 0.375 hr$^{-1}$ in xylose-glucose growth media that includes 10 g/L glucose. The recombinant yeast cells may have a growth rate of about 0.4 hr$^{-1}$ in xylose-glucose growth media that includes 10 g/L glucose. The recombinant yeast cells may have a growth rate of about 0.425 hr$^{-1}$ in xylose-glucose growth media that includes 10 g/L glucose. The recombinant yeast cells may have a growth rate of about 0.45 hr$^{-1}$ in xylose-glucose growth media that includes 10 g/L glucose. The recombinant yeast cells may have a growth rate of about 0.475 hr$^{-1}$ in xylose-glucose growth media that includes 10 g/L glucose. The recombinant yeast cells may have a growth rate of about 0.5 hr$^{-1}$ in xylose-glucose growth media that includes 10 g/L glucose. The recombinant yeast cells may have a growth rate of about 0.525 hr$^{-1}$ in xylose-glucose growth media that includes 10 g/L glucose. The recombinant yeast cells may have a growth rate of about 0.5 hr$^{-1}$ in xylose-glucose growth media that includes 10 g/L glucose. The recombinant yeast cells may have a growth rate of about 0.575 hr$^{-1}$ in xylose-glucose growth media that includes 10 g/L glucose. The recombinant yeast cells may have a growth rate of about 0.6 hr$^{-1}$ in xylose-glucose growth media that includes 10 g/L glucose. The recombinant yeast cells may have a growth rate of about 0.65 hr$^{-1}$ in xylose-glucose growth media that includes 10 g/L glucose. The recombinant yeast cells may have a growth rate of about 0.7 hr$^{-1}$ in xylose-glucose growth media that includes 10 g/L glucose. The recombinant yeast cells may have a growth rate of about 0.75 hr$^{-1}$ in xylose-glucose growth media that includes 10 g/L glucose. The recombinant yeast cells may have a growth rate of about 0.8 hr$^{-1}$ in xylose-glucose growth media that includes 10 g/L glucose. The recombinant yeast cells may have a growth rate of about 0.85 hr$^{-1}$ in xylose-glucose growth media that includes 10 g/L glucose. The recombinant yeast cells may have a growth rate of about 0.9 hr$^{-1}$ in xylose-glucose growth media that includes 10 g/L glucose. The recombinant yeast cells may have a growth rate of about 0.95 hr$^{-1}$ in xylose-glucose growth media that includes 10 g/L glucose. The recombinant yeast cells may have a growth rate of about 1 hr$^{-1}$ in xylose-glucose growth media that includes 10 g/L glucose.

In embodiments, the recombinant yeast cells have a growth rate of about 0.005 hr$^{-1}$ in xylose-glucose growth media that includes 20 g/L glucose. The recombinant yeast cells may have a growth rate of about 0.0075 hr$^{-1}$ in xylose-glucose growth media that includes 20 g/L glucose. The recombinant yeast cells may have a growth rate of about 0.01 hr$^{-1}$ in xylose-glucose growth media that includes 20 g/L glucose. The recombinant yeast cells may have a growth rate of about 0.0125 hr$^{-1}$ in xylose-glucose growth media that includes 20 g/L glucose. The recombinant yeast cells may have a growth rate of about 0.015 hr$^{-1}$ in xylose-glucose growth media that includes 20 g/L glucose. The recombinant yeast cells may have a growth rate of about 0.0175 hr$^{-1}$ in xylose-glucose growth media that includes 20 g/L glucose. The recombinant yeast cells may have a growth rate of about 0.02 hr$^{-1}$ in xylose-glucose growth media that includes 20 g/L glucose. The recombinant yeast cells may have a growth rate of about 0.0225 hr$^{-1}$ in xylose-glucose growth media that includes 20 g/L glucose. The recombinant yeast cells may have a growth rate of about 0.025 hr$^{-1}$ in xylose-glucose growth media that includes 20 g/L glucose. The recombinant yeast cells may have a growth rate of about 0.0275 hr$^{-1}$ in xylose-glucose growth media that includes 20 g/L glucose. The recombinant yeast cells may have a growth rate of about 0.03 hr$^{-1}$ in xylose-glucose growth media that includes 20 g/L glucose. The recombinant yeast cells may have a growth rate of about 0.0325 hr$^{-1}$ in xylose-glucose growth media that includes 20 g/L glucose. The recombinant yeast cells may have a growth rate of about 0.035 hr$^{-1}$ in xylose-glucose growth media that includes 20 g/L glucose. The recombinant yeast cells may have a growth rate of about 0.0375 hr$^{-1}$ in xylose-glucose growth media that includes 20 g/L glucose. The recombinant yeast cells may have a growth rate of about 0.04 hr$^{-1}$ in xylose-glucose growth media that includes 20 g/L glucose. The recombinant yeast cells may have a growth rate of about 0.0425 hr$^{-1}$ in xylose-glucose growth media that includes 20 g/L glucose. The recombinant yeast cells may have a growth rate of about 0.045 hr$^{-1}$. The recombinant yeast cells may have a growth rate of about 0.0475 hr$^{-1}$ in xylose-glucose growth media that includes 20 g/L glucose. The recombinant yeast cells may have a growth rate of about 0.05 hr$^{-1}$ in xylose-glucose growth media that includes 20 g/L glucose.

In embodiments, the recombinant yeast cells have a growth rate of about 0.1 hr$^{-1}$ in xylose-glucose growth media that includes 20 g/L glucose. The recombinant yeast cells may have a growth rate of about 0.125 hr$^{-1}$ in xylose-glucose growth media that includes 20 g/L glucose. The recombinant yeast cells may have a growth rate of about 0.15 hr$^{-1}$ in xylose-glucose growth media that includes 20 g/L glucose. The recombinant yeast cells may have a growth rate of about 0.175 hr$^{-1}$ in xylose-glucose growth media that includes 20 g/L glucose. The recombinant yeast cells may have a growth rate of about 0.2 hr$^{-1}$ in xylose-glucose growth media that includes 20 g/L glucose. The recombinant yeast cells may have a growth rate of about 0.225 hr$^{-1}$ in xylose-glucose growth media that includes 20 g/L glucose. The recombinant yeast cells may have a growth rate of about 0.25 hr$^{-1}$ in xylose-glucose growth media that includes 20 g/L glucose. The recombinant yeast cells may have a growth rate of about 0.275 hr$^{-1}$ in xylose-glucose growth media that includes 20 g/L glucose. The recombinant yeast cells may have a growth rate of about 0.3 hr$^{-1}$ in xylose-glucose growth media that includes 20 g/L glucose. The recombinant yeast cells may have a growth rate of about 0.325 hr$^{-1}$ in xylose-glucose growth media that includes 20 g/L glucose. The recombinant yeast cells may have a growth rate of about 0.35 hr$^{-1}$ in xylose-glucose growth media that includes 20 g/L glucose. The recombinant yeast cells may have a growth rate of about 0.375 hr$^{-1}$ in xylose-glucose growth media that includes 20 g/L glucose. The recombinant yeast cells may have a growth rate of about 0.4 hr$^{-1}$ in xylose-glucose growth media that includes 20 g/L glucose. The recombinant yeast cells may have a growth rate of about 0.425 hr$^{-1}$ in xylose-glucose growth media that includes 20 g/L glucose. The recombinant yeast cells may have a growth rate of about 0.45 hr$^{-1}$ in xylose-glucose growth media that includes 20 g/L glucose. The recombinant yeast cells may have a growth rate of about 0.475 hr$^{-1}$ in xylose-glucose growth media that includes 20 g/L glucose. The recombinant yeast cells may have a growth rate of about 0.5 hr$^{-1}$ in xylose-glucose growth media that includes 20 g/L glucose. The recombinant yeast cells may have a growth rate of about 0.525 hr$^{-1}$ in xylose-glucose growth media that includes 20 g/L glucose. The recombinant yeast cells may have a growth rate of about 0.5 hr$^{-1}$ in xylose-glucose growth media that includes 20 g/L glucose. The recombinant yeast cells may have a growth rate of about 0.575 hr$^{-1}$ in xylose-glucose growth media that includes 20 g/L glucose. The recombinant yeast cells may have a growth rate of about 0.6 hr$^{-1}$ in xylose-glucose growth media that includes 20 g/L glucose. The recombinant yeast cells may have a growth rate of about 0.65 hr$^{-1}$ in xylose-glucose growth media that includes 20 g/L glucose. The recombinant yeast cells may have a growth rate of about 0.7 hr$^{-1}$ in xylose-glucose growth media that includes 20 g/L glucose. The recombinant yeast cells may have a growth rate of about 0.75 hr$^{-1}$ in xylose-glucose growth media that includes 20 g/L glucose. The recombinant yeast cells may have a growth rate of about 0.8 hr$^{-1}$ in xylose-glucose growth media that includes 20 g/L glucose. The recombinant yeast cells may have a growth rate of about 0.85 hr$^{-1}$ in xylose-glucose growth media that includes 20 g/L glucose. The recombinant yeast cells may have a growth rate of about 0.9 hr$^{-1}$ in xylose-glucose growth media that includes 20 g/L glucose. The recombinant yeast cells may have a growth rate of about 0.95 hr$^{-1}$ in xylose-glucose growth media that includes 20 g/L glucose. The recombinant yeast cells may have a growth rate of about 1 hr$^{-1}$ in xylose-glucose growth media that includes 20 g/L glucose.

In embodiments, the recombinant yeast cells have a growth rate of about 0.005 hr$^{-1}$ in xylose-glucose growth media that includes 30 g/L glucose. The recombinant yeast cells may have a growth rate of about 0.0075 hr$^{-1}$ in xylose-glucose growth media that includes 30 g/L glucose. The recombinant yeast cells may have a growth rate of about 0.01 hr$^{-1}$ in xylose-glucose growth media that includes 30 g/L glucose. The recombinant yeast cells may have a growth rate of about 0.0125 hr$^{-1}$ in xylose-glucose growth media that includes 30 g/L glucose. The recombinant yeast cells may have a growth rate of about 0.015 hr$^{-1}$ in xylose-glucose growth media that includes 30 g/L glucose. The recombinant yeast cells may have a growth rate of about 0.0175 hr$^{-1}$ in xylose-glucose growth media that includes 30 g/L glucose. The recombinant yeast cells may have a growth rate of about 0.02 hr$^{-1}$ in xylose-glucose growth media that includes 30 g/L glucose. The recombinant yeast cells may have a growth rate of about 0.0225 hr$^{-1}$ in growth media that includes 30 g/L glucose. The recombinant yeast cells may have a growth rate of about 0.025 hr$^{-1}$ in xylose-glucose growth media that includes 30 g/L glucose. The recombinant yeast cells may have a growth rate of about 0.0275 hr$^{-1}$ in xylose-glucose growth media that includes 30 g/L glucose. The recombinant yeast cells may have a growth rate of about 0.03 hr$^{-1}$ in xylose-glucose growth media that includes 30 g/L glucose. The recombinant yeast cells may have a growth rate of about 0.0325 hr$^{-1}$ in xylose-glucose growth media that includes 30 g/L glucose. The recombinant yeast cells may have a growth rate of about 0.035 hr$^{-1}$ in xylose-glucose growth media that includes 30 g/L glucose. The recombinant yeast cells may have a growth rate of about 0.0375 hr$^{-1}$ in xylose-glucose growth media that includes 30 g/L glucose. The recombinant yeast cells may have a growth rate of about 0.04 hr$^{-1}$ in xylose-glucose growth media that includes 30 g/L glucose. The recombinant yeast cells may have a growth rate of about 0.0425 hr$^{-1}$ in xylose-glucose growth media that includes 30 g/L glucose. The recombinant yeast cells may have a growth rate of about 0.045 hr$^{-1}$. The recombinant yeast cells may have a growth rate of about 0.0475 hr$^{-1}$ in xylose-glucose growth media that includes 30 g/L glucose. The recombinant yeast cells may have a growth rate of about 0.05 hr$^{-1}$ in xylose-glucose growth media that includes 30 g/L glucose.

In embodiments, the recombinant yeast cells have a growth rate of about 0.1 hr$^{-1}$ in xylose-glucose growth media that includes 30 g/L glucose. The recombinant yeast cells may have a growth rate of about 0.125 hr$^{-1}$ in xylose-glucose growth media that includes 30 g/L glucose. The recombinant yeast cells may have a growth rate of about 0.15 hr$^{-1}$ in xylose-glucose growth media that includes 30 g/L glucose. The recombinant yeast cells may have a growth rate of about 0.175 hr$^{-1}$ in xylose-glucose growth media that includes 30 g/L glucose. The recombinant yeast cells may have a growth rate of about 0.2 hr$^{-1}$ in xylose-glucose growth media that includes 30 g/L glucose. The recombinant yeast cells may have a growth rate of about 0.225 hr$^{-1}$ in xylose-glucose growth media that includes 30 g/L glucose. The recombinant yeast cells may have a growth rate of about 0.25 hr$^{-1}$ in xylose-glucose growth media that includes 30 g/L glucose. The recombinant yeast cells may have a growth rate of about 0.275 hr$^{-1}$ in xylose-glucose growth media that includes 30 g/L glucose. The recombinant yeast cells may have a growth rate of about 0.3 hr$^{-1}$ in xylose-glucose growth media that includes 30 g/L glucose. The recombinant yeast cells may have a growth rate of about 0.325 hr$^{-1}$ in xylose-glucose growth media that includes 30 g/L glucose. The recombinant yeast cells may have a growth rate of about 0.35 hr$^{-1}$ in xylose-glucose growth media that includes 30 g/L glucose. The recombinant yeast cells may have a growth rate of about 0.375 hr$^{-1}$ in xylose-glucose growth media that includes 30 g/L glucose. The recombinant yeast cells may have a growth rate of about 0.4 hr$^{-1}$ in xylose-glucose growth media that includes 30 g/L glucose. The recombinant yeast cells may have a growth rate of about 0.425 hr$^{-1}$ in xylose-glucose growth media that includes 30 g/L glucose. The recombinant yeast cells may have a growth rate of about 0.45 hr$^{-1}$ in xylose-glucose growth media that includes 30 g/L glucose. The recombinant yeast cells may have a growth rate of about 0.475 hr$^{-1}$ in xylose-glucose growth media that includes 30 g/L glucose. The recombinant yeast cells may have a growth rate of about 0.5 hr$^{-1}$ in xylose-glucose growth media that includes 30 g/L glucose. The recombinant yeast cells may have a growth rate of about 0.525 hr$^{-1}$ in xylose-glucose growth media that includes 30 g/L glucose. The recombinant yeast cells may have a growth rate of about 0.5 hr$^{-1}$ in xylose-glucose growth media that includes 30 g/L glucose. The recombinant yeast cells may have a growth rate of about 0.575 hr$^{-1}$ in xylose-glucose growth media that includes 30 g/L glucose. The recombinant yeast cells may have a growth rate of about 0.6 hr$^{-1}$ in xylose-glucose growth media that includes 30 g/L glucose. The recombinant yeast cells may have a growth rate of about 0.65 hr$^{-1}$ in xylose-glucose growth media that includes 30 g/L glucose. The recombinant yeast cells may have a growth rate of about 0.7 hr$^{-1}$ in xylose-glucose growth media that includes 30 g/L glucose. The recombinant yeast cells may have a growth rate of about 0.75 hr$^{-1}$ in xylose-glucose growth media that includes 30 g/L glucose. The recombinant yeast cells may have a growth rate of about 0.8 hr$^{-1}$ in xylose-glucose growth media that includes 30 g/L glucose. The recombinant yeast cells may have a growth rate of about 0.85 hr$^{-1}$ in xylose-glucose growth media that includes 30 g/L glucose. The recombinant yeast cells may have a growth rate of about 0.9 hr$^{-1}$ in xylose-glucose growth media that includes 30 g/L glucose. The recombinant yeast cells may have a growth rate of about 0.95 hr$^{-1}$ in xylose-glucose growth media that includes 30 g/L glucose. The recombinant yeast cells may have a growth rate of about 1 hr$^{-1}$ in xylose-glucose growth media that includes 30 g/L glucose.

In embodiments, the recombinant yeast cells have a growth rate of about 0.005 hr$^{-1}$ in xylose-glucose growth media that includes 50 g/L glucose. The recombinant yeast cells may have a growth rate of about 0.0075 hr$^{-1}$ in xylose-glucose growth media that includes 50 g/L glucose. The recombinant yeast cells may have a growth rate of about 0.01 hr$^{-1}$ in xylose-glucose growth media that includes 50 g/L glucose. The recombinant yeast cells may have a growth rate of about 0.0125 hr$^{-1}$ in xylose-glucose growth media that includes 50 g/L glucose. The recombinant yeast cells may have a growth rate of about 0.015 hr$^{-1}$ in xylose-glucose growth media that includes 50 g/L glucose. The recombinant yeast cells may have a growth rate of about 0.0175 hr$^{-1}$ in xylose-glucose growth media that includes 50 g/L glucose. The recombinant yeast cells may have a growth rate of about 0.02 hr$^{-1}$ in xylose-glucose growth media that includes 50 g/L glucose. The recombinant yeast cells may have a growth rate of about 0.0225 hr$^{-1}$ in xylose-glucose growth media that includes 50 g/L glucose. The recombinant yeast cells may have a growth rate of about 0.025 hr$^{-1}$ in xylose-glucose growth media that includes 50 g/L glucose. The recombinant yeast cells may have a growth rate of about 0.0275 hr$^{-1}$ in xylose-glucose growth media that includes 50 g/L glucose. The recombinant yeast cells may have a growth rate of about 0.03 hr$^{-1}$ in xylose-glucose growth media that includes 50 g/L glucose. The recombinant yeast cells may have a growth rate of about 0.0325 hr$^{-1}$ in xylose-glucose growth media that includes 50 g/L glucose. The recombinant yeast cells may have a growth rate of about 0.035 hr$^{-1}$ in xylose-glucose growth media that includes 50 g/L glucose. The recombinant yeast cells may have a growth rate of about 0.0375 hr$^{-1}$ in xylose-glucose growth media that includes 50 g/L glucose. The recombinant yeast cells may have a growth rate of about 0.04 hr$^{-1}$ in xylose-glucose growth media that includes 50 g/L glucose. The recombinant yeast cells may have a growth rate of about 0.0425 hr$^{-1}$ in xylose-glucose growth media that includes 50 g/L glucose. The recombinant yeast cells may have a growth rate of about 0.045 hr$^{-1}$. The recombinant yeast cells may have a growth rate of about 0.0475 hr$^{-1}$ in xylose-glucose growth media that includes 50 g/L glucose. The recombinant yeast cells may have a growth rate of about 0.05 hr$^{-1}$ in xylose-glucose growth media that includes 50 g/L glucose.

In embodiments, the recombinant yeast cells have a growth rate of about 0.1 hr$^{-1}$ in xylose-glucose growth media that includes 50 g/L glucose. The recombinant yeast cells may have a growth rate of about 0.125 hr$^{-1}$ in xylose-glucose growth media that includes 50 g/L glucose. The recombinant yeast cells may have a growth rate of about 0.15 hr$^{-1}$ in xylose-glucose growth media that includes 50 g/L glucose. The recombinant yeast cells may have a growth rate of about 0.175 hr$^{-1}$ in xylose-glucose growth media that includes 50 g/L glucose. The recombinant yeast cells may have a growth rate of about 0.2 hr$^{-1}$ in xylose-glucose growth media that includes 50 g/L glucose. The recombinant yeast cells may have a growth rate of about 0.225 hr$^{-1}$ in xylose-glucose growth media that includes 50 g/L glucose. The recombinant yeast cells may have a growth rate of about 0.25 hr$^{-1}$ in xylose-glucose growth media that includes 50 g/L glucose. The recombinant yeast cells may have a growth rate of about 0.275 hr$^{-1}$ in xylose-glucose growth media that includes 50 g/L glucose. The recombinant yeast cells may have a growth rate of about 0.3 hr$^{-1}$ in xylose-glucose growth media that includes 50 g/L glucose. The recombinant yeast cells may have a growth rate of about 0.325 hr$^{-1}$ in xylose-glucose growth media that includes 50 g/L glucose. The recombinant yeast cells may have a growth rate of about 0.35 hr$^{-1}$ in xylose-glucose growth media that includes 50 g/L glucose. The recombinant yeast cells may have a growth rate of about 0.375 hr$^{-1}$ in xylose-glucose growth media that includes 50 g/L glucose. The recombinant yeast cells may have a growth rate of about 0.4 hr$^{-1}$ in xylose-glucose growth media that includes 50 g/L glucose. The recombinant yeast cells may have a growth rate of about 0.425 hr$^{-1}$ in xylose-glucose growth media that includes 50 g/L glucose. The recombinant yeast cells may have a growth rate of about 0.45 hr$^{-1}$ in xylose-glucose growth media that includes 50 g/L glucose. The recombinant yeast cells may have a growth rate of about 0.475 hr$^{-1}$ in xylose-glucose growth media that includes 50 g/L glucose. The recombinant yeast cells may have a growth rate of about 0.5 hr$^{-1}$ in xylose-glucose growth media that includes 50 g/L glucose. The recombinant yeast cells may have a growth rate of about 0.525 hr$^{-1}$ in xylose-glucose growth media that includes 50 g/L glucose. The recombinant yeast cells may have a growth rate of about 0.5 hr$^{-1}$ in xylose-glucose growth media that includes 50 g/L glucose. The recombinant yeast cells may have a growth rate of about 0.575 hr$^{-1}$ in xylose-glucose growth media that includes 50 g/L glucose. The recombinant yeast cells may have a growth rate of about 0.6 hr$^{-1}$ in xylose-glucose growth media that includes 50 g/L glucose. The recombinant yeast cells may have a growth rate of about 0.65 hr$^{-1}$ in xylose-glucose growth media that includes 50 g/L glucose. The recombinant yeast cells may have a growth rate of about 0.7 hr$^{-1}$ in xylose-glucose growth media that includes 50 g/L glucose. The recombinant yeast cells may have a growth rate of about 0.75 hr$^{-1}$ in xylose-glucose growth media that includes 50 g/L glucose. The recombinant yeast cells may have a growth rate of about 0.8 hr$^{-1}$ in xylose-glucose growth media that includes 50 g/L glucose. The recombinant yeast cells may have a growth rate of about 0.85 hr$^{-1}$ in xylose-glucose growth media that includes 50 g/L glucose. The recombinant yeast cells may have a growth rate of about 0.9 hr$^{-1}$ in xylose-glucose growth media that includes 50 g/L glucose. The recombinant yeast cells may have a growth rate of about 0.95 hr$^{-1}$ in xylose-glucose growth media that includes 50 g/L glucose. The recombinant yeast cells may have a growth rate of about 1 hr$^{-1}$ in xylose-glucose growth media that includes 50 g/L glucose.

In embodiments, the recombinant yeast cells have a growth rate of about 0.005 hr$^{-1}$ in xylose-glucose growth media that includes 75 g/L glucose. The recombinant yeast cells may have a growth rate of about 0.0075 hr$^{-1}$ in xylose-glucose growth media that includes 75 g/L glucose. The recombinant yeast cells may have a growth rate of about 0.01 hr$^{-1}$ in xylose-glucose growth media that includes 75 g/L glucose. The recombinant yeast cells may have a growth rate of about 0.0125 hr$^{-1}$ in xylose-glucose growth media that includes 75 g/L glucose. The recombinant yeast cells may have a growth rate of about 0.015 hr$^{-1}$ in xylose-glucose growth media that includes 75 g/L glucose. The recombinant yeast cells may have a growth rate of about 0.0175 hr$^{-1}$ in xylose-glucose growth media that includes 75 g/L glucose. The recombinant yeast cells may have a growth rate of about 0.02 hr$^{-1}$ in xylose-glucose growth media that includes 75 g/L glucose. The recombinant yeast cells may have a growth rate of about 0.0225 hr$^{-1}$ in xylose-glucose growth media that includes 75 g/L glucose. The recombinant yeast cells may have a growth rate of about 0.025 hr$^{-1}$ in xylose-glucose growth media that includes 75 g/L glucose. The recombinant yeast cells may have a growth rate of about 0.0275 hr$^{-1}$ in xylose-glucose growth media that includes 75 g/L glucose. The recombinant yeast cells may have a growth rate of about 0.03 hr$^{-1}$ in xylose-glucose growth media that includes 75 g/L glucose. The recombinant yeast cells may have a growth rate of about 0.0325 hr$^{-1}$ in xylose-glucose growth media that includes 75 g/L glucose. The recombinant yeast cells may have a growth rate of about 0.035 hr$^{-1}$ in xylose-glucose growth media that includes 75 g/L glucose. The recombinant yeast cells may have a growth rate of about 0.0375 hr$^{-1}$ in xylose-glucose growth media that includes 75 g/L glucose. The recombinant yeast cells may have a growth rate of about 0.04 hr$^{-1}$ in xylose-glucose growth media that includes 75 g/L glucose. The recombinant yeast cells may have a growth rate of about 0.0425 hr$^{-1}$ in xylose-glucose growth media that includes 75 g/L glucose. The recombinant yeast cells may have a growth rate of about 0.045 hr$^{-1}$. The recombinant yeast cells may have a growth rate of about 0.0475 hr$^{-1}$ in xylose-glucose growth media that includes 75 g/L glucose. The recombinant yeast cells may have a growth rate of about 0.05 hr$^{-1}$ in xylose-glucose growth media that includes 75 g/L glucose.

In embodiments, the recombinant yeast cells have a growth rate of about 0.1 hr$^{-1}$ in xylose-glucose growth media that includes 75 g/L glucose. The recombinant yeast cells may have a growth rate of about 0.125 hr$^{-1}$ in xylose-glucose growth media that includes 75 g/L glucose. The recombinant yeast cells may have a growth rate of about 0.15 hr$^{-1}$ in xylose-glucose growth media that includes 75 g/L glucose. The recombinant yeast cells may have a growth rate of about 0.175 hr$^{-1}$ in xylose-glucose growth media that includes 75 g/L glucose. The recombinant yeast cells may have a growth rate of about 0.2 hr$^{-1}$ in xylose-glucose growth media that includes 75 g/L glucose. The recombinant yeast cells may have a growth rate of about 0.225 hr$^{-1}$ in xylose-glucose growth media that includes 75 g/L glucose. The recombinant yeast cells may have a growth rate of about 0.25 hr$^{-1}$ in xylose-glucose growth media that includes 75 g/L glucose. The recombinant yeast cells may have a growth rate of about 0.275 hr$^{-1}$ in xylose-glucose growth media that includes 75 g/L glucose. The recombinant yeast cells may have a growth rate of about 0.3 hr$^{-1}$ in xylose-glucose growth media that includes 75 g/L glucose. The recombinant yeast cells may have a growth rate of about 0.325 hr$^{-1}$ in xylose-glucose growth media that includes 75 g/L glucose. The recombinant yeast cells may have a growth rate of about 0.35 hr$^{-1}$ in xylose-glucose growth media that includes 75 g/L glucose. The recombinant yeast cells may have a growth rate of about 0.375 hr$^{-1}$ in xylose-glucose growth media that includes 75 g/L glucose. The recombinant yeast cells may have a growth rate of about 0.4 hr$^{-1}$ in xylose-glucose growth media that includes 75 g/L glucose. The recombinant yeast cells may have a growth rate of about 0.425 hr$^{-1}$ in xylose-glucose growth media that includes 75 g/L glucose. The recombinant yeast cells may have a growth rate of about 0.45 hr$^{-1}$ in xylose-glucose growth media that includes 75 g/L glucose. The recombinant yeast cells may have a growth rate of about 0.475 hr$^{-1}$ in xylose-glucose growth media that includes 75 g/L glucose. The recombinant yeast cells may have a growth rate of about 0.5 hr$^{-1}$ in xylose-glucose growth media that includes 75 g/L glucose. The recombinant yeast cells may have a growth rate of about 0.525 hr$^{-1}$ in xylose-glucose growth media that includes 75 g/L glucose. The recombinant yeast cells may have a growth rate of about 0.5 hr$^{-1}$ in xylose-glucose growth media that includes 75 g/L glucose. The recombinant yeast cells may have a growth rate of about 0.575 hr$^{-1}$ in xylose-glucose growth media that includes 75 g/L glucose. The recombinant yeast cells may have a growth rate of about 0.6 hr$^{-1}$ in xylose-glucose growth media that includes 75 g/L glucose. The recombinant yeast cells may have a growth rate of about 0.65 hr$^{-1}$ in xylose-glucose growth media that includes 75 g/L glucose. The recombinant yeast cells may have a growth rate of about 0.7 hr$^{-1}$ in xylose-glucose growth media that includes 75 g/L glucose. The recombinant yeast cells may have a growth rate of about 0.75 hr$^{-1}$ in xylose-glucose growth media that includes 75 g/L glucose. The recombinant yeast cells may have a growth rate of about 0.8 hr$^{-1}$ in xylose-glucose growth media that includes 75 g/L glucose. The recombinant yeast cells may have a growth rate of about 0.85 hr$^{-1}$ in xylose-glucose growth media that includes 75 g/L glucose. The recombinant yeast cells may have a growth rate of about 0.9 hr$^{-1}$ in xylose-glucose growth media that includes 75 g/L glucose. The recombinant yeast cells may have a growth rate of about 0.95 hr$^{-1}$ in xylose-glucose growth media that includes 75 g/L glucose. The recombinant yeast cells may have a growth rate of about 1 hr$^{-1}$ in xylose-glucose growth media that includes 75 g/L glucose.

In embodiments, the recombinant yeast cells have a growth rate of about 0.005 hr$^{-1}$ in xylose-glucose growth media that includes 100 g/L glucose. The recombinant yeast cells may have a growth rate of about 0.0075 hr$^{-1}$ in xylose-glucose growth media that includes 100 g/L glucose. The recombinant yeast cells may have a growth rate of about 0.01 hr$^{-1}$ in xylose-glucose growth media that includes 100 g/L glucose. The recombinant yeast cells may have a growth rate of about 0.0125 hr$^{-1}$ in xylose-glucose growth media that includes 100 g/L glucose. The recombinant yeast cells may have a growth rate of about 0.015 hr$^{-1}$ in xylose-glucose growth media that includes 100 g/L glucose. The recombinant yeast cells may have a growth rate of about 0.0175 hr$^{-1}$ in xylose-glucose growth media that includes 100 g/L glucose. The recombinant yeast cells may have a growth rate of about 0.02 hr$^{-1}$ in xylose-glucose growth media that includes 100 g/L glucose. The recombinant yeast cells may have a growth rate of about 0.0225 hr$^{-1}$ in xylose-glucose growth media that includes 100 g/L glucose. The recombinant yeast cells may have a growth rate of about 0.025 hr$^{-1}$ in xylose-glucose growth media that includes 100 g/L glucose. The recombinant yeast cells may have a growth rate of about 0.0275 hr$^{-1}$ in xylose-glucose growth media that includes 100 g/L glucose. The recombinant yeast cells may have a growth rate of about 0.03 hr$^{-1}$ in xylose-glucose growth media that includes 100 g/L glucose. The recombinant yeast cells may have a growth rate of about 0.0325 hr$^{-1}$ in xylose-glucose growth media that includes 100 g/L glucose. The recombinant yeast cells may have a growth rate of about 0.035 hr$^{-1}$ in xylose-glucose growth media that includes 100 g/L glucose. The recombinant yeast cells may have a growth rate of about 0.0375 hr$^{-1}$ in xylose-glucose growth media that includes 100 g/L glucose. The recombinant yeast cells may have a growth rate of about 0.04 hr$^{-1}$ in xylose-glucose growth media that includes 100 g/L glucose. The recombinant yeast cells may have a growth rate of about 0.0425 hr$^{-1}$ in xylose-glucose growth media that includes 100 g/L glucose. The recombinant yeast cells may have a growth rate of about 0.045 hr$^{-1}$. The recombinant yeast cells may have a growth rate of about 0.0475 hr$^{-1}$ in xylose-glucose growth media that includes 100 g/L glucose. The recombinant yeast cells may have a growth rate of about 0.05 hr$^{-1}$ in xylose-glucose growth media that includes 100 g/L glucose.

In embodiments, the recombinant yeast cells have a growth rate of about 0.1 hr$^{-1}$ in xylose-glucose growth media that includes 100 g/L glucose. The recombinant yeast cells may have a growth rate of about 0.125 hr$^{-1}$ in xylose-glucose growth media that includes 100 g/L glucose. The recombinant yeast cells may have a growth rate of about 0.15 hr$^{-1}$ in xylose-glucose growth media that includes 100 g/L glucose. The recombinant yeast cells may have a growth rate of about 0.175 hr$^{-1}$ in xylose-glucose growth media that includes 100 g/L glucose. The recombinant yeast cells may have a growth rate of about 0.2 hr$^{-1}$ in xylose-glucose growth media that includes 100 g/L glucose. The recombinant yeast cells may have a growth rate of about 0.225 hr$^{-1}$ in xylose-glucose growth media that includes 100 g/L glucose. The recombinant yeast cells may have a growth rate of about 0.25 hr$^{-1}$ in xylose-glucose growth media that includes 100 g/L glucose. The recombinant yeast cells may have a growth rate of about 0.275 hr$^{-1}$ in xylose-glucose growth media that includes 100 g/L glucose. The recombinant yeast cells may have a growth rate of about 0.3 hr$^{-1}$ in xylose-glucose growth media that includes 100 g/L glucose. The recombinant yeast cells may have a growth rate of about 0.325 hr$^{-1}$ in xylose-glucose growth media that includes 100 g/L glucose. The recombinant yeast cells may have a growth rate of about 0.35 hr$^{-1}$ in xylose-glucose growth media that includes 100 g/L glucose. The recombinant yeast cells may have a growth rate of about 0.375 hr$^{-1}$ in xylose-glucose growth media that includes 100 g/L glucose. The recombinant yeast cells may have a growth rate of about 0.4 hr$^{-1}$ in xylose-glucose growth media that includes 100 g/L glucose. The recombinant yeast cells may have a growth rate of about 0.425 hr$^{-1}$ in xylose-glucose growth media that includes 100 g/L glucose. The recombinant yeast cells may have a growth rate of about 0.45 hr$^{-1}$ in xylose-glucose growth media that includes 100 g/L glucose. The recombinant yeast cells may have a growth rate of about 0.475 hr$^{-1}$ in xylose-glucose growth media that includes 100 g/L glucose. The recombinant yeast cells may have a growth rate of about 0.5 hr$^{-1}$ in xylose-glucose growth media that includes 100 g/L glucose. The recombinant yeast cells may have a growth rate of about 0.525 hr$^{-1}$ in xylose-glucose growth media that includes 100 g/L glucose. The recombinant yeast cells may have a growth rate of about 0.5 hr$^{-1}$ in xylose-glucose growth media that includes 100 g/L glucose. The recombinant yeast cells may have a growth rate of about 0.575 hr$^{-1}$ in xylose-glucose growth media that includes 100 g/L glucose. The recombinant yeast cells may have a growth rate of about 0.6 hr$^{-1}$ in xylose-glucose growth media that includes 100 g/L glucose. The recombinant yeast cells may have a growth rate of about 0.65 hr$^{-1}$ in xylose-glucose growth media that includes 100 g/L glucose. The recombinant yeast cells may have a growth rate of about 0.7 hr$^{-1}$ in xylose-glucose growth media that includes 100 g/L glucose. The recombinant yeast cells may have a growth rate of about 0.75 hr$^{-1}$ in xylose-glucose growth media that includes 100 g/L glucose. The recombinant yeast cells may have a growth rate of about 0.8 hr$^{-1}$ in xylose-glucose growth media that includes 100 g/L glucose. The recombinant yeast cells may have a growth rate of about 0.85 hr$^{-1}$ in xylose-glucose growth media that includes 100 g/L glucose. The recombinant yeast cells may have a growth rate of about 0.9 hr$^{-1}$ in xylose-glucose growth media that includes 100 g/L glucose. The recombinant yeast cells may have a growth rate of about 0.95 hr$^{-1}$ in xylose-glucose growth media that includes 100 g/L glucose. The recombinant yeast cells may have a growth rate of about 1 hr$^{-1}$ in xylose-glucose growth media that includes 100 g/L glucose.

In embodiments, the growth rate of the recombinant yeast cell in xylose-glucose growth media is about 0.1× fold greater than a wildtype yeast cell (i.e. a yeast cell without a recombinant transporter protein described herein) in xylose-glucose growth media. The growth rate of the recombinant yeast cell in xylose-glucose growth media may be about 0.2× fold greater than a wildtype yeast cell in xylose-glucose growth media. The growth rate of the recombinant yeast cell in xylose-glucose growth media may be about 0.3× fold greater than a wildtype yeast cell in xylose-glucose growth media. The growth rate of the recombinant yeast cell in xylose-glucose growth media may be about 0.4× fold greater than a wildtype yeast cell in xylose-glucose growth media. The growth rate of the recombinant yeast cell in xylose-glucose growth media may be about 0.5× fold greater than a wildtype yeast cell in xylose-glucose growth media. The growth rate of the recombinant yeast cell in xylose-glucose growth media may be about 0.6× fold greater than a wildtype yeast cell in xylose-glucose growth media. The growth rate of the recombinant yeast cell in xylose-glucose growth media may be about 0.7× fold greater than a wildtype yeast cell in xylose-glucose growth media. The growth rate of the recombinant yeast cell in xylose-glucose growth media may be about 0.8× fold greater than a wildtype yeast cell in xylose-glucose growth media. The growth rate of the recombinant yeast cell in xylose-glucose growth media may be about 0.9× fold greater than a wildtype yeast cell in xylose-glucose growth media. The growth rate of the recombinant yeast cell in xylose-glucose growth media may be about 1× fold greater than a wildtype yeast cell in xylose-glucose growth media.

The growth rate of the recombinant yeast cell in xylose-glucose growth media may be about 2× fold greater than a wildtype yeast cell in xylose-glucose growth media. The growth rate of the recombinant yeast cell in xylose-glucose growth media may be about 3× fold greater than a wildtype yeast cell in xylose-glucose growth media. The growth rate of the recombinant yeast cell in xylose-glucose growth media may be about 4× fold greater than a wildtype yeast cell in xylose-glucose growth media. The growth rate of the recombinant yeast cell in xylose-glucose growth media may be about 5× fold greater than a wildtype yeast cell in xylose-glucose growth media. The growth rate of the recombinant yeast cell in xylose-glucose growth media may be about 6× fold greater than a wildtype yeast cell in xylose-glucose growth media. The growth rate of the recombinant yeast cell in xylose-glucose growth media may be about 7× fold greater than a wildtype yeast cell in xylose-glucose growth media. The growth rate of the recombinant yeast cell in xylose-glucose growth media may be about 8× fold greater than a wildtype yeast cell in xylose-glucose growth media. The growth rate of the recombinant yeast cell in xylose-glucose growth media may be about 9× fold greater than a wildtype yeast cell in xylose-glucose growth media. The growth rate of the recombinant yeast cell in xylose-glucose growth media may be about 10× fold greater than a wildtype yeast cell in xylose-glucose growth media.

The growth rate of the recombinant yeast cell in xylose-glucose growth media may be about 11× fold greater than a wildtype yeast cell in xylose-glucose growth media. The growth rate of the recombinant yeast cell in xylose-glucose growth media may be about 12× fold greater than a wildtype yeast cell in xylose-glucose growth media. The growth rate of the recombinant yeast cell in xylose-glucose growth media may be about 13× fold greater than a wildtype yeast cell in xylose-glucose growth media. The growth rate of the recombinant yeast cell in xylose-glucose growth media may be about 14× fold greater than a wildtype yeast cell in xylose-glucose growth media. The growth rate of the recombinant yeast cell in xylose-glucose growth media may be about 15× fold greater than a wildtype yeast cell in xylose-glucose growth media. The growth rate of the recombinant yeast cell in xylose-glucose growth media may be about 16× fold greater than a wildtype yeast cell in xylose-glucose growth media. The growth rate of the recombinant yeast cell in xylose-glucose growth media may be about 17× fold greater than a wildtype yeast cell in xylose-glucose growth media. The growth rate of the recombinant yeast cell in xylose-glucose growth media may be about 18× fold greater than a wildtype yeast cell in xylose-glucose growth media. The growth rate of the recombinant yeast cell in xylose-glucose growth media may be about 19× fold greater than a wildtype yeast cell in xylose-glucose growth media. The growth rate of the recombinant yeast cell in xylose-glucose growth media may be about 20× fold greater than a wildtype yeast cell in xylose-glucose growth media.

In embodiments, the recombinant xylose transporter transports a xylose compound into a recombinant yeast in a xylose-glucose growth media at a rate of about 5% to about 150% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 140% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 130% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 120% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 110% of the rate the recombinant xylose transporter transports the xylose compound into the recombinant yeast in a xylose growth media.

The recombinant xylose transporter may transport a xylose compound into a recombinant yeast in a xylose-glucose growth media at a rate of about 5% to about 100% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 90% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 80% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 70% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 60% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 50% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 40% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 30% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 20% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 5% to about 10% of the rate the recombinant xylose transporter transports the xylose compound into the recombinant yeast in a xylose growth media.

The recombinant xylose transporter may transport a xylose compound into a recombinant yeast in a xylose-glucose growth media at a rate of about 5% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 10% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 20% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 30% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 40% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 50% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 60% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 70% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 80% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 90% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 100% of the rate the recombinant xylose transporter transports the xylose compound into the recombinant yeast in a xylose growth media. In embodiments, a recombinant xylose transporter transports a xylose compound into a recombinant yeast in a xylose-glucose growth media at a rate about equal to the rate the recombinant xylose transporter transports the xylose compound into the recombinant yeast in a xylose growth media. In embodiments, a recombinant xylose transporter transports a xylose compound into a recombinant yeast in a xylose-glucose growth media at a rate greater to the rate the recombinant xylose transporter transports the xylose compound into the recombinant yeast in a xylose growth media.

The recombinant xylose transporter may transport a xylose compound into a recombinant yeast in a xylose-glucose growth media at a rate of about 110% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 120% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 130% of the rate the recombinant xylose transporter transports the xylose compound into the recombinant yeast in a xylose growth media.

The recombinant xylose transporter may transport a xylose compound into a recombinant yeast in a xylose-glucose growth media at a rate of about 140% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 150% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 160% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 170% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 180% of the rate the recombinant xylose transporter transports the xylose compound into the recombinant yeast in a xylose growth media. The recombinant xylose transporter may transport a xylose compound into a recombinant yeast in a xylose-glucose growth media at a rate of about 190% of the rate the recombinant xylose transporter transports the xylose compound into the recombinant yeast in a xylose growth media. The recombinant xylose transporter may transport a xylose compound into a recombinant yeast in a xylose-glucose growth media at a rate about 200% of the rate the recombinant xylose transporter transports the xylose compound into the recombinant yeast in a xylose growth media.

In embodiments, the xylose growth media includes xylose at a concentration of about 0.05 g/L to about 100 g/L. The xylose growth media may include xylose at a concentration of about 0.05 g/L to about 90 g/L. The xylose growth media may include xylose at a concentration of about 0.05 g/L to about 80 g/L. The xylose growth media may include xylose at a concentration of about 0.05 g/L to about 70 g/L. The xylose growth media may include xylose at a concentration of about 0.05 g/L to about 60 g/L. The xylose growth media may include xylose at a concentration of about 0.05 g/L to about 50 g/L. The xylose growth media may include xylose at a concentration of about 0.05 g/L to about 40 g/L. The xylose growth media may include xylose at a concentration of about 0.05 g/L to about 30 g/L. The xylose growth media may include xylose at a concentration of about 0.05 g/L to about 25 g/L.

In embodiments, the xylose growth media includes xylose at a concentration of about 0.05 g/L to about 20 g/L. The xylose growth media may include xylose at a concentration of about 0.05 g/L to about 15 g/L. The xylose growth media may include xylose at a concentration of about 0.05 g/L to about 10 g/L. The xylose growth media may include xylose at a concentration of about 0.05 g/L to about 5 g/L. The xylose growth media may include xylose at a concentration of about 0.05 g/L to about 4 g/L. The xylose growth media may include xylose at a concentration of about 0.05 g/L to about 3 g/L. The xylose growth media may include xylose at a concentration of about 0.05 g/L to about 2 g/L. The xylose growth media may include xylose at a concentration of about 0.05 g/L to about 1 g/L. The xylose growth media may include xylose at a concentration of about 0.05 g/L to about 0.5 g/L. The xylose growth media may include xylose at a concentration of about 0.05 g/L to about 0.1 g/L.

The xylose growth media may include xylose at a concentration of about 0.05 g/L. The xylose growth media may include xylose at a concentration of about 0.1 g/L. The xylose growth media may include xylose at a concentration of about 0.5 g/L. The xylose growth media may include xylose at a concentration of about 1 g/L. The xylose growth media may include xylose at a concentration of about 2 g/L. The xylose growth media may include xylose at a concentration of about 3 g/L. The xylose growth media may include xylose at a concentration of about 4 g/L. The xylose growth media may include xylose at a concentration of about 5 g/L. The xylose growth media may include xylose at a concentration of about 10 g/L. The xylose growth media may include xylose at a concentration of about 15 g/L. The xylose growth media may include xylose at a concentration of about 20 g/L. The xylose growth media may include xylose at a concentration of about 25 g/L. The xylose growth media may include xylose at a concentration of about 30 g/L. The xylose growth media may include xylose at a concentration of about 40 g/L. The xylose growth media may include xylose at a concentration of about 50 g/L. The xylose growth media may include xylose at a concentration of about 60 g/L. The xylose growth media may include xylose at a concentration of about 70 g/L. The xylose growth media may include xylose at a concentration of about 80 g/L. The xylose growth media may include xylose at a concentration of about 90 g/L. The xylose growth media may include xylose at a concentration of about 100 g/L.

In embodiments, the xylose growth media includes xylose at a concentration of about 0.05 g/L to about 300 g/L. The xylose growth media may include xylose at a concentration of about 0.05 g/L to about 250 g/L. The xylose growth media may include xylose at a concentration of about 0.05 g/L to about 200 g/L. The xylose growth media may include xylose at a concentration of about 0.05 g/L to about 150 g/L. The xylose growth media may include xylose at a concentration of about 0.05 g/L to about 100 g/L. The xylose growth media may include xylose at a concentration of about 0.05 g/L to about 50 g/L. The xylose growth media may include xylose at a concentration of about 0.05 g/L to about 25 g/L. The xylose growth media may include xylose at a concentration of about 1 g/L to about 300 g/L. The xylose growth media may include xylose at a concentration of about 10 g/L to about 300 g/L. The xylose growth media may include xylose at a concentration of about 20 g/L to about 300 g/L. The xylose growth media may include xylose at a concentration of about 30 g/L to about 300 g/L. The xylose growth media may include xylose at a concentration of about 40 g/L to about 300 g/L. The xylose growth media may include xylose at a concentration of about 50 g/L to about 300 g/L. The xylose growth media may include xylose at a concentration of about 75 g/L to about 300 g/L. The xylose growth media may include xylose at a concentration of about 100 g/L to about 300 g/L. The xylose growth media may include xylose at a concentration of about 125 g/L to about 300 g/L. The xylose growth media may include xylose at a concentration of about 150 g/L to about 300 g/L. The xylose growth media may include xylose at a concentration of about 175 g/L to about 300 g/L. The xylose growth media may include xylose at a concentration of about 200 g/L to about 300 g/L. The xylose growth media may include xylose at a concentration of about 225 g/L to about 300 g/L. The xylose growth media may include xylose at a concentration of about 250 g/L to about 300 g/L. The xylose growth media may include xylose at a concentration of about 275 g/L to about 300 g/L.

In embodiments, the xylose growth media includes xylose at a concentration of about 10 g/L to about 275 g/L. The xylose growth media may include xylose at a concentration of about 10 g/L to about 250 g/L. The xylose growth media may include xylose at a concentration of about 10 g/L to about 225 g/L. The xylose growth media may include xylose at a concentration of about 10 g/L to about 200 g/L. The xylose growth media may include xylose at a concentration of about 10 g/L to about 175 g/L. The xylose growth media may include xylose at a concentration of about 10 g/L to about 150 g/L. The xylose growth media may include xylose at a concentration of about 10 g/L to about 125 g/L. The xylose growth media may include xylose at a concentration of about 10 g/L to about 100 g/L. The xylose growth media may include xylose at a concentration of about 10 g/L to about 75 g/L. The xylose growth media may include xylose at a concentration of about 10 g/L to about 50 g/L. The xylose growth media may include xylose at a concentration of about 10 g/L to about 25 g/L.

The xylose growth media may include xylose at a concentration of about 125 g/L. The xylose growth media may include xylose at a concentration of about 150 g/L. The xylose growth media may include xylose at a concentration of about 175 g/L. The xylose growth media may include xylose at a concentration of about 200 g/L. The xylose growth media may include xylose at a concentration of about 225 g/L. The xylose growth media may include xylose at a concentration of about 250 g/L. The xylose growth media may include xylose at a concentration of about 275 g/L. The xylose growth media may include xylose at a concentration of about 300 g/L.

In embodiments, the xylose-glucose growth media includes xylose at a concentration as described herein for xylose growth media. In embodiments, the xylose-glucose growth media includes glucose at a concentration of about 0.05 g/L to about 20 g/L. The xylose-glucose growth media may include glucose at a concentration of about 0.05 g/L to about 15 g/L. The xylose-glucose growth media may include glucose at a concentration of about 0.05 g/L to about 10 g/L. The xylose-glucose growth media may include glucose at a concentration of about 0.05 g/L to about 5 g/L. The xylose-glucose growth media may include glucose at a concentration of about 0.05 g/L to about 4 g/L. The xylose-glucose growth media may include glucose at a concentration of about 0.05 g/L to about 3 g/L. The xylose-glucose growth media may include glucose at a concentration of about 0.05 g/L to about 2 g/L. The xylose-glucose growth media may include glucose at a concentration of about 0.05 g/L to about 1 g/L. The xylose-glucose growth media may include glucose at a concentration of about 0.05 g/L to about 0.5 g/L. The xylose-glucose growth media may include glucose at a concentration of about 0.05 g/L to about 0.1 g/L. The xylose-glucose growth media may include glucose at a concentration of about 0.05 g/L. The xylose-glucose growth media may include glucose at a concentration of about 0.1 g/L. The xylose-glucose growth media may include glucose at a concentration of about 0.5 g/L. The xylose-glucose growth media may include glucose at a concentration of about 1 g/L. The xylose-glucose growth media may include glucose at a concentration of about 2 g/L. The xylose-glucose growth media may include glucose at a concentration of about 3 g/L. The xylose-glucose growth media may include glucose at a concentration of about 4 g/L. The xylose-glucose growth media may include glucose at a concentration of about 5 g/L. The xylose-glucose growth media may include glucose at a concentration of about 10 g/L. The xylose-glucose growth media may include glucose at a concentration of about 15 g/L. The xylose-glucose growth media may include glucose at a concentration of about 20 g/L.

In embodiments, the xylose-glucose growth media includes glucose at a concentration of about 0.05 g/L to about 100 g/L. The xylose-glucose growth media may include glucose at a concentration of about 0.05 g/L to about 90 g/L. The xylose-glucose growth media may include glucose at a concentration of about 0.05 g/L to about 80 g/L. The xylose-glucose growth media may include glucose at a concentration of about 0.05 g/L to about 70 g/L. The xylose-glucose growth media may include glucose at a concentration of about 0.05 g/L to about 60 g/L. The xylose-glucose growth media may include glucose at a concentration of about 0.05 g/L to about 50 g/L. The xylose-glucose growth media may include glucose at a concentration of about 0.05 g/L to about 40 g/L. The xylose-glucose growth media may include glucose at a concentration of about 0.05 g/L to about 30 g/L. The xylose-glucose growth media may include glucose at a concentration of about 0.05 g/L to about 25 g/L.

The xylose-glucose growth media may include glucose at a concentration of about 25 g/L. The xylose-glucose growth media may include glucose at a concentration of about 30 g/L. The xylose-glucose growth media may include glucose at a concentration of about 40 g/L. The xylose-glucose growth media may include glucose at a concentration of about 50 g/L. The xylose-glucose growth media may include glucose at a concentration of about 60 g/L. The xylose-glucose growth media may include glucose at a concentration of about 70 g/L. The xylose-glucose growth media may include glucose at a concentration of about 80 g/L. The xylose-glucose growth media may include glucose at a concentration of about 90 g/L. The xylose-glucose growth media may include glucose at a concentration of about 100 g/L.

2. Recombinant Yeast Cell Including a Recombinant Arabinose Transporter Protein

In another aspect is a recombinant yeast cell that includes a recombinant arabinose transporter protein as described herein, including embodiments thereof. In embodiments, the growth rate of the recombinant yeast cell including a recombinant arabinose transporter protein as described herein can be measured. The growth rate may be determined in arabinose growth media (i.e. in the absence of glucose). The growth rate may be determined in arabinose-glucose growth media. In embodiments, the growth rates (i.e. growth rate in the absence and presence of glucose) are compared to determine the differential growth rate of the recombinant yeast cells. If the growth rate of recombinant yeast cells grown in arabinose-glucose growth media is less than the growth rate of recombinant yeast cells grown in arabinose growth media, the differential growth rate may indicate glucose inhibits the activity of the recombinant arabinose transporter protein. As described herein, inclusion of a glucose mitigating mutation decreases, minimizes, or may eliminate glucose inhibition of the recombinant arabinose transporter protein.

In embodiments, the growth rate of the recombinant yeast cell in an arabinose-glucose growth media is about 5% to about 150% of the growth rate of the recombinant yeast cell in arabinose growth media. The growth rate of the recombinant yeast cell in an arabinose-glucose growth media may be about 5% to about 140% of the growth rate of the recombinant yeast cell in arabinose growth media. The growth rate of the recombinant yeast cell in an arabinose-glucose growth media may be about 5% to about 130% of the growth rate of the recombinant yeast cell in arabinose growth media. The growth rate of the recombinant yeast cell in an arabinose-glucose growth media may be about 5% to about 120% of the growth rate of the recombinant yeast cell in arabinose growth media. The growth rate of the recombinant yeast cell in an arabinose-glucose growth media may be about 5% to about 110% of the growth rate of the recombinant yeast cell in arabinose growth media.

The growth rate of the recombinant yeast cell in an arabinose-glucose growth media may be about 5% to about 100% of the growth rate of the recombinant yeast cell in arabinose growth media. The growth rate of the recombinant yeast cell in an arabinose-glucose growth media may be about 5% to about 90% of the growth rate of the recombinant yeast cell in arabinose growth media. The growth rate of the recombinant yeast cell in an arabinose-glucose growth media may be about 5% to about 80% of the growth rate of the recombinant yeast cell in arabinose growth media. The growth rate of the recombinant yeast cell in an arabinose-glucose growth media may be about 5% to about 70% of the growth rate of the recombinant yeast cell in arabinose growth media. The growth rate of the recombinant yeast cell in an arabinose-glucose growth media may be about 5% to about 60% of the growth rate of the recombinant yeast cell in arabinose growth media. The growth rate of the recombinant yeast cell in an arabinose-glucose growth media may be about 5% to about 50% of the growth rate of the recombinant yeast cell in arabinose growth media. The growth rate of the recombinant yeast cell in an arabinose-glucose growth media may be about 5% to about 40% of the growth rate of the recombinant yeast cell in arabinose growth media. The growth rate of the recombinant yeast cell in an arabinose-glucose growth media may be about 5% to about 30% of the growth rate of the recombinant yeast cell in arabinose growth media. The growth rate of the recombinant yeast cell in an arabinose-glucose growth media may be about 5% to about 20% of the growth rate of the recombinant yeast cell in arabinose growth media. The growth rate of the recombinant yeast cell in an arabinose-glucose growth media may be about 5% to about 10% of the growth rate of the recombinant yeast cell in arabinose growth media.

The growth rate of the recombinant yeast cell in an arabinose-glucose growth media may be about 10% to about 150% of the growth rate of the recombinant yeast cell in arabinose growth media. The growth rate of the recombinant yeast cell in an arabinose-glucose growth media may be about 10% to about 140% of the growth rate of the recombinant yeast cell in arabinose growth media. The growth rate of the recombinant yeast cell in an arabinose-glucose growth media may be about 10% to about 130% of the growth rate of the recombinant yeast cell in arabinose growth media. The growth rate of the recombinant yeast cell in an arabinose-glucose growth media may be about 10% to about 120% of the growth rate of the recombinant yeast cell in arabinose growth media. The growth rate of the recombinant yeast cell in an arabinose-glucose growth media may be about 10% to about 110% of the growth rate of the recombinant yeast cell in arabinose growth media.

The growth rate of the recombinant yeast cell in an arabinose-glucose growth media may be about 10% to about 100% of the growth rate of the recombinant yeast cell in arabinose growth media. The growth rate of the recombinant yeast cell in an arabinose-glucose growth media may be about 10% to about 90% of the growth rate of the recombinant yeast cell in arabinose growth media. The growth rate of the recombinant yeast cell in an arabinose-glucose growth media may be about 10% to about 80% of the growth rate of the recombinant yeast cell in arabinose growth media. The growth rate of the recombinant yeast cell in an arabinose-glucose growth media may be about 10% to about 70% of the growth rate of the recombinant yeast cell in arabinose growth media. The growth rate of the recombinant yeast cell in an arabinose-glucose growth media may be about 10% to about 60% of the growth rate of the recombinant yeast cell in arabinose growth media. The growth rate of the recombinant yeast cell in an arabinose-glucose growth media may be about 10% to about 50% of the growth rate of the recombinant yeast cell in arabinose growth media. The growth rate of the recombinant yeast cell in an arabinose-glucose growth media may be about 10% to about 40% of the growth rate of the recombinant yeast cell in arabinose growth media. The growth rate of the recombinant yeast cell in an arabinose-glucose growth media may be about 10% to about 30% of the growth rate of the recombinant yeast cell in arabinose growth media. The growth rate of the recombinant yeast cell in an arabinose-glucose growth media may be about 10% to about 20% of the growth rate of the recombinant yeast cell in arabinose growth media.

The growth rate of the recombinant yeast cell in an arabinose-glucose growth media may be about 5% of the growth rate of the recombinant yeast cell in arabinose growth media. The growth rate of the recombinant yeast cell in an arabinose-glucose growth media may be about 10% of the growth rate of the recombinant yeast cell in arabinose growth media. The growth rate of the recombinant yeast cell in an arabinose-glucose growth media may be about 20% of the growth rate of the recombinant yeast cell in arabinose growth media. The growth rate of the recombinant yeast cell in an arabinose-glucose growth media may be about 30% of the growth rate of the recombinant yeast cell in arabinose growth media. The growth rate of the recombinant yeast cell in an arabinose-glucose growth media may be about 40% of the growth rate of the recombinant yeast cell in arabinose growth media. The growth rate of the recombinant yeast cell in an arabinose-glucose growth media may be about 50% of the growth rate of the recombinant yeast cell in arabinose growth media. The growth rate of the recombinant yeast cell in an arabinose-glucose growth media may be about 60% of the growth rate of the recombinant yeast cell in arabinose growth media. The growth rate of the recombinant yeast cell in an arabinose-glucose growth media may be about 70% of the growth rate of the recombinant yeast cell in arabinose growth media. The growth rate of the recombinant yeast cell in an arabinose-glucose growth media may be about 80% of the growth rate of the recombinant yeast cell in arabinose growth media. The growth rate of the recombinant yeast cell in an arabinose-glucose growth media may be about 90% of the growth rate of the recombinant yeast cell in arabinose growth media. The growth rate of the recombinant yeast cell in an arabinose-glucose growth media may be about 100% of the growth rate of the recombinant yeast cell in arabinose growth media.

The growth rate of the recombinant yeast cell in an arabinose-glucose growth media may be about 110% of the growth rate of the recombinant yeast cell in arabinose growth media. The growth rate of the recombinant yeast cell in an arabinose-glucose growth media may be about 120% of the growth rate of the recombinant yeast cell in arabinose growth media. The growth rate of the recombinant yeast cell in an arabinose-glucose growth media may be about 130% of the growth rate of the recombinant yeast cell in arabinose growth media. The growth rate of the recombinant yeast cell in an arabinose-glucose growth media may be about 140% of the growth rate of the recombinant yeast cell in arabinose growth media. The growth rate of the recombinant yeast cell in an arabinose-glucose growth media may be about 150% of the growth rate of the recombinant yeast cell in arabinose growth media. The growth rate of the recombinant yeast cell in an arabinose-glucose growth media may be about 160% of the growth rate of the recombinant yeast cell in arabinose growth media. The growth rate of the recombinant yeast cell in an arabinose-glucose growth media may be about 170% of the growth rate of the recombinant yeast cell in arabinose growth media. The growth rate of the recombinant yeast cell in an arabinose-glucose growth media may be about 180% of the growth rate of the recombinant yeast cell in arabinose growth media. The growth rate of the recombinant yeast cell in an arabinose-glucose growth media may be about 190% of the growth rate of the recombinant yeast cell in arabinose growth media. The growth rate of the recombinant yeast cell in an arabinose-glucose growth media may be about 200% of the growth rate of the recombinant yeast cell in arabinose growth media.

In embodiments, the recombinant yeast cells have a growth rate of about 0.005 $hr^{-1}$ in arabinose-glucose growth media that includes about 2.5, 5, 10, or 20 g/L glucose. The recombinant yeast cells may have a growth rate of about 0.0075 $hr^{-1}$ in arabinose-glucose growth media that includes about 2.5, 5, 10, or 20 g/L glucose. The recombinant yeast cells may have a growth rate of about 0.01 $hr^{-1}$ in arabinose-glucose growth media that includes about 2.5, 5, 10, or 20 g/L glucose. The recombinant yeast cells may have a growth rate of about 0.0125 $hr^{-1}$ in arabinose-glucose growth media that includes about 2.5, 5, 10, or 20 g/L glucose. The recombinant yeast cells may have a growth rate of about 0.015 $hr^{-1}$ in arabinose-glucose growth media that includes about 2.5, 5, 10, or 20 g/L glucose. The recombinant yeast cells may have a growth rate of about 0.0175 $hr^{-1}$ in arabinose-glucose growth media that includes about 2.5, 5, 10, or 20 g/L glucose. The recombinant yeast cells may have a growth rate of about 0.02 $hr^{-1}$ in arabinose-glucose growth media that includes about 2.5, 5, 10, or 20 g/L glucose. The recombinant yeast cells may have a growth rate of about 0.0225 $hr^{-1}$ in arabinose-glucose growth media that includes about 2.5, 5, 10, or 20 g/L glucose. The recombinant yeast cells may have a growth rate of about 0.025 $hr^{-1}$ in arabinose-glucose growth media that includes about 2.5, 5, 10, or 20 g/L glucose. The recombinant yeast cells may have a growth rate of about 0.0275 $hr^{-1}$ in arabinose-glucose growth media that includes about 2.5, 5, 10, or 20 g/L glucose. The recombinant yeast cells may have a growth rate of about 0.03 $hr^{-1}$ in arabinose-glucose growth media that includes about 2.5, 5, 10, or 20 g/L glucose. The recombinant yeast cells may have a growth rate of about 0.0325 $hr^{-1}$ in arabinose-glucose growth media that includes about 2.5, 5, 10, or 20 g/L glucose. The recombinant yeast cells may have a growth rate of about 0.035 $hr^{-1}$ in arabinose-glucose growth media that includes about 2.5, 5, 10, or 20 g/L glucose. The recombinant yeast cells may have a growth rate of about 0.0375 $hr^{-1}$ in arabinose-glucose growth media that includes about 2.5, 5, 10, or 20 g/L glucose. The recombinant yeast cells may have a growth rate of about 0.04 $hr^{-1}$ in arabinose-glucose growth media that includes about 2.5, 5, 10, or 20 g/L glucose. The recombinant yeast cells may have a growth rate of about 0.0425 $hr^{-1}$ in arabinose-glucose growth media that includes about 2.5, 5, 10, or 20 g/L glucose. The recombinant yeast cells may have a growth rate of about 0.045 $hr^{-1}$. The recombinant yeast cells may have a growth rate of about 0.0475 $hr^{-1}$ in arabinose-glucose growth media that includes about 2.5, 5, 10, or 20 g/L glucose. The recombinant yeast cells may have a growth rate of about 0.05 $hr^{-1}$ in arabinose-glucose growth media that includes about 2.5, 5, 10, or 20 g/L glucose.

In embodiments, the recombinant yeast cells have a growth rate of about 0.1 $hr^{-1}$ in arabinose-glucose growth media that includes about 2.5, 5, 10, or 20 g/L glucose. The recombinant yeast cells may have a growth rate of about 0.125 $hr^{-1}$ in arabinose-glucose growth media that includes about 2.5, 5, 10, or 20 g/L glucose. The recombinant yeast cells may have a growth rate of about 0.15 $hr^{-1}$ in arabinose-glucose growth media that includes about 2.5, 5, 10, or 20 g/L glucose. The recombinant yeast cells may have a growth rate of about 0.175 $hr^{-1}$ in arabinose-glucose growth media that includes about 2.5, 5, 10, or 20 g/L glucose. The recombinant yeast cells may have a growth rate of about 0.2 $hr^{-1}$ in arabinose-glucose growth media that includes about 2.5, 5, 10, or 20 g/L glucose. The recombinant yeast cells may have a growth rate of about 0.225 $hr^{-1}$ in arabinose-glucose growth media that includes about 2.5, 5, 10, or 20 g/L glucose. The recombinant yeast cells may have a growth rate of about 0.25 $hr^{-1}$ in arabinose-glucose growth media that includes about 2.5, 5, 10, or 20 g/L glucose. The recombinant yeast cells may have a growth rate of about 0.275 $hr^{-1}$ in arabinose-glucose growth media that includes about 2.5, 5, 10, or 20 g/L glucose. The recombinant yeast cells may have a growth rate of about 0.3 $hr^{-1}$ in arabinose-glucose growth media that includes about 2.5, 5, 10, or 20 g/L glucose. The recombinant yeast cells may have a growth rate of about 0.325 $hr^{-1}$ in arabinose-glucose growth media that includes about 2.5, 5, 10, or 20 g/L glucose. The recombinant yeast cells may have a growth rate of about 0.35 $hr^{-1}$ in arabinose-glucose growth media that includes about 2.5, 5, 10, or 20 g/L glucose. The recombinant yeast cells may have a growth rate of about 0.375 $hr^{-1}$ in arabinose-glucose growth media that includes about 2.5, 5, 10, or 20 g/L glucose. The recombinant yeast cells may have a growth rate of about 0.4 $hr^{-1}$ in arabinose-glucose growth media that includes about 2.5, 5, 10, or 20 g/L glucose. The recombinant yeast cells may have a growth rate of about 0.425 $hr^{-1}$ in arabinose-glucose growth media that includes about 2.5, 5, 10, or 20 g/L glucose. The recombinant yeast cells may have a growth rate of about 0.45 $hr^{-1}$ in arabinose-glucose growth media that includes about 2.5, 5, 10, or 20 g/L glucose. The recombinant yeast cells may have a growth rate of about 0.475 $hr^{-1}$ in arabinose-glucose growth media that includes about 2.5, 5, 10, or 20 g/L glucose. The recombinant yeast cells may have a growth rate of about 0.5 $hr^{-1}$ in arabinose-glucose growth media that includes about 2.5, 5, 10, or 20 g/L glucose. The recombinant yeast cells may have a growth rate of about 0.525 $hr^{-1}$ in arabinose-glucose growth media that includes about 2.5, 5, 10, or 20 g/L glucose. The recombinant yeast cells may have a growth rate of about 0.5 $hr^{-1}$ in arabinose-glucose growth media that includes about 2.5, 5, 10, or 20 g/L glucose. The recombinant yeast cells may have a growth rate of about 0.575 $hr^{-1}$ in arabinose-glucose growth media that includes about 2.5, 5, 10, or 20 g/L glucose. The recombinant yeast cells may have a growth rate of about 0.6 $hr^{-1}$ in arabinose-glucose growth media that includes about 2.5, 5, 10, or 20 g/L glucose. The recombinant yeast cells may have a growth rate of about 0.65 $hr^{-1}$ in arabinose-glucose growth media that includes about 2.5, 5, 10, or 20 g/L glucose. The recombinant yeast cells may have a growth rate of about 0.7 $hr^{-1}$ in arabinose-glucose growth media that includes about 2.5, 5, 10, or 20 g/L glucose. The recombinant yeast cells may have a growth rate of about 0.75 $hr^{-1}$ in arabinose-glucose growth media that includes about 2.5, 5, 10, or 20 g/L glucose. The recombinant yeast cells may have a growth rate of about 0.8 $hr^{-1}$ in arabinose-glucose growth media that includes about 2.5, 5, 10, or 20 g/L glucose. The recombinant yeast cells may have a growth rate of about 0.85 $hr^{-1}$ in arabinose-glucose growth media that includes about 2.5, 5, 10, or 20 g/L glucose. The recombinant yeast cells may have a growth rate of about 0.9 $hr^{-1}$ in arabinose-glucose growth media that includes about 2.5, 5, 10, or 20 g/L glucose. The recombinant yeast cells may have a growth rate of about 0.95 $hr^{-1}$ in arabinose-glucose growth media that includes about 2.5, 5, 10, or 20 g/L glucose. The recombinant yeast cells may have a growth rate of about 1 $hr^{-1}$ in arabinose-glucose growth media that includes about 2.5, 5, 10, or 20 g/L glucose.

The recombinant yeast cells may have a growth rate of about 0.005 $hr^{-1}$ in arabinose-glucose growth media that includes about 25 to about 100 g/L glucose. The recombinant yeast cells may have a growth rate of about 0.0075 $hr^{-1}$ in arabinose-glucose growth media that includes about 25 to about 100 g/L glucose. The recombinant yeast cells may have a growth rate of about 0.01 $hr^{-1}$ in arabinose-glucose growth media that includes about 25 to about 100 g/L glucose. The recombinant yeast cells may have a growth rate of about 0.0125 $hr^{-1}$ in arabinose-glucose growth media that includes about 25 to about 100 g/L glucose. The recombinant yeast cells may have a growth rate of about 0.015 $hr^{-1}$ in arabinose-glucose growth media that includes about 25 to about 100 g/L glucose. The recombinant yeast cells may have a growth rate of about 0.0175 $hr^{-1}$ in arabinose-glucose growth media that includes about 25 to about 100 g/L glucose. The recombinant yeast cells may have a growth rate of about 0.02 $hr^{-1}$ in arabinose-glucose growth media that includes about 25 to about 100 g/L glucose. The recombinant yeast cells may have a growth rate of about 0.0225 $hr^{-1}$ in arabinose-glucose growth media that includes about 25 to about 100 g/L glucose. The recombinant yeast cells may have a growth rate of about 0.025 $hr^{-1}$ in arabinose-glucose growth media that includes about 25 to about 100 g/L glucose. The recombinant yeast cells may have a growth rate of about 0.0275 $hr^{-1}$ in arabinose-glucose growth media that includes about 25 to about 100 g/L glucose. The recombinant yeast cells may have a growth rate of about 0.03 $hr^{-1}$ in arabinose-glucose growth media that includes about 25 to about 100 g/L glucose. The recombinant yeast cells may have a growth rate of about 0.0325 $hr^{-1}$ in arabinose-glucose growth media that includes about 25 to about 100 g/L glucose. The recombinant yeast cells may have a growth rate of about 0.035 $hr^{-1}$ in arabinose-glucose growth media that includes about 25 to about 100 g/L glucose. The recombinant yeast cells may have a growth rate of about 0.0375 $hr^{-1}$ in arabinose-glucose growth media that includes about 25 to about 100 g/L glucose. The recombinant yeast cells may have a growth rate of about 0.04 $hr^{-1}$ in arabinose-glucose growth media that includes about 25 to about 100 g/L glucose. The recombinant yeast cells may have a growth rate of about 0.0425 $hr^{-1}$ in arabinose-glucose growth media that includes about 25 to about 100 g/L glucose. The recombinant yeast cells may have a growth rate of about 0.045 $hr^{-1}$. The recombinant yeast cells may have a growth rate of about 0.0475 $hr^{-1}$ in arabinose-glucose growth media that includes about 25 to about 100 g/L glucose. The recombinant yeast cells may have a growth rate of about 0.05 $hr^{-1}$ in arabinose-glucose growth media that includes about 25 to about 100 g/L glucose.

In embodiments, the recombinant yeast cells have a growth rate of about 0.1 $hr^{-1}$ in arabinose-glucose growth media that includes about 25 to about 100 g/L glucose. The recombinant yeast cells may have a growth rate of about 0.125 $hr^{-1}$ in arabinose-glucose growth media that includes about 25 to about 100 g/L glucose. The recombinant yeast cells may have a growth rate of about 0.15 $hr^{-1}$ in arabinose-glucose growth media that includes about 25 to about 100 g/L glucose. The recombinant yeast cells may have a growth rate of about 0.175 $hr^{-1}$ in arabinose-glucose growth media that includes about 25 to about 100 g/L glucose. The recombinant yeast cells may have a growth rate of about 0.2 $hr^{-1}$ in arabinose-glucose growth media that includes about 25 to about 100 g/L glucose. The recombinant yeast cells may have a growth rate of about 0.225 $hr^{-1}$ in arabinose-glucose growth media that includes about 25 to about 100 g/L glucose. The recombinant yeast cells may have a growth rate of about 0.25 $hr^{-1}$ in arabinose-glucose growth media that includes about 25 to about 100 g/L glucose. The recombinant yeast cells may have a growth rate of about 0.275 $hr^{-1}$ in arabinose-glucose growth media that includes about 25 to about 100 g/L glucose. The recombinant yeast cells may have a growth rate of about 0.3 $hr^{-1}$ in arabinose-glucose growth media that includes about 25 to about 100 g/L glucose. The recombinant yeast cells may have a growth rate of about 0.325 $hr^{-1}$ in arabinose-glucose growth media that includes about 25 to about 100 g/L glucose. The recombinant yeast cells may have a growth rate of about 0.35 $hr^{-1}$ in arabinose-glucose growth media that includes about 25 to about 100 g/L glucose. The recombinant yeast cells may have a growth rate of about 0.375 $hr^{-1}$ in arabinose-glucose growth media that includes about 25 to about 100 g/L glucose. The recombinant yeast cells may have a growth rate of about 0.4 $hr^{-1}$ in arabinose-glucose growth media that includes about 25 to about 100 g/L glucose. The recombinant yeast cells may have a growth rate of about 0.425 $hr^{-1}$ in arabinose-glucose growth media that includes about 25 to about 100 g/L glucose. The recombinant yeast cells may have a growth rate of about 0.45 $hr^{-1}$ in arabinose-glucose growth media that includes about 25 to about 100 g/L glucose. The recombinant yeast cells may have a growth rate of about 0.475 $hr^{-1}$ in arabinose-glucose growth media that includes about 25 to about 100 g/L glucose. The recombinant yeast cells may have a growth rate of about 0.5 $hr^{-1}$ in arabinose-glucose growth media that includes about 25 to about 100 g/L glucose. The recombinant yeast cells may have a growth rate of about 0.525 $hr^{-1}$ in arabinose-glucose growth media that includes about 25 to about 100 g/L glucose. The recombinant yeast cells may have a growth rate of about 0.5 $hr^{-1}$ in arabinose-glucose growth media that includes about 25 to about 100 g/L glucose. The recombinant yeast cells may have a growth rate of about 0.575 $hr^{-1}$ in arabinose-glucose growth media that includes about 25 to about 100 g/L glucose. The recombinant yeast cells may have a growth rate of about 0.6 $hr^{-1}$ in arabinose-glucose growth media that includes about 25 to about 100 g/L glucose. The recombinant yeast cells may have a growth rate of about 0.65 $hr^{-1}$ in arabinose-glucose growth media that includes about 25 to about 100 g/L glucose. The recombinant yeast cells may have a growth rate of about 0.7 $hr^{-1}$ in arabinose-glucose growth media that includes about 25 to about 100 g/L glucose. The recombinant yeast cells may have a growth rate of about 0.75 $hr^{-1}$ in arabinose-glucose growth media that includes about 25 to about 100 g/L glucose. The recombinant yeast cells may have a growth rate of about 0.8 $hr^{-1}$ in arabinose-glucose growth media that includes about 25 to about 100 g/L glucose. The recombinant yeast cells may have a growth rate of about 0.85 $hr^{-1}$ in arabinose-glucose growth media that includes about 25 to about 100 g/L glucose. The recombinant yeast cells may have a growth rate of about 0.9 hr$^{-1}$ in arabinose-glucose growth media that includes about 25 to about 100 g/L glucose. The recombinant yeast cells may have a growth rate of about 0.95 hr$^{-1}$ in arabinose-glucose growth media that includes about 25 to about 100 g/L glucose. The recombinant yeast cells may have a growth rate of about 1 hr$^{-1}$ in arabinose-glucose growth media that includes about 25 to about 100 g/L glucose.

In embodiments, the growth rate of the recombinant yeast cell in arabinose-glucose growth media is about 0.1× fold greater than a wildtype yeast cell (i.e. a yeast cell without a recombinant transporter protein described herein) in arabinose-glucose growth media. The growth rate of the recombinant yeast cell in arabinose-glucose growth media may be about 0.2× fold greater than a wildtype yeast cell in arabinose-glucose growth media. The growth rate of the recombinant yeast cell in arabinose-glucose growth media may be about 0.3× fold greater than a wildtype yeast cell in arabinose-glucose growth media. The growth rate of the recombinant yeast cell in arabinose-glucose growth media may be about 0.4× fold greater than a wildtype yeast cell in arabinose-glucose growth media. The growth rate of the recombinant yeast cell in arabinose-glucose growth media may be about 0.5× fold greater than a wildtype yeast cell in arabinose-glucose growth media. The growth rate of the recombinant yeast cell in arabinose-glucose growth media may be about 0.6× fold greater than a wildtype yeast cell in arabinose-glucose growth media. The growth rate of the recombinant yeast cell in arabinose-glucose growth media may be about 0.7× fold greater than a wildtype yeast cell in arabinose-glucose growth media. The growth rate of the recombinant yeast cell in arabinose-glucose growth media may be about 0.8× fold greater than a wildtype yeast cell in arabinose-glucose growth media. The growth rate of the recombinant yeast cell in arabinose-glucose growth media may be about 0.9× fold greater than a wildtype yeast cell in arabinose-glucose growth media. The growth rate of the recombinant yeast cell in arabinose-glucose growth media may be about 1× fold greater than a wildtype yeast cell in arabinose-glucose growth media.

The growth rate of the recombinant yeast cell in arabinose-glucose growth media may be about 2× fold greater than a wildtype yeast cell in arabinose-glucose growth media. The growth rate of the recombinant yeast cell in arabinose-glucose growth media may be about 3× fold greater than a wildtype yeast cell in arabinose-glucose growth media. The growth rate of the recombinant yeast cell in arabinose-glucose growth media may be about 4× fold greater than a wildtype yeast cell in arabinose-glucose growth media. The growth rate of the recombinant yeast cell in arabinose-glucose growth media may be about 5× fold greater than a wildtype yeast cell in arabinose-glucose growth media. The growth rate of the recombinant yeast cell in arabinose-glucose growth media may be about 6× fold greater than a wildtype yeast cell in arabinose-glucose growth media. The growth rate of the recombinant yeast cell in arabinose-glucose growth media may be about 7× fold greater than a wildtype yeast cell in arabinose-glucose growth media. The growth rate of the recombinant yeast cell in arabinose-glucose growth media may be about 8× fold greater than a wildtype yeast cell in arabinose-glucose growth media. The growth rate of the recombinant yeast cell in arabinose-glucose growth media may be about 9× fold greater than a wildtype yeast cell in arabinose-glucose growth media. The growth rate of the recombinant yeast cell in arabinose-glucose growth media may be about 10× fold greater than a wildtype yeast cell in arabinose-glucose growth media.

The growth rate of the recombinant yeast cell in arabinose-glucose growth media may be about 11× fold greater than a wildtype yeast cell in arabinose-glucose growth media. The growth rate of the recombinant yeast cell in arabinose-glucose growth media may be about 12× fold greater than a wildtype yeast cell in arabinose-glucose growth media. The growth rate of the recombinant yeast cell in arabinose-glucose growth media may be about 13× fold greater than a wildtype yeast cell in arabinose-glucose growth media. The growth rate of the recombinant yeast cell in arabinose-glucose growth media may be about 14× fold greater than a wildtype yeast cell in arabinose-glucose growth media. The growth rate of the recombinant yeast cell in arabinose-glucose growth media may be about 15× fold greater than a wildtype yeast cell in arabinose-glucose growth media. The growth rate of the recombinant yeast cell in arabinose-glucose growth media may be about 16× fold greater than a wildtype yeast cell in arabinose-glucose growth media. The growth rate of the recombinant yeast cell in arabinose-glucose growth media may be about 17× fold greater than a wildtype yeast cell in arabinose-glucose growth media. The growth rate of the recombinant yeast cell in arabinose-glucose growth media may be about 18× fold greater than a wildtype yeast cell in arabinose-glucose growth media. The growth rate of the recombinant yeast cell in arabinose-glucose growth media may be about 19× fold greater than a wildtype yeast cell in arabinose-glucose growth media. The growth rate of the recombinant yeast cell in arabinose-glucose growth media may be about 20× fold greater than a wildtype yeast cell in arabinose-glucose growth media.

In embodiments, the recombinant arabinose transporter transports an arabinose compound into a recombinant yeast in an arabinose-glucose growth media at a rate of about 5% to about 150% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 140% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 130% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 120% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 110% of the rate the recombinant arabinose transporter transports the arabinose compound into the recombinant yeast in an arabinose growth media.

The recombinant arabinose transporter may transport an arabinose compound into a recombinant yeast in an arabinose-glucose growth media at a rate of about 5% to about 100% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 90% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 80% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 70% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 60% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 50% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 40% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 30% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 20% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 5% to about 10% of the rate the recombinant arabinose transporter transports the arabinose compound into the recombinant yeast in an arabinose growth media.

The recombinant arabinose transporter may transport an arabinose compound into a recombinant yeast in an arabinose-glucose growth media at a rate of about 5% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 10% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 20% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 30% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 40% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 50% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 60% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 70% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 80% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 90% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 100% of the rate the recombinant arabinose transporter transports the arabinose compound into the recombinant yeast in an arabinose growth media.

The recombinant arabinose transporter may transport an arabinose compound into a recombinant yeast in an arabinose-glucose growth media at a rate of about 110% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 120% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 130% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 140% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 150% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 160% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 170% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 180% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate of about 190% of the rate the recombinant arabinose transporter transports the arabinose compound into the recombinant yeast in an arabinose growth media. The recombinant arabinose transporter may transport an arabinose compound into a recombinant yeast in an arabinose-glucose growth media at a rate about 200% of the rate the recombinant arabinose transporter transports the arabinose compound into the recombinant yeast in an arabinose growth media.

In embodiments, the arabinose growth media includes arabinose at a concentration of about 0.05 g/L to about 20 g/L. The arabinose growth media may include arabinose at a concentration of about 0.05 g/L to about 15 g/L. The arabinose growth media may include arabinose at a concentration of about 0.05 g/L to about 10 g/L. The arabinose growth media may include arabinose at a concentration of about 0.05 g/L to about 5 g/L. The arabinose growth media may include arabinose at a concentration of about 0.05 g/L to about 4 g/L. The arabinose growth media may include arabinose at a concentration of about 0.05 g/L to about 3 g/L. The arabinose growth media may include arabinose at a concentration of about 0.05 g/L to about 2 g/L. The arabinose growth media may include arabinose at a concentration of about 0.05 g/L to about 1 g/L. The arabinose growth media may include arabinose at a concentration of about 0.05 g/L to about 0.5 g/L. The arabinose growth media may include arabinose at a concentration of about 0.05 g/L to about 0.1 g/L.

The arabinose growth media may include arabinose at a concentration of about 0.05 g/L. The arabinose growth media may include arabinose at a concentration of about 0.1 g/L. The arabinose growth media may include arabinose at a concentration of about 0.5 g/L. The arabinose growth media may include arabinose at a concentration of about 1 g/L. The arabinose growth media may include arabinose at a concentration of about 2 g/L. The arabinose growth media may include arabinose at a concentration of about 3 g/L. The arabinose growth media may include arabinose at a concentration of about 4 g/L. The arabinose growth media may include arabinose at a concentration of about 5 g/L. The arabinose growth media may include arabinose at a concentration of about 10 g/L. The arabinose growth media may include arabinose at a concentration of about 15 g/L. The arabinose growth media may include arabinose at a concentration of about 20 g/L.

In embodiments, the arabinose growth media includes arabinose at a concentration of about 0.05 g/L to about 300 g/L. The arabinose growth media may include arabinose at a concentration of about 0.05 g/L to about 250 g/L. The arabinose growth media may include arabinose at a concentration of about 0.05 g/L to about 200 g/L. The arabinose growth media may include arabinose at a concentration of about 0.05 g/L to about 150 g/L. The arabinose growth media may include arabinose at a concentration of about 0.05 g/L to about 100 g/L. The arabinose growth media may include arabinose at a concentration of about 0.05 g/L to about 50 g/L. The arabinose growth media may include arabinose at a concentration of about 0.05 g/L to about 25 g/L. The arabinose growth media may include arabinose at a concentration of about 1 g/L to about 300 g/L. The arabinose growth media may include arabinose at a concentration of about 10 g/L to about 300 g/L. The arabinose growth media may include arabinose at a concentration of about 20 g/L to about 300 g/L. The arabinose growth media may include arabinose at a concentration of about 30 g/L to about 300 g/L. The arabinose growth media may include arabinose at a concentration of about 40 g/L to about 300 g/L. The arabinose growth media may include arabinose at a concentration of about 50 g/L to about 300 g/L. The arabinose growth media may include arabinose at a concentration of about 75 g/L to about 300 g/L. The arabinose growth media may include arabinose at a concentration of about 100 g/L to about 300 g/L. The arabinose growth media may include arabinose at a concentration of about 125 g/L to about 300 g/L. The arabinose growth media may include arabinose at a concentration of about 150 g/L to about 300 g/L. The arabinose growth media may include arabinose at a concentration of about 175 g/L to about 300 g/L. The arabinose growth media may include arabinose at a concentration of about 200 g/L to about 300 g/L. The arabinose growth media may include arabinose at a concentration of about 225 g/L to about 300 g/L. The arabinose growth media may include arabinose at a concentration of about 250 g/L to about 300 g/L. The arabinose growth media may include arabinose at a concentration of about 275 g/L to about 300 g/L.

In embodiments, the arabinose growth media includes arabinose at a concentration of about 10 g/L to about 275 g/L. The arabinose growth media may include arabinose at a concentration of about 10 g/L to about 250 g/L. The arabinose growth media may include arabinose at a concentration of about 10 g/L to about 225 g/L. The arabinose growth media may include arabinose at a concentration of about 10 g/L to about 200 g/L. The arabinose growth media may include arabinose at a concentration of about 10 g/L to about 175 g/L. The arabinose growth media may include arabinose at a concentration of about 10 g/L to about 150 g/L. The arabinose growth media may include arabinose at a concentration of about 10 g/L to about 125 g/L. The arabinose growth media may include arabinose at a concentration of about 10 g/L to about 100 g/L. The arabinose growth media may include arabinose at a concentration of about 10 g/L to about 75 g/L. The arabinose growth media may include arabinose at a concentration of about 10 g/L to about 50 g/L. The arabinose growth media may include arabinose at a concentration of about 10 g/L to about 25 g/L.

The arabinose growth media may include arabinose at a concentration of about 25 g/L. The arabinose growth media may include arabinose at a concentration of about 50 g/L. The arabinose growth media may include arabinose at a concentration of about 75 g/L. The arabinose growth media may include arabinose at a concentration of about 100 g/L.

The arabinose growth media may include arabinose at a concentration of about 125 g/L. The arabinose growth media may include arabinose at a concentration of about 150 g/L. The arabinose growth media may include arabinose at a concentration of about 175 g/L. The arabinose growth media may include arabinose at a concentration of about 200 g/L. The arabinose growth media may include arabinose at a concentration of about 225 g/L. The arabinose growth media may include arabinose at a concentration of about 250 g/L. The arabinose growth media may include arabinose at a concentration of about 275 g/L. The arabinose growth media may include arabinose at a concentration of about 300 g/L.

In embodiments, the arabinose-glucose growth media includes arabinose at a concentration described herein for an arabinose growth media. In embodiments, the arabinose-glucose growth media includes glucose at a concentration of about 0.05 g/L to about 100 g/L. The arabinose-glucose growth media may include glucose at a concentration of about 0.05 g/L to about 90 g/L. The arabinose-glucose growth media may include glucose at a concentration of about 0.05 g/L to about 80 g/L. The arabinose-glucose growth media may include glucose at a concentration of about 0.05 g/L to about 70 g/L. The arabinose-glucose growth media may include glucose at a concentration of about 0.05 g/L to about 60 g/L. The arabinose-glucose growth media may include glucose at a concentration of about 0.05 g/L to about 50 g/L. The arabinose-glucose growth media may include glucose at a concentration of about 0.05 g/L to about 40 g/L. The arabinose-glucose growth media may include glucose at a concentration of about 0.05 g/L to about 30 g/L. The arabinose-glucose growth media may include glucose at a concentration of about 0.05 g/L to about 25 g/L.

The arabinose-glucose growth media may include glucose at a concentration of about 25 g/L. The arabinose-glucose growth media may include glucose at a concentration of about 30 g/L. The arabinose-glucose growth media may include glucose at a concentration of about 40 g/L. The arabinose-glucose growth media may include glucose at a concentration of about 50 g/L. The arabinose-glucose growth media may include glucose at a concentration of about 60 g/L. The arabinose-glucose growth media may include glucose at a concentration of about 70 g/L. The arabinose-glucose growth media may include glucose at a concentration of about 80 g/L. The arabinose-glucose growth media may include glucose at a concentration of about 90 g/L. The arabinose-glucose growth media may include glucose at a concentration of about 100 g/L.

In embodiments, the arabinose-glucose growth media includes glucose at a concentration of about 0.05 g/L to about 20 g/L. The arabinose-glucose growth media may include glucose at a concentration of about 0.05 g/L to about 15 g/L. The arabinose-glucose growth media may include glucose at a concentration of about 0.05 g/L to about 10 g/L. The arabinose-glucose growth media may include glucose at a concentration of about 0.05 g/L to about 5 g/L. The arabinose-glucose growth media may include glucose at a concentration of about 0.05 g/L to about 4 g/L. The arabinose-glucose growth media may include glucose at a concentration of about 0.05 g/L to about 3 g/L. The arabinose-glucose growth media may include glucose at a concentration of about 0.05 g/L to about 2 g/L. The arabinose-glucose growth media may include glucose at a concentration of about 0.05 g/L to about 1 g/L. The arabinose-glucose growth media may include glucose at a concentration of about 0.05 g/L to about 0.5 g/L. The arabinose-glucose growth media may include glucose at a concentration of about 0.05 g/L to about 0.1 g/L. The arabinose-glucose growth media may include glucose at a concentration of about 0.5 g/L. The arabinose-glucose growth media may include glucose at a concentration of about 1 g/L. The arabinose-glucose growth media may include glucose at a concentration of about 2 g/L. The arabinose-glucose growth media may include glucose at a concentration of about 3 g/L. The arabinose-glucose growth media may include glucose at a concentration of about 4 g/L. The arabinose-glucose growth media may include glucose at a concentration of about 5 g/L. The arabinose-glucose growth media may include glucose at a concentration of about 10 g/L. The arabinose-glucose growth media may include glucose at a concentration of about 15 g/L. The arabinose-glucose growth media may include glucose at a concentration of about 20 g/L.

3. Recombinant Yeast Cell Including a Recombinant Galactose Transporter Protein

In another aspect is a recombinant yeast cell that includes a recombinant galactose transporter protein as described herein, including embodiments thereof. In embodiments, the growth rate of the recombinant yeast cell including a recombinant transporter protein as described herein can be measured. The growth rate may be determined in galactose growth media (i.e. in the absence of glucose). The growth rate may be determined in galactose-glucose growth media. In embodiments, the growth rates (i.e. growth rate in the absence and presence of glucose) are compared to determine the differential growth rate of the recombinant yeast cells. If the growth rate of recombinant yeast cells grown in galactose-glucose growth media is less than the growth rate of recombinant yeast cells grown in galactose growth media, the differential growth rate may indicate glucose inhibits the activity of the recombinant galactose transporter protein. As described herein, inclusion of a glucose mitigating mutation decreases, minimizes, or may eliminate glucose inhibition experienced by the recombinant galactose transporter protein.

In embodiments, the growth rate of the recombinant yeast cell in a galactose-glucose growth media is about 5% to about 150% of the growth rate of the recombinant yeast cell in galactose growth media. The growth rate of the recombinant yeast cell in a galactose-glucose growth media may be about 5% to about 140% of the growth rate of the recombinant yeast cell in galactose growth media. The growth rate of the recombinant yeast cell in a galactose-glucose growth media may be about 5% to about 130% of the growth rate of the recombinant yeast cell in galactose growth media. The growth rate of the recombinant yeast cell in a galactose-glucose growth media may be about 5% to about 120% of the growth rate of the recombinant yeast cell in galactose growth media. The growth rate of the recombinant yeast cell in a galactose-glucose growth media may be about 5% to about 110% of the growth rate of the recombinant yeast cell in galactose growth media.

The growth rate of the recombinant yeast cell in a galactose-glucose growth media may be about 5% to about 100% of the growth rate of the recombinant yeast cell in galactose growth media. The growth rate of the recombinant yeast cell in a galactose-glucose growth media may be about 5% to about 90% of the growth rate of the recombinant yeast cell in galactose growth media. The growth rate of the recombinant yeast cell in a galactose-glucose growth media may be about 5% to about 80% of the growth rate of the recombinant yeast cell in galactose growth media. The growth rate of the recombinant yeast cell in a galactose-glucose growth media may be about 5% to about 70% of the growth rate of the recombinant yeast cell in galactose growth media. The growth rate of the recombinant yeast cell in a galactose-glucose growth media may be about 5% to about 60% of the growth rate of the recombinant yeast cell in galactose growth media. The growth rate of the recombinant yeast cell in a galactose-glucose growth media may be about 5% to about 50% of the growth rate of the recombinant yeast cell in galactose growth media. The growth rate of the recombinant yeast cell in a galactose-glucose growth media may be about 5% to about 40% of the growth rate of the recombinant yeast cell in galactose growth media. The growth rate of the recombinant yeast cell in a galactose-glucose growth media may be about 5% to about 30% of the growth rate of the recombinant yeast cell in galactose growth media. The growth rate of the recombinant yeast cell in a galactose-glucose growth media may be about 5% to about 20% of the growth rate of the recombinant yeast cell in galactose growth media. The growth rate of the recombinant yeast cell in a galactose-glucose growth media may be about 5% to about 10% of the growth rate of the recombinant yeast cell in galactose growth media.

The growth rate of the recombinant yeast cell in a galactose-glucose growth media may be about 10% to about 150% of the growth rate of the recombinant yeast cell in galactose growth media. The growth rate of the recombinant yeast cell in a galactose-glucose growth media may be about 10% to about 140% of the growth rate of the recombinant yeast cell in galactose growth media. The growth rate of the recombinant yeast cell in a galactose-glucose growth media may be about 10% to about 130% of the growth rate of the recombinant yeast cell in galactose growth media. The growth rate of the recombinant yeast cell in a galactose-glucose growth media may be about 10% to about 120% of the growth rate of the recombinant yeast cell in galactose growth media. The growth rate of the recombinant yeast cell in a galactose-glucose growth media may be about 10% to about 110% of the growth rate of the recombinant yeast cell in galactose growth media.

The growth rate of the recombinant yeast cell in a galactose-glucose growth media may be about 10% to about 100% of the growth rate of the recombinant yeast cell in galactose growth media. The growth rate of the recombinant yeast cell in a galactose-glucose growth media may be about 10% to about 90% of the growth rate of the recombinant yeast cell in galactose growth media. The growth rate of the recombinant yeast cell in a galactose-glucose growth media may be about 10% to about 80% of the growth rate of the recombinant yeast cell in galactose growth media. The growth rate of the recombinant yeast cell in a galactose-glucose growth media may be about 10% to about 70% of the growth rate of the recombinant yeast cell in galactose growth media. The growth rate of the recombinant yeast cell in a galactose-glucose growth media may be about 10% to about 60% of the growth rate of the recombinant yeast cell in galactose growth media. The growth rate of the recombinant yeast cell in a galactose-glucose growth media may be about 10% to about 50% of the growth rate of the recombinant yeast cell in galactose growth media. The growth rate of the recombinant yeast cell in a galactose-glucose growth media may be about 10% to about 40% of the growth rate of the recombinant yeast cell in galactose growth media. The growth rate of the recombinant yeast cell in a galactose-glucose growth media may be about 10% to about 30% of the growth rate of the recombinant yeast cell in galactose growth media. The growth rate of the recombinant yeast cell in a galactose-glucose growth media may be about 10% to about 20% of the growth rate of the recombinant yeast cell in galactose growth media.

The growth rate of the recombinant yeast cell in a galactose-glucose growth media may be about 5% of the growth rate of the recombinant yeast cell in galactose growth media. The growth rate of the recombinant yeast cell in a galactose-glucose growth media may be about 10% of the growth rate of the recombinant yeast cell in galactose growth media. The growth rate of the recombinant yeast cell in a galactose-glucose growth media may be about 20% of the growth rate of the recombinant yeast cell in galactose growth media. The growth rate of the recombinant yeast cell in a galactose-glucose growth media may be about 30% of the growth rate of the recombinant yeast cell in galactose growth media. The growth rate of the recombinant yeast cell in a galactose-glucose growth media may be about 40% of the growth rate of the recombinant yeast cell in galactose growth media. The growth rate of the recombinant yeast cell in a galactose-glucose growth media may be about 50% of the growth rate of the recombinant yeast cell in galactose growth media. The growth rate of the recombinant yeast cell in a galactose-glucose growth media may be about 60% of the growth rate of the recombinant yeast cell in galactose growth media. The growth rate of the recombinant yeast cell in a galactose-glucose growth media may be about 70% of the growth rate of the recombinant yeast cell in galactose growth media. The growth rate of the recombinant yeast cell in a galactose-glucose growth media may be about 80% of the growth rate of the recombinant yeast cell in galactose growth media. The growth rate of the recombinant yeast cell in a galactose-glucose growth media may be about 90% of the growth rate of the recombinant yeast cell in galactose growth media. The growth rate of the recombinant yeast cell in a galactose-glucose growth media may be about 100% of the growth rate of the recombinant yeast cell in galactose growth media.

The growth rate of the recombinant yeast cell in a galactose-glucose growth media may be about 110% of the growth rate of the recombinant yeast cell in galactose growth media. The growth rate of the recombinant yeast cell in a galactose-glucose growth media may be about 120% of the growth rate of the recombinant yeast cell in galactose growth media. The growth rate of the recombinant yeast cell in a galactose-glucose growth media may be about 130% of the growth rate of the recombinant yeast cell in galactose growth media. The growth rate of the recombinant yeast cell in a galactose-glucose growth media may be about 140% of the growth rate of the recombinant yeast cell in galactose growth media. The growth rate of the recombinant yeast cell in a galactose-glucose growth media may be about 150% of the growth rate of the recombinant yeast cell in galactose growth media. The growth rate of the recombinant yeast cell in a galactose-glucose growth media may be about 160% of the growth rate of the recombinant yeast cell in galactose growth media. The growth rate of the recombinant yeast cell in a galactose-glucose growth media may be about 170% of the growth rate of the recombinant yeast cell in galactose growth media. The growth rate of the recombinant yeast cell in a galactose-glucose growth media may be about 180% of the growth rate of the recombinant yeast cell in galactose growth media. The growth rate of the recombinant yeast cell in a galactose-glucose growth media may be about 190% of the growth rate of the recombinant yeast cell in galactose growth media. The growth rate of the recombinant yeast cell in a galactose-glucose growth media may be about 200% of the growth rate of the recombinant yeast cell in galactose growth media.

In embodiments, the recombinant yeast cells have a growth rate of about 0.005 hr$^{-1}$ in galactose-glucose growth media that includes about 2.5, 5, 10, or 20 g/L glucose. The recombinant yeast cells may have a growth rate of about 0.0075 hr$^{-1}$ in galactose-glucose growth media that includes about 2.5, 5, 10, or 20 g/L glucose. The recombinant yeast cells may have a growth rate of about 0.01 hr$^{-1}$ in galactose-glucose growth media that includes about 2.5, 5, 10, or 20 g/L glucose. The recombinant yeast cells may have a growth rate of about 0.0125 hr$^{-1}$ in galactose-glucose growth media that includes about 2.5, 5, 10, or 20 g/L glucose. The recombinant yeast cells may have a growth rate of about 0.015 hr$^{-1}$ in galactose-glucose growth media that includes about 2.5, 5, 10, or 20 g/L glucose. The recombinant yeast cells may have a growth rate of about 0.0175 hr$^{-1}$ in galactose-glucose growth media that includes about 2.5, 5, 10, or 20 g/L glucose. The recombinant yeast cells may have a growth rate of about 0.02 hr$^{-1}$ in galactose-glucose growth media that includes about 2.5, 5, 10, or 20 g/L glucose. The recombinant yeast cells may have a growth rate of about 0.0225 hr$^{-1}$ in galactose-glucose growth media that includes about 2.5, 5, 10, or 20 g/L glucose. The recombinant yeast cells may have a growth rate of about 0.025 hr$^{-1}$ in galactose-glucose growth media that includes about 2.5, 5, 10, or 20 g/L glucose. The recombinant yeast cells may have a growth rate of about 0.0275 hr$^{-1}$ in galactose-glucose growth media that includes about 2.5, 5, 10, or 20 g/L glucose. The recombinant yeast cells may have a growth rate of about 0.03 hr$^{-1}$ in galactose-glucose growth media that includes about 2.5, 5, 10, or 20 g/L glucose. The recombinant yeast cells may have a growth rate of about 0.0325 hr$^{-1}$ in galactose-glucose growth media that includes about 2.5, 5, 10, or 20 g/L glucose. The recombinant yeast cells may have a growth rate of about 0.035 hr$^{-1}$ in galactose-glucose growth media that includes about 2.5, 5, 10, or 20 g/L glucose. The recombinant yeast cells may have a growth rate of about 0.0375 hr$^{-1}$ in galactose-glucose growth media that includes about 2.5, 5, 10, or 20 g/L glucose. The recombinant yeast cells may have a growth rate of about 0.04 hr$^{-1}$ in galactose-glucose growth media that includes about 2.5, 5, 10, or 20 g/L glucose. The recombinant yeast cells may have a growth rate of about 0.0425 hr$^{-1}$ in galactose-glucose growth media that includes about 2.5, 5, 10, or 20 g/L glucose. The recombinant yeast cells may have a growth rate of about 0.045 hr$^{-1}$. The recombinant yeast cells may have a growth rate of about 0.0475 hr$^{-1}$ in galactose-glucose growth media that includes about 2.5, 5, 10, or 20 g/L glucose. The recombinant yeast cells may have a growth rate of about 0.05 hr$^{-1}$ in galactose-glucose growth media that includes about 2.5, 5, 10, or 20 g/L glucose.

In embodiments, the recombinant yeast cells have a growth rate of about 0.1 hr$^{-1}$ in galactose-glucose growth media that includes about 2.5, 5, 10, or 20 g/L glucose. The recombinant yeast cells may have a growth rate of about 0.125 hr$^{-1}$ in galactose-glucose growth media that includes about 2.5, 5, 10, or 20 g/L glucose. The recombinant yeast cells may have a growth rate of about 0.15 hr$^{-1}$ in galactose-glucose growth media that includes about 2.5, 5, 10, or 20 g/L glucose. The recombinant yeast cells may have a growth rate of about 0.175 hr$^{-1}$ in galactose-glucose growth media that includes about 2.5, 5, 10, or 20 g/L glucose. The recombinant yeast cells may have a growth rate of about 0.2 hr$^{-1}$ in galactose-glucose growth media that includes about 2.5, 5, 10, or 20 g/L glucose. The recombinant yeast cells may have a growth rate of about 0.225 hr$^{-1}$ in galactose-glucose growth media that includes about 2.5, 5, 10, or 20 g/L glucose. The recombinant yeast cells may have a growth rate of about 0.25 hr$^{-1}$ in galactose-glucose growth media that includes about 2.5, 5, 10, or 20 g/L glucose. The recombinant yeast cells may have a growth rate of about 0.275 hr$^{-1}$ in galactose-glucose growth media that includes about 2.5, 5, 10, or 20 g/L glucose. The recombinant yeast cells may have a growth rate of about 0.3 hr$^{-1}$ in galactose-glucose growth media that includes about 2.5, 5, 10, or 20 g/L glucose. The recombinant yeast cells may have a growth rate of about 0.325 hr$^{-1}$ in galactose-glucose growth media that includes about 2.5, 5, 10, or 20 g/L glucose. The recombinant yeast cells may have a growth rate of about 0.35 hr$^{-1}$ in galactose-glucose growth media that includes about 2.5, 5, 10, or 20 g/L glucose. The recombinant yeast cells may have a growth rate of about 0.375 hr$^{-1}$ in galactose-glucose growth media that includes about 2.5, 5, 10, or 20 g/L glucose. The recombinant yeast cells may have a growth rate of about 0.4 hr$^{-1}$ in galactose-glucose growth media that includes about 2.5, 5, 10, or 20 g/L glucose. The recombinant yeast cells may have a growth rate of about 0.425 hr$^{-1}$ in galactose-glucose growth media that includes about 2.5, 5, 10, or 20 g/L glucose. The recombinant yeast cells may have a growth rate of about 0.45 hr$^{-1}$ in galactose-glucose growth media that includes about 2.5, 5, 10, or 20 g/L glucose. The recombinant yeast cells may have a growth rate of about 0.475 hr$^{-1}$ in galactose-glucose growth media that includes about 2.5, 5, 10, or 20 g/L glucose. The recombinant yeast cells may have a growth rate of about 0.5 hr$^{-1}$ in galactose-glucose growth media that includes about 2.5, 5, 10, or 20 g/L glucose. The recombinant yeast cells may have a growth rate of about 0.525 hr$^{-1}$ in galactose-glucose growth media that includes about 2.5, 5, 10, or 20 g/L glucose. The recombinant yeast cells may have a growth rate of about 0.5 hr$^{-1}$ in galactose-glucose growth media that includes about 2.5, 5, 10, or 20 g/L glucose. The recombinant yeast cells may have a growth rate of about 0.575 hr$^{-1}$ in galactose-glucose growth media that includes about 2.5, 5, 10, or 20 g/L glucose. The recombinant yeast cells may have a growth rate of about 0.6 hr$^{-1}$ in galactose-glucose growth media that includes about 2.5, 5, 10, or 20 g/L glucose. The recombinant yeast cells may have a growth rate of about 0.65 hr$^{-1}$ in galactose-glucose growth media that includes about 2.5, 5, 10, or 20 g/L glucose. The recombinant yeast cells may have a growth rate of about 0.7 hr$^{-1}$ in galactose-glucose growth media that includes about 2.5, 5, 10, or 20 g/L glucose. The recombinant yeast cells may have a growth rate of about 0.75 hr$^{-1}$ in galactose-glucose growth media that includes about 2.5, 5, 10, or 20 g/L glucose. The recombinant yeast cells may have a growth rate of about 0.8 hr$^{-1}$ in galactose-glucose growth media that includes about 2.5, 5, 10, or 20 g/L glucose. The recombinant yeast cells may have a growth rate of about 0.85 hr$^{-1}$ in galactose-glucose growth media that includes about 2.5, 5, 10, or 20 g/L glucose. The recombinant yeast cells may have a growth rate of about 0.9 hr$^{-1}$ in galactose-glucose growth media that includes about 2.5, 5, 10, or 20 g/L glucose. The recombinant yeast cells may have a growth rate of about 0.95 hr$^{-1}$ in galactose-glucose growth media that includes about 2.5, 5, 10, or 20 g/L glucose. The recombinant yeast cells may have a growth rate of about 1 hr$^{-1}$ in galactose-glucose growth media that includes about 2.5, 5, 10, or 20 g/L glucose.

In embodiments, the recombinant yeast cells have a growth rate of about 0.005 hr$^{-1}$ in galactose-glucose growth media that includes about 25 to about 100 g/L glucose. The recombinant yeast cells may have a growth rate of about 0.0075 hr$^{-1}$ in galactose-glucose growth media that includes about 25 to about 100 g/L glucose. The recombinant yeast cells may have a growth rate of about 0.01 hr$^{-1}$ in galactose-glucose growth media that includes about 25 to about 100 g/L glucose. The recombinant yeast cells may have a growth rate of about 0.0125 hr$^{-1}$ in galactose-glucose growth media that includes about 25 to about 100 g/L glucose. The recombinant yeast cells may have a growth rate of about 0.015 hr$^{-1}$ in galactose-glucose growth media that includes about 25 to about 100 g/L glucose. The recombinant yeast cells may have a growth rate of about 0.0175 hr$^{-1}$ in galactose-glucose growth media that includes about 25 to about 100 g/L glucose. The recombinant yeast cells may have a growth rate of about 0.02 hr$^{-1}$ in galactose-glucose growth media that includes about 25 to about 100 g/L glucose. The recombinant yeast cells may have a growth rate of about 0.0225 hr$^{-1}$ in galactose-glucose growth media that includes about 25 to about 100 g/L glucose. The recombinant yeast cells may have a growth rate of about 0.025 hr$^{-1}$ in galactose-glucose growth media that includes about 25 to about 100 g/L glucose. The recombinant yeast cells may have a growth rate of about 0.0275 hr$^{-1}$ in galactose-glucose growth media that includes about 25 to about 100 g/L glucose. The recombinant yeast cells may have a growth rate of about 0.03 hr$^{-1}$ in galactose-glucose growth media that includes about 25 to about 100 g/L glucose. The recombinant yeast cells may have a growth rate of about 0.0325 hr$^{-1}$ in galactose-glucose growth media that includes about 25 to about 100 g/L glucose. The recombinant yeast cells may have a growth rate of about 0.035 hr$^{-1}$ in galactose-glucose growth media that includes about 25 to about 100 g/L glucose. The recombinant yeast cells may have a growth rate of about 0.0375 hr$^{-1}$ in galactose-glucose growth media that includes about 25 to about 100 g/L glucose. The recombinant yeast cells may have a growth rate of about 0.04 hr$^{-1}$ in galactose-glucose growth media that includes about 25 to about 100 g/L glucose. The recombinant yeast cells may have a growth rate of about 0.0425 hr$^{-1}$ in galactose-glucose growth media that includes about 25 to about 100 g/L glucose. The recombinant yeast cells may have a growth rate of about 0.045 hr$^{-1}$. The recombinant yeast cells may have a growth rate of about 0.0475 hr$^{-1}$ in galactose-glucose growth media that includes about 25 to about 100 g/L glucose. The recombinant yeast cells may have a growth rate of about 0.05 hr$^{-1}$ in galactose-glucose growth media that includes about 25 to about 100 g/L glucose.

In embodiments, the recombinant yeast cells have a growth rate of about 0.1 hr$^{-1}$ in galactose-glucose growth media that includes about 25 to about 100 g/L glucose. The recombinant yeast cells may have a growth rate of about 0.125 hr$^{-1}$ in galactose-glucose growth media that includes about 25 to about 100 g/L glucose. The recombinant yeast cells may have a growth rate of about 0.15 hr$^{-1}$ in galactose-glucose growth media that includes about 25 to about 100 g/L glucose. The recombinant yeast cells may have a growth rate of about 0.175 hr$^{-1}$ in galactose-glucose growth media that includes about 25 to about 100 g/L glucose. The recombinant yeast cells may have a growth rate of about 0.2 hr$^{-1}$ in galactose-glucose growth media that includes about 25 to about 100 g/L glucose. The recombinant yeast cells may have a growth rate of about 0.225 hr$^{-1}$ in galactose-glucose growth media that includes about 25 to about 100 g/L glucose. The recombinant yeast cells may have a growth rate of about 0.25 hr$^{-1}$ in galactose-glucose growth media that includes about 25 to about 100 g/L glucose. The recombinant yeast cells may have a growth rate of about 0.275 hr$^{-1}$ in galactose-glucose growth media that includes about 25 to about 100 g/L glucose. The recombinant yeast cells may have a growth rate of about 0.3 hr$^{-1}$ in galactose-glucose growth media that includes about 25 to about 100 g/L glucose. The recombinant yeast cells may have a growth rate of about 0.325 hr$^{-1}$ in galactose-glucose growth media that includes about 25 to about 100 g/L glucose. The recombinant yeast cells may have a growth rate of about 0.35 hr$^{-1}$ in galactose-glucose growth media that includes about 25 to about 100 g/L glucose. The recombinant yeast cells may have a growth rate of about 0.375 hr$^{-1}$ in galactose-glucose growth media that includes about 25 to about 100 g/L glucose. The recombinant yeast cells may have a growth rate of about 0.4 hr$^{-1}$ in galactose-glucose growth media that includes about 25 to about 100 g/L glucose. The recombinant yeast cells may have a growth rate of about 0.425 hr$^{-1}$ in galactose-glucose growth media that includes about 25 to about 100 g/L glucose. The recombinant yeast cells may have a growth rate of about 0.45 hr$^{-1}$ in galactose-glucose growth media that includes about 25 to about 100 g/L glucose. The recombinant yeast cells may have a growth rate of about 0.475 hr$^{-1}$ in galactose-glucose growth media that includes about 25 to about 100 g/L glucose. The recombinant yeast cells may have a growth rate of about 0.5 hr$^{-1}$ in galactose-glucose growth media that includes about 25 to about 100 g/L glucose. The recombinant yeast cells may have a growth rate of about 0.525 hr$^{-1}$ in galactose-glucose growth media that includes about 25 to about 100 g/L glucose. The recombinant yeast cells may have a growth rate of about 0.5 hr$^{-1}$ in galactose-glucose growth media that includes about 25 to about 100 g/L glucose. The recombinant yeast cells may have a growth rate of about 0.575 hr$^{-1}$ in galactose-glucose growth media that includes about 25 to about 100 g/L glucose. The recombinant yeast cells may have a growth rate of about 0.6 hr$^{-1}$ in galactose-glucose growth media that includes about 25 to about 100 g/L glucose. The recombinant yeast cells may have a growth rate of about 0.65 hr$^{-1}$ in galactose-glucose growth media that includes about 25 to about 100 g/L glucose. The recombinant yeast cells may have a growth rate of about 0.7 hr$^{-1}$ in galactose-glucose growth media that includes about 25 to about 100 g/L glucose. The recombinant yeast cells may have a growth rate of about 0.75 hr$^{-1}$ in galactose-glucose growth media that includes about 25 to about 100 g/L glucose. The recombinant yeast cells may have a growth rate of about 0.8 hr$^{-1}$ in galactose-glucose growth media that includes about 25 to about 100 g/L glucose. The recombinant yeast cells may have a growth rate of about 0.85 hr$^{-1}$ in galactose-glucose growth media that includes about 25 to about 100 g/L glucose. The recombinant yeast cells may have a growth rate of about 0.9 hr$^{-1}$ in galactose-glucose growth media that includes about 25 to about 100 g/L glucose. The recombinant yeast cells may have a growth rate of about 0.95 hr$^{-1}$ in galactose-glucose growth media that includes about 25 to about 100 g/L glucose. The recombinant yeast cells may have a growth rate of about 1 hr$^{-1}$ in galactose-glucose growth media that includes about 25 to about 100 g/L glucose.

In embodiments, the growth rate of the recombinant yeast cell in galactose-glucose growth media is about 0.1× fold greater than a wildtype yeast cell (i.e. a yeast cell without a recombinant transporter protein described herein) in galactose-glucose growth media. The growth rate of the recombinant yeast cell in galactose-glucose growth media may be about 0.2× fold greater than a wildtype yeast cell in galactose-glucose growth media. The growth rate of the recombinant yeast cell in galactose-glucose growth media may be about 0.3× fold greater than a wildtype yeast cell in galactose-glucose growth media. The growth rate of the recombinant yeast cell in galactose-glucose growth media may be about 0.4× fold greater than a wildtype yeast cell in galactose-glucose growth media. The growth rate of the recombinant yeast cell in galactose-glucose growth media may be about 0.5× fold greater than a wildtype yeast cell in galactose-glucose growth media. The growth rate of the recombinant yeast cell in galactose-glucose growth media may be about 0.6× fold greater than a wildtype yeast cell in galactose-glucose growth media. The growth rate of the recombinant yeast cell in galactose-glucose growth media may be about 0.7× fold greater than a wildtype yeast cell in galactose-glucose growth media. The growth rate of the recombinant yeast cell in galactose-glucose growth media may be about 0.8× fold greater than a wildtype yeast cell in galactose-glucose growth media. The growth rate of the recombinant yeast cell in galactose-glucose growth media may be about 0.9× fold greater than a wildtype yeast cell in galactose-glucose growth media. The growth rate of the recombinant yeast cell in galactose-glucose growth media may be about 1× fold greater than a wildtype yeast cell in galactose-glucose growth media.

The growth rate of the recombinant yeast cell in galactose-glucose growth media may be about 2× fold greater than a wildtype yeast cell in galactose-glucose growth media. The growth rate of the recombinant yeast cell in galactose-glucose growth media may be about 3× fold greater than a wildtype yeast cell in galactose-glucose growth media. The growth rate of the recombinant yeast cell in galactose-glucose growth media may be about 4× fold greater than a wildtype yeast cell in galactose-glucose growth media. The growth rate of the recombinant yeast cell in galactose-glucose growth media may be about 5× fold greater than a wildtype yeast cell in galactose-glucose growth media. The growth rate of the recombinant yeast cell in galactose-glucose growth media may be about 6× fold greater than a wildtype yeast cell in galactose-glucose growth media. The growth rate of the recombinant yeast cell in galactose-glucose growth media may be about 7× fold greater than a wildtype yeast cell in galactose-glucose growth media. The growth rate of the recombinant yeast cell in galactose-glucose growth media may be about 8× fold greater than a wildtype yeast cell in galactose-glucose growth media. The growth rate of the recombinant yeast cell in galactose-glucose growth media may be about 9× fold greater than a wildtype yeast cell in galactose-glucose growth media. The growth rate of the recombinant yeast cell in galactose-glucose growth media may be about 10× fold greater than a wildtype yeast cell in galactose-glucose growth media.

The growth rate of the recombinant yeast cell in galactose-glucose growth media may be about 11× fold greater than a wildtype yeast cell in galactose-glucose growth media. The growth rate of the recombinant yeast cell in galactose-glucose growth media may be about 12× fold greater than a wildtype yeast cell in galactose-glucose growth media. The growth rate of the recombinant yeast cell in galactose-glucose growth media may be about 13× fold greater than a wildtype yeast cell in galactose-glucose growth media. The growth rate of the recombinant yeast cell in galactose-glucose growth media may be about 14× fold greater than a wildtype yeast cell in galactose-glucose growth media. The growth rate of the recombinant yeast cell in galactose-glucose growth media may be about 15× fold greater than a wildtype yeast cell in galactose-glucose growth media. The growth rate of the recombinant yeast cell in galactose-glucose growth media may be about 16× fold greater than a wildtype yeast cell in galactose-glucose growth media. The growth rate of the recombinant yeast cell in galactose-glucose growth media may be about 17× fold greater than a wildtype yeast cell in galactose-glucose growth media. The growth rate of the recombinant yeast cell in galactose-glucose growth media may be about 18× fold greater than a wildtype yeast cell in galactose-glucose growth media. The growth rate of the recombinant yeast cell in galactose-glucose growth media may be about 19× fold greater than a wildtype yeast cell in galactose-glucose growth media. The growth rate of the recombinant yeast cell in galactose-glucose growth media may be about 20× fold greater than a wildtype yeast cell in galactose-glucose growth media.

In embodiments, the recombinant galactose transporter transports an galactose compound into a recombinant yeast in a galactose-glucose growth media at a rate of about 5% to about 150% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 140% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 130% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 120% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 110% of the rate the recombinant galactose transporter transports the galactose compound into the recombinant yeast in a galactose growth media.

The recombinant galactose transporter may transport an galactose compound into a recombinant yeast in a galactose-glucose growth media at a rate of about 5% to about 100% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 90% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 80% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 70% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 60% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 50% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 40% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 30% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 20% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 5% to about 10% of the rate the recombinant galactose transporter transports the galactose compound into the recombinant yeast in a galactose growth media.

The recombinant galactose transporter may transport an galactose compound into a recombinant yeast in a galactose-glucose growth media at a rate of about 5% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 10% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 20% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 30% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 40% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 50% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 60% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 70% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 80% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 90% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 100% of the rate the recombinant galactose transporter transports the galactose compound into the recombinant yeast in a galactose growth media.

The recombinant galactose transporter may transport an galactose compound into a recombinant yeast in a galactose-glucose growth media at a rate of about 110% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 120% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 130% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 140% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 150% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 160% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 170% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 180% of the rate the recombinant galactose transporter transports the galactose compound into the recombinant yeast in a galactose growth media. The recombinant galactose transporter may transport an galactose compound into a recombinant yeast in a galactose-glucose growth media at a rate of about 190% of the rate the recombinant galactose transporter transports the galactose compound into the recombinant yeast in a galactose growth media. The recombinant galactose transporter may transport an galactose compound into a recombinant yeast in a galactose-glucose growth media at a rate about 200% of the rate the recombinant galactose transporter transports the galactose compound into the recombinant yeast in a galactose growth media.

In embodiments, the galactose growth media includes galactose a concentration of about 0.05 g/L to about 20 g/L. The galactose growth media may include galactose a concentration of about 0.05 g/L to about 15 g/L. The galactose growth media may include galactose a concentration of about 0.05 g/L to about 10 g/L. The galactose growth media may include galactose a concentration of about 0.05 g/L to about 5 g/L. The galactose growth media may include galactose a concentration of about 0.05 g/L to about 4 g/L. The galactose growth media may include galactose a concentration of about 0.05 g/L to about 3 g/L. The galactose growth media may include galactose a concentration of about 0.05 g/L to about 2 g/L. The galactose growth media may include galactose a concentration of about 0.05 g/L to about 1 g/L. The galactose growth media may include galactose a concentration of about 0.05 g/L to about 0.5 g/L. The galactose growth media may include galactose a concentration of about 0.05 g/L to about 0.1 g/L.

The galactose growth media may include galactose a concentration of about 0.05 g/L. The galactose growth media may include galactose a concentration of about 0.1 g/L. The galactose growth media may include galactose a concentration of about 0.5 g/L. The galactose growth media may include galactose a concentration of about 1 g/L. The galactose growth media may include galactose a concentration of about 2 g/L. The galactose growth media may include galactose a concentration of about 3 g/L. The galactose growth media may include galactose a concentration of about 4 g/L. The galactose growth media may include galactose a concentration of about 5 g/L. The galactose growth media may include galactose a concentration of about 10 g/L. The galactose growth media may include galactose a concentration of about 15 g/L. The galactose growth media may include galactose a concentration of about 20 g/L.

In embodiments, the galactose growth media includes galactose a concentration of about 0.05 g/L to about 300 g/L. The galactose growth media may include galactose a concentration of about 0.05 g/L to about 250 g/L. The galactose growth media may include galactose a concentration of about 0.05 g/L to about 200 g/L. The galactose growth media may include galactose a concentration of about 0.05 g/L to about 150 g/L. The galactose growth media may include galactose a concentration of about 0.05 g/L to about 100 g/L. The galactose growth media may include galactose a concentration of about 0.05 g/L to about 50 g/L. The galactose growth media may include galactose a concentration of about 0.05 g/L to about 25 g/L. The galactose growth media may include galactose a concentration of about 1 g/L to about 300 g/L. The galactose growth media may include galactose a concentration of about 10 g/L to about 300 g/L. The galactose growth media may include galactose a concentration of about 20 g/L to about 300 g/L. The galactose growth media may include galactose a concentration of about 30 g/L to about 300 g/L. The galactose growth media may include galactose a concentration of about 40 g/L to about 300 g/L. The galactose growth media may include galactose a concentration of about 50 g/L to about 300 g/L. The galactose growth media may include galactose a concentration of about 75 g/L to about 300 g/L. The galactose growth media may include galactose a concentration of about 100 g/L to about 300 g/L. The galactose growth media may include galactose a concentration of about 125 g/L to about 300 g/L. The galactose growth media may include galactose a concentration of about 150 g/L to about 300 g/L. The galactose growth media may include galactose a concentration of about 175 g/L to about 300 g/L. The galactose growth media may include galactose a concentration of about 200 g/L to about 300 g/L. The galactose growth media may include galactose a concentration of about 225 g/L to about 300 g/L. The galactose growth media may include galactose a concentration of about 250 g/L to about 300 g/L. The galactose growth media may include galactose a concentration of about 275 g/L to about 300 g/L.

In embodiments, the galactose growth media includes galactose a concentration of about 10 g/L to about 275 g/L. The galactose growth media may include galactose a concentration of about 10 g/L to about 250 g/L. The galactose growth media may include galactose a concentration of about 10 g/L to about 225 g/L. The galactose growth media may include galactose a concentration of about 10 g/L to about 200 g/L. The galactose growth media may include galactose a concentration of about 10 g/L to about 175 g/L. The galactose growth media may include galactose a concentration of about 10 g/L to about 150 g/L. The galactose growth media may include galactose a concentration of about 10 g/L to about 125 g/L. The galactose growth media may include galactose a concentration of about 10 g/L to about 100 g/L. The galactose growth media may include galactose a concentration of about 10 g/L to about 75 g/L. The galactose growth media may include galactose a concentration of about 10 g/L to about 50 g/L. The galactose growth media may include galactose a concentration of about 10 g/L to about 25 g/L.

The galactose growth media may include galactose a concentration of about 25 g/L. The galactose growth media may include galactose a concentration of about 50 g/L. The galactose growth media may include galactose a concentration of about 75 g/L. The galactose growth media may include galactose a concentration of about 100 g/L. The galactose growth media may include galactose a concentration of about 125 g/L. The galactose growth media may include galactose a concentration of about 150 g/L. The galactose growth media may include galactose a concentration of about 175 g/L. The galactose growth media may include galactose a concentration of about 200 g/L. The galactose growth media may include galactose a concentration of about 225 g/L. The galactose growth media may include galactose a concentration of about 250 g/L. The galactose growth media may include galactose a concentration of about 275 g/L. The galactose growth media may include galactose a concentration of about 300 g/L.

In embodiments, the galactose-glucose growth media includes galactose at a concentration as described herein for a galactose growth media. In embodiments, the galactose-glucose growth media includes glucose at a concentration of about 0.05 g/L to about 100 g/L. The galactose-glucose growth media may include glucose at a concentration of about 0.05 g/L to about 90 g/L. The galactose-glucose growth media may include glucose at a concentration of about 0.05 g/L to about 80 g/L. The galactose-glucose growth media may include glucose at a concentration of about 0.05 g/L to about 70 g/L. The galactose-glucose growth media may include glucose at a concentration of about 0.05 g/L to about 60 g/L. The galactose-glucose growth media may include glucose at a concentration of about 0.05 g/L to about 50 g/L. The galactose-glucose growth media may include glucose at a concentration of about 0.05 g/L to about 40 g/L. The galactose-glucose growth media may include glucose at a concentration of about 0.05 g/L to about 30 g/L. The galactose-glucose growth media may include glucose at a concentration of about 0.05 g/L to about 25 g/L.

The galactose-glucose growth media may include glucose at a concentration of about 25 g/L. The galactose-glucose growth media may include glucose at a concentration of about 30 g/L. The galactose-glucose growth media may include glucose at a concentration of about 40 g/L. The galactose-glucose growth media may include glucose at a concentration of about 50 g/L. The galactose-glucose growth media may include glucose at a concentration of about 60 g/L. The galactose-glucose growth media may include glucose at a concentration of about 70 g/L. The galactose-glucose growth media may include glucose at a concentration of about 80 g/L. The galactose-glucose growth media may include glucose at a concentration of about 90 g/L. The galactose-glucose growth media may include glucose at a concentration of about 100 g/L.

In embodiments, the galactose-glucose growth media includes glucose at a concentration of about 0.05 g/L to about 20 g/L. The galactose-glucose growth media may include glucose at a concentration of about 0.05 g/L to about 15 g/L. The galactose-glucose growth media may include glucose at a concentration of about 0.05 g/L to about 10 g/L. The galactose-glucose growth media may include glucose at a concentration of about 0.05 g/L to about 5 g/L. The galactose-glucose growth media may include glucose at a concentration of about 0.05 g/L to about 4 g/L. The galactose-glucose growth media may include glucose at a concentration of about 0.05 g/L to about 3 g/L. The galactose-glucose growth media may include glucose at a concentration of about 0.05 g/L to about 2 g/L. The galactose-glucose growth media may include glucose at a concentration of about 0.05 g/L to about 1 g/L. The galactose-glucose growth media may include glucose at a concentration of about 0.05 g/L to about 0.5 g/L. The galactose-glucose growth media may include glucose at a concentration of about 0.05 g/L to about 0.1 g/L. The galactose-glucose growth media may include glucose at a concentration of about 0.05 g/L. The galactose-glucose growth media may include glucose at a concentration of about 0.1 g/L. The galactose-glucose growth media may include glucose at a concentration of about 0.5 g/L. The galactose-glucose growth media may include glucose at a concentration of about 1 g/L. The galactose-glucose growth media may include glucose at a concentration of about 2 g/L. The galactose-glucose growth media may include glucose at a concentration of about 3 g/L. The galactose-glucose growth media may include glucose at a concentration of about 4 g/L. The galactose-glucose growth media may include glucose at a concentration of about 5 g/L. The galactose-glucose growth media may include glucose at a concentration of about 10 g/L. The galactose-glucose growth media may include glucose at a concentration of about 15 g/L. The galactose-glucose growth media may include glucose at a concentration of about 20 g/L.

IV. Methods

Also provided herein are methods of transporting xylose into a recombinant yeast cell. In one aspect, the method includes contacting a recombinant yeast cell with a xylose compound described herein, where the recombinant yeast cell includes a recombinant xylose transporter protein as described herein, including embodiments thereof. The recombinant xylose transporter protein transports the xylose compound into the recombinant yeast cell. In embodiments, the only sugar (i.e. carbon source) present is a xylose compound. The recombinant xylose transporter protein is as described herein, including embodiments thereof. By extension, the xylose transporter motif sequence and the glucose mitigation mutation are as described herein, including embodiments thereof.

In another aspect, the method includes contacting a recombinant yeast cell with a xylose compound, where the xylose compound is the only sugar (i.e. carbon source) in the media, and where the recombinant yeast cell includes a recombinant xylose transporter protein as described herein, including embodiments thereof.

1. Transporting Xylose into a Recombinant Yeast Cell

The xylose compound may be derived from lignocellulosic biomass, hemicellulose, or xylan. Thus, in embodiments, the xylose compound is not the only sugar (i.e. carbon source) present. The xylose compound may be derived from lignocellulosic biomass. The xylose compound may be derived from hemicellulose. The xylose compound may be derived from xylan. In embodiments, the recombinant yeast cell metabolizes the xylose compound. The xylose compound may be present at a concentration as described hereinabove for the "xylose growth media". In embodiments, the recombinant yeast cell converts the xylose compound to a biofuel as described herein (e.g. ethanol) or to a biochemical as described herein. The recombinant yeast cell may convert the xylose compound to a biofuel as described herein (e.g. ethanol). The recombinant yeast cell may convert the xylose compound to a biochemical as described herein. In embodiments, the only sugar (i.e. carbon source) available is the xylose compound.

In embodiments, the recombinant xylose transporter transports a xylose compound into a recombinant yeast cell in a xylose-glucose growth media at a rate of at least 1 nmol min$^{-1}$ gDCW$^{-1}$ to 15 nmol min$^{-1}$ gDCW$^{-1}$. The term "gDCW" provided herein is well known in the art and refers to gram dry cell weight. The recombinant xylose transporter may transport a xylose compound into a recombinant yeast cell in a xylose-glucose growth media at a rate of at least 2 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 3 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 4 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 5 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 6 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 7 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 8 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 9 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 10 nmol min$^{-1}$ gDCW$^{-1}$ to 15 nmol min$^{-1}$ gDCW$^{-1}$.

The recombinant xylose transporter may transport a xylose compound into a recombinant yeast cell in a xylose-glucose growth media at a rate of at least 11 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 12 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 13 nmol min$^{-1}$ gDCW$^{-1}$ to 15 nmol min$^{-1}$ gDCW$^{-1}$. The recombinant xylose transporter may transport a xylose compound into a recombinant yeast cell in a xylose-glucose growth media at a rate of at least 14 nmol min$^{-1}$ gDCW$^{-1}$ to 15 nmol min$^{-1}$ gDCW$^{-1}$.

The recombinant xylose transporter may transport a xylose compound into a recombinant yeast cell in a xylose-glucose growth media at a rate of at least 1 nmol min$^{-1}$ gDCW$^{-1}$. The recombinant xylose transporter may transport a xylose compound into a recombinant yeast cell in a xylose-glucose growth media at a rate of at least 2 nmol min$^{-1}$ gDCW$^{-1}$. The recombinant xylose transporter may transport a xylose compound into a recombinant yeast cell in a xylose-glucose growth media at a rate of at least 3 nmol min$^{-1}$ gDCW$^{-1}$. The recombinant xylose transporter may transport a xylose compound into a recombinant yeast cell in a xylose-glucose growth media at a rate of at least 4 nmol min$^{-1}$ gDCW$^{-1}$. The recombinant xylose transporter may transport a xylose compound into a recombinant yeast cell in a xylose-glucose growth media at a rate of at least 5 nmol min$^{-1}$ gDCW$^{-1}$. The recombinant xylose transporter may transport a xylose compound into a recombinant yeast cell in a xylose-glucose growth media at a rate of at least 6 nmol min$^{-1}$ gDCW$^{-1}$. The recombinant xylose transporter may transport a xylose compound into a recombinant yeast cell in a xylose-glucose growth media at a rate of at least 7 nmol min$^{-1}$ gDCW$^{-1}$. The recombinant xylose transporter may transport a xylose compound into a recombinant yeast cell in a xylose-glucose growth media at a rate of at least 8 nmol min$^{-1}$ gDCW$^{-1}$. The recombinant xylose transporter may transport a xylose compound into a recombinant yeast cell in a xylose-glucose growth media at a rate of at least 9 nmol min$^{-1}$ gDCW$^{-1}$. The recombinant xylose transporter may transport a xylose compound into a recombinant yeast cell in a xylose-glucose growth media at a rate of at least 10 nmol min$^{-1}$ gDCW$^{-1}$. The recombinant xylose transporter may transport a xylose compound into a recombinant yeast cell in a xylose-glucose growth media at a rate of at least 11 nmol min$^{-1}$ gDCW$^{-1}$. The recombinant xylose transporter may transport a xylose compound into a recombinant yeast cell in a xylose-glucose growth media at a rate of at least 12 nmol min$^{-1}$ gDCW$^{-1}$. The recombinant xylose transporter may transport a xylose compound into a recombinant yeast cell in a xylose-glucose growth media at a rate of at least 13 nmol min$^{-1}$ gDCW$^{-1}$. The recombinant xylose transporter may transport a xylose compound into a recombinant yeast cell in a xylose-glucose growth media at a rate of at least 14 nmol min$^{-1}$ gDCW$^{-1}$. The recombinant xylose transporter may transport a xylose compound into a recombinant yeast cell in a xylose-glucose growth media at a rate of at least 15 nmol min$^{-1}$ gDCW$^{-1}$.

In embodiments, the recombinant xylose transporter transports a xylose compound into a recombinant yeast cell in a xylose-glucose growth media at a rate of at least 1 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 2.5 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 5 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 10 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 12 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 15 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 20 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 25 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 30 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 35 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 40 nmol min$^{-1}$ gDCW$^{-1}$ to 50 nmol min$^{-1}$ gDCW$^{-1}$. The recombinant xylose transporter may transport a xylose compound into a recombinant yeast cell in a xylose-glucose growth media at a rate of at least 45 nmol min$^{-1}$ gDCW$^{-1}$ to 50 nmol min$^{-1}$ gDCW$^{-1}$.

The recombinant xylose transporter may transport a xylose compound into a recombinant yeast cell in a xylose-glucose growth media at a rate of at least 2.5 nmol min$^{-1}$ gDCW$^{-1}$. The recombinant xylose transporter may transport a xylose compound into a recombinant yeast cell in a xylose-glucose growth media at a rate of at least 17 nmol min$^{-1}$ gDCW$^{-1}$. The recombinant xylose transporter may transport a xylose compound into a recombinant yeast cell in a xylose-glucose growth media at a rate of at least 18 nmol min$^{-1}$ gDCW$^{-1}$. The recombinant xylose transporter may transport a xylose compound into a recombinant yeast cell in a xylose-glucose growth media at a rate of at least 19 nmol min$^{-1}$ gDCW$^{-1}$. The recombinant xylose transporter may transport a xylose compound into a recombinant yeast cell in a xylose-glucose growth media at a rate of at least 20 nmol min$^{-1}$ gDCW$^{-1}$. The recombinant xylose transporter may transport a xylose compound into a recombinant yeast cell in a xylose-glucose growth media at a rate of at least 22 nmol min$^{-1}$ gDCW$^{-1}$. The recombinant xylose transporter may transport a xylose compound into a recombinant yeast cell in a xylose-glucose growth media at a rate of at least 25 nmol min$^{-1}$ gDCW$^{-1}$. The recombinant xylose transporter may transport a xylose compound into a recombinant yeast cell in a xylose-glucose growth media at a rate of at least 30 nmol min$^{-1}$ gDCW$^{-1}$. The recombinant xylose transporter may transport a xylose compound into a recombinant yeast cell in a xylose-glucose growth media at a rate of at least 35 nmol min$^{-1}$ gDCW$^{-1}$. The recombinant xylose transporter may transport a xylose compound into a recombinant yeast cell in a xylose-glucose growth media at a rate of at least 40 nmol min$^{-1}$ gDCW$^{-1}$. The recombinant xylose transporter may transport a xylose compound into a recombinant yeast cell in a xylose-glucose growth media at a rate of at least 45 nmol $min^{-1}$ $gDCW^{-1}$. The recombinant xylose transporter may transport a xylose compound into a recombinant yeast cell in a xylose-glucose growth media at a rate of at least 50 nmol $min^{-1}$ $gDCW^{-1}$.

In embodiments, the recombinant xylose transporter transports a xylose compound into a recombinant yeast cell in a xylose-glucose growth media at a rate of at least 10 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 20 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 30 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 40 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 50 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 60 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 70 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 80 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 90 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 100 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 110 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 120 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 130 nmol $min^{-1}$ $gDCW^{-1}$ to 150 nmol $min^{-1}$ $gDCW^{-1}$. The recombinant xylose transporter may transport a xylose compound into a recombinant yeast cell in a xylose-glucose growth media at a rate of at least 140 nmol $min^{-1}$ $gDCW^{-1}$ to 150 nmol $min^{-1}$ $gDCW^{-1}$.

The recombinant xylose transporter may transport a xylose compound into a recombinant yeast cell in a xylose-glucose growth media at a rate of at least 60 nmol $min^{-1}$ $gDCW^{-1}$. The recombinant xylose transporter may transport a xylose compound into a recombinant yeast cell in a xylose-glucose growth media at a rate of at least 70 nmol $min^{-1}$ $gDCW^{-1}$. The recombinant xylose transporter may transport a xylose compound into a recombinant yeast cell in a xylose-glucose growth media at a rate of at least 80 nmol $min^{-1}$ $gDCW^{-1}$. The recombinant xylose transporter may transport a xylose compound into a recombinant yeast cell in a xylose-glucose growth media at a rate of at least 90 nmol $min^{-1}$ $gDCW^{-1}$. The recombinant xylose transporter may transport a xylose compound into a recombinant yeast cell in a xylose-glucose growth media at a rate of at least 100 nmol $min^{-1}$ $gDCW^{-1}$. The recombinant xylose transporter may transport a xylose compound into a recombinant yeast cell in a xylose-glucose growth media at a rate of at least 110 nmol $min^{-1}$ $gDCW^{-1}$. The recombinant xylose transporter may transport a xylose compound into a recombinant yeast cell in a xylose-glucose growth media at a rate of at least 120 nmol $min^{-1}$ $gDCW^{-1}$. The recombinant xylose transporter may transport a xylose compound into a recombinant yeast cell in a xylose-glucose growth media at a rate of at least 130 nmol $min^{-1}$ $gDCW^{-1}$. The recombinant xylose transporter may transport a xylose compound into a recombinant yeast cell in a xylose-glucose growth media at a rate of at least 140 nmol $min^{-1}$ $gDCW^{-1}$. The recombinant xylose transporter may transport a xylose compound into a recombinant yeast cell in a xylose-glucose growth media at a rate of at least 150 nmol $min^{-1}$ $gDCW^{-1}$.

2. Transporting Arabinose into a Recombinant Yeast Cell

Also provided herein are methods of transporting arabinose into a recombinant yeast cell. In one aspect, the method includes contacting a recombinant yeast cell with an arabinose compound described herein, where the recombinant yeast cell includes a recombinant arabinose transporter protein as described herein, including embodiments thereof. The recombinant arabinose transporter protein transports the arabinose compound into the recombinant yeast cell. In embodiments, the only sugar (i.e. carbon source) present is an arabinose compound. The recombinant arabinose transporter protein is as described herein, including embodiments thereof. By extension, the arabinose transporter motif sequence and the glucose mitigation mutation are as described herein, including embodiments thereof.

In another aspect, the method includes contacting a recombinant yeast cell with an arabinose compound, where the arabinose compound is the only sugar (i.e. carbon source) in the media, and where the recombinant yeast cell includes a recombinant arabinose transporter protein as described herein, including embodiments thereof.

The arabinose compound may be derived from lignocellulosic biomass, hemicellulose, pectin, or xylan. Thus, in embodiments, the arabinose compound is not the only sugar (i.e. carbon source) present. The arabinose compound may be derived from lignocellulosic biomass. The arabinose compound may be derived from hemicellulose. The arabinose compound may be derived from pectin. The arabinose compound may be derived from xylan. In embodiments, the recombinant yeast cell metabolizes the arabinose compound. The arabinose compound may be present at a concentration as described hereinabove for the "arabinose growth media". In embodiments, the recombinant yeast cell converts the arabinose compound to a biofuel (e.g. ethanol) or to a biochemical as described herein, including embodiments thereof. The recombinant yeast cell may convert the arabinose compound to a biofuel (e.g. ethanol). The recombinant yeast cell may convert the arabinose compound to a biochemical as described herein, including embodiments thereof.

In embodiments, the recombinant arabinose transporter transports an arabinose compound into a recombinant yeast cell in an arabinose-glucose growth media at a rate of at least 1 nmol $min^{-1}$ $gDCW^{-1}$ to 15 nmol $min^{-1}$ $gDCW^{-1}$. The recombinant arabinose transporter may transport an arabinose compound into a recombinant yeast cell in an arabinose-glucose growth media at a rate of at least 2 nmol $min^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 3 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 4 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 5 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 6 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 7 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 8 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 9 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 10 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 11 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 12 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 13 nmol min$^{-1}$ gDCW$^{-1}$ to 15 nmol min$^{-1}$ gDCW$^{-1}$. The recombinant arabinose transporter may transport an arabinose compound into a recombinant yeast cell in an arabinose-glucose growth media at a rate of at least 14 nmol min$^{-1}$ gDCW$^{-1}$ to 15 nmol min$^{-1}$ gDCW$^{-1}$.

The recombinant arabinose transporter may transport an arabinose compound into a recombinant yeast cell in an arabinose-glucose growth media at a rate of at least 1 nmol min$^{-1}$ gDCW$^{-1}$. The recombinant arabinose transporter may transport an arabinose compound into a recombinant yeast cell in an arabinose-glucose growth media at a rate of at least 2 nmol min$^{-1}$ gDCW$^{-1}$. The recombinant arabinose transporter may transport an arabinose compound into a recombinant yeast cell in an arabinose-glucose growth media at a rate of at least 3 nmol min$^{-1}$ gDCW$^{-1}$. The recombinant arabinose transporter may transport an arabinose compound into a recombinant yeast cell in an arabinose-glucose growth media at a rate of at least 4 nmol min$^{-1}$ gDCW$^{-1}$. The recombinant arabinose transporter may transport an arabinose compound into a recombinant yeast cell in an arabinose-glucose growth media at a rate of at least 5 nmol min$^{-1}$ gDCW$^{-1}$. The recombinant arabinose transporter may transport an arabinose compound into a recombinant yeast cell in an arabinose-glucose growth media at a rate of at least 6 nmol min$^{-1}$ gDCW$^{-1}$. The recombinant arabinose transporter may transport an arabinose compound into a recombinant yeast cell in an arabinose-glucose growth media at a rate of at least 7 nmol min$^{-1}$ gDCW$^{-1}$. The recombinant arabinose transporter may transport an arabinose compound into a recombinant yeast cell in an arabinose-glucose growth media at a rate of at least 8 nmol min$^{-1}$ gDCW$^{-1}$. The recombinant arabinose transporter may transport an arabinose compound into a recombinant yeast cell in an arabinose-glucose growth media at a rate of at least 9 nmol min$^{-1}$ gDCW$^{-1}$. The recombinant arabinose transporter may transport an arabinose compound into a recombinant yeast cell in an arabinose-glucose growth media at a rate of at least 10 nmol min$^{-1}$ gDCW$^{-1}$. The recombinant arabinose transporter may transport an arabinose compound into a recombinant yeast cell in an arabinose-glucose growth media at a rate of at least 11 nmol min$^{-1}$ gDCW$^{-1}$. The recombinant arabinose transporter may transport an arabinose compound into a recombinant yeast cell in an arabinose-glucose growth media at a rate of at least 12 nmol min$^{-1}$ gDCW$^{-1}$. The recombinant arabinose transporter may transport an arabinose compound into a recombinant yeast cell in an arabinose-glucose growth media at a rate of at least 13 nmol min$^{-1}$ gDCW$^{-1}$. The recombinant arabinose transporter may transport an arabinose compound into a recombinant yeast cell in an arabinose-glucose growth media at a rate of at least 14 nmol min$^{-1}$ gDCW$^{-1}$. The recombinant arabinose transporter may transport an arabinose compound into a recombinant yeast cell in an arabinose-glucose growth media at a rate of at least 15 nmol min$^{-1}$ gDCW$^{-1}$.

In embodiments, the recombinant arabinose transporter transports an arabinose compound into a recombinant yeast cell in an arabinose-glucose growth media at a rate of at least 1 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 2.5 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 5 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 10 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 12 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 15 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 20 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 25 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 30 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 35 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 40 nmol min$^{-1}$ gDCW$^{-1}$ to 50 nmol min$^{-1}$ gDCW$^{-1}$. The recombinant arabinose transporter may transport an arabinose compound into a recombinant yeast cell in an arabinose-glucose growth media at a rate of at least 45 nmol min$^{-1}$ gDCW$^{-1}$ to 50 nmol min$^{-1}$ gDCW$^{-1}$.

The recombinant arabinose transporter may transport an arabinose compound into a recombinant yeast cell in an arabinose-glucose growth media at a rate of at least 2.5 nmol min$^{-1}$ gDCW$^{-1}$. The recombinant arabinose transporter may transport an arabinose compound into a recombinant yeast cell in an arabinose-glucose growth media at a rate of at least 17 nmol min$^{-1}$ gDCW$^{-1}$. The recombinant arabinose transporter may transport an arabinose compound into a recombinant yeast cell in an arabinose-glucose growth media at a rate of at least 18 nmol min$^{-1}$ gDCW$^{-1}$. The recombinant arabinose transporter may transport an arabinose compound into a recombinant yeast cell in an arabinose-glucose growth media at a rate of at least 19 nmol min$^{-1}$ gDCW$^{-1}$. The recombinant arabinose transporter may transport an arabinose compound into a recombinant yeast cell in an arabinose-glucose growth media at a rate of at least 20 nmol min$^{-1}$ gDCW$^{-1}$. The recombinant arabinose transporter may transport an arabinose compound into a recombinant yeast cell in an arabinose-glucose growth media at a rate of at least 22 nmol min$^{-1}$ gDCW$^{-1}$. The recombinant arabinose transporter may transport an arabinose compound into a recombinant yeast cell in an arabinose-glucose growth media at a rate of at least 25 nmol min$^{-1}$ gDCW$^{-1}$. The recombinant arabinose transporter may transport an arabinose compound into a recombinant yeast cell in an arabinose-glucose growth media at a rate of at least 30 nmol min$^{-1}$ gDCW$^{-1}$. The recombinant arabinose transporter may transport an arabinose compound into a recombinant yeast cell in an arabinose-glucose growth media at a rate of at least 35 nmol min$^{-1}$ gDCW$^{-1}$. The recombinant arabinose transporter may transport an arabinose compound into a recombinant yeast cell in an arabinose-glucose growth media at a rate of at least 40 nmol min$^{-1}$ gDCW$^{-1}$. The recombinant arabinose transporter may transport an arabinose compound into a recombinant yeast cell in an arabinose-glucose growth media at a rate of at least 45 nmol min$^{-1}$ gDCW$^{-1}$. The recombinant arabinose transporter may transport an arabinose compound into a recombinant yeast cell in an arabinose-glucose growth media at a rate of at least 50 nmol min$^{-1}$ gDCW$^{-1}$.

In embodiments, the recombinant arabinose transporter transports an arabinose compound into a recombinant yeast cell in an arabinose-glucose growth media at a rate of at least 10 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 20 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 30 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 40 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 50 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 60 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 70 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 80 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 90 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 100 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 110 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 120 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 130 nmol min$^{-1}$ gDCW$^{-1}$ to 150 nmol min$^{-1}$ gDCW$^{-1}$. The recombinant arabinose transporter may transport an arabinose compound into a recombinant yeast cell in an arabinose-glucose growth media at a rate of at least 140 nmol min$^{-1}$ gDCW$^{-1}$ to 150 nmol min$^{-1}$ gDCW$^{-1}$.

The recombinant arabinose transporter may transport an arabinose compound into a recombinant yeast cell in an arabinose-glucose growth media at a rate of at least 60 nmol min$^{-1}$ gDCW$^{-1}$. The recombinant arabinose transporter may transport an arabinose compound into a recombinant yeast cell in an arabinose-glucose growth media at a rate of at least 70 nmol min$^{-1}$ gDCW$^{-1}$. The recombinant arabinose transporter may transport an arabinose compound into a recombinant yeast cell in an arabinose-glucose growth media at a rate of at least 80 nmol min$^{-1}$ gDCW$^{-1}$. The recombinant arabinose transporter may transport an arabinose compound into a recombinant yeast cell in an arabinose-glucose growth media at a rate of at least 90 nmol min$^{-1}$ gDCW$^{-1}$. The recombinant arabinose transporter may transport an arabinose compound into a recombinant yeast cell in an arabinose-glucose growth media at a rate of at least 100 nmol min$^{-1}$ gDCW$^{-1}$. The recombinant arabinose transporter may transport an arabinose compound into a recombinant yeast cell in an arabinose-glucose growth media at a rate of at least 110 nmol min$^{-1}$ gDCW$^{-1}$. The recombinant arabinose transporter may transport an arabinose compound into a recombinant yeast cell in an arabinose-glucose growth media at a rate of at least 120 nmol min$^{-1}$ gDCW$^{-1}$. The recombinant arabinose transporter may transport an arabinose compound into a recombinant yeast cell in an arabinose-glucose growth media at a rate of at least 130 nmol min$^{-1}$ gDCW$^{-1}$. The recombinant arabinose transporter may transport an arabinose compound into a recombinant yeast cell in an arabinose-glucose growth media at a rate of at least 140 nmol min$^{-1}$ gDCW$^{-1}$. The recombinant arabinose transporter may transport an arabinose compound into a recombinant yeast cell in an arabinose-glucose growth media at a rate of at least 150 nmol min$^{-1}$ gDCW$^{-1}$.

3. Transporting Galactose into a Recombinant Yeast Cell

Also provided herein are methods of transporting galactose into a recombinant yeast cell. In one aspect, the method includes contacting a recombinant yeast cell with a galactose compound described herein, where the recombinant yeast cell includes a recombinant galactose transporter protein as described herein, including embodiments thereof. The recombinant galactose transporter protein transports the galactose compound into the recombinant yeast cell. In embodiments, the only sugar (i.e. carbon source) present is a galactose compound. The recombinant galactose transporter protein is as described herein, including embodiments thereof. By extension, the galactose transporter motif sequence and the glucose mitigation mutation are as described herein, including embodiments thereof.

In another aspect, the method includes contacting a recombinant yeast cell with a galactose compound, where the galactose compound is the only sugar (i.e. carbon source) in the media, and where the recombinant yeast cell includes a recombinant galactose transporter protein as described herein, including embodiments thereof.

The galactose compound may be derived from lignocellulosic biomass, hemicellulose, or marine biomass. Thus, in embodiments, the galactose compound is not the only sugar (i.e. carbon source) present. The galactose compound may be derived from lignocellulosic biomass. The galactose compound may be derived from hemicellulose. The galactose compound may be derived from marine biomass. In embodiments, the recombinant yeast cell metabolizes the galactose compound. The galactose compound may be present at a concentration as described hereinabove for the "galactose growth media". In embodiments, the recombinant yeast cell converts the galactose compound to a biofuel (e.g. ethanol) or to a biochemical as described herein, including embodiments thereof. The recombinant yeast cell may convert the galactose compound to a biofuel (e.g. ethanol). The recombinant yeast cell may convert the galactose compound to a biochemical as described herein, including embodiments thereof.

In embodiments, the recombinant galactose transporter transports a galactose compound into a recombinant yeast cell in a galactose-glucose growth media at a rate of at least 1 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 2 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 3 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 4 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 5 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 6 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 7 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 8 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 9 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 10 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 11 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 12 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 13 nmol min$^{-1}$ gDCW$^{-1}$ to about 15 nmol min$^{-1}$ gDCW$^{-1}$. The recombinant galactose transporter may transport a galactose compound into a recombinant yeast cell in a galactose-glucose growth media at a rate of at least 14 nmol min$^{-1}$ gDCW$^{-1}$ to about 15 nmol min$^{-1}$ gDCW$^{-1}$.

The recombinant galactose transporter may transport a galactose compound into a recombinant yeast cell in a galactose-glucose growth media at a rate of at least 1 nmol min$^{-1}$ gDCW$^{-1}$. The recombinant galactose transporter may transport a galactose compound into a recombinant yeast cell in a galactose-glucose growth media at a rate of at least 2 nmol min$^{-1}$ gDCW$^{-1}$. The recombinant galactose transporter may transport a galactose compound into a recombinant yeast cell in a galactose-glucose growth media at a rate of at least 3 nmol min$^{-1}$ gDCW$^{-1}$. The recombinant galactose transporter may transport a galactose compound into a recombinant yeast cell in a galactose-glucose growth media at a rate of at least 4 nmol min$^{-1}$ gDCW$^{-1}$. The recombinant galactose transporter may transport a galactose compound into a recombinant yeast cell in a galactose-glucose growth media at a rate of at least 5 nmol min$^{-1}$ gDCW$^{-1}$. The recombinant galactose transporter may transport a galactose compound into a recombinant yeast cell in a galactose-glucose growth media at a rate of at least 6 nmol min$^{-1}$ gDCW$^{-1}$. The recombinant galactose transporter may transport a galactose compound into a recombinant yeast cell in a galactose-glucose growth media at a rate of at least 7 nmol min$^{-1}$ gDCW$^{-1}$. The recombinant galactose transporter may transport a galactose compound into a recombinant yeast cell in a galactose-glucose growth media at a rate of at least 8 nmol min$^{-1}$ gDCW$^{-1}$. The recombinant galactose transporter may transport a galactose compound into a recombinant yeast cell in a galactose-glucose growth media at a rate of at least 9 nmol min$^{-1}$ gDCW$^{-1}$. The recombinant galactose transporter may transport a galactose compound into a recombinant yeast cell in a galactose-glucose growth media at a rate of at least 10 nmol min$^{-1}$ gDCW$^{-1}$. The recombinant galactose transporter may transport a galactose compound into a recombinant yeast cell in a galactose-glucose growth media at a rate of at least 11 nmol min$^{-1}$ gDCW$^{-1}$. The recombinant galactose transporter may transport a galactose compound into a recombinant yeast cell in a galactose-glucose growth media at a rate of at least 12 nmol min$^{-1}$ gDCW$^{-1}$. The recombinant galactose transporter may transport a galactose compound into a recombinant yeast cell in a galactose-glucose growth media at a rate of at least 13 nmol min$^{-1}$ gDCW$^{-1}$. The recombinant galactose transporter may transport a galactose compound into a recombinant yeast cell in a galactose-glucose growth media at a rate of at least 14 nmol min$^{-1}$ gDCW$^{-1}$. The recombinant galactose transporter may transport a galactose compound into a recombinant yeast cell in a galactose-glucose growth media at a rate of at least 15 nmol min$^{-1}$ gDCW$^{-1}$.

In embodiments, the recombinant galactose transporter transports a galactose compound into a recombinant yeast cell in a galactose-glucose growth media at a rate of at least 1 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 2.5 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 5 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 10 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 12 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 15 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 20 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 25 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 30 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 35 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 40 nmol min$^{-1}$ gDCW$^{-1}$ to 50 nmol min$^{-1}$ gDCW$^{-1}$. The recombinant galactose transporter may transport a galactose compound into a recombinant yeast cell in a galactose-glucose growth media at a rate of at least 45 nmol min$^{-1}$ gDCW$^{-1}$ to 50 nmol min$^{-1}$ gDCW$^{-1}$.

The recombinant galactose transporter may transport a galactose compound into a recombinant yeast cell in a galactose-glucose growth media at a rate of at least 2.5 nmol min$^{-1}$ gDCW$^{-1}$. The recombinant galactose transporter may transport a galactose compound into a recombinant yeast cell in a galactose-glucose growth media at a rate of at least 17 nmol min$^{-1}$ gDCW$^{-1}$. The recombinant galactose transporter may transport a galactose compound into a recombinant yeast cell in a galactose-glucose growth media at a rate of at least 18 nmol min$^{-1}$ gDCW$^{-1}$. The recombinant galactose transporter may transport a galactose compound into a recombinant yeast cell in a galactose-glucose growth media at a rate of at least 19 nmol min$^{-1}$ gDCW$^{-1}$. The recombinant galactose transporter may transport a galactose compound into a recombinant yeast cell in a galactose-glucose growth media at a rate of at least 20 nmol min$^{-1}$ gDCW$^{-1}$. The recombinant galactose transporter may transport a galactose compound into a recombinant yeast cell in a galactose-glucose growth media at a rate of at least 22 nmol min$^{-1}$ gDCW$^{-1}$. The recombinant galactose transporter may transport a galactose compound into a recombinant yeast cell in a galactose-glucose growth media at a rate of at least 25 nmol min$^{-1}$ gDCW$^{-1}$. The recombinant galactose transporter may transport a galactose compound into a recombinant yeast cell in a galactose-glucose growth media at a rate of at least 30 nmol min$^{-1}$ gDCW$^{-1}$. The recombinant galactose transporter may transport a galactose compound into a recombinant yeast cell in a galactose-glucose growth media at a rate of at least 35 nmol min$^{-1}$ gDCW$^{-1}$. The recombinant galactose transporter may transport a galactose compound into a recombinant yeast cell in a galactose-glucose growth media at a rate of at least 40 nmol min$^{-1}$ gDCW$^{-1}$. The recombinant galactose transporter may transport a galactose compound into a recombinant yeast cell in a galactose-glucose growth media at a rate of at least 45 nmol min$^{-1}$ gDCW$^{-1}$. The recombinant galactose transporter may transport a galactose compound into a recombinant yeast cell in a galactose-glucose growth media at a rate of at least 50 nmol min$^{-1}$ gDCW$^{-1}$.

In embodiments, the recombinant galactose transporter transports a galactose compound into a recombinant yeast cell in a galactose-glucose growth media at a rate of at least 10 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 20 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 30 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 40 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 50 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 60 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 70 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 80 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 90 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 100 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 110 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 120 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 130 nmol min$^{-1}$ gDCW$^{-1}$ to 150 nmol min$^{-1}$ gDCW$^{-1}$. The recombinant galactose transporter may transport a galactose compound into a recombinant yeast cell in a galactose-glucose growth media at a rate of at least 140 nmol min$^{-1}$ gDCW$^{-1}$ to 150 nmol min$^{-1}$ gDCW$^{-1}$.

The recombinant galactose transporter may transport a galactose compound into a recombinant yeast cell in a galactose-glucose growth media at a rate of at least 60 nmol min$^{-1}$ gDCW$^{-1}$. The recombinant galactose transporter may transport a galactose compound into a recombinant yeast cell in a galactose-glucose growth media at a rate of at least 70 nmol min$^{-1}$ gDCW$^{-1}$. The recombinant galactose transporter may transport a galactose compound into a recombinant yeast cell in a galactose-glucose growth media at a rate of at least 80 nmol min$^{-1}$ gDCW$^{-1}$. The recombinant galactose transporter may transport a galactose compound into a recombinant yeast cell in a galactose-glucose growth media at a rate of at least 90 nmol min$^{-1}$ gDCW$^{-1}$. The recombinant galactose transporter may transport a galactose compound into a recombinant yeast cell in a galactose-glucose growth media at a rate of at least 100 nmol min$^{-1}$ gDCW$^{-1}$. The recombinant galactose transporter may transport a galactose compound into a recombinant yeast cell in a galactose-glucose growth media at a rate of at least 110 nmol min$^{-1}$ gDCW$^{-1}$. The recombinant galactose transporter may transport a galactose compound into a recombinant yeast cell in a galactose-glucose growth media at a rate of at least 120 nmol min$^{-1}$ gDCW$^{-1}$. The recombinant galactose transporter may transport a galactose compound into a recombinant yeast cell in a galactose-glucose growth media at a rate of at least 130 nmol min$^{-1}$ gDCW$^{-1}$. The recombinant galactose transporter may transport a galactose compound into a recombinant yeast cell in a galactose-glucose growth media at a rate of at least 140 nmol min$^{-1}$ gDCW$^{-1}$. The recombinant galactose transporter may transport a galactose compound into a recombinant yeast cell in a galactose-glucose growth media at a rate of at least 150 nmol min$^{-1}$ gDCW$^{-1}$.

V. Examples

In previous research, was developed a xylose specific transporter hereafter termed "CiGXS1-FIM" ("FIM"), based on a hexose transporter from *C. intermedia*, GXS1. The FIM mutation imparted specificity in transporting xylose over glucose. (11) The presence of glucose, however, inhibited the performance of FIM in transporting xylose. Herein directed evolution was conducted to reduce the observed glucose inhibition.

A library of randomly mutated FIM was generated by error-prone PCR with a library size of over 1×10$^5$ mutants (as measured by independent *E. coli* colonies post-transformation). The mutant FIM was then transformed into *S. cerevisiae* ETKXG strain, a triple hexokinase knockout strain which is not able to grow on glucose, and screened on the xylose dependent growth based advantage on the dropout plates with 20 g/L of xylose and 2.5 g/L of glucose. The 140 selected mutants from the plates were then tested for the growth on the medium with 20 g/L of xylose and 2.5 g/L glucose using Bioscreen C and the top 6 mutants were selected for further confirmation. The growth rates of the selected mutants on xylose in the presence of various concentration of glucose were then confirmed using Bioscreen C (FIG. 1).

Figure 2:
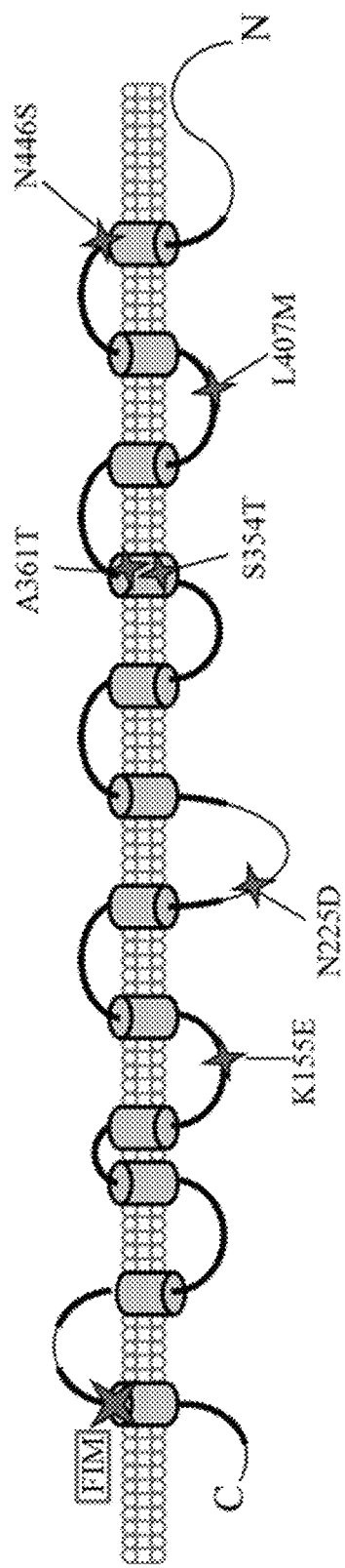
FIG. 2: SACS HMMTOP Prediction of the mutant 105 xylose transporter and mutant positions: mutations are indicated with arrows.
Figure 3:
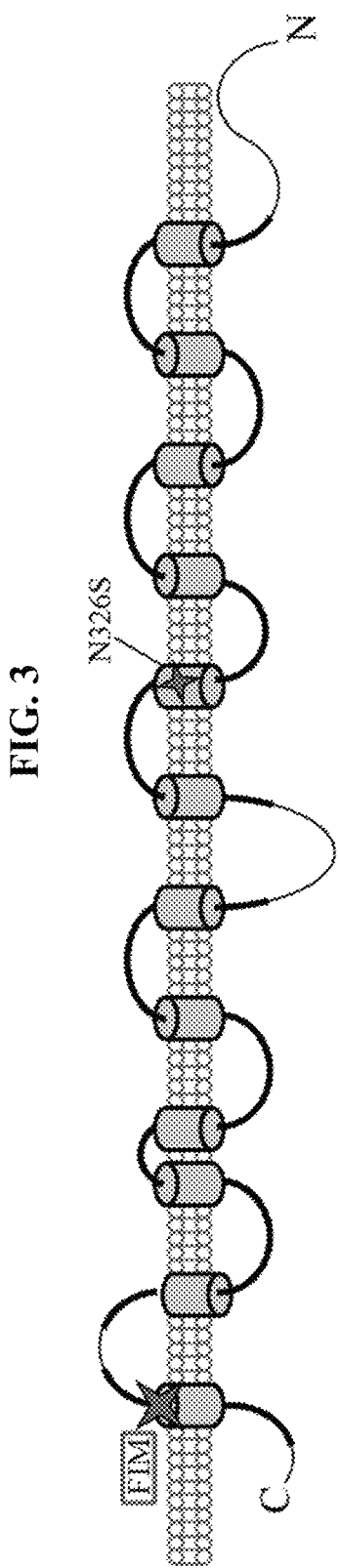
FIG. 3: SACS HMMTOP Prediction of the mutant 78 xylose transporter and mutant positions: mutations are indicated with arrows.
Figure 4:
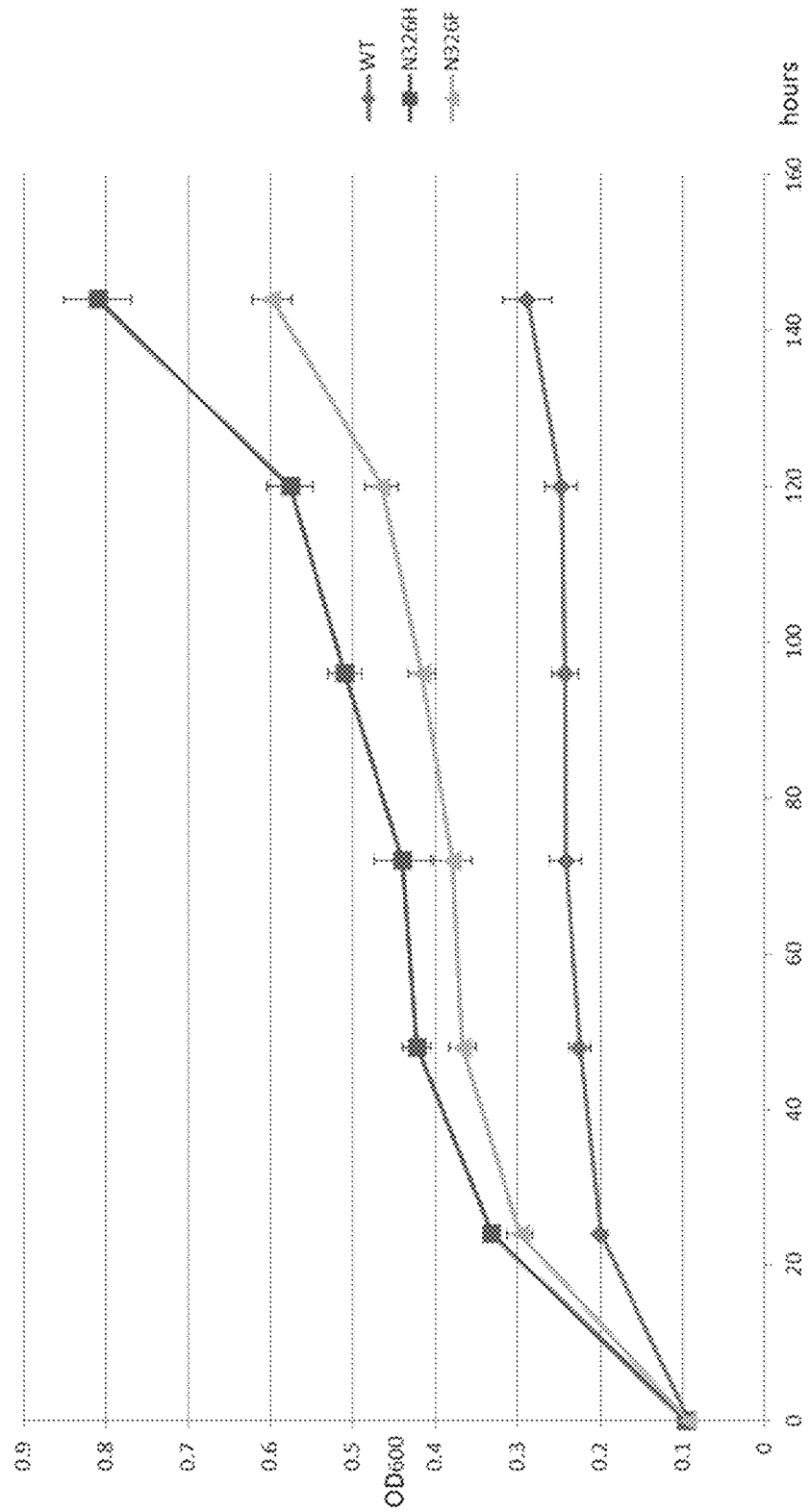
FIG. 4: Mutations to residue N326 to convert to a histidine or phenylalanine were explored in the background of the gxs1 (FIM) mutant containing the xylose transporter motif sequence G-G-F-I-M-G (SEQ ID NO:107). Mutations in residue N326 improve assimilation rates and growth rates in pure xylose over the wild-type GXS1 and N326H is a better mutation than N326F.
Figure 5:
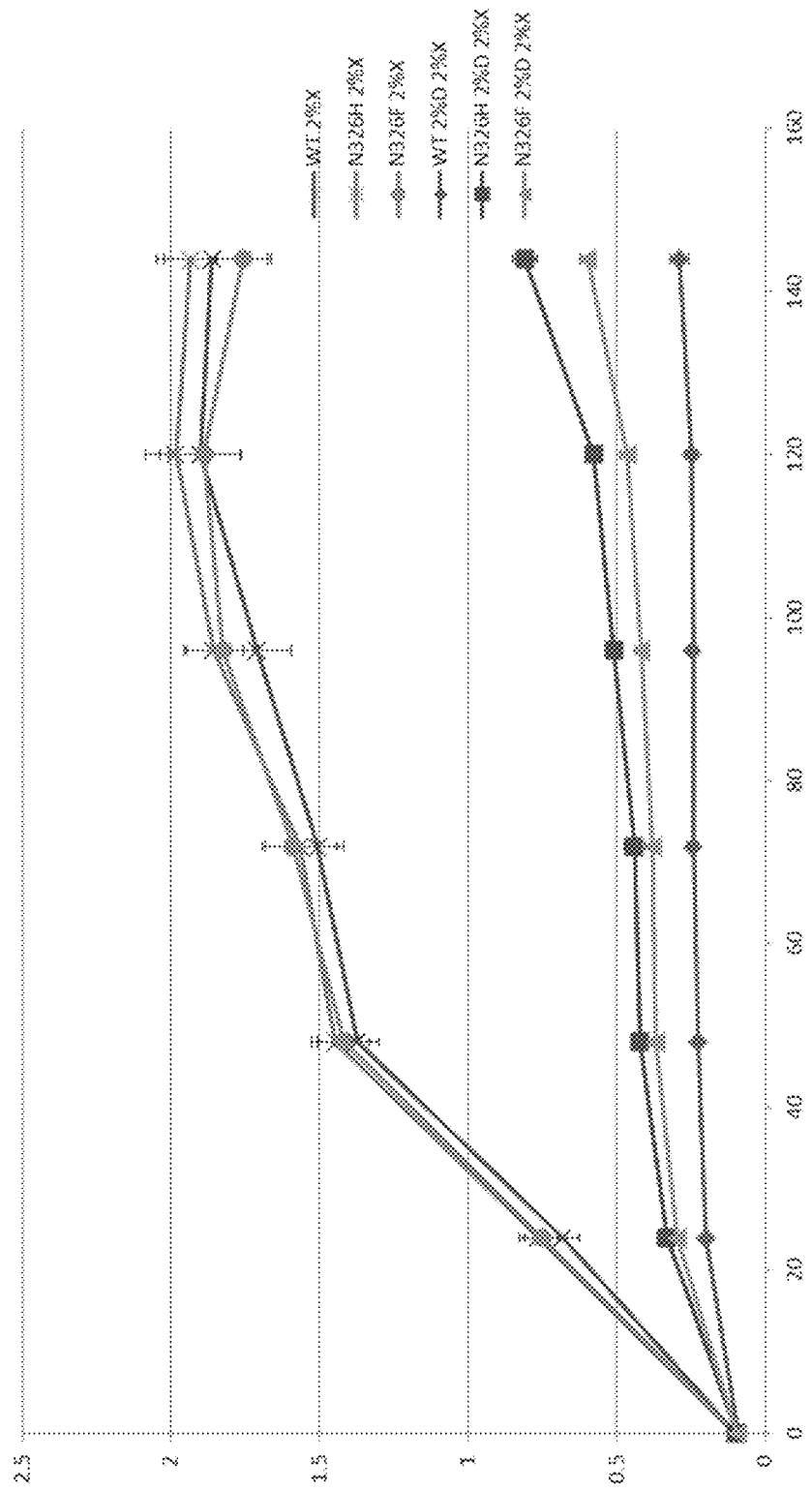
FIG. 5: Mutations to residue N326 to convert to a histidine or phenylalanine were explored in the background of the gxs1 (FIM) mutant containing the xylose transporter motif sequence G-G-F-I-M-G (SEQ ID NO:107). Mutations in residue N326 improve assimilation rates and growth rates in a mixture of 2% glucose and 2% xylose over the wild-type GXS1 and N326H is a better mutation than N326F.
Figure 6:
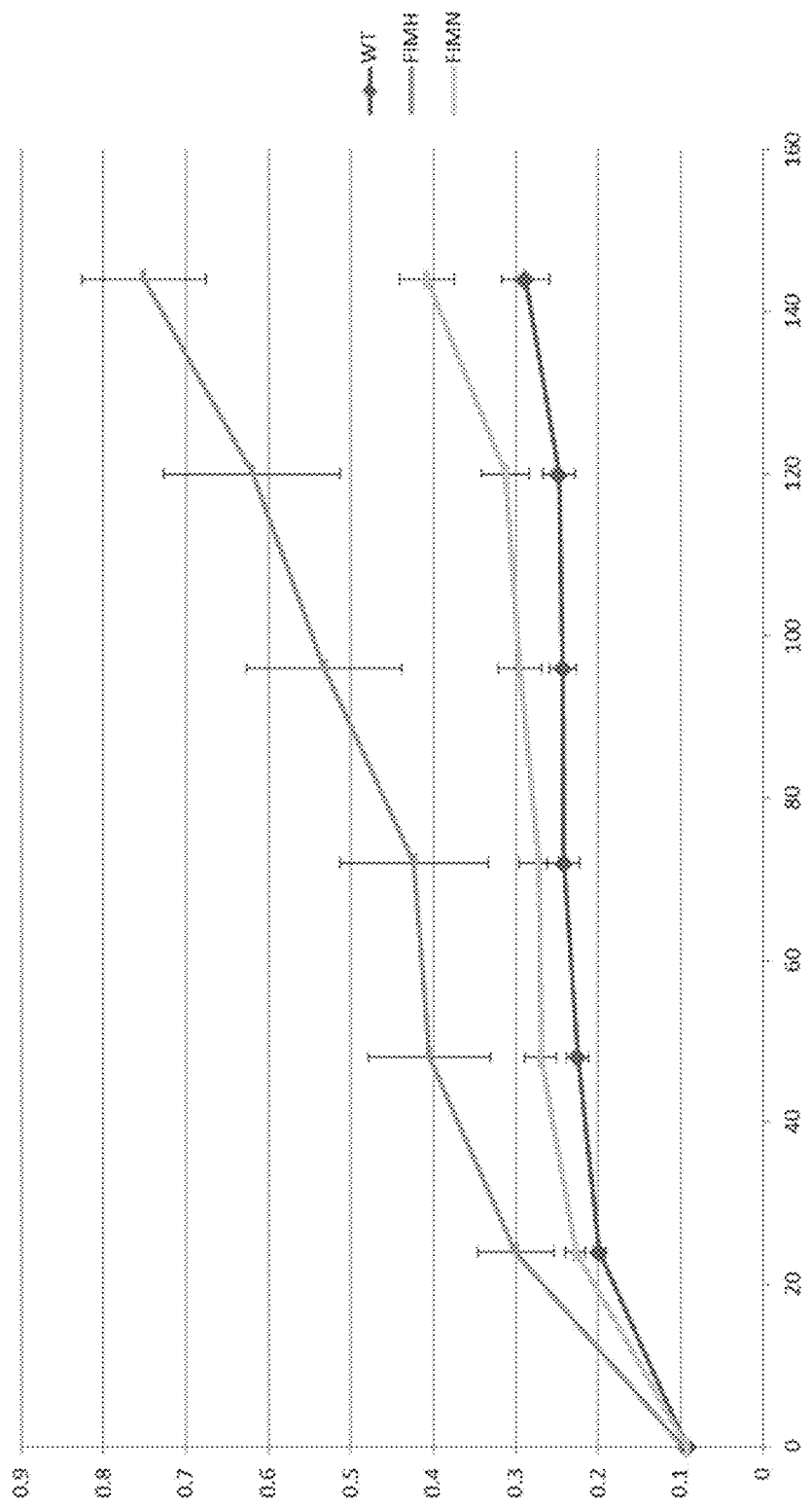
FIG. 6: Mutations to residue N326 to convert to a histidine (N326H) are compared with an additionally discovered mutation T170N in the background of the gxs1 (FIM) mutant containing the xylose transporter motif sequence G-G-F-I-M-G (SEQ ID NO:107). Both mutants improved xylose growth rates over the wild-type transporter with the mutation of N326H stronger than T170N.
Figure 7:
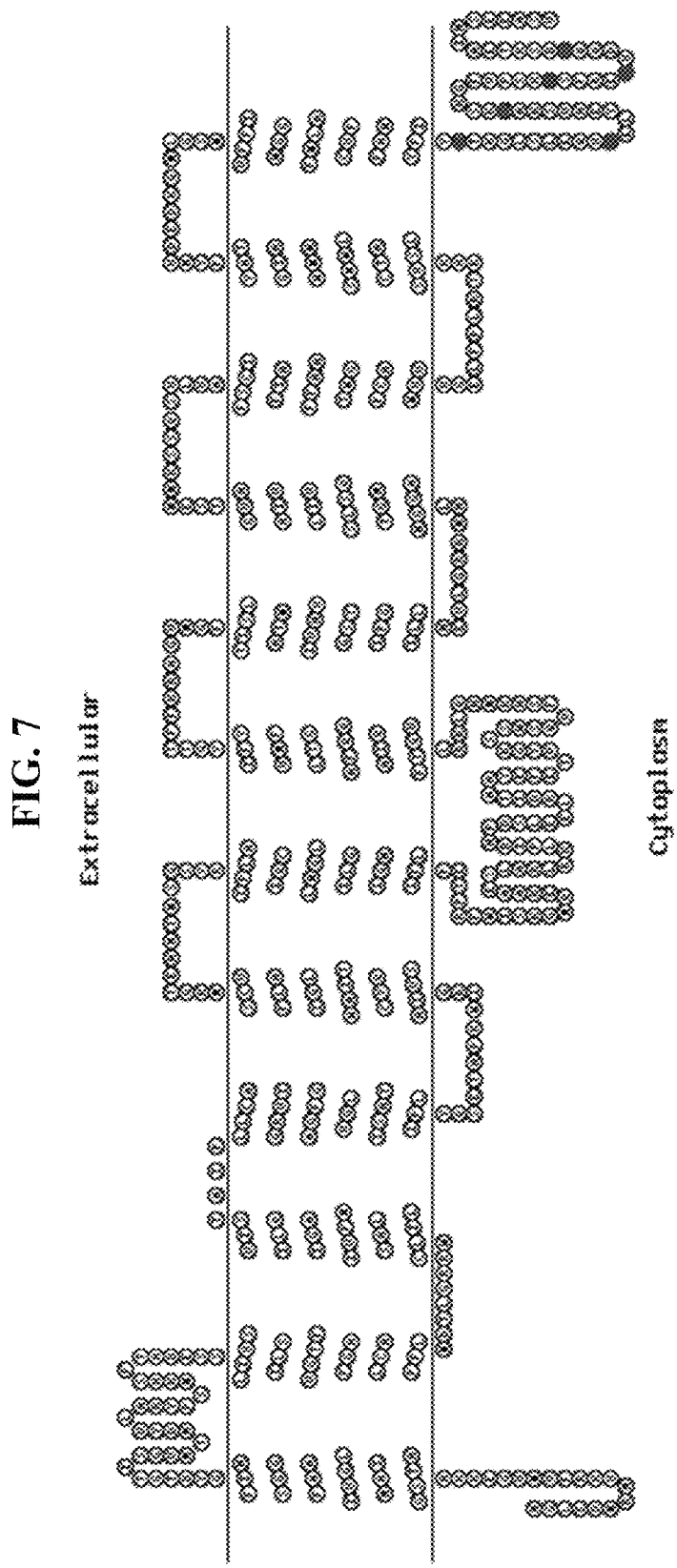
FIG. 7: An additional round of mutagenesis and selection was completed in the background of gxs1 (FIM) containing N326H (SEQ ID NO:3). These experiments were conducted in the presence of 4% glucose and 2% xylose. Several mutations in the tail region of the transporter were identified including a stop codon (dark dots on schematic of tail with circle indicating location of stop codon). To assess the potential inhibition of this tail region, several truncations of this transporter protein were created (see vertical lines in the sequence on the bottom).
Figure 8:
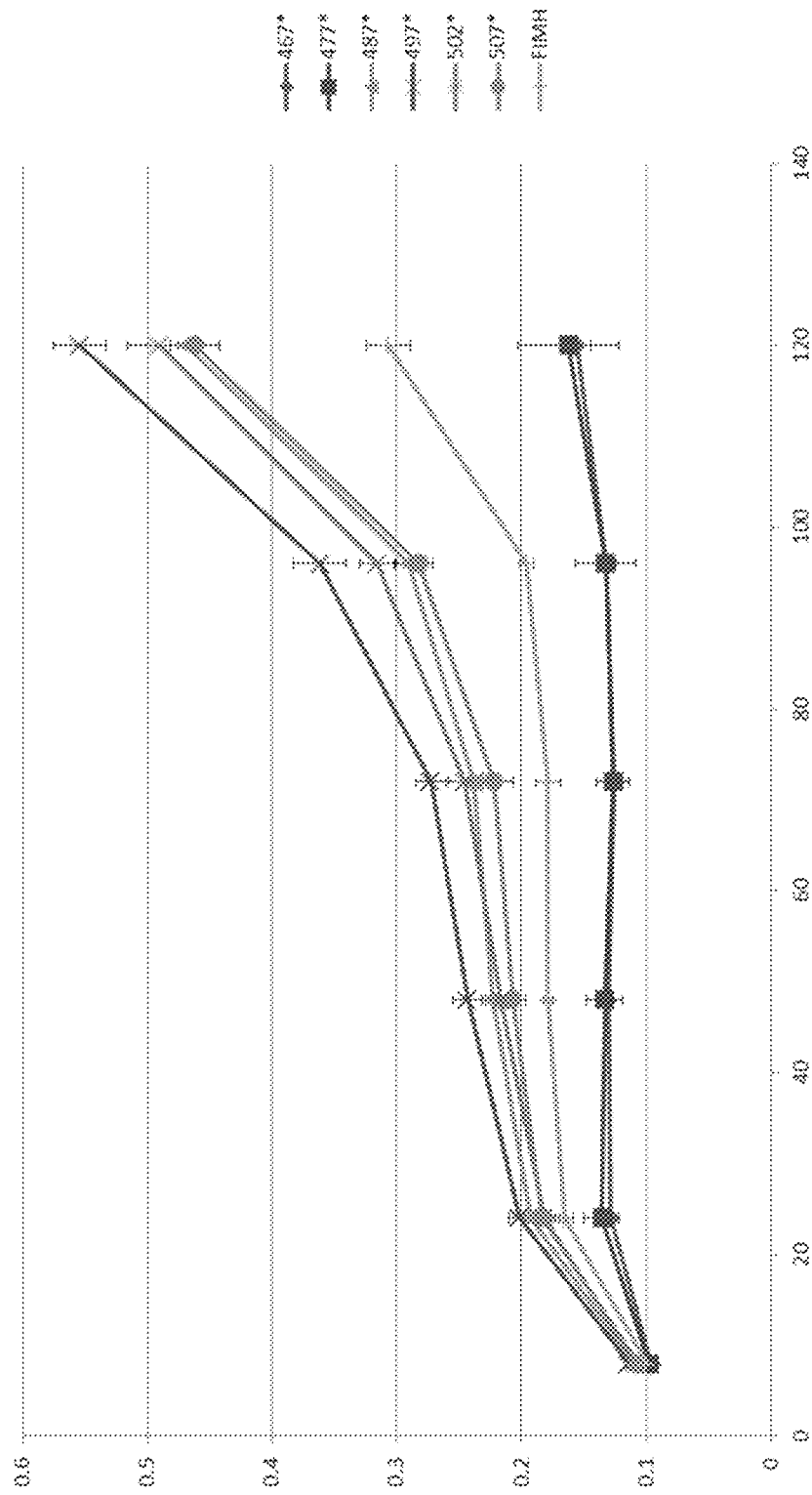
FIG. 8: The gxs1 (FIM) strain with the N326H mutation was truncated at various amino acid residues (indicated by number) and assessed for growth in the presence of 4% glucose, 2% xylose. Several truncations were superior with respect to growth over the starting transporter with a truncation after amino acid residue 497 giving the highest performance. Truncations before residue 487 were detrimental to performance.
Figure 9A:
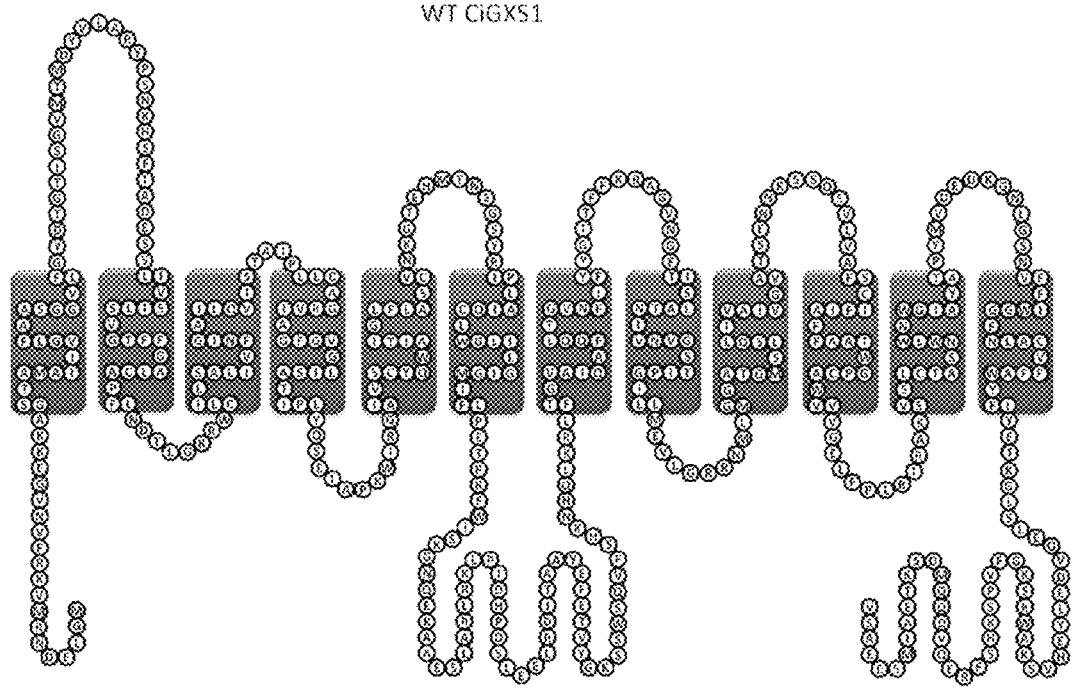
Figure 9B:
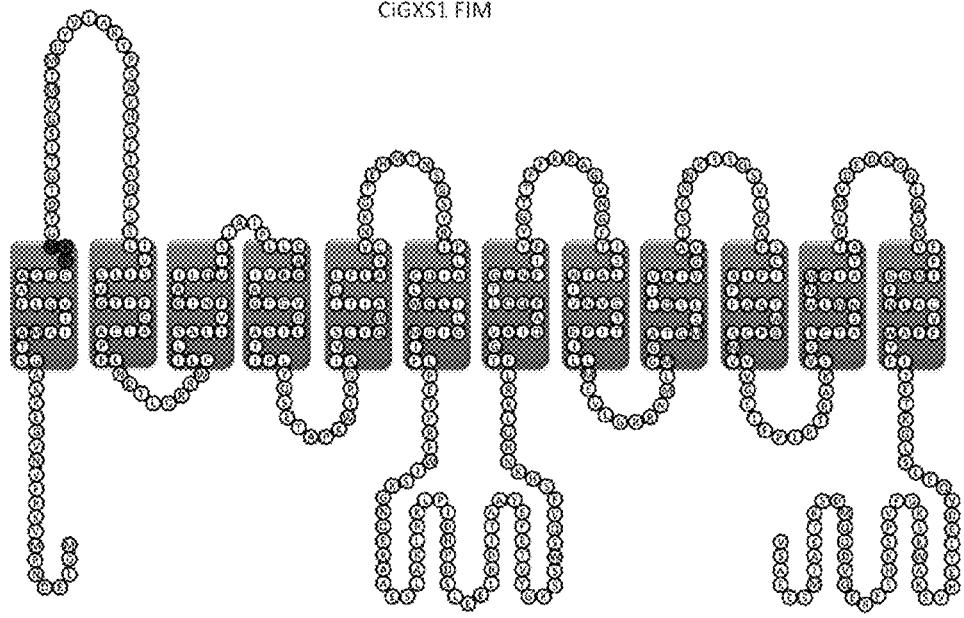
Figures 9C, 9D:
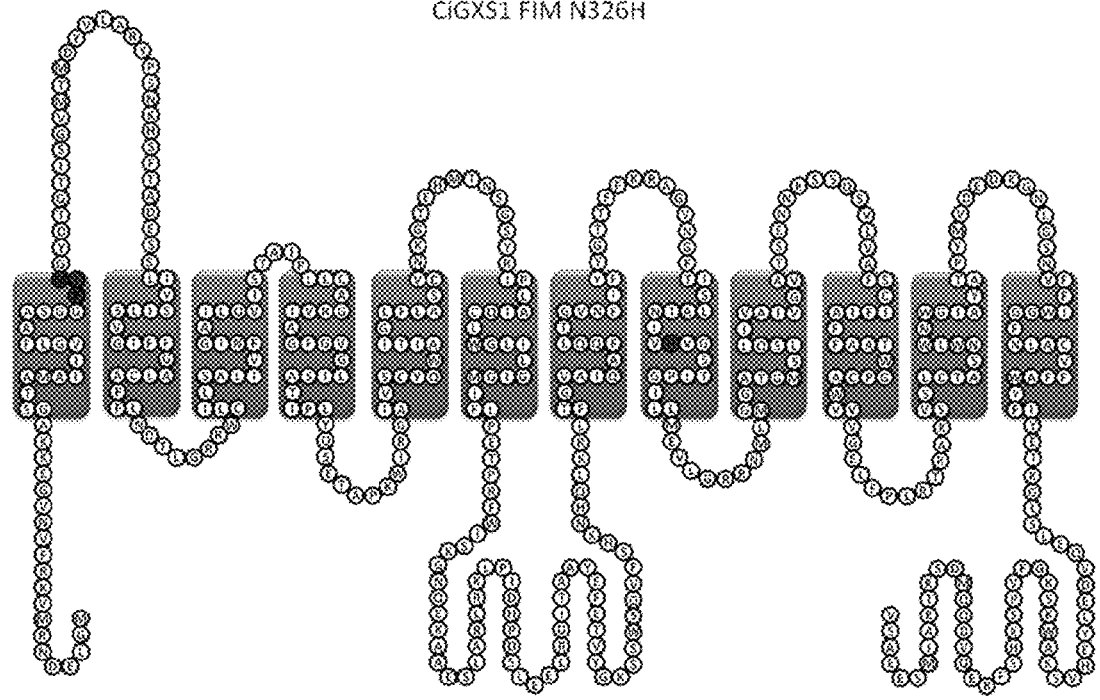
Figure 10:
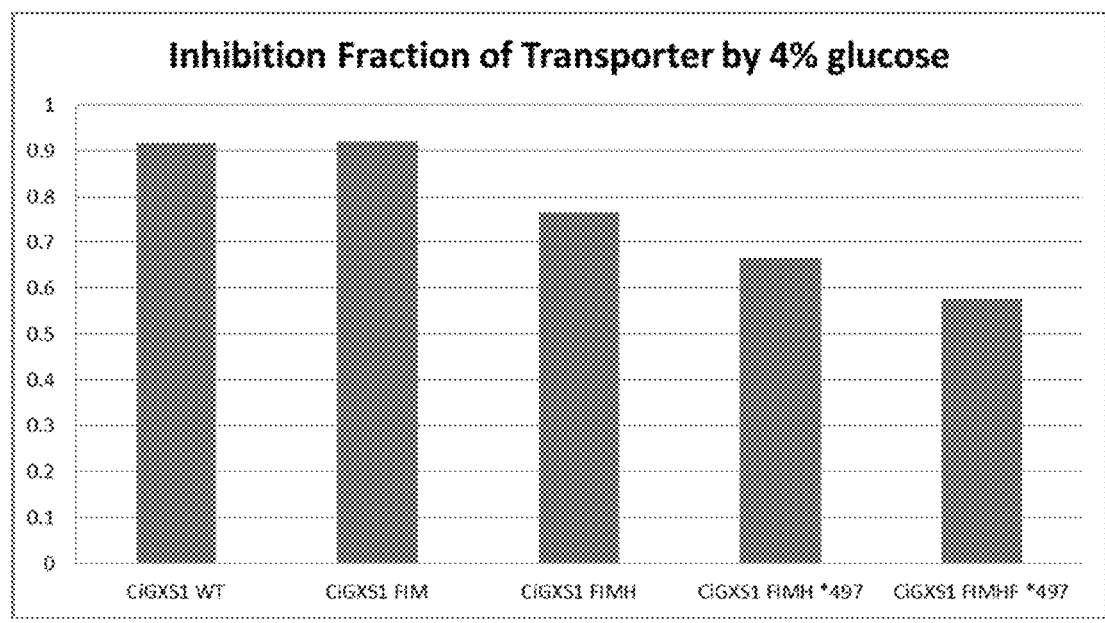
FIG. 10: The inhibition fraction (the ratio of the transporter capacity in 4% glucose compared to the transporter capacity in pure xylose) for various mutants. The gxs1 mutant with the F-I-M xylose transporter sequence motif and the N326H mutation along with the tail region after truncating past residue 497 and the T171F mutation performed best and was the least inhibited by high glucose levels.

The mutant 105, which has 6 mutations: K155E, N225D, S354T, A361T, L407M, N446S (FIG. 2), showed reduced glucose inhibition. Indeed, the mutant 105 showed significantly higher growth rates in the all tested conditions compared to FIM and wild-type transporters. Mutant 105 shows nearly a 30-fold increase in the growth rate on a xylose medium with the presence of glucose. The growth rate of the mutant 105 in the xylose 20 g/L+glucose 2.5 g/L medium was slightly higher than the growth rate of the wild-type transporter in the xylose only medium. Though the mutant 105 showed the highest reduction in glucose inhibition, the growth rate on xylose only was slightly reduced compared to FIM and wild-type. See FIG. 1

The mutant 78, which has a single mutation, N326S, showed reduced glucose inhibition without decrease in xylose transport capability. In contrast to mutant 105, mutant 78 showed no reduction in the xylose transport performance. This suggests the mutant 78 represents a promising candidate for further round of directed evolution to develop xylose transporters with reduced glucose inhibition.

REFERENCES

1. Reijenga K A, et al. (2001) Control of glycolytic dynamics by hexose transport in *Saccharomyces cerevisiae*. *Biophysical Journal* 80(2):626-634.
2. Gardonyi M, Jeppsson M, Liden G, Gorwa-Grausland M F, & Hahn-Hagerdal B (2003) Control of xylose consumption by xylose transport in recombinant *Saccharomyces cerevisiae*. *Biotechnology and Bioengineering* 82(7):818-824.
3. Elbing K, et al. (2004) Role of hexose transport in control of glycolytic flux in *Saccharomyces cerevisiae*. *Applied and Environmental Microbiology* 70(9):5323-5330.
4. Wahlbom C F, Otero R R C, van Zyl W H, Hahn-Hagerdal B, & Jonsson L J (2003) Molecular analysis of a *Saccharomyces cerevisiae* mutant with improved ability to utilize xylose shows enhanced expression of proteins involved in transport, initial xylose metabolism, and the pentose phosphate pathway. *Applied and Environmental Microbiology* 69(2):740-746.
5. Bengtsson O, et al. (2008) Identification of common traits in improved xylose-growing *Saccharomyces cerevisiae* for inverse metabolic engineering. *Yeast* 25(11):835-847.
6. Jeffries T W & Jin Y S (2004) Metabolic engineering for improved fermentation of pentoses by yeasts. *Applied Microbiology and Biotechnology* 63(5):495-509.
7. Hahn-Hagerdal B, Karhumaa K, Fonseca C, Spencer-Martins I, & Gorwa-Grauslund M F (2007) Towards industrial pentose-fermenting yeast strains. *Applied Microbiology and Biotechnology* 74(5):937-953.
8. Martin C H, Nielsen D R, Solomon K V, & Prather K L J (2009) Synthetic metabolism: engineering biology at the protein and pathway scales. *Chemistry & Biology* 16(3): 277-286.
9. Tyo K E J, Kocharin K, & Nielsen J (2010) Toward design-based engineering of industrial microbes. *Current Opinion in Microbiology* 13(3):255-262.
10. Curran K A & Alper H S (2012) Expanding the chemical palate of cells by combining systems biology and metabolic engineering. *Metabolic Engineering* 14(4):289-297.
11. Eric Young, Alice Tong, Hang Bui, Caitlin Spofford, and Hal Alper, 2014. *Rewiring yeast sugar transporter preference through modifying a conserved protein motif.* PNAS 111(1), 131-136

VI. P Embodiments

Embodiment P 1

A recombinant xylose transporter protein comprising a xylose transporter motif sequence and a glucose mitigation mutation.

Embodiment P 2

The recombinant xylose transporter protein of embodiment P 1, wherein said xylose transporter motif sequence corresponds to amino acid residue positions 36, 37, 38, 39, 40, and 41 of *Candida intermedia* GXS1 protein, and wherein said xylose transporter motif sequence is -G-G/F-$X^1$-$X^2$-$X^3$-G-; wherein, $X^1$ is D, C, G, H, I, L, or F; $X^2$ is A, D, C, E, G, H, or I; and $X^3$ is N, C, Q, F, G, L, M, S, T, or P.

Embodiment P 3

The recombinant xylose transporter protein of embodiment P 1 or embodiment P 2, wherein said xylose transporter motif sequence is -G-G-F-I-M-G- (SEQ ID NO:107), -G-F-F-I-M-G- (SEQ ID NO:108), -G-G-F-I-S-G- (SEQ ID NO:109), -G-F-F-I-S-G- (SEQ ID NO:110), -G-G-F-I-T-G- (SEQ ID NO:111), -G-F-F-I-T-G- (SEQ ID NO:112), -G-G-F-L-M-G- (SEQ ID NO:113), -G-F-F-L-M-G- (SEQ ID NO:114), -G-G-F-L-S-G- (SEQ ID NO:115), -G-F-F-L-S-G- (SEQ ID NO:116), -G-G-F-L-T-G- (SEQ ID NO:117), -G-F-F-L-T-G- (SEQ ID NO:118), -G-G-F-H-M-G- (SEQ ID NO:119), -G-F-F-H-M-G- (SEQ ID NO:120), -G-G-F-H-S-G- (SEQ ID NO:121), -G-F-F-H-S-G- (SEQ ID NO:122), -G-G-F-H-T-G- (SEQ ID NO:123) or -G-F-F-H-T-G- (SEQ ID NO:124).

Embodiment P 4

The recombinant xylose transporter protein of any one of embodiments P 1 to 3, wherein said xylose transporter motif sequence is -G-G-F-I-M-G- (SEQ ID NO:107), -G-F-F-I-M-G- (SEQ ID NO:108), -G-G-F-I-S-G- (SEQ ID NO:109), or -G-F-F-I-S-G- (SEQ ID NO:110).

Embodiment P 5

The recombinant xylose transporter protein of any one of embodiments P 1 to 4, wherein said xylose transporter motif sequence is -G-G-F-I-M-G- (SEQ ID NO:107).

Embodiment P 6

The recombinant xylose transporter protein of any one of embodiments P 1 to 5, wherein said glucose mitigation mutation is within a protein domain corresponding to transmembrane 9 of *Candida intermedia* GXS1 protein.

Embodiment P 7

The recombinant xylose transporter protein of any one of embodiments P 1 to 6, wherein said glucose mitigation mutation is at a position corresponding to K155, N225, S354, A361, L407, or N446 of *Candida intermedia* GXS1 protein.

Embodiment P 8

The recombinant xylose transporter protein of any one of embodiments P 1 to 5, wherein said glucose mitigation mutation is within a protein domain corresponding to transmembrane 8 of *Candida intermedia* GXS1 protein.

Embodiment P 9

The recombinant xylose transporter protein of any one of embodiments P 1 to 5, or embodiment P 8, wherein said glucose mitigation mutation is at a position corresponding N326 of *Candida intermedia* GXS1 protein.

Embodiment P 10

The recombinant xylose transporter protein of embodiment P 9, wherein said glucose mitigation mutation is a N326S mutation.

Embodiment P 11

A recombinant yeast cell comprising a recombinant xylose transporter protein of any one of embodiments P 1 to 10.

Embodiment P 12

The recombinant yeast cell of embodiment P 11, wherein the growth rate of said recombinant yeast cell in a xylose-glucose growth media is at least about 10% of the growth rate of said recombinant yeast cell in a xylose growth media.

Embodiment P 13

The recombinant yeast cell of embodiment P 11, wherein the growth rate of said recombinant yeast cell in a xylose-glucose growth media is at least about 20% of the growth rate of said recombinant yeast cell in a xylose growth media.

Embodiment P 14

The recombinant yeast cell of embodiment P 11, wherein the growth rate of said recombinant yeast cell in a xylose-glucose growth media is at least about 30% of the growth rate of said recombinant yeast cell in a xylose growth media.

Embodiment P 15

The recombinant yeast cell of embodiment P 11, wherein the growth rate of said recombinant yeast cell in a xylose-glucose growth media is at least about 40% of the growth rate of said recombinant yeast cell in a xylose growth media.

Embodiment P 16

The recombinant yeast cell of embodiment P 11, wherein the growth rate of said recombinant yeast cell in a xylose-glucose growth media is at least about 50% of the growth rate of said recombinant yeast cell in a xylose growth media.

Embodiment P 17

The recombinant yeast cell of embodiment P 11, wherein the growth rate of said recombinant yeast cell in a xylose-glucose growth media is at least about 60% of the growth rate of said recombinant yeast cell in a xylose growth media.

Embodiment P 18

The recombinant yeast cell of embodiment P 11, wherein the growth rate of said recombinant yeast cell in a xylose-

Embodiment P 19

The recombinant yeast cell of embodiment P 11, wherein the growth rate of said recombinant yeast cell in a xylose-glucose growth media is at least about 80% of the growth rate of said recombinant yeast cell in a xylose growth media.

Embodiment P 20

The recombinant yeast cell of embodiment P 11, wherein the growth rate of said recombinant yeast cell in a xylose-glucose growth media is at least about 90% of the growth rate of said recombinant yeast cell in a xylose growth media.

Embodiment P 21

The recombinant yeast cell of embodiment P 11, wherein the growth rate of said recombinant yeast cell in a xylose-glucose growth media is at least about 100% of the growth rate of said recombinant yeast cell in a xylose growth media.

Embodiment P 22

The recombinant yeast cell of embodiment P 11, wherein the growth rate of said recombinant yeast cell in a xylose-glucose growth media is at least about 110% of the growth rate of said recombinant yeast cell in a xylose growth media.

Embodiment P 23

The recombinant yeast cell of embodiment P 11, wherein the growth rate of said recombinant yeast cell in a xylose-glucose growth media is at least about 120% of the growth rate of said recombinant yeast cell in a xylose growth media.

Embodiment P 24

The recombinant yeast cell of any one of embodiments P 11 to 23, wherein said xylose-glucose growth media comprises about 0.05 g/L to about 20 g/L glucose.

Embodiment P 25

The recombinant yeast cell of any one of embodiments P 11 to 24, wherein said xylose-glucose growth media comprises about 2.5 g/L glucose.

Embodiment P 26

The recombinant yeast cell of any one of embodiments P 11 to 25, wherein said xylose-glucose growth media comprises about 5 g/L glucose.

Embodiment P 27

The recombinant yeast cell of any one of embodiments P 11 to 26, wherein said xylose-glucose growth media comprises about 10 g/L glucose.

Embodiment P 28

The recombinant yeast cell of any one of embodiments P 11 to 27, wherein said xylose-glucose growth media comprises about 20 g/L glucose.

Embodiment P 29

The recombinant yeast cell of any one of embodiments P 11 to 28, wherein said xylose-glucose growth media comprises about 0.05 g/L to about 300 g/L xylose.

Embodiment P 30

The recombinant yeast cell of any one of embodiments P 11 to 29, wherein said xylose growth media comprises about 0.05 g/L to about 300 g/L xylose.

Embodiment P 31

The recombinant yeast cell of any one of embodiments P 11 to 30, wherein said xylose growth media comprises about 20 g/L xylose.

Embodiment P 32

A method of transporting xylose into a recombinant yeast cell, said method comprising: i) contacting a recombinant yeast cell with a xylose compound, wherein said recombinant yeast cell comprises a recombinant xylose transporter protein, said recombinant xylose transporter protein comprising a xylose transporter motif sequence and a glucose mitigation mutation; and ii) allowing said recombinant xylose transporter protein to transport said xylose compound into said recombinant yeast cell.

Embodiment P 33

The method of embodiment P 32, wherein said xylose transporter motif sequence corresponds to amino acid residue positions 36, 37, 38, 39, 40, and 41 of *Candida intermedia* GXS1 protein, and wherein said xylose transporter motif sequence is -G-G/F-$X^1$-$X^2$-$X^3$-G-; wherein, $X^1$ is D, C, G, H, I, L, or F; $X^2$ is A, D, C, E, G, H, or I; and $X^3$ is N, C, Q, F, G, L, M, S, T, or P.

Embodiment P 34

The method of embodiment P 32 or embodiment P 33, wherein said xylose transporter motif sequence is -G-G-F-I-M-G- (SEQ ID NO:107), -G-F-F-I-M-G- (SEQ ID NO:108), -G-G-F-I-S-G- (SEQ ID NO:109), -G-F-F-I-S-G- (SEQ ID NO:110), -G-G-F-I-T-G- (SEQ ID NO:111), -G-F-F-I-T-G- (SEQ ID NO:112), -G-G-F-L-M-G- (SEQ ID NO:113), -G-F-F-L-M-G- (SEQ ID NO:114), -G-G-F-L-S-G- (SEQ ID NO:115), -G-F-F-L-S-G- (SEQ ID NO:116), -G-G-F-L-T-G- (SEQ ID NO:117), -G-F-F-L-T-G- (SEQ ID NO:118), -G-G-F-H-M-G- (SEQ ID NO:119), -G-F-F-H-M-G- (SEQ ID NO:120), -G-G-F-H-S-G- (SEQ ID NO:121), -G-F-F-H-S-G- (SEQ ID NO:122), -G-G-F-H-T-G- (SEQ ID NO:123) or -G-F-F-H-T-G- (SEQ ID NO:124).

Embodiment P 35

The method of any one of embodiments P 32 to 34, wherein said xylose transporter motif sequence is -G-G-F-I-M-G- (SEQ ID NO:107), -G-F-F-I-M-G- (SEQ ID NO:108), -G-G-F-I-S-G- (SEQ ID NO:109), or -G-F-F-I-S-G- (SEQ ID NO:110).

Embodiment P 36

The method of any one of embodiments P 32 to 35, wherein said xylose transporter motif sequence is -G-G-F-I-M-G- (SEQ ID NO:107).

Embodiment P 37

The method of any one of embodiments P 32 to 36, wherein said glucose mitigation mutation is within a protein domain corresponding to transmembrane 9 of *Candida intermedia* GXS1 protein.

Embodiment P 38

The method of any one of embodiments P 32 to 37, wherein said glucose mitigation mutation is at a position corresponding to K155, N225, S354, A361, L407, or N446 of *Candida intermedia* GXS1 protein.

Embodiment P 39

The method of any one of embodiments P 32 to 36, wherein said glucose mitigation mutation is within a protein domain corresponding to transmembrane 8 of *Candida intermedia* GXS1 protein.

Embodiment P 40

The method of any one of embodiments P 32 to 36, or embodiment P 39, wherein said glucose mitigation mutation is at a position corresponding N326 of *Candida intermedia* GXS1 protein.

Embodiment P 41

The method of embodiment P 40, wherein said glucose mitigation mutation is a N326S mutation.

Embodiment P 42

The method of any one of embodiments P 32 to 41, wherein said recombinant yeast cell metabolizes said xylose compound.

Embodiment P 43

The method of any one of embodiments P 32 to 42, wherein said recombinant yeast cell converts said xylose compound to a biofuel.

Embodiment P 44

The method of any one of embodiments P 32 to 43, wherein said xylose compound forms part of lignocellulosic biomass, hemicellulose, or xylan.

Embodiment P 45

The method of any one of embodiments P 32 to 44, wherein said recombinant xylose transporter transports said xylose compound into said yeast in a xylose-glucose growth media at a rate at least about 10% of the rate said recombinant xylose transporter transports said xylose compound into said yeast in a xylose growth media.

Embodiment P 46

The method of any one of embodiments P 32 to 44, wherein said recombinant xylose transporter transports said xylose compound into said yeast in a xylose-glucose growth media at a rate at least about 20% of the rate said recombinant xylose transporter transports said xylose compound into said yeast in a xylose growth media.

Embodiment P 47

The method of any one of embodiments P 32 to 44, wherein said recombinant xylose transporter transports said xylose compound into said yeast in a xylose-glucose growth media at a rate at least about 30% of the rate said recombinant xylose transporter transports said xylose compound into said yeast in a xylose growth media.

Embodiment P 48

The method of any one of embodiments P 32 to 44, wherein said recombinant xylose transporter transports said xylose compound into said yeast in a xylose-glucose growth media at a rate at least about 40% of the rate said recombinant xylose transporter transports said xylose compound into said yeast in a xylose growth media.

Embodiment P 49

The method of any one of embodiments P 32 to 44, wherein said recombinant xylose transporter transports said xylose compound into said yeast in a xylose-glucose growth media at a rate at least about 50% of the rate said recombinant xylose transporter transports said xylose compound into said yeast in a xylose growth media.

Embodiment P 50

The method of any one of embodiments P 32 to 44, wherein said recombinant xylose transporter transports said xylose compound into said yeast in a xylose-glucose growth media at a rate at least about 60% of the rate said recombinant xylose transporter transports said xylose compound into said yeast in a xylose growth media.

Embodiment P 51

The method of any one of embodiments P 32 to 44, wherein said recombinant xylose transporter transports said xylose compound into said yeast in a xylose-glucose growth media at a rate at least about 70% of the rate said recombinant xylose transporter transports said xylose compound into said yeast in a xylose growth media.

Embodiment P 52

The method of any one of embodiments P 32 to 44, wherein said recombinant xylose transporter transports said xylose compound into said yeast in a xylose-glucose growth media at a rate at least about 80% of the rate said recombinant xylose transporter transports said xylose compound into said yeast in a xylose growth media.

Embodiment P 53

The method of any one of embodiments P 32 to 44, wherein said recombinant xylose transporter transports said xylose compound into said yeast in a xylose-glucose growth media at a rate at least about 90% of the rate said recombinant xylose transporter transports said xylose compound into said yeast in a xylose growth media.

Embodiment P 54

The method of any one of embodiments P 32 to 44, wherein said recombinant xylose transporter transports said xylose compound into said yeast in a xylose-glucose growth media at a rate at least about 100% of the rate said recombinant xylose transporter transports said xylose compound into said yeast in a xylose growth media.

Embodiment P 55

The method of any one of embodiments P 32 to 44, wherein said recombinant xylose transporter transports said xylose compound into said yeast in a xylose-glucose growth media at a rate at least about 110% of the rate said recombinant xylose transporter transports said xylose compound into said yeast in a xylose growth media.

Embodiment P 56

The method of any one of embodiments P 32 to 44, wherein said recombinant xylose transporter transports said xylose compound into said yeast in a xylose-glucose growth media at a rate at least about 120% of the rate said recombinant xylose transporter transports said xylose compound into said yeast in a xylose growth media.

Embodiment P 57

The method of any one of embodiments P 45 to 56, wherein said xylose-glucose growth media comprises about 0.05 g/L to about 20 g/L glucose.

Embodiment P 58

The method of any one of embodiments P 45 to 57, wherein said xylose-glucose growth media comprises about 2.5 g/L glucose.

Embodiment P 59

The method of any one of embodiments P 45 to 58, wherein said xylose-glucose growth media comprises about 5 g/L glucose.

Embodiment P 60

The method of any one of embodiments P 45 to 59, wherein said xylose-glucose growth media comprises about 10 g/L glucose.

Embodiment P 61

The method of any one of embodiments P 45 to 60, wherein said xylose-glucose growth media comprises about 20 g/L glucose.

Embodiment P 62

The method of any one of embodiments P 45 to 61, wherein said xylose-glucose growth media comprises about 0.05 g/L to about 300 g/L xylose.

Embodiment P 63

The method of any one of embodiments P 45 to 62, wherein said xylose growth media comprises about 0.05 g/L to about 300 g/L xylose.

Embodiment P 64

The method of any one of embodiments P 45 to 63, wherein said xylose growth media comprises about 20 g/L xylose.

Embodiment P 65

The method of any one of embodiments P 32 to 64, wherein said recombinant xylose transporter protein transports said xylose compound into said recombinant yeast cell in a xylose-glucose growth media growth media at a rate of at least 5 nmol min$^{-1}$ gDCW$^{-1}$.

Embodiment P 66

A nucleic acid encoding the recombinant xylose transporter protein of one of embodiments P 1 to 10.

VII. Further Embodiments

Embodiment 1

A recombinant xylose transporter protein comprising a xylose transporter motif sequence and a glucose mitigation mutation.

Embodiment 2

The recombinant xylose transporter protein of embodiment 1, wherein said xylose transporter motif sequence corresponds to amino acid residue positions 36, 37, 38, 39, 40, and 41 of *Candida intermedia* GXS1 protein.

Embodiment 3

The recombinant xylose transporter protein of embodiment 1 or embodiment 2, wherein said xylose transporter motif sequence is -G-G/F-X$^1$-X$^2$-X$^3$-G-; wherein, X$^1$ is D, C, G, H, I, L, or F; X$^2$ is A, D, C, E, G, H, or I; and X$^3$ is N, C, Q, F, G, L, M, S, T, or P.

Embodiment 4

The recombinant xylose transporter protein of one of embodiments 1-3, wherein said xylose transporter motif sequence is G-G-F-I-M-G- (SEQ ID NO:107), -G-F-F-I-M-G- (SEQ ID NO:108), -G-G-F-I-S-G- (SEQ ID NO:109), -G-F-F-I-S-G- (SEQ ID NO:110), -G-G-F-I-T-G- (SEQ ID NO:111), -G-F-F-I-T-G- (SEQ ID NO:112), -G-G-F-L-M-G- (SEQ ID NO:113), -G-F-F-L-M-G- (SEQ ID NO:114), -G-G-F-L-S-G- (SEQ ID NO:115), -G-F-F-L-S-G- (SEQ ID NO:116), -G-G-F-L-T-G- (SEQ ID NO:117), -G-F-F-L-T-G- (SEQ ID NO:118), -G-G-F-H-M-G- (SEQ ID NO:119), -G-F-F-H-M-G- (SEQ ID NO:120), -G-G-F-H-S-G- (SEQ ID NO:121), -G-F-F-H-S-G- (SEQ ID NO:122), -G-G-F-H-T-G- (SEQ ID NO:123) or -G-F-F-H-T-G- (SEQ ID NO:124).

Embodiment 5

The recombinant xylose transporter protein of any one of embodiments 2 to 4, wherein said xylose transporter motif sequence is G-G-F-I-M-G- (SEQ ID NO:107), -G-F-F-I-M-G- (SEQ ID NO:108), -G-G-F-I-S-G- (SEQ ID NO:109), or -G-F-F-I-S-G- (SEQ ID NO:110).

Embodiment 6

The recombinant xylose transporter protein of any one of embodiments 1 to 5, wherein said xylose transporter motif sequence is -G-G-F-I-M-G- (SEQ ID NO:107).

Embodiment 7

The recombinant xylose transporter protein of any one of embodiments 1 to 6, wherein said glucose mitigation mutation is within a protein domain corresponding to transmembrane 9 of *Candida intermedia* GXS1 protein.

Embodiment 8

The recombinant xylose transporter protein of any one of embodiments 1 to 7, wherein said glucose mitigation mutation is at a position corresponding to K155, N225, S354, A361, L407, or N446 of *Candida intermedia* GXS1 protein.

Embodiment 9

The recombinant xylose transporter protein of any one of embodiments 1 to 6, wherein said glucose mitigation mutation is within a protein domain corresponding to transmembrane 8 of *Candida intermedia* GXS1 protein.

Embodiment 10

The recombinant xylose transporter protein of any one of embodiments 1 to 6, or embodiment 9, wherein said glucose mitigation mutation is at a position corresponding to N326 of *Candida intermedia* GXS1 protein.

Embodiment 11

The recombinant xylose transporter protein of embodiment 10, wherein said glucose mitigation mutation is a N326H mutation.

Embodiment 12

The recombinant xylose transporter protein of embodiment 10, wherein said glucose mitigation mutation is a N326S mutation.

Embodiment 13

The recombinant xylose transporter protein of any one of embodiments 1 to 6, wherein said glucose mitigation mutation is within a protein domain corresponding to transmembrane 5 of *Candida intermedia* GXS1 protein.

Embodiment 14

The recombinant xylose transporter protein of any one of embodiments 1 to 6, or embodiment 13, wherein said glucose mitigation mutation is within a protein domain corresponding to residue 160-179 of *Candida intermedia* GXS1 protein.

Embodiment 15

The recombinant xylose transporter protein of any one of embodiments 1 to 6, 13 or 14, wherein said glucose mitigation mutation is at a position corresponding to T170 or I171 of *Candida intermedia* GXS1 protein.

Embodiment 16

The recombinant xylose transporter protein of embodiment 15, wherein said glucose mitigation mutation is a T170N mutation.

Embodiment 17

The recombinant xylose transporter protein of embodiment 15, wherein said glucose mitigation mutation is a I171F mutation.

Embodiment 18

The recombinant xylose transporter protein of one of embodiments 1-17 further comprising an amino acid deletion.

Embodiment 19

The recombinant xylose transporter protein of embodiment 18, wherein said deletion is within a protein domain corresponding to residue 497-522 of *Candida intermedia* GXS1 protein.

Embodiment 20

The recombinant xylose transporter protein of embodiment 18 or embodiment 19, wherein said deletion is at least 10 amino acids in length.

Embodiment 21

A recombinant yeast cell comprising a recombinant xylose transporter protein of any one of embodiments 1 to 20

Embodiment 22

The recombinant yeast cell of embodiment 21, wherein the growth rate of said recombinant yeast cell in a xylose-glucose growth media is at least about 10% of the growth rate of said recombinant yeast cell in a xylose growth media.

Embodiment 23

The recombinant yeast cell of embodiment 21, wherein the growth rate of said recombinant yeast cell in a xylose-glucose growth media is at least about 20% of the growth rate of said recombinant yeast cell in a xylose growth media.

Embodiment 24

The recombinant yeast cell of embodiment 21, wherein the growth rate of said recombinant yeast cell in a xylose-glucose growth media is at least about 30% of the growth rate of said recombinant yeast cell in a xylose growth media.

Embodiment 25

The recombinant yeast cell of embodiment 21, wherein the growth rate of said recombinant yeast cell in a xylose-glucose growth media is at least about 40% of the growth rate of said recombinant yeast cell in a xylose growth media.

Embodiment 26

The recombinant yeast cell of embodiment 21, wherein the growth rate of said recombinant yeast cell in a xylose-glucose growth media is at least about 50% of the growth rate of said recombinant yeast cell in a xylose growth media.

Embodiment 27

The recombinant yeast cell of embodiment 21, wherein the growth rate of said recombinant yeast cell in a xylose-glucose growth media is at least about 60% of the growth rate of said recombinant yeast cell in a xylose growth media.

Embodiment 28

The recombinant yeast cell of embodiment 21, wherein the growth rate of said recombinant yeast cell in a xylose-glucose growth media is at least about 70% of the growth rate of said recombinant yeast cell in a xylose growth media.

Embodiment 29

The recombinant yeast cell of embodiment 21, wherein the growth rate of said recombinant yeast cell in a xylose-glucose growth media is at least about 80% of the growth rate of said recombinant yeast cell in a xylose growth media.

Embodiment 30

The recombinant yeast cell of embodiment 21, wherein the growth rate of said recombinant yeast cell in a xylose-glucose growth media is at least about 90% of the growth rate of said recombinant yeast cell in a xylose growth media.

Embodiment 31

The recombinant yeast cell of embodiment 21, wherein the growth rate of said recombinant yeast cell in a xylose-glucose growth media is at least about 100% of the growth rate of said recombinant yeast cell in a xylose growth media.

Embodiment 32

The recombinant yeast cell of embodiment 21, wherein the growth rate of said recombinant yeast cell in a xylose-glucose growth media is at least about 110% of the growth rate of said recombinant yeast cell in a xylose growth media.

Embodiment 33

The recombinant yeast cell of embodiment 21, wherein the growth rate of said recombinant yeast cell in a xylose-glucose growth media is at least about 120% of the growth rate of said recombinant yeast cell in a xylose growth media.

Embodiment 34

The recombinant yeast cell of any one of embodiments 21 to 33, wherein said xylose-glucose growth media comprises about 0.05 g/L to about 20 g/L glucose.

Embodiment 35

The recombinant yeast cell of any one of embodiments 21 to 34, wherein said xylose-glucose growth media comprises about 2.5 g/L glucose.

Embodiment 36

The recombinant yeast cell of any one of embodiments 21 to 35, wherein said xylose-glucose growth media comprises about 5 g/L glucose.

Embodiment 37

The recombinant yeast cell of any one of embodiments 21 to 36, wherein said xylose-glucose growth media comprises about 10 g/L glucose.

Embodiment 38

The recombinant yeast cell of any one of embodiments 21 to 37, wherein said xylose-glucose growth media comprises about 20 g/L glucose.

Embodiment 39

The recombinant yeast cell of any one of embodiments 21 to 38, wherein said xylose-glucose growth media comprises about 0.05 g/L to about 300 g/L xylose.

Embodiment 40

The recombinant yeast cell of any one of embodiments 21 to 39, wherein said xylose growth media comprises about 0.05 g/L to about 300 g/L xylose.

Embodiment 41

The recombinant yeast cell of any one of embodiments 21 to 40, wherein said xylose growth media comprises about 20 g/L xylose.

Embodiment 42

A method of transporting xylose into a recombinant yeast cell, said method comprising: i) contacting a recombinant yeast cell with a xylose compound, wherein said recombinant yeast cell comprises a recombinant xylose transporter protein, said recombinant xylose transporter protein comprising a xylose transporter motif sequence and a glucose mitigation mutation; and ii) allowing said recombinant xylose transporter protein to transport said xylose compound into said recombinant yeast cell.

Embodiment 43

The method of embodiment 42, wherein said xylose transporter motif sequence corresponds to amino acid residue positions 36, 37, 38, 39, 40, and 41 of *Candida intermedia* GXS1 protein.

Embodiment 44

The method of embodiment 42 or embodiment 43, wherein said xylose transporter motif sequence is -G-G/F-$X^1$-$X^2$-$X^3$-G-; wherein, $X^1$ is D, C, G, H, I, L, or F; $X^2$ is A, D, C, E, G, H, or I; and $X^3$ is N, C, Q, F, G, L, M, S, T, or P.

Embodiment 45

The method of one of embodiments 42-44, wherein said xylose transporter motif sequence is -G-G-F-I-M-G- (SEQ ID NO:107), -G-F-F-I-M-G- (SEQ ID NO:108), -G-G-F-I-S-G- (SEQ ID NO:109), -G-F-F-I-S-G- (SEQ ID NO:110), -G-G-F-I-T-G- (SEQ ID NO:111), -G-F-F-I-T-G- (SEQ ID NO:112), -G-G-F-L-M-G- (SEQ ID NO:113), -G-F-F-L-M-G- (SEQ ID NO:114), -G-G-F-L-S-G- (SEQ ID NO:115), -G-F-F-L-S-G- (SEQ ID NO:116), -G-G-F-L-T-G- (SEQ ID NO:117), -G-F-F-L-T-G- (SEQ ID NO:118), -G-G-F-H-M-G- (SEQ ID NO:119), -G-F-F-H-M-G- (SEQ ID NO:120), -G-G-F-H-S-G- (SEQ ID NO:121), -G-F-F-H-S-G- (SEQ ID NO:122), -G-G-F-H-T-G- (SEQ ID NO:123) or -G-F-F-H-T-G- (SEQ ID NO:124).

Embodiment 46

The method of any one of embodiments 42 to 45, wherein said xylose transporter motif sequence is -G-G-F-I-M-G- (SEQ ID NO:107), -G-F-F-I-M-G- (SEQ ID NO:108), -G-G-F-I-S-G- (SEQ ID NO:109), or -G-F-F-I-S-G- (SEQ ID NO:110).

Embodiment 47

The method of any one of embodiments 42 to 46, wherein said xylose transporter motif sequence is -G-G-F-I-M-G- (SEQ ID NO:107).

Embodiment 48

The method of any one of embodiments 42 to 47, wherein said glucose mitigation mutation is within a protein domain corresponding to transmembrane 9 of *Candida intermedia* GXS1 protein.

Embodiment 49

The method of any one of embodiments 42 to 48, wherein said glucose mitigation mutation is at a position corresponding to K155, N225, S354, A361, L407, or N446 of *Candida intermedia* GXS1 protein.

Embodiment 50

The method of any one of embodiments 42 to 47, wherein said glucose mitigation mutation is within a protein domain corresponding to transmembrane 8 of *Candida intermedia* GXS1 protein.

Embodiment 51

The method of any one of embodiments 42 to 47, or embodiment 50, wherein said glucose mitigation mutation is at a position corresponding N326 of *Candida intermedia* GXS1 protein.

Embodiment 52

The method of embodiment 51, wherein said glucose mitigation mutation is a N326H mutation.

Embodiment 53

The method of embodiment 51, wherein said glucose mitigation mutation is a N326S mutation.

Embodiment 54

The method of any one of embodiments 42 to 47, wherein said glucose mitigation mutation is within a protein domain corresponding to transmembrane 5 of *Candida intermedia* GXS1 protein.

Embodiment 55

The method of one of embodiments 42 to 47, or embodiment 54, wherein said glucose mitigation mutation is within a protein domain corresponding to residue 160-179 of *Candida intermedia* GXS1 protein.

Embodiment 56

The method of embodiment 54 or 55, wherein said glucose mitigation mutation is at a position corresponding to T170 or I171 of *Candida intermedia* GXS1 protein.

Embodiment 57

The method of embodiment 56, wherein said glucose mitigation mutation is a T170N mutation.

Embodiment 58

The method of embodiment 56, wherein said glucose mitigation mutation is a I171F mutation.

Embodiment 59

The method of any one of embodiments 42 to 58, further comprising an amino acid deletion.

Embodiment 60

The method of embodiment 59, wherein said deletion is within a protein domain corresponding to residue 497-522 of *Candida intermedia* GXS1 protein.

Embodiment 61

The method of any one of embodiments 42 to 53, wherein said recombinant yeast cell metabolizes said xylose compound.

Embodiment 62

The method of any one of embodiments 42 to 61, wherein said recombinant yeast cell converts said xylose compound to a biofuel.

Embodiment 63

The method of any one of embodiments 42 to 62, wherein said xylose compound forms part of lignocellulosic biomass, hemicellulose, or xylan.

Embodiment 64

The method of any one of embodiments 42 to 63, wherein said recombinant xylose transporter transports said xylose compound into said yeast in a xylose-glucose growth media at a rate at least about 10% of the rate said recombinant xylose transporter transports said xylose compound into said yeast in a xylose growth media.

Embodiment 65

The method of any one of embodiments 42 to 63, wherein said recombinant xylose transporter transports said xylose compound into said yeast in a xylose-glucose growth media at a rate at least about 20% of the rate said recombinant xylose transporter transports said xylose compound into said yeast in a xylose growth media.

Embodiment 66

The method of any one of embodiments 42 to 63, wherein said recombinant xylose transporter transports said xylose compound into said yeast in a xylose-glucose growth media at a rate at least about 30% of the rate said recombinant xylose transporter transports said xylose compound into said yeast in a xylose growth media.

Embodiment 67

The method of any one of embodiments 42 to 63, wherein said recombinant xylose transporter transports said xylose compound into said yeast in a xylose-glucose growth media at a rate at least about 40% of the rate said recombinant xylose transporter transports said xylose compound into said yeast in a xylose growth media.

Embodiment 68

The method of any one of embodiments 42 to 63, wherein said recombinant xylose transporter transports said xylose compound into said yeast in a xylose-glucose growth media at a rate at least about 50% of the rate said recombinant xylose transporter transports said xylose compound into said yeast in a xylose growth media.

Embodiment 69

The method of any one of embodiments 42 to 63, wherein said recombinant xylose transporter transports said xylose compound into said yeast in a xylose-glucose growth media at a rate at least about 60% of the rate said recombinant xylose transporter transports said xylose compound into said yeast in a xylose growth media.

Embodiment 70

The method of any one of embodiments 42 to 63, wherein said recombinant xylose transporter transports said xylose compound into said yeast in a xylose-glucose growth media at a rate at least about 70% of the rate said recombinant xylose transporter transports said xylose compound into said yeast in a xylose growth media.

Embodiment 71

The method of any one of embodiments 42 to 63, wherein said recombinant xylose transporter transports said xylose compound into said yeast in a xylose-glucose growth media at a rate at least about 80% of the rate said recombinant xylose transporter transports said xylose compound into said yeast in a xylose growth media.

Embodiment 72

The method of any one of embodiments 42 to 63, wherein said recombinant xylose transporter transports said xylose compound into said yeast in a xylose-glucose growth media at a rate at least about 90% of the rate said recombinant xylose transporter transports said xylose compound into said yeast in a xylose growth media.

Embodiment 73

The method of any one of embodiments 42 to 63, wherein said recombinant xylose transporter transports said xylose compound into said yeast in a xylose-glucose growth media at a rate at least about 100% of the rate said recombinant xylose transporter transports said xylose compound into said yeast in a xylose growth media.

Embodiment 74

The method of any one of embodiments 42 to 63, wherein said recombinant xylose transporter transports said xylose compound into said yeast in a xylose-glucose growth media at a rate at least about 110% of the rate said recombinant xylose transporter transports said xylose compound into said yeast in a xylose growth media.

Embodiment 75

The method of any one of embodiments 42 to 63, wherein said recombinant xylose transporter transports said xylose compound into said yeast in a xylose-glucose growth media at a rate at least about 120% of the rate said recombinant xylose transporter transports said xylose compound into said yeast in a xylose growth media.

Embodiment 76

The method of any one of embodiments 64 to 75, wherein said xylose-glucose growth media comprises about 0.05 g/L to about 20 g/L glucose.

Embodiment 77

The method of any one of embodiments 64 to 76, wherein said xylose-glucose growth media comprises about 2.5 g/L glucose.

Embodiment 78

The method 1 of any one of embodiments 64 to 77, wherein said xylose-glucose growth media comprises about 5 g/L glucose.

Embodiment 79

The method of any one of embodiments 64 to 78, wherein said xylose-glucose growth media comprises about 10 g/L glucose.

Embodiment 80

The method of any one of embodiments 64 to 79, wherein said xylose-glucose growth media comprises about 20 g/L glucose.

Embodiment 81

The method of any one of embodiments 64 to 80, wherein said xylose-glucose growth media comprises about 0.05 g/L to about 300 g/L xylose.

Embodiment 82

The method of any one of embodiments 64 to 81, wherein said xylose growth media comprises about 0.05 g/L to about 300 g/L xylose.

Embodiment 83

The method of any one of embodiments 64 to 82, wherein said xylose growth media comprises about 20 g/L xylose.

Embodiment 84

The method of any one of embodiments 42 to 83, wherein said recombinant xylose transporter protein transports said xylose compound into said recombinant yeast cell in a xylose-glucose growth media growth media at a rate of at least 5 nmol min$^{-1}$ gDCW$^{-1}$

Embodiment 85

A nucleic acid encoding the recombinant xylose transporter protein of one of embodiments 1 to 21.

---

What is claimed is:

1. A recombinant xylose transporter protein comprising a xylose transporter motif sequence and at least one glucose mitigation mutation; wherein said xylose transporter motif sequence corresponds to amino acid residue positions 36, 37, 38, 39, 40, and 41 of SEQ ID NO: 1, and wherein the xylose transporter motif comprises the sequence -G-G/F-$X^1$-$X^2$-$X^3$-G-;

wherein,
$X^1$ is D, C, G, H, I, L, or F;
$X^2$ is A, D, C, E, G, H, or I; and
$X^3$ is N, C, Q, F, G, L, M, S, T, or P;

and further wherein said glucose mitigation mutation is at a position corresponding to N326, T170, I171, K155, N225, S354, A361, L407, and/or N446 of SEQ ID NO: 1 wherein the xylose transporter protein is at least 95% identical to the sequence of SEQ ID NO: 1 and has xylose transporter protein activity.

2. The recombinant xylose transporter protein of claim 1, wherein said xylose transporter motif sequence is G-G-F-I-M-G- (SEQ ID NO:107), -G-F-F-I-M-G- (SEQ ID NO:108), -G-G-F-I-S-G- (SEQ ID NO:109), or -G-F-F-I-S-G- (SEQ ID NO: 110).

3. The recombinant xylose transporter protein of claim 1, wherein said glucose mitigation mutation is a N326H mutation.

4. The recombinant xylose transporter protein of claim 1, wherein said glucose mitigation mutation is a N326S mutation.

5. The recombinant xylose transporter protein of claim 1 further comprising an amino acid deletion.

6. The recombinant xylose transporter protein of claim 5, wherein said deletion is within a protein domain corresponding to residue 497-522 of SEQ ID NO: 1.

7. A recombinant yeast cell comprising a recombinant xylose transporter protein of claim 1.

8. The recombinant yeast cell of claim 7, wherein the growth rate of said recombinant yeast cell in a xylose-glucose growth media is at least about 50% of the growth rate of said recombinant yeast cell in a xylose growth media.

9. A nucleic acid encoding the recombinant xylose transporter protein of claim 1.

* * * * *